(12) United States Patent
Van de Bittner et al.

(10) Patent No.: US 10,519,160 B2
(45) Date of Patent: Dec. 31, 2019

(54) IMAGING AGENTS FOR NEURAL FLUX

(71) Applicant: The General Hospital Corporation, Boston, MA (US)

(72) Inventors: Genevieve Van de Bittner, Stoneham, MA (US); Jacob M. Hooker, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/326,890

(22) PCT Filed: Jul. 17, 2015

(86) PCT No.: PCT/US2015/040971
§ 371 (c)(1),
(2) Date: Jan. 17, 2017

(87) PCT Pub. No.: WO2016/011394
PCT Pub. Date: Jan. 21, 2016

(65) Prior Publication Data
US 2018/0258090 A1 Sep. 13, 2018

Related U.S. Application Data

(60) Provisional application No. 62/074,853, filed on Nov. 4, 2014, provisional application No. 62/026,147, filed on Jul. 18, 2014.

(51) Int. Cl.
| | | |
|---|---|---|
| C07D 473/40 | (2006.01) | |
| C07D 473/16 | (2006.01) | |
| C07D 487/04 | (2006.01) | |
| C07D 473/34 | (2006.01) | |
| C07B 59/00 | (2006.01) | |
| A61K 51/04 | (2006.01) | |

(52) U.S. Cl.
CPC ........ *C07D 473/40* (2013.01); *A61K 51/0459* (2013.01); *C07B 59/002* (2013.01); *C07D 473/16* (2013.01); *C07D 473/34* (2013.01); *C07D 487/04* (2013.01); *C07B 2200/05* (2013.01)

(58) Field of Classification Search
CPC ... C07D 473/16; C07D 473/40; C07D 487/04
See application file for complete search history.

(56) References Cited

U.S. PATENT DOCUMENTS

| | | |
|---|---|---|
| 2004/0096436 A1 | 5/2004 | Carson et al. |
| 2010/0184760 A1 | 7/2010 | Ren et al. |
| 2011/0053941 A1 | 3/2011 | Mautino et al. |
| 2012/0289496 A1 | 11/2012 | Nagarathnam et al. |

FOREIGN PATENT DOCUMENTS

| | | | | |
|---|---|---|---|---|
| WO | WO-2011028507 A2 * | 3/2011 | ........... | C07D 473/18 |

OTHER PUBLICATIONS

Stuart Wilson et al. Design, Synthesis and biological evaluation of 6-oyridylmethylaminopurines as CDK inhibitors, Bioorganic & Medicinal Chemistry, 19, 6949-6965. (Year: 2011).*
ILibor Havlicek et al., Cytokinin-Derived Cyclin-Dependent Kinase Inhibitors: Synthesis and cdc2 Inhibitory Activity of Olomoucine and Related Compounds, J. Med. Chem. 40, 408-412. (Year: 1997).*
Alexoff et al., "Reproducibility of 11C-raclopride binding in the rat brain measured with the microPET R4: effects of scatter correction and tracer specific activity," J Nucl Med., May 2003, 44(5):815-22.
Ansari and Johnson, "Olfactory function in patients with Parkinson's disease," Journal of Chronic Diseases, Oct. 1975, 28:493-7.
Aoki et al., "Drebrin A is a postsynaptic protein that localizes in vivo to the submembranous surface of dendritic sites forming excitatory synapses," Journal of Comparative Neurology, 2005, 483:383-402.
Bretin et al., "Preclinical radiation dosimetry for the novel SV2A radiotracer [18F]UCB-H," EJNMMI Research, 2013, 3(1):35.
Brown et al., "Metabotropic glutamate subtype 5 receptors are quantified in the human brain with a novel radioligand for PET," Journal ofNuclear Medicine, 2008, 49:2042-8.
Cai et al., "Radiosynthesis and preliminary evaluation of 11C-levetiracetam for PET imaging of SV2A expression," The Journal of Nuclear Medicine, 2014, 55: 1795.
Cesca et al., "The synapsins: key actors of synapse function and plasticity," Progress in Neurobiology, 2010, 91:313-48.
Day et al., "Selective elimination of glutamatergic synapses on striatopallidal neurons in Parkinson's disease models," Nature Neuroscience, 2006, 9:251-9.
De Franchi et al., "Binding of protein kinase inhibitors to synapsin I inferred from pair-wise binding site similarity measurments," PLoS One, 2010, 5(8):e12214.
Dean and Scheiffele, "Imaging Synaptogenesis by Measuring Accumulation of Synaptic Proteins," Cold Spring Harbor Protocols, Nov. 2009, 4(11):1-4.
Duda et al., "The expression of alpha-, beta-, and gamma-synucleins in olfactory mucosa from patients with and without neurodegenerative diseases," Experimental Neurology, Dec. 1999, 160(2):515-22.
Dunn et al., "Establishing test-retest reliability of an adapted [(18)F]fallypride imaging protocol in older people," J Cereb Blood Flow Metab, Jul. 2013, 33(7):1098-103.
Eastwood and Harrison, "Decreased synaptophysin in the medial temporal lobe in schizophrenia demonstrated using immunoautoradiography," Neuroscience, 1995, 69:339-43.

(Continued)

*Primary Examiner* — Michael G. Hartley
*Assistant Examiner* — Jagadishwar R Samala
(74) *Attorney, Agent, or Firm* — Fish & Richardson P.C.

(57) ABSTRACT

Provided herein are radiolabeled compounds useful for non-invasive imaging techniques. An exemplary radiolabeled compound provided herein is useful as a radiotracer for positron emission tomography. The present application also provides unlabeled compounds useful in methods of treating diseases of the central nervous system or disease of the peripheral nervous system. Methods for preparing radiolabeled compounds, preparing unlabeled compounds, and diagnostic methods using labeled or unlabeled compounds are also provided.

12 Claims, 34 Drawing Sheets

(56) References Cited

OTHER PUBLICATIONS

Farrell et al., "Non-motor parkinsonian pathology in aging A53T α-synuclein mice is associated with progressive synucleinopathy and altered enzymatic function," Journal of Neurochemistry, 2014, 128(4):536-46.
Ferrante et al., "Proliferative and Degenerative Changes in Striatal Spiny Neurons in Huntington's Disease: A Combined Study Using the Section-Golgi Method and Calbindin D28k Immunocytochemistry," The Journal of Neuroscience, Dec. 1991, 11(12):3877-87.
Ferreira and Rapoport, "The synapsins: beyond the regulation of neurotransmitter release," Cellular and Molecular Life Sciences, Apr. 2002,59:589-95.
Fletcher et al., "The distribution of synapsin I and synaptophysin in hippocampal neurons developing in culture," The Journal of Neuroscience, Jun. 1991,11(6):1617-26.
Frank et al., "New approaches for studying synaptic development, function, and plasticity using *Drosophila* as a model system," The Journal of Neuroscience, 2013, 33(45):17560-8.
Gage et al., "Reproducibility of Repeated Measures of Cholinergic Terminal Density Using [18F](+)-4-Fluorobenzyltrozamicol and PET in the Rhesus Monkey Brain," J Nucl Med, 2000, 41(12):2069-76.
Glantz et al., "Apoptotic mechanisms and the synaptic pathology of schizophrenia," Schizophrenia Research, 2006, 81:47-63.
Goelz et al., "Distribution of protein I in mammalian brain as determined by a detergent-based radioimmunoassay," PNAS, 1981;78:2130-4.
Grabrucker et al., "Synaptogenesis of hippocampal neurons in primary cell culture," Cell and Tissue Research, Dec. 2009, 338(3):333-41.
Graveland et al., "Evidence for Degenerative and Regenerative Changes in Neostriatal Spiny Neurons in Huntington's Disease," Science, Feb. 1985, 227:770-3.
Graziadei and Graziadei, "Neurogenesis and neuron regeneration in the olfactory system of mammals. I. Morphological aspects of differentiation and structural organization of the olfactory sensory neurons," J. Neurocytol, Feb. 1979, 8: 1-18.
Hawkes, "Olfaction in Neurodegenerative Disorder," Movement Disorders, Apr. 2003, 18:364-72.
Herzog and Van Den Hoff, "Combined PET/MR systems: an overview and comparison of currently available options," The Quarterly Journal of Nuclear Medicine and Molecular Imaging, Jun. 2012, 56(3):247-67.
Hinds et al., "Aging in the rat olfactory system: Correlation of changes in the olfactory epithelium and olfactory bulb," J. Comp. Neural., Dec. 1981, 203: 441-453.
Ho et al., "In vivo imaging of adult human hippocampal neurogenesis: progress, pitfalls and promise," Molecular Psychiatry, 2013, 18:404-16.
Hosaka and Sudhof, "Synapsins I and II are ATP-binding proteins with differential Ca2+ regulation," Journal of Biological Chemistry, 1998, 273:1425-9.
Howard et al., "Plasma Protein Binding in Drug Discovery and Development," Comb Chem High Throughput Screen, 2010, 13: 170-187.
Huang et al., "Late Stage Benzylic C—H Fluorination with [18F]Fluoride for PET Imaging," Journal of the American Chemical Society, 2014, 136(19):6842-5.
International Preliminary Report on Patentability in International Application No. PCT/US2015/040971, dated Jan. 24, 2017, 8 pages.
Kang et al., "Decreased expression of synapse-related genes and loss of synapses in major depressive disorder," Nature Medicine, 2012, 18(9):1413-7.
Kassem et al., "Stress-induced grey matter loss determined by MRI is primarily due to loss of dendrites and their synapses," Molecular Neurobiology, 2013, 47:645-61.
Knockaert et al., "Pharmacological inhibitors of cyclin-dependent kinases," Trends in Pharmacological Sciences, 2002, 23(9):417-25.
Kolomeets e al., "Decreased Numerical Density of CA3 Hippocampal Mossy Fiber Synapses in Schizophrenia," Synapse, 2007, 61:615-21.
Kovacs et al., "β-Amyloid deposition and neurofibrillary tangle formation in the olfactory bulb in ageing and Alzheimer's disease," Neuropathology and Applied Neurobiology, 1999, 25(6):481-91.
Lane-Guermonprez et al., "Synapsin associates with cyclophilin B in an ATP- and cyclosporin A-dependent manner," Journal of Neurochemistry, 2005, 93:1401-11.
Lara et al., "Antidepressant, mood stabilizing and procognitive effects of very low dose sublingual ketamine in refractory unipolar and bipolar depression," International Journal of Neuropsychopharmacology, 2013, 16(9):2111-7.
Larson et al., "Soluble α-Synuclein Is a Novel Modulator of Alzheimer's Disease Pathophysiology," The Journal of Neuroscience, 2012, 32(30):10253-66.
Lee et al., "Human alpha-synuclein-harboring familial Parkinson's disease-linked Ala-53 --> Thr mutation causes neurodegenerative disease with alpha-synuclein aggregation in transgenic mice," PNAS, 2002, 99(13):8968-73.
Lee et al., "Olfactory-related cortical atrophy is associated with olfactory dysfunction in Parkinson's disease," Movement Disorders, Aug. 2014, 29: 1205-1208.
Lelan et al., "Effects of Human Alpha-Synuclein A53T-A30P Mutations on SVZ and Local Olfactory Bulb Cell Proliferation in a Transgenic Rat Model of Parkinson Disease," Parkinson's Disease, 2011, 2011: 1-11.
Li et al., "Glutamate N-methyl-D-aspartate receptor antagonists rapidly reverse behavioral and synaptic deficits caused by chronic stress exposure," Biological Psychiatry, 2011;69(8):754-61.
Lim et al., "Forebrain overexpression of alpha-synuclein leads to early postnatal hippocampal neuron loss and synaptic disruption," Experimental Neurology, 2010, 221:86-97.
Logan, "Graphical analysis of Pet data applied to reversible and irreversible tracers," Nuclear Medicine and Biology, Oct. 2000, 27(7):661-70.
Magen and Chesselet, "Genetic mouse models of Parkinson's disease: The state of the art," Progress in Brain Research, 2010, 184:53-87.
Marcucci et al., "Sequential onset of presynaptic molecules during olfactory sensory neuron maturation," The Journal of Comparative Neurology, 2009, 516:187-98.
Masliah and Terry, "The role of synaptic proteins in the pathogenesis of disorders of the central nervous system," Brain Pathology, Jan. 1993, 3:77-85.
McCann et al., "α-Synucleinopathy phenotypes," Parkinsonism and Related Disorders, Jan. 2014, 20 (Suppl 1): S62-7.
McLaren et al., "A population-average MRI-based atlas collection of the rhesus macaque," Neuroimage, Mar. 2009, 45(1):52-9.
Melloni Jr et al., "Dynamics of synapsin I gene expression during the establishment and restoration of functional synapses in the rat hippocampus," Neuroscience, Feb. 1994, 58:683-703.
Mochalkin et al., "Discovery of Antibacterial Biotin Carboxylase Inhibitors by Virtual Screening and Fragment-Based Approaches," ACS Chemical Biology, Jun. 2009, 4(6):473-83.
Murrell et al., "Neurogenesis in adult human," Neuroreport., Apr. 1996, 7(6):1189-94.
Narendran et al., "PET Imaging of dopamine D2/3 receptors in the human cortex with [11C]FLB 457: reproducibility studies," Synapse, Jan. 2011, 65(1):35-40.
Neelamegam et al., "Imaging Evaluation of 5HT2C Agonists,[11C] WAY-163909 and [11C] Vabicaserin, Formed by Pictet-Spengler Cyclization," Journal of Medicinal Chemistry, 2014, 57(4):1488-94.
Nemani et al., "Increased expression of alpha-synuclein reduces neurotransmitter release by inhibiting synaptic vesicle reclustering after endocytosis," Neuron, Jan. 2010, 65(1):66-79.
Nithianantharajah and Hannan, "Dysregulation of synaptic proteins, dendritic spine abnormalities, and pathological plasticity of synapses as experience-dependent mediators of cognitive and psychiatric symptoms in Huntington's Disease," Neuroscience, Oct. 2013, 251:66-74.

(56) References Cited

OTHER PUBLICATIONS

Nord et al., "Test-retest reliability of [11C]AZ10419369 binding to 5-HT(1B) receptors in human brain," Eur J Nucl Med Mol Imaging, Feb. 2014, 41(2):301-7.
Nuber et al., "A progressive dopaminergic phenotype associated with neurotoxic conversion of α-synuclein in BAC-transgenic rats," Brain, 2013, 136:412-32.
Oaks et al., "Age-dependent effects of A53T alpha-synuclein on behavior and dopaminergic function," PLoS ONE, 2013, 8(4):e60378.
Petit et al., "Rasagiline Ameliorates Olfactory Deficits in an AlphaSynuclein Mouse Model of Parkinson's Disease," PLOS One, 2013, 8:e60691.
Pettersen et al., "UCSF Chimera—a visualization system for exploratory research and analysis," Journal of Computational Chemistry, 2004, 25(13):1605-12.
Pike, "PET radiotracers: crossing the blood-brain barrier and surviving metabolism," Trends in Pharmacological Sciences, Aug. 2009, 30(8):431-40.
Ren et al., "Synthesis and Imaging Validation of [18F]MDL100907 Enabled by Ni-Mediated Fluorination," ACS Chemical Neuroscience, 2014, 5: 611-615.
Roberts et al., "Synaptic differences in the postmortem striatum of subjects with Schizophrenia: a stereological ultrastructural analysis," Synapse, 2005, 56:185-97.
Roisen et al., "Adult human olfactory stem cells," Brain Research, 2001, 890(1):11-22.
Schoch et al., "Neuron-specific gene expression of synapsin I," The Journal of Biological Chemistry, 1996, 271:3317-23.
Selkoe, "Alzheimer's disease is a synaptic failure," Science, Oct. 2002, 298:789-91.
Seo et al., "Image-guided synthesis reveals potent blood-brain barrier permeable histone deacetylase inhibitors," ACS Chemical Neuroscience, 2014, 5: 588-596.
Sudo et al., "Reproducibility of [11 C]FLB 457 binding in extrastriatal regions," Nucl Med Commun, Nov. 2001, 22(11):1215-21.
Sultana et al., "Decreased levels of PSD95 and two associated proteins and increased levels of BC12 and caspase 3 in hippocampus from subjects with amnestic mild cognitive impairment: Insights into their potential roles for loss of synapses and memory, accumulation of Aβ, and neurodegeneration in a prodromal stage of Alzheimer's disease," Journal of Neuroscience Research, 2009, 88(3):469-77.
Syvänen et al., "Species differences in blood-brain barrier transport of three positron emission tomography radioligands with emphasis on P-glycoprotein transport," Drug Metabolism and Disposition, 2009, 37:635-43.
Terry et al., "Physical basis of cognitive alterations in Alzheimer's disease: Synapse loss is the major correlate of cognitive impairment," Annals of Neurology, Oct. 1991, 30:572-80.
Thiebaut et al., "Cellular localization of the multidrug-resistance gene product P-glycoprotein in normal human tissues," PNAS, Nov. 1987, 84(21):7735-8.
Trott and Olson, "AutoDock Vina: improving the speed and accuracy of docking with a new scoring function, efficient optimization and multithreading," Journal of Computational Chemistry, Jan. 2010, 31:455-61.
Wang et al., "Design, synthesis, and evaluation of hydroxamic acid-based molecular probes for in vivo imaging of histone deacetylase (HDAC) in brain," American Journal of Nuclear Medicine and Molecular Imaging, 2014, 4(1):29-38.
Weiler and Benali, "Olfactory epithelia differentially express neuronal markers," Journal of Neurocytology, Sep. 2005, 34:217-40.
Williams et al., "Retinal ganglion cell dendritic degeneration in a mouse model of Alzheimer's disease," Neurobiology of Aging, 2013, 34(7):1799-806.
Wilson et al., "Design, synthesis and biological evaluation of 6-pyridylmethylaminopurines as CDK inhibitors," Bioorg. Med. Chem, Nov. 2011, 19: 6949-6965.
Witt et al., "Biopsies of olfactory epithelium in patients with Parkinson's disease," Movement Disorders, 2009, 24(6):906-14.
Yamada et al., "Synaptic adhesion molecule OBCAM; synaptogenesis and dynamic internalization," Brain Research, Aug. 2007, 1165:5-14.
Zaja-Milatovic et al., "Dendritic degeneration in neostriatal medium spiny neurons in Parkinson disease," Neurology, Feb. 2005, 64:545-547.
International Search Report and Written Opinion dated Dec. 18, 2015 in international application No. PCT/US2015/040971, 15 pgs.

\* cited by examiner

%ID/cc = percent injected dose/cc

DVR = distribution volume ratio

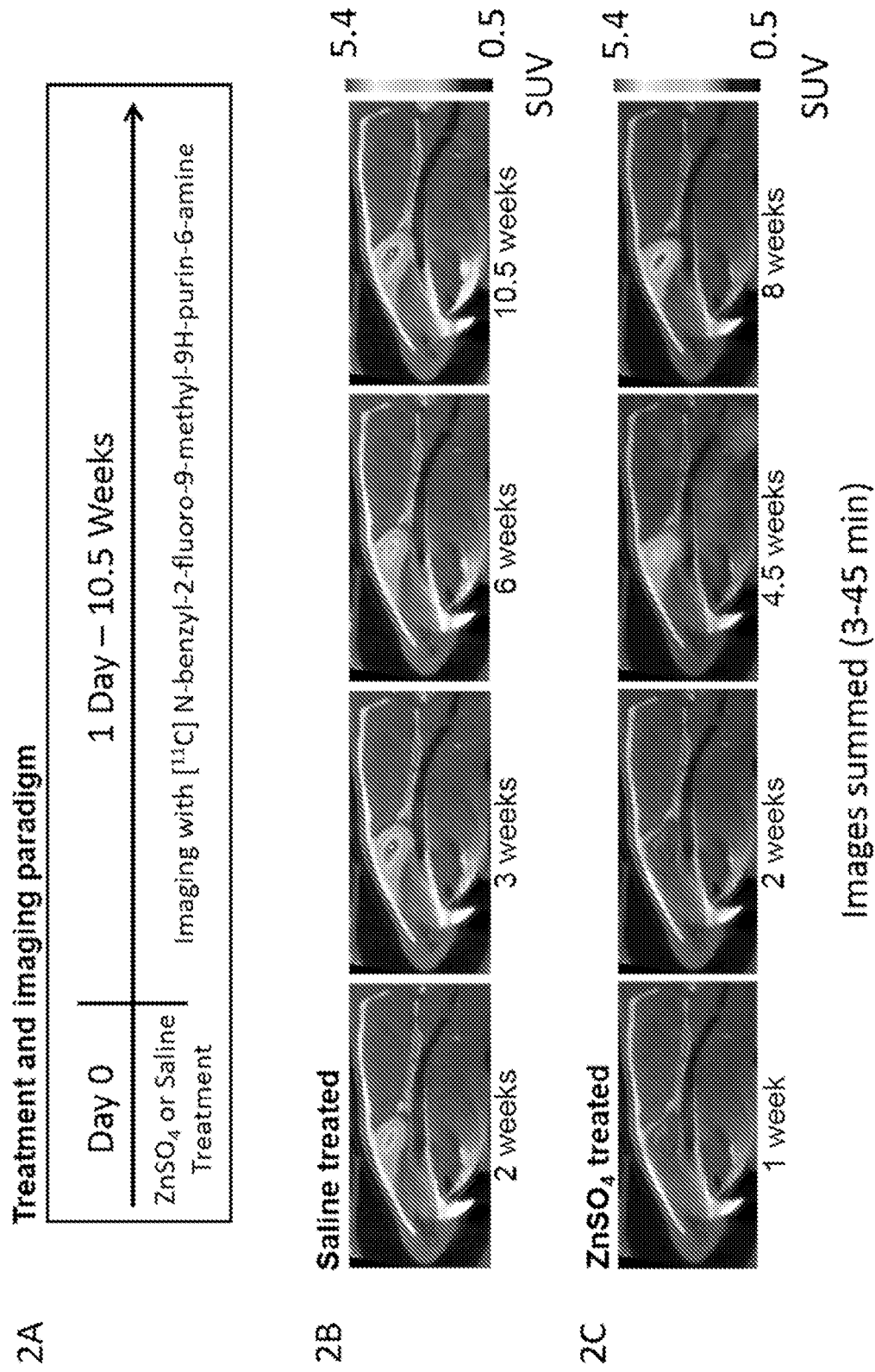
FIG. 2A-C

FIG. 4A-B
4A SUV changes in rats
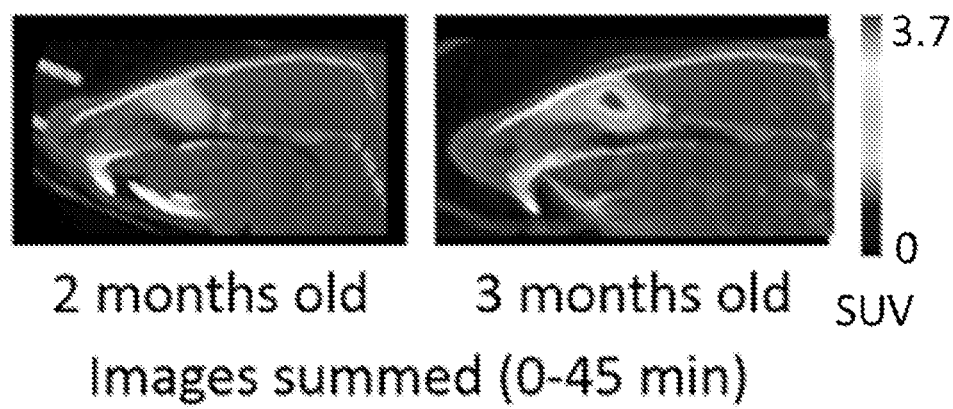
2 months old    3 months old
Images summed (0-45 min)
4B Logan Analysis - Rat
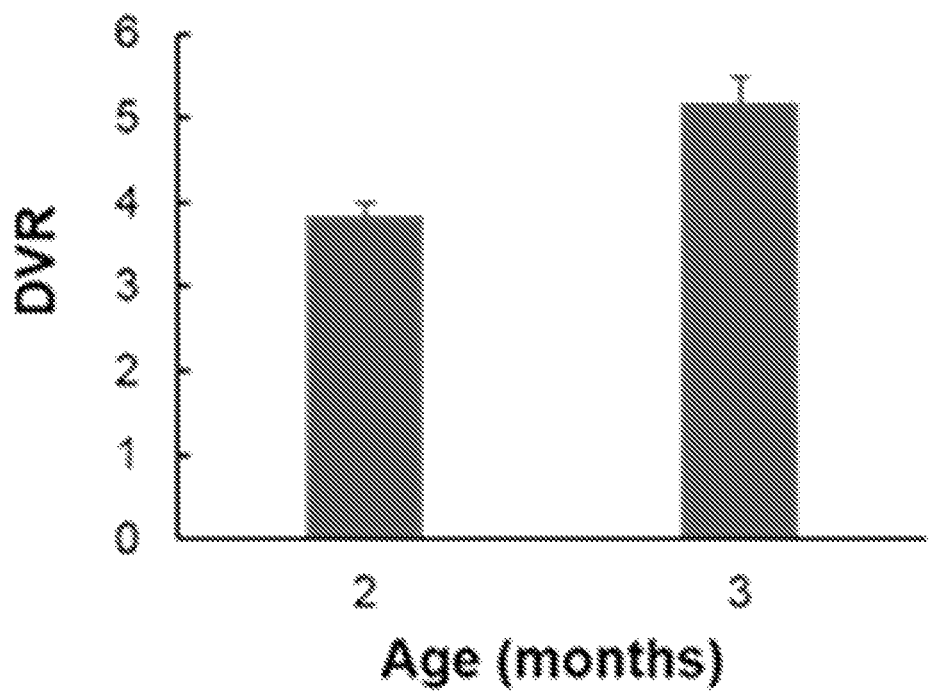

4C SUV changes in mice

1.7 months old    4.2 months old    24 months old    SUV

4D 1.7 mo: n=1    4.2 mo: n=3
12 mo: n=2    24 mo> n=1

DVR = distribution volume ratio

%ID/cc = percent injected dose/cc

FIG. 9
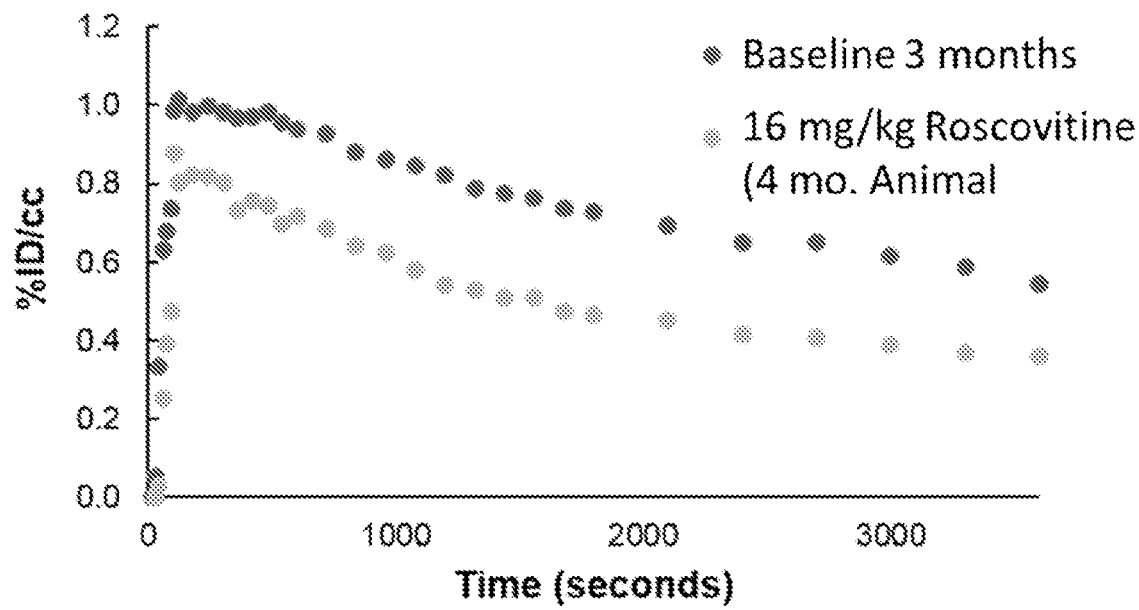
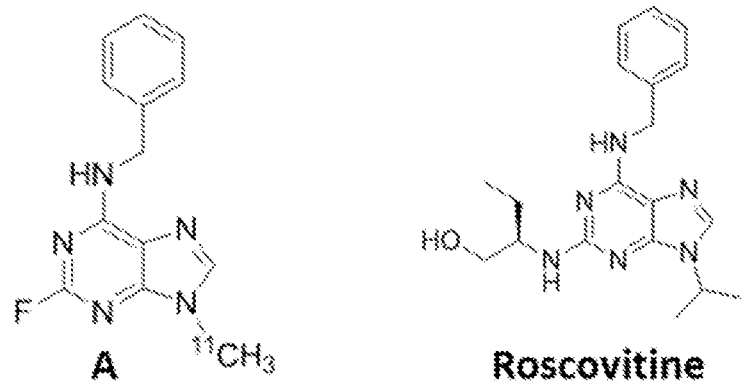
%ID/cc = percent injected dose/cc

FIG. 10B
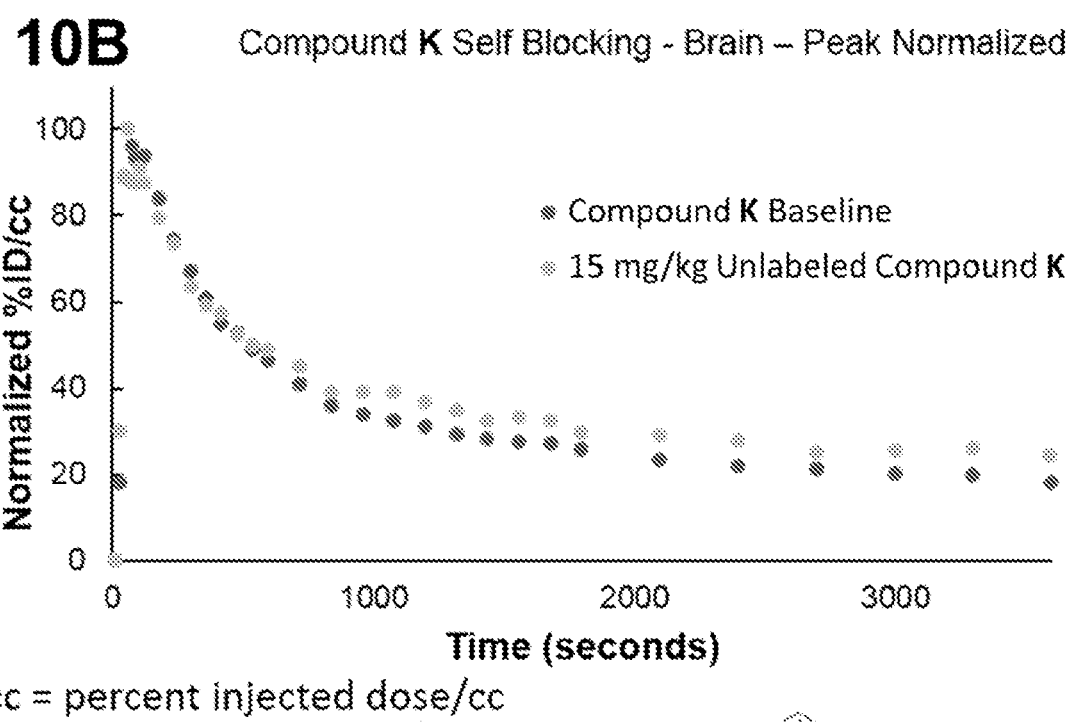
%ID/cc = percent injected dose/cc
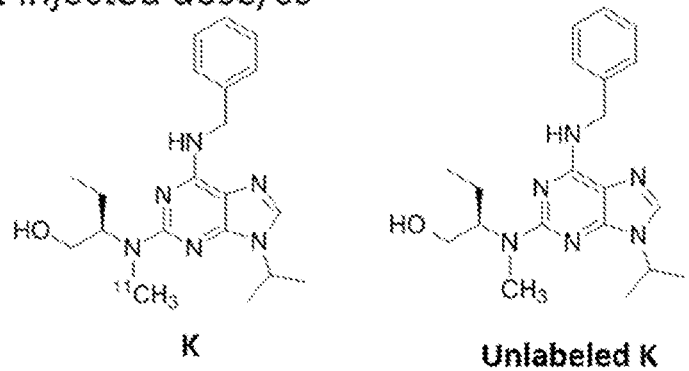

FIG. 11
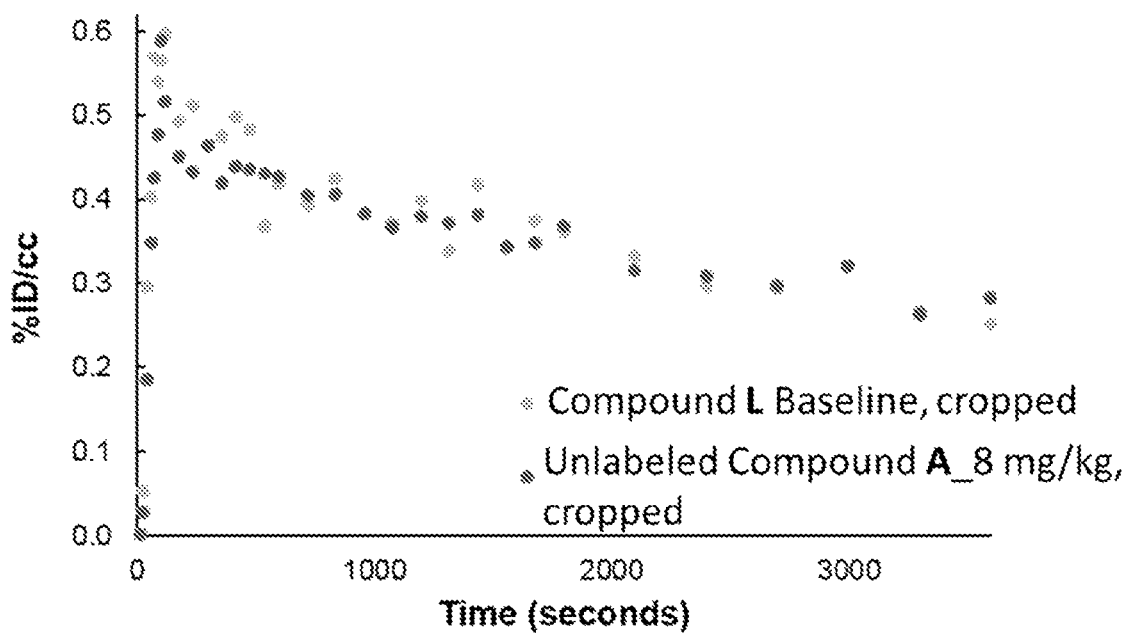
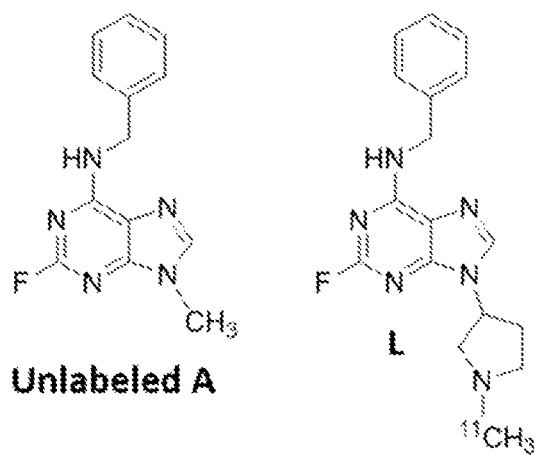
%ID/cc = percent injected dose/cc

FIG. 12A
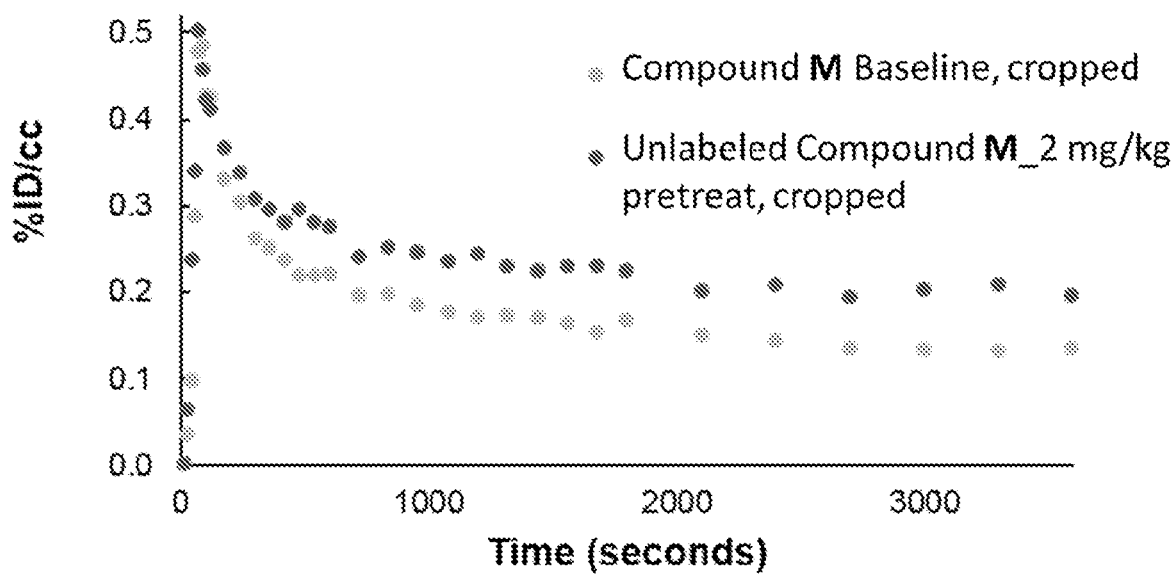
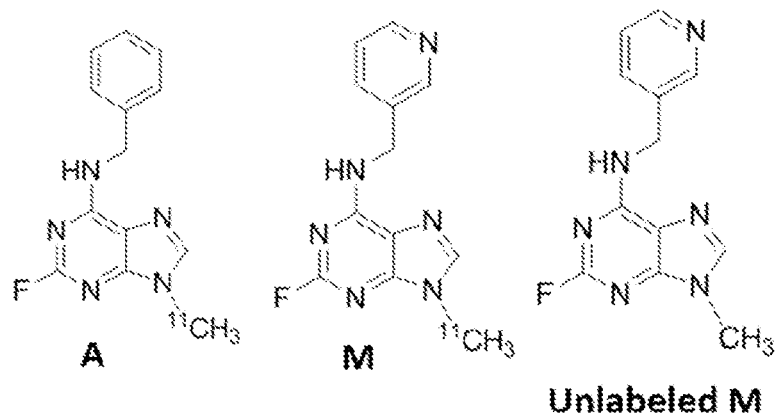

FIG. 12B
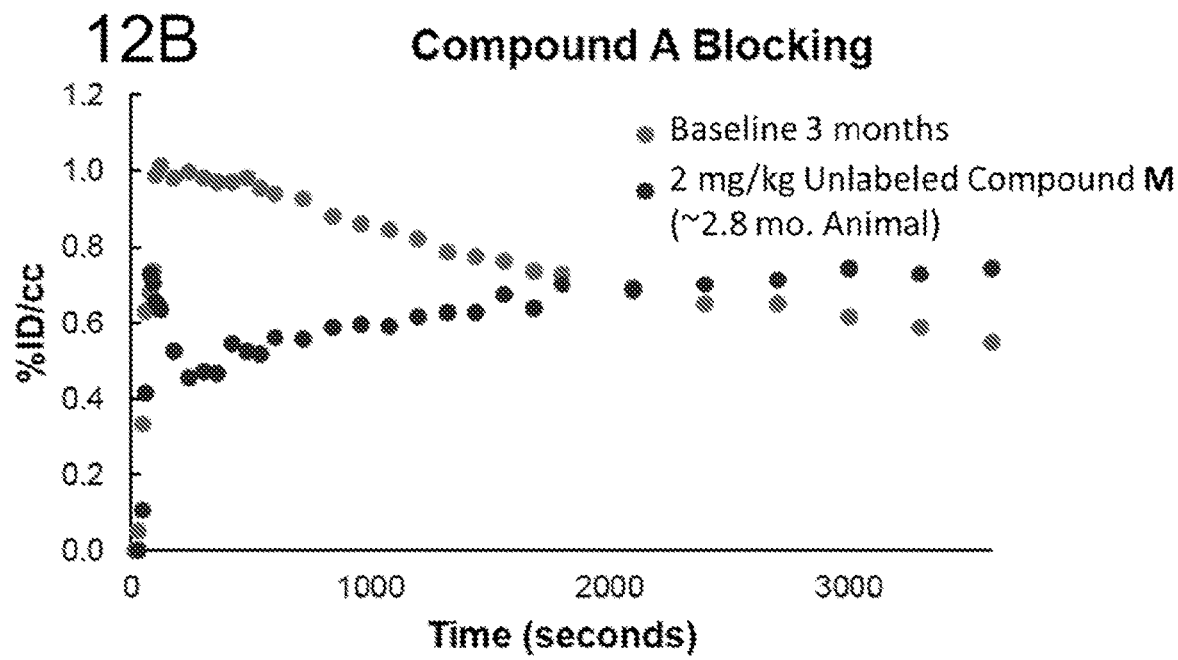
% ID/cc = percent injected dose/cc
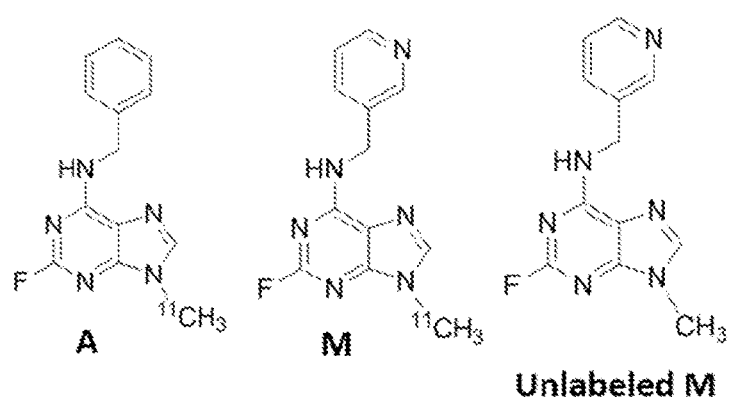

FIG. 13B
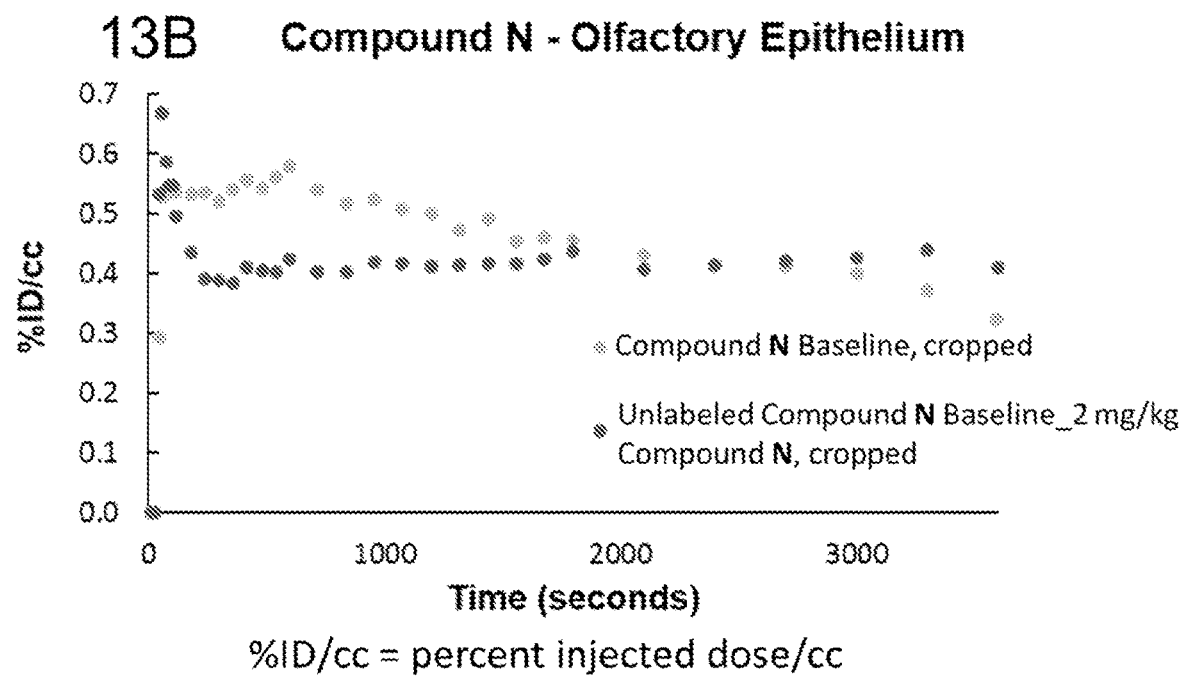
%ID/cc = percent injected dose/cc
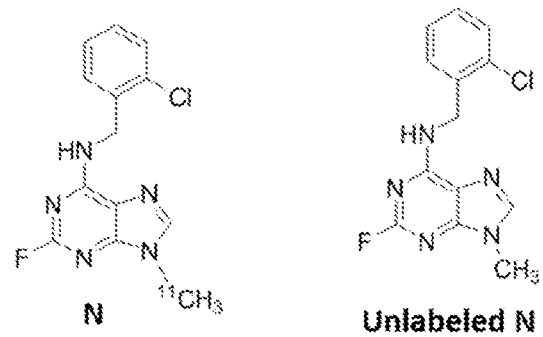

FIG. 13C
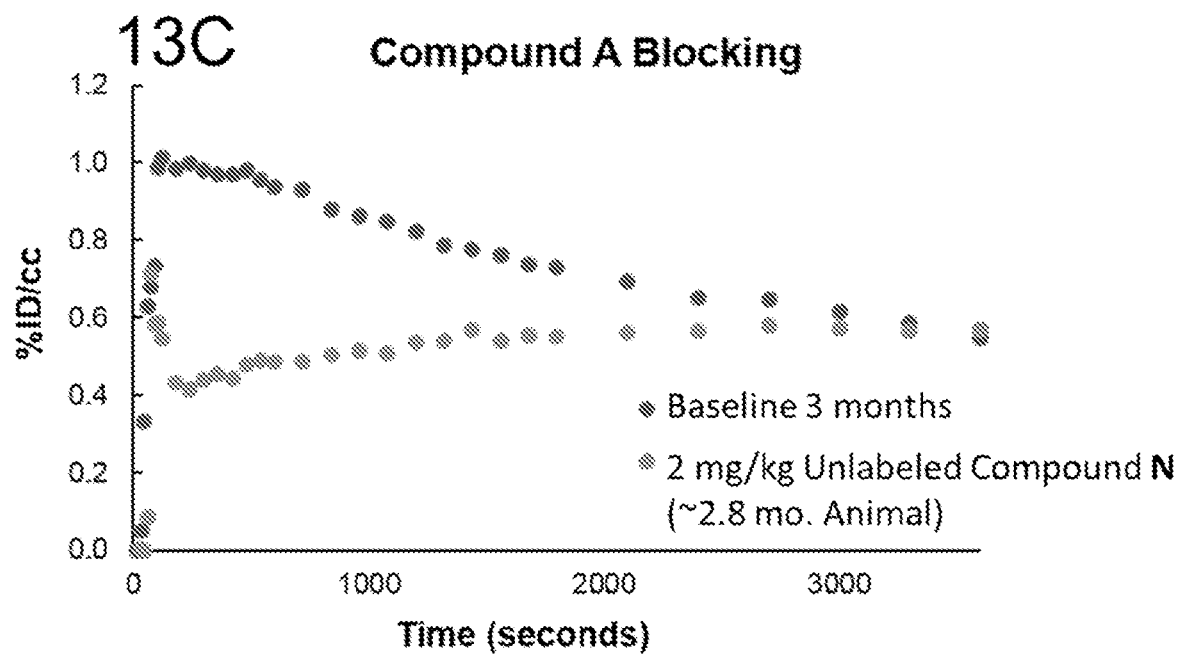
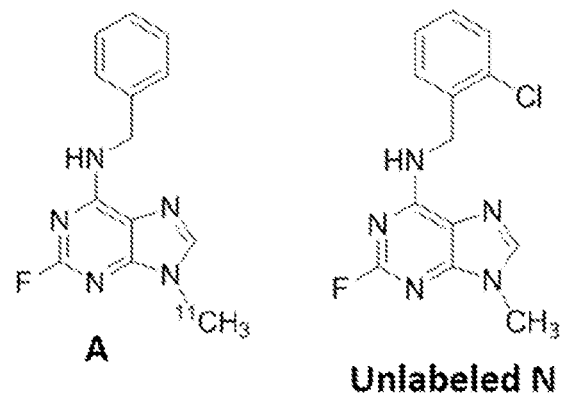
%ID/cc = percent injected dose/cc

%ID/cc = percent injected dose/cc

FIG. 14B
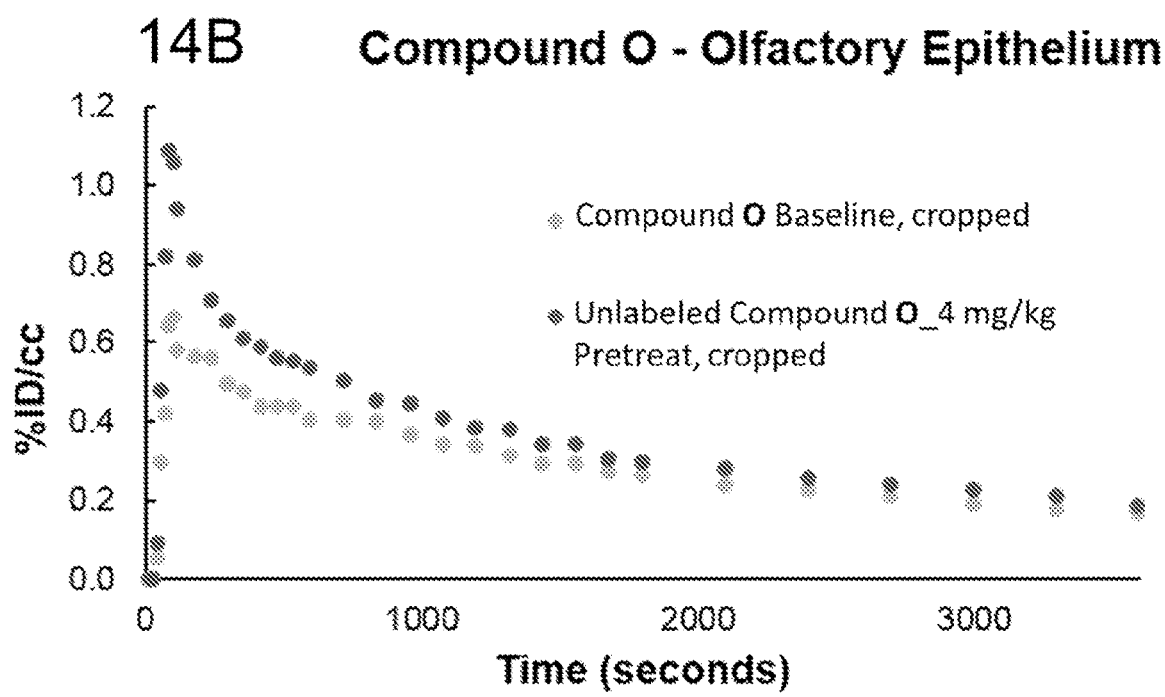
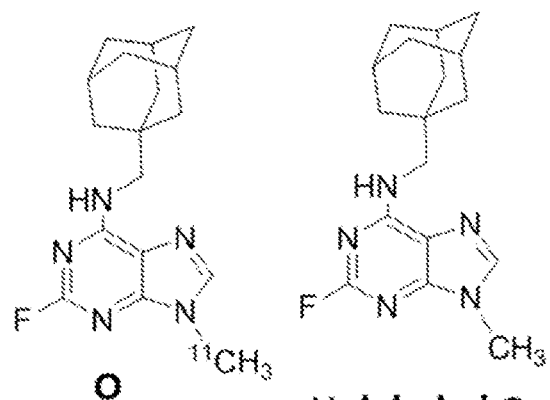
%ID/cc = percent injected dose/cc

FIG. 14C
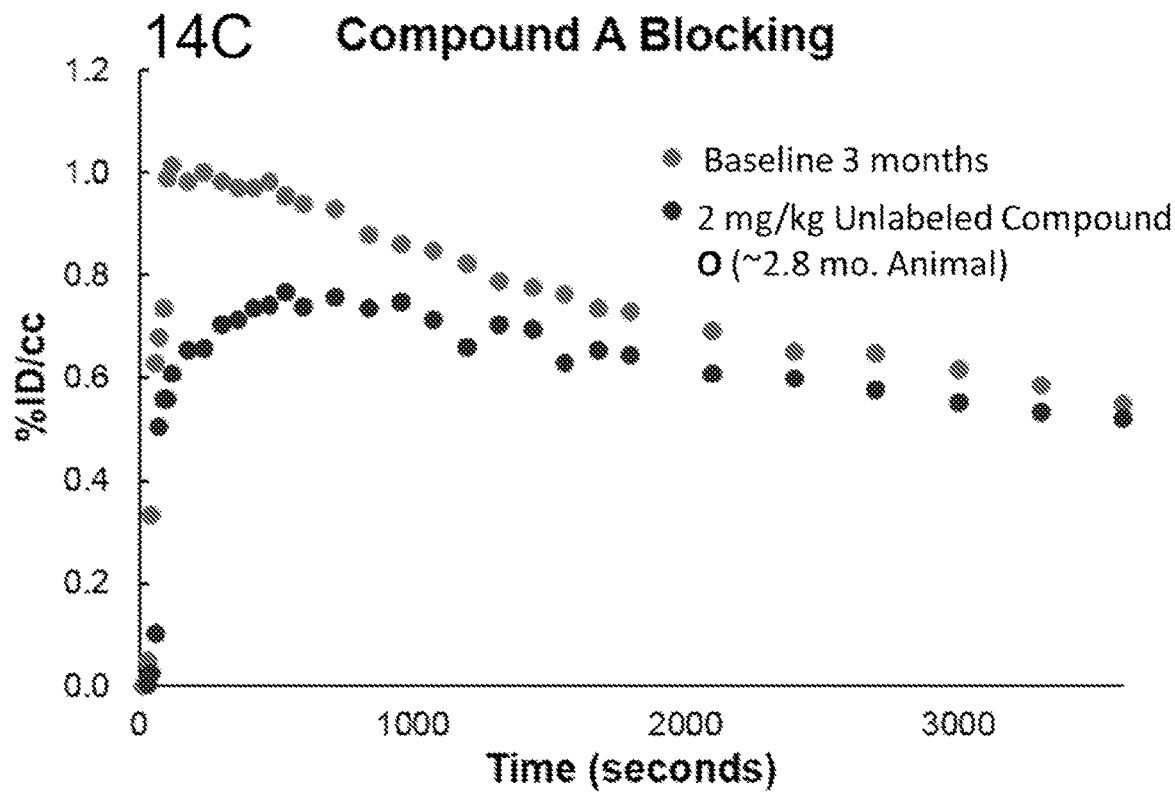
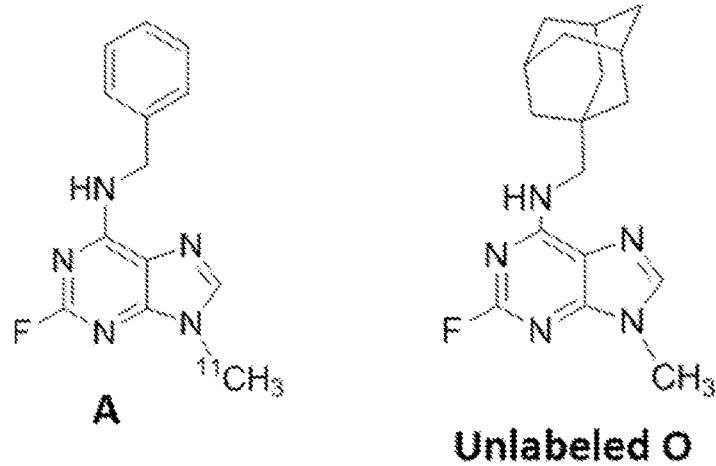
%ID/cc = percent injected dose/cc

FIG. 15

| | | | | | | |
|---|---|---|---|---|---|---|
| %ID/cc OE (highest) | 1.0 | N/A | 0.5 | 0.6 | 0.5 | 0.5 |
| %ID/cc Brain (highest) | 1.0 | 0.4 | 0.6 | 0.8 | 0.4 | 0.8 |
| GV1-57 Blocking | Yes | No | N/A | Yes | Yes | Yes |
| Self Blocking | Yes | No | No | Probably | No | Yes - OE |
| Estimated in vivo "IC₅₀" | - | < Cmpd A | N/A | ≈ Cmpd A | > Cmpd A | > Cmpd A |
| LogP | 2.04(m), 2.22 (e) | 2.12(m), 3.54 (e) | 2.06 (e) | 3 (e) | 0.88 (e) | 2.78 (e) |
| tPSA | 52.35 | 75.82 | 55.59 | 52.35 | 64.71 | 52.35 |

N/A = not available
OE = olfactory epithelium
LogP = partition coefficient (m = measured; (e) = estimated)
tPSA = Topological Polar Surface Area (estimated value)

FIG. 16A-B
*Synapsin 1 – ATP bound (key interacting residues shown)*
*Synapsin 1 – N-benzyl-2-fluoro-9-methyl-9H-purin-6-amine bound (energy minimum from AutoDock Vina®)*

FIG. 18A-B
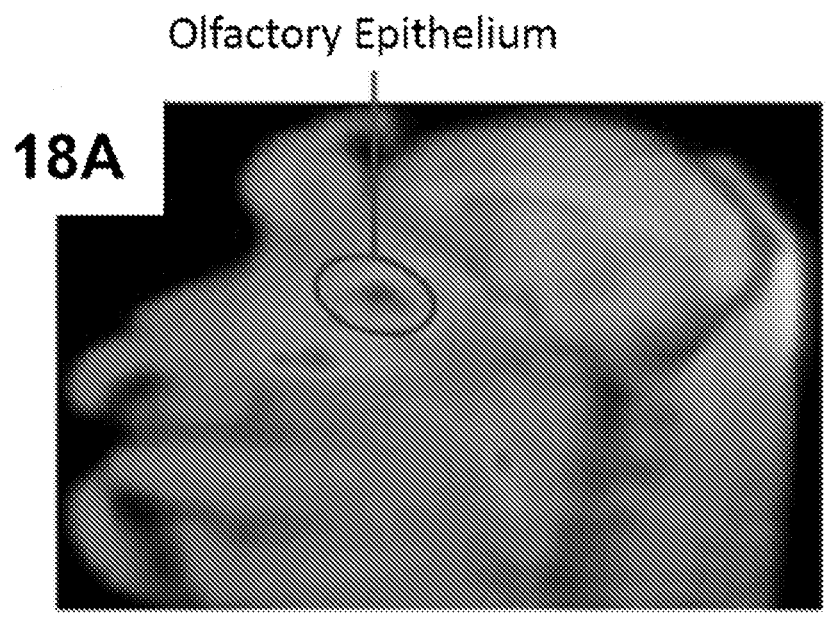
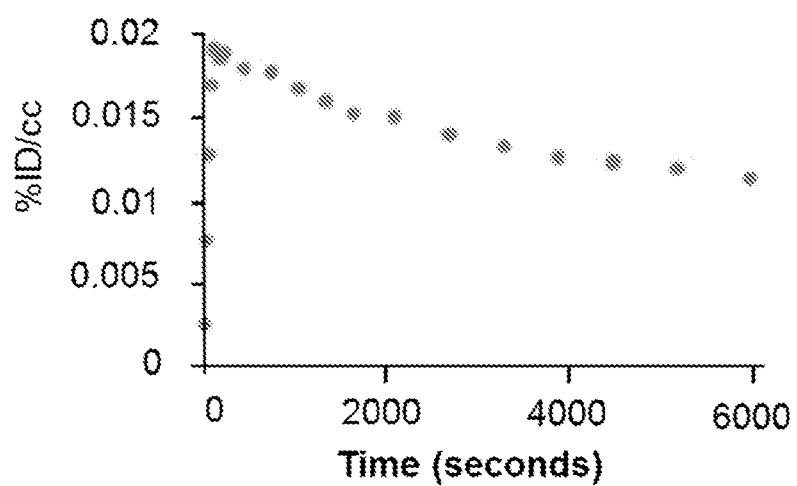

FIG. 20A-B
20A
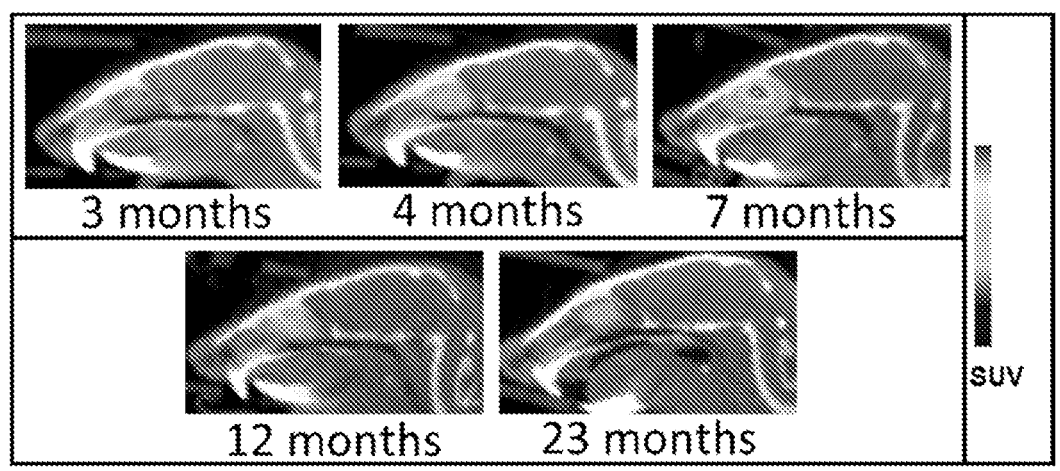
20B
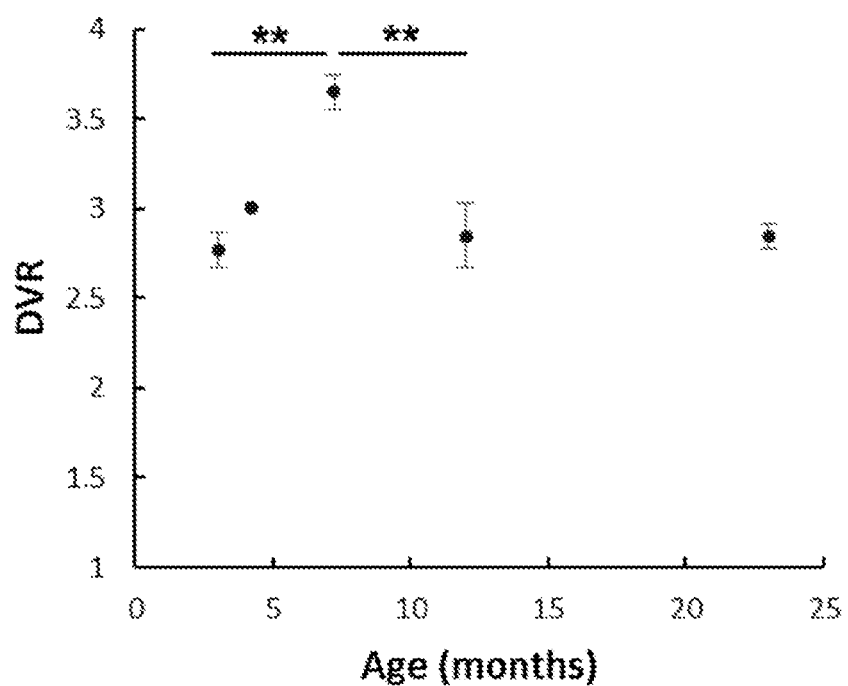

FIG. 21A-B
21A
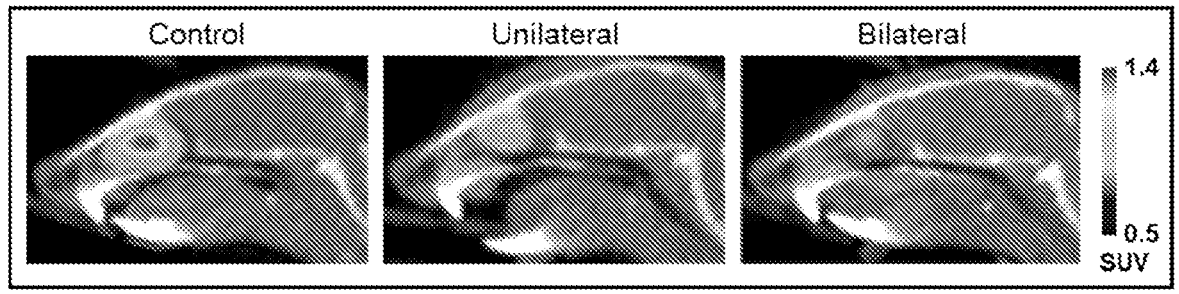
21B
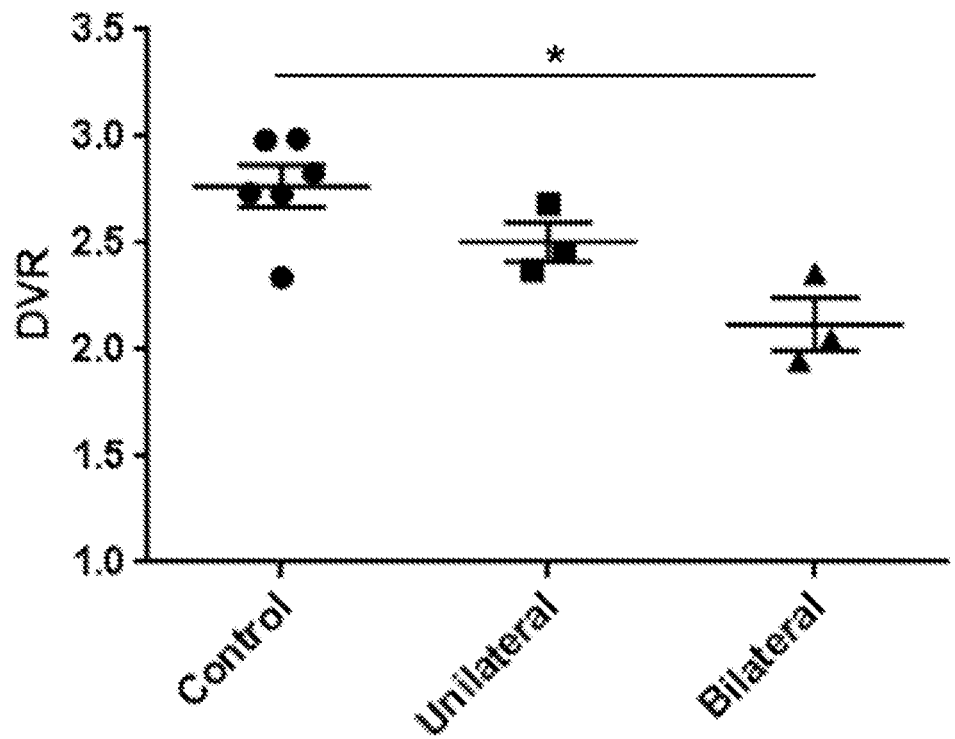

FIG. 22A-B
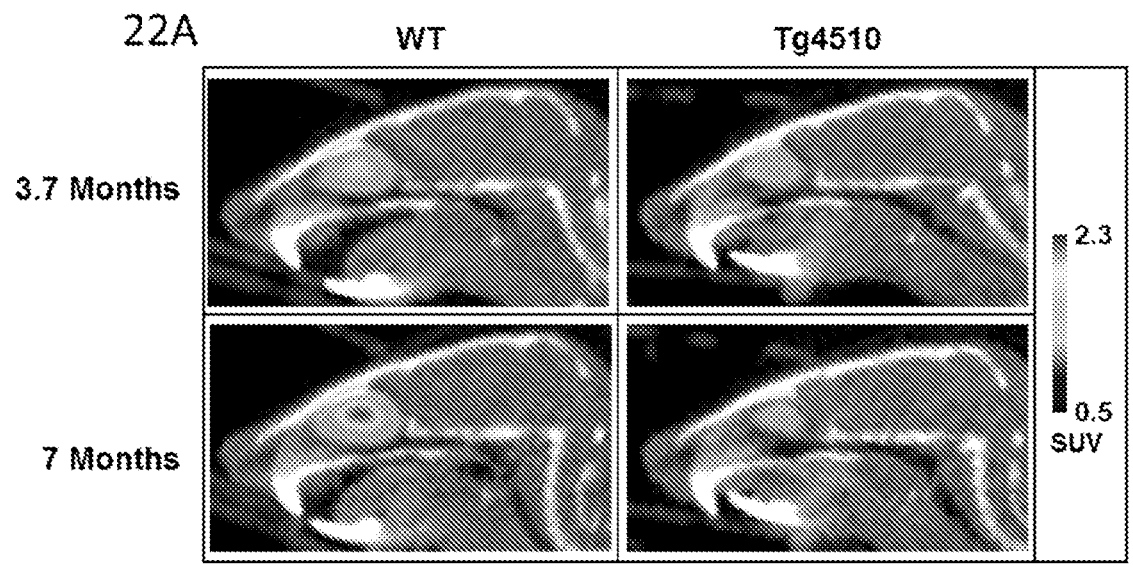
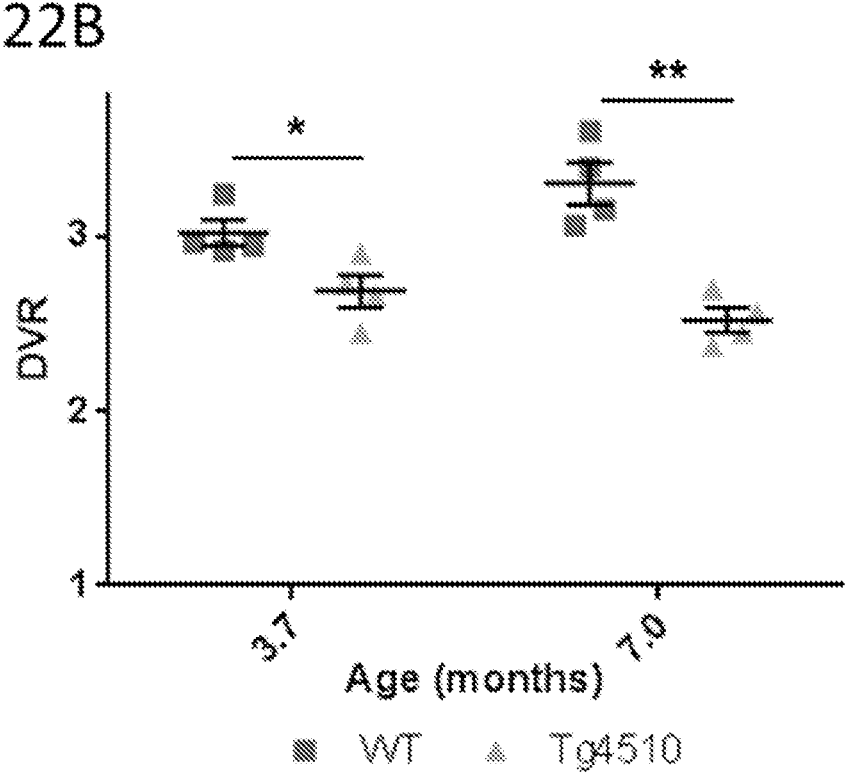

IMAGING AGENTS FOR NEURAL FLUX

CROSS-REFERENCE TO RELATED APPLICATIONS

This application is a § 371 National Stage Application of PCT/US2015/040971, filed Jul. 17, 2015, which claims the benefit of U.S. Provisional Application Ser. No. 62/026,147, filed Jul. 18, 2014, and 62/074,853, filed Nov. 4, 2014, the disclosures of each of which are incorporated herein by reference in their entirety.

FEDERALLY SPONSORED RESEARCH OR DEVELOPMENT

This invention was made with Government support under Grant No. DE-SC0008430, awarded by the National Institutes of Health. The Government has certain rights in the invention.

TECHNICAL FIELD

The present disclosure relates to radiolabeled compounds useful for imaging techniques, and more particularly to radiolabeled compounds that are useful for imaging neural density using positron emission tomography. The present disclosure further relates to compounds (e.g., labeled or unlabeled compounds) useful for the treatment of diseases of the central and peripheral nervous system.

BACKGROUND

Olfactory sensory neurons (OSNs) have been studied due to their relationship to disease processes, for example, Alzheimer's disease and other neurodegenerative diseases. Initial symptoms may include a decreased sense of smell due to OSN loss and/or processing impairments of sensory circuits. Studies have shown a decrease in OSN neural density in the olfactory epithelium of Alzheimer's patients, while others have attributed neuron loss in other regions of the sensory circuit as a source of olfaction deficits. Although biopsies of the olfactory epithelium offer potential for OSN analysis in living humans, these biopsies do not offer a global picture of the OSN neural density status in a patient, and they have a large sample bias that can make it difficult to interpret the results.

SUMMARY

The present application provides, inter alia, a compound of Formula (II):

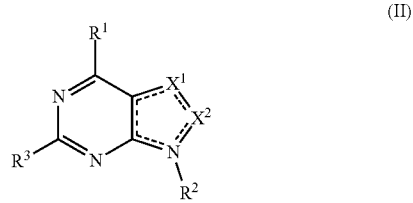

(II)

or a pharmaceutically acceptable salt thereof, wherein:
═══ represents a single- or double-bond;
$X^1$ is $CR^A$ or $NR^B$;
$X^2$ is $CR^A$ or $NR^B$; wherein
one of $X^1$ and $X^2$ is $CR^A$ and the other is $NR^B$;

$R^A$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^B$ is absent; or $R^B$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^1$ is selected from the group consisting of $NR^NR^{N'}$, —($C_{1-6}$ alkylene)-$NR^NR^{N'}$, —($C_{2-6}$ alkenylene)-$NR^NR^{N'}$, —($C_{2-6}$ alkynylene)-$NR^NR^{N'}$, —O-Cy, —O—($C_{1-6}$ alkylene)-Cy, —S-Cy, and —S—($C_{1-6}$ alkylene)-Cy;

$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;

$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^2$ is absent; or $R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

wherein at least two of $R^A$, $R^B$, and $R^2$ are independently H or absent;

$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$, and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

each $R^{a2}$, $R^{b2}$, $R^{c2}$, and $R^{d2}$ is independently selected from the group consisting of H, $C_{1-6}$ alkyl, $C_{2-6}$ alkenyl, and $C_{2-6}$ alkynyl;

$R^{c3}$ and $R^{d3}$ are each independently selected from the group consisting of H, $C_{1-6}$ alkyl, $C_{2-6}$ alkenyl, $C_{2-6}$ alkynyl, and $C(=O)OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; wherein the compound of Formula (II) comprises at least one radioisotope.

In some embodiments, the compound of Formula (II) is a compound of Formula (IIa):

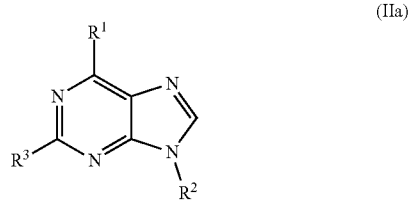

(IIa)

or a pharmaceutically acceptable salt thereof, wherein:

$R^1$ is selected from the group consisting of $NR^NR^{N'}$, —($C_{1-6}$ alkylene)-$NR^NR^{N'}$, —($C_{2-6}$ alkenylene)-$NR^NR^{N'}$, —($C_{2-6}$ alkynylene)-$NR^NR^{N'}$, —O-Cy, —O—($C_{1-6}$ alkylene)-Cy, —S-Cy, and —S—($C_{1-6}$ alkylene)-Cy;

$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;

$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$, and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

each $R^{a2}$, $R^{b2}$, $R^2$, and $R^{d2}$ is independently selected from the group consisting of H, $C_{1-6}$ alkyl, $C_{2-6}$ alkenyl, and $C_{2-6}$ alkynyl;

$R^{c3}$ and $R^{d3}$ are each independently selected from the group consisting of H, $C_{1-6}$ alkyl, $C_{2-6}$ alkenyl, $C_{2-6}$ alkynyl, and $C(=O)OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

wherein the compound of Formula (IIa) comprises at least one radioisotope.

In some embodiments, $R^1$ is $NR^NR^{N'}$. In some embodiments, $R^N$ is H or $C_{1-6}$ alkyl. In some embodiments, $R^N$ is H. In some embodiments, $R^{N'}$ is selected from the group consisting of $C_{3-10}$ cycloalkyl, $C_{6-10}$ aryl, 4-10 membered heteroaryl, 4-10 membered heterocycloalkyl, and —($C_{1-6}$ alkylene)-$Cy^1$. In some embodiments, $R^{N'}$ is —($C_{1-6}$ alkylene)-$Cy^1$. In some embodiments, $R^{N'}$ is —($CH_2$)—$Cy^1$.

In some embodiments, $Cy^1$ is selected from the group consisting of $C_{3-10}$ cycloalkyl, $C_{6-10}$ aryl, and 4-10 membered heteroaryl, and each is optionally substituted by 1, 2, 3, or 4 independently selected $R^4$ groups In some embodiments, $Cy^1$ is selected from the group consisting of $C_{3-10}$ cycloalkyl, $C_{6-10}$ aryl, and 4-10 membered heteroaryl, wherein the $C_{6-10}$ aryl is optionally substituted by one substituent selected from the group consisting of halo, $C_{1-6}$ alkyl, and $C_{1-6}$ alkoxy. In some embodiments, $Cy^1$ is selected from the group consisting of adamantyl, phenyl, 2-methylphenyl, 2-methoxyphenyl, 2-chlorophenyl, 4-chlorophenyl, 4-fluorophenyl, and pyridin-3-yl.

In some embodiments, $R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups. In some embodiments, $R^2$ is selected from the group consisting of H, $C_{1-6}$ alkyl, —C(=O)($C_{1-6}$ alkyl), and $NH_2$, wherein the $C_{1-6}$ alkyl is optionally substituted by one substituent selected from the group consisting of OH, —$OCH_3$, —C(=O)$CH_3$. In some embodiments, $R^2$ is selected from the group consisting of H, methyl, isopropyl, pentyl, —$CH_2OH$, —$CH_2CH_2OH$, —$CH_2OCH_3$, —CH(OH)$CH_3$, —CH($OCH_3$)$CH_3$, —$CH_2$C(=O)$CH_3$, —C(=O)$CH_3$, and —C(=O)$CH_2CH_3$. In some embodiments, $R^2$ is selected from the group consisting of —($C_{1-6}$ alkylene)-$Cy^2$, $C_{3-10}$ cycloalkyl, $C_{6-10}$ aryl, 4-10 membered heteroaryl, and 4-10 membered heterocycloalkyl, wherein the 4-10 membered heteroaryl and 4-10 membered heterocycloalkyl are each optionally substituted by one or two substituents independently selected from the group consisting of halo, oxo, $C_{1-3}$ alkyl, and $C_{1-6}$ alkoxycarbonyl. In some embodiments, $R^2$ is selected from the group consisting of:

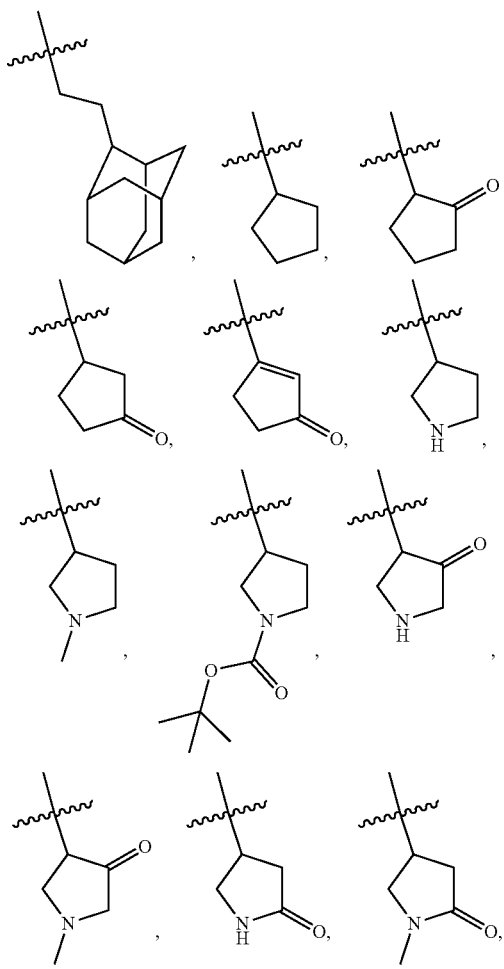

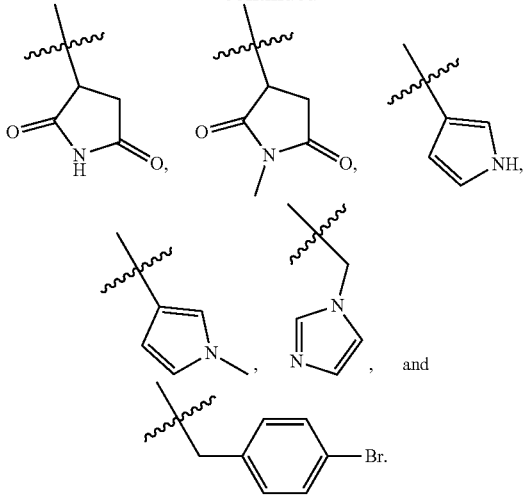

In some embodiments, $R^3$ is selected from the group consisting of H, halo, $NR^{c3}R^{d3}$, and $NO_2$. In some embodiments, $R^3$ is selected from the group consisting of H, fluoro, chloro, $NH_2$, —NHC(=O)O-tert-butyl, and $NO_2$. In some embodiments, $R^3$ forms a group selected from:

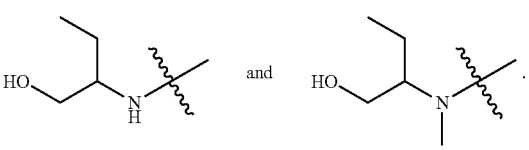

In some embodiments, $R^3$ forms a group selected from:

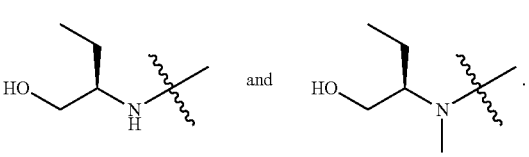

In some embodiments:
$R^1$ is $NR^NR^{N'}$;
$R^N$ is H;
$R^{N'}$ is —($C_{1-6}$ alkylene)-$Cy^1$;
$R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups; and
$R^3$ is selected from the group consisting of H, halo, $NR^{c3}R^{d3}$, and $NO_2$.

In some embodiments:
$R^1$ is $NR^NR^{N'}$;
$R^N$ is H;
$R^{N'}$ is selected from the group consisting of —($C_{1-6}$ alkylene)-phenyl, —($C_{1-6}$ alkylene)adamantyl, and —($C_{1-6}$ alkylene)-pyridin-3-yl, wherein said phenyl is optionally substituted by 1, 2, 3, or 4 independently selected $R^4$ groups;
$R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —(C$_{1-6}$ alkylene)-Cy$^2$, C(=O)R$^{b2}$, and NR$^{c2}$R$^{d2}$, wherein the C$_{1-6}$ alkyl, 4-10 membered heteroaryl, and 4-10 membered heterocycloalkyl are each optionally substituted by 1, 2, 3, or 4 independently selected R$^4$ groups; and R$^3$ is selected from the group consisting of H, halo, NR$^{c3}$R$^{d3}$, and NO$_2$.

In some embodiments, the compound of Formula (II) is a compound of Formula (IIb):

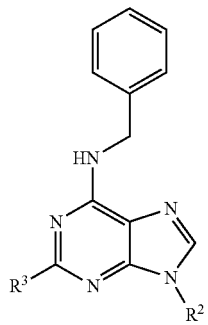

(IIb)

or a pharmaceutically acceptable salt thereof.

In some embodiments, the compound of Formula (II) is a compound of Formula (IIc):

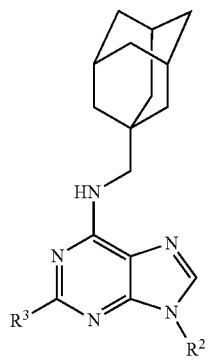

(IIc)

or a pharmaceutically acceptable salt thereof.

In some embodiments, the compound of Formula (II) is a compound of Formula (IId):

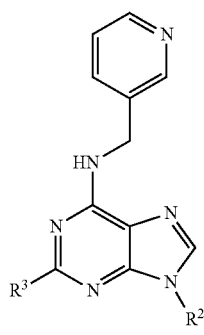

(IId)

or a pharmaceutically acceptable salt thereof.

In some embodiments, the compound of Formula (II) is a compound of Formula (IIe):

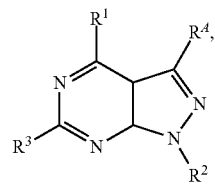

(IIe)

or a pharmaceutically acceptable salt thereof.

In some embodiments, the compound of Formula (II) is a compound of Formula (IIf):

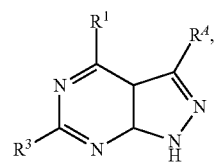

(IIf)

or a pharmaceutically acceptable salt thereof.

In some embodiments, the compound of Formula (II) is a compound of Formula (IIg):

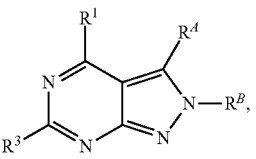

(IIg)

or a pharmaceutically acceptable salt thereof.

In some embodiments, R$^2$ comprises at least one radioisotope. In some embodiments, R$^2$ comprises one radioisotope. In some embodiments, R$^2$ comprises two independently selected radioisotopes. In some embodiments, R$^3$ comprises at least one radioisotope. In some embodiments, R$^3$ comprises one radioisotope. In some embodiments, R$^2$ and R$^3$ each comprise at least one radioisotope. In some embodiments, R$^2$ and R$^3$ each comprise one independently selected radioisotope. In some embodiments, the radioisotope is a positron emitter. In some embodiments, the positron emitter is selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I. In some embodiments, the positron emitter is $^{11}$C or $^{18}$F.

In some embodiments, the compound of Formula (II) is selected from the group consisting of:

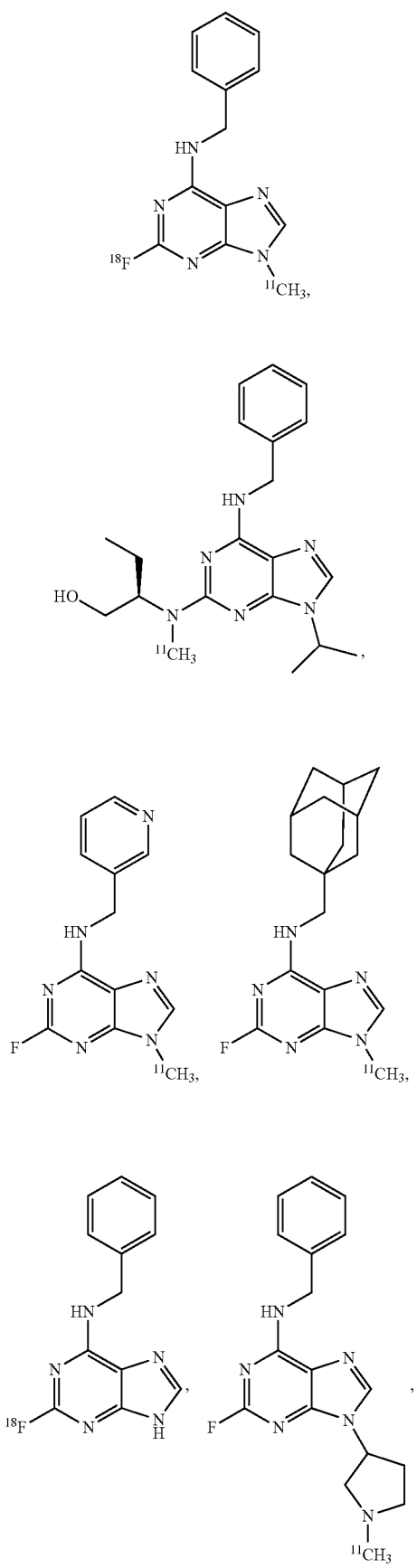
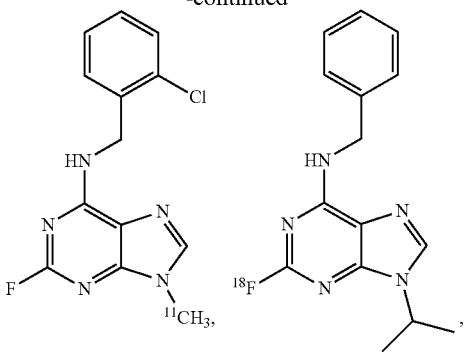
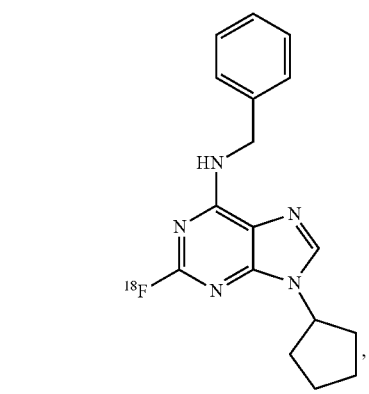
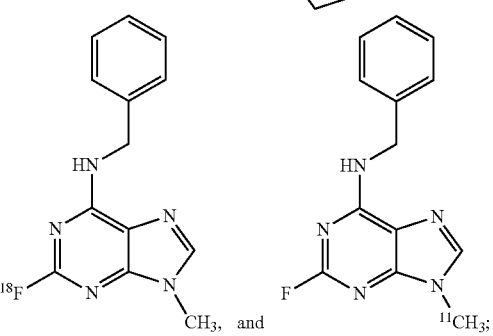

or a pharmaceutically acceptable salt thereof.

The present application further provides a pharmaceutical composition comprising a compound of Formula (II), or a pharmaceutically acceptable salt thereof, and at least one pharmaceutically acceptable carrier.

The present application further provides a method of imaging neural density in a subject, comprising:

i) administering to the subject a compound of Formula (II), or a pharmaceutically acceptable salt thereof;

ii) waiting a time sufficient to allow the compound to accumulate at a tissue or cell site to be imaged; and iii) imaging the cell or tissue with an imaging technique.

In some embodiments, the imaging technique is selected from the group consisting of magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of positron emission tomography imaging, positron emission tomography with computed tomography imaging, or positron emission tomography with magnetic resonance imaging.

In some embodiments, the neural density comprises synaptic density. In some embodiments, the neural density is synaptic density.

In some embodiments, the cell or tissue is localized in the olfactory epithelium. In some embodiments, the cell or tissue comprises olfactory sensory neurons.

In some embodiments, the time sufficient is from about 30 seconds to about 60 minutes. In some embodiments, the time sufficient is from about 30 seconds to about 48 hours.

The present application further provides a method of diagnosing a disease of the central nervous system or a disease of the peripheral nervous system in a subject, comprising:
i) administering to the subject a compound of Formula (II), or a pharmaceutically acceptable salt thereof;
ii) waiting a time sufficient to allow the compound to accumulate at a tissue or cell site associated with the disease; and
iii) imaging the cell or tissue with an imaging technique.

In some embodiments, the disease of the central nervous system or the disease of the peripheral nervous system comprises a neurodegenerative disease. In some embodiments, the disease of the central nervous system or the disease of the peripheral nervous system is a neurodegenerative disease. In some embodiments, the disease of the central nervous system is selected from the group consisting of schizophrenia, major depressive disorder, depression, dementia, Alzheimer's disease, Huntington's disease, and Parkinson's disease. In some embodiments, the disease of the peripheral nervous system is selected from the group consisting of accessory nerve disorder, autonomic dysreflexia, peripheral neuropathy, mononeuropathy, polyneuropathy, radial neuropathy, ulnar neuropathy, Villaret's syndrome, Charcot-Marie-Tooth disease, diabetic neuropathy, nerve paralysis, and Horner's syndrome. In some embodiments, the disease of the central nervous system or the disease of the peripheral nervous system is associated with hyposmia or anosmia.

In some embodiments, the imaging technique is selected from the group consisting of magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of positron emission tomography imaging, positron emission tomography with computed tomography imaging, or positron emission tomography with magnetic resonance imaging.

The present application further provides a compound of Formula (I):

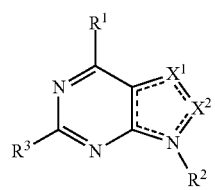

(I)

or a pharmaceutically acceptable salt thereof, wherein:
═══ represents a single- or double-bond;
$X^1$ is $CR^A$ or $NR^B$;
$X^2$ is $CR^A$ or $NR^B$; wherein
one of $X^1$ and $X^2$ is $CR^A$ and the other is $NR^B$;

$R^A$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^B$ is absent; or
$R^B$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^1$ is selected from the group consisting of $NR^NR^{N'}$, —($C_{1-6}$ alkylene)-$NR^NR^{N'}$, —($C_{2-6}$ alkenylene)-$NR^NR^{N'}$, —($C_{2-6}$ alkynylene)-$NR^NR^{N'}$, —O-Cy, —O—($C_{1-6}$ alkylene)-Cy, —S-Cy, and —S—($C_{1-6}$ alkylene)-Cy;

$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;

$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^2$ is absent; or
$R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

wherein at least two of $R^A$, $R^B$, and $R^2$ are independently H or absent;

$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$, and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

each $R^{a2}$, $R^{b2}$, $R^{c2}$, and $R^{d2}$ is independently selected from the group consisting of H, $C_{1-6}$ alkyl, $C_{2-6}$ alkenyl, and $C_{2-6}$ alkynyl;

$R^{c3}$ and $R^{d3}$ are each independently selected from the group consisting of H, $C_{1-6}$ alkyl, $C_{2-6}$ alkenyl, $C_{2-6}$ alkynyl, and $C(=O)OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

with the proviso that when $X^1$ is N, $X^2$ is CH, $R^2$ is isopropyl and $R^1$ is —N(H)$CH_2$-phenyl, then $R^3$ cannot form the group:

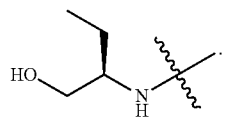

In some embodiments, the compound of Formula (I) is a compound of Formula (Ia):

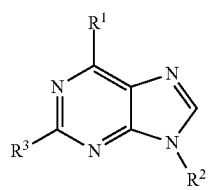

(Ia)

or a pharmaceutically acceptable salt thereof, wherein:

$R^1$ is selected from the group consisting of $NR^NR^{N'}$, —($C_{1-6}$ alkylene)-$NR^NR^{N'}$, —($C_{2-6}$ alkenylene)-$NR^NR^{N'}$, —($C_{2-6}$ alkynylene)-$NR^NR^{N'}$, —O-Cy, —O—($C_{1-6}$ alkylene)-Cy, —S-Cy, and —S—($C_{1-6}$ alkylene)-Cy;

$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;

$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, C(=O)$R^{b2}$, C(=O)$OR^{b2}$, $NR^{c2}R^{d2}$, C(=O)$NR^{c2}R^{d2}$, $NR^{c2}$C(=O)$R^{b2}$, $NR^{c2}$C(=O)$OR^{b2}$, $NR^{c2}$C(=O)$NR^{c2}R^{d2}$, $NR^{c2}$S(=O)$_2R^{b2}$, $NR^{c2}$S(=O)$_2NR^{c2}R^{d2}$, S(O)$R^{a2}$, S(O)$_2R^{a2}$, S(O)$NR^{c2}R^{d2}$, and S(O)$_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$, and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

each $R^{a2}$, $R^{b2}$, $R^2$, and $R^{d2}$ is independently selected from the group consisting of H, $C_{1-6}$ alkyl, $C_{2-6}$ alkenyl, and $C_{2-6}$ alkynyl;

$R^{c3}$ and $R^{d3}$ are each independently selected from the group consisting of H, $C_{1-6}$ alkyl, $C_{2-6}$ alkenyl, $C_{2-6}$ alkynyl, and C(=O)$OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; with the proviso that when $R^2$ is isopropyl and $R^3$ is —N(H)$CH_2$-phenyl, then $R^1$ cannot form the group:

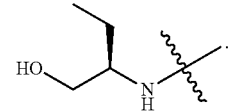

In some embodiments, $R^1$ is $NR^NR^{N'}$. In some embodiments, $R^N$ is H or $C_{1-6}$ alkyl. In some embodiments, $R^N$ is H. In some embodiments, $R^{N'}$ is selected from the group consisting of $C_{3-10}$ cycloalkyl, $C_{6-10}$ aryl, 4-10 membered heteroaryl, 4-10 membered heterocycloalkyl, and —($C_{1-6}$ alkylene)-$Cy^1$. In some embodiments, $R^{N'}$ is —($C_{1-6}$ alkylene)-$Cy^1$. In some embodiments, $R^{N'}$ is —($CH_2$)—$Cy^1$.

In some embodiments, $Cy^1$ is selected from the group consisting of $C_{3-10}$ cycloalkyl, $C_{6-10}$ aryl, and 4-10 membered heteroaryl, and each is optionally substituted by 1, 2, 3, or 4 independently selected $R^4$ groups. In some embodiments, $Cy^1$ is selected from the group consisting of $C_{3-10}$ cycloalkyl, $C_{6-10}$ aryl, and 4-10 membered heteroaryl, wherein the $C_{6-10}$ aryl is optionally substituted by one substituent selected from the group consisting of halo, $C_{1-6}$ alkyl, and $C_{1-6}$ alkoxy. In some embodiments, $Cy^1$ is selected from the group consisting of adamantyl, phenyl, 2-methylphenyl, 2-methoxyphenyl, 2-chlorophenyl, 4-chlorophenyl, 4-fluorophenyl, and pyridin-3-yl.

In some embodiments, $R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $C(=O)R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups. In some embodiments, $R^2$ is selected from the group consisting of H, $C_{1-6}$ alkyl, —$C(=O)(C_{1-6}$ alkyl), and $NH_2$, wherein the $C_{1-6}$ alkyl is optionally substituted by one substituent selected from the group consisting of OH, —$OCH_3$, —$C(=O)CH_3$. In some embodiments, $R^2$ is selected from the group consisting of H, methyl, isopropyl, pentyl, —$CH_2OH$, —$CH_2CH_2OH$, —$CH_2OCH_3$, —$CH(OH)CH_3$, —$CH(OCH_3)CH_3$, —$CH_2C(=O)CH_3$, —$C(=O)CH_3$, and —$C(=O)CH_2CH_3$. In some embodiments, $R^2$ is selected from the group consisting of —($C_{1-6}$ alkylene)-$Cy^2$, $C_{3-10}$ cycloalkyl, $C_{6-10}$ aryl, 4-10 membered heteroaryl, and 4-10 membered heterocycloalkyl, wherein the 4-10 membered heteroaryl and 4-10 membered heterocycloalkyl are each optionally substituted by one or two substituents independently selected from the group consisting of halo, oxo, $C_{1-3}$ alkyl, and $C_{1-6}$ alkoxycarbonyl. In some embodiments, $R^2$ is selected from the group consisting of:

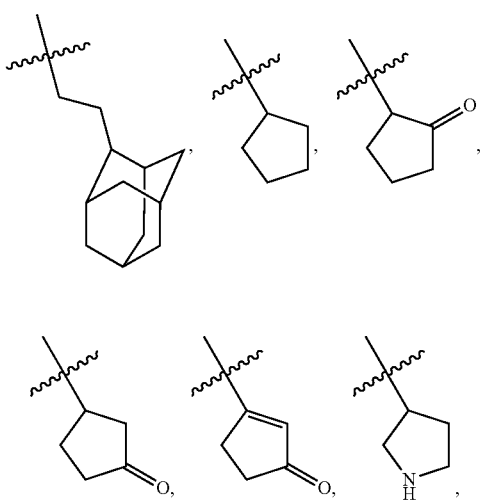

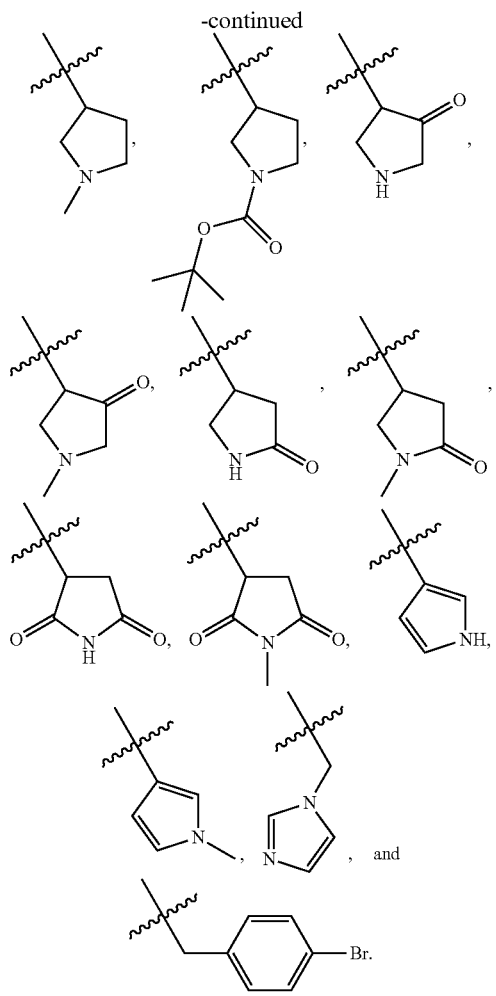

In some embodiments, $R^3$ is selected from the group consisting of H, halo, $NR^{c3}R^{d3}$, and $NO_2$. In some embodiments, $R^3$ is selected from the group consisting of H, fluoro, chloro, $NH_2$, —$NHC(=O)O$-tert-butyl, and $NO_2$. In some embodiments, $R^3$ forms a 5 group selected from:

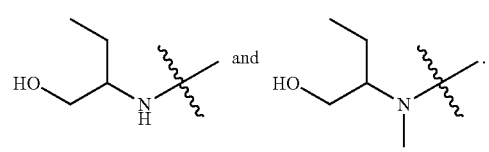

In some embodiments, $R^3$ forms a group selected from:

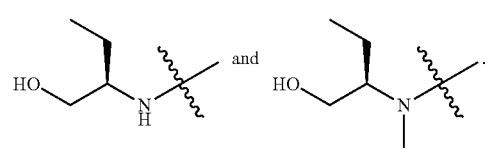

In some embodiments:
$R^1$ is $NR^NR^{N'}$;
$R^N$ is H;
$R^{N'}$ is —($C_{1-6}$ alkylene)-$Cy^1$;

R² is selected from the group consisting of H, C₁₋₆ alkyl, C₃₋₁₀ cycloalkyl, C₆₋₁₀ aryl, 4-10 membered heteroaryl, 4-10 membered heterocycloalkyl, —(C₁₋₆ alkylene)-Cy², C(=O)R$^{b2}$, and NR$^{c2}$R$^{d2}$, wherein the C₁₋₆ alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR$^{c3}$R$^{d3}$, and NO₂.

In some embodiments:

R¹ is NR$^{N}$R$^{N'}$;

R$^{N}$ is H;

R$^{N'}$ is selected from the group consisting of —(C₁₋₆ alkylene)-phenyl, —(C₁₋₆ alkylene)adamantyl, and —(C₁₋₆ alkylene)-pyridin-3-yl, wherein said phenyl is optionally substituted by 1, 2, 3, or 4 independently selected R⁴ groups;

R² is selected from the group consisting of H, C₁₋₆ alkyl, C₃₋₁₀ cycloalkyl, C₆₋₁₀ aryl, 4-10 membered heteroaryl, 4-10 membered heterocycloalkyl, —(C₁₋₆ alkylene)-Cy², C(=O)R$^{b2}$, and NR$^{c2}$R$^{d2}$, wherein the C₁₋₆ alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR$^{c3}$R$^{d3}$, and NO₂.

In some embodiments, the compound of Formula (I) is a compound of Formula (Ib):

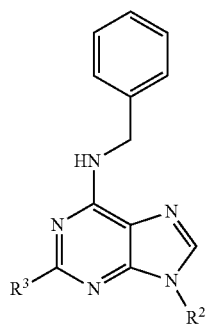

(Ib)

or a pharmaceutically acceptable salt thereof.

In some embodiments, the compound of Formula (I) is a compound of Formula

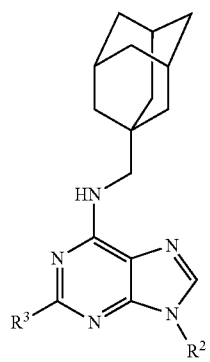

(Ic)

or a pharmaceutically acceptable salt thereof.

In some embodiments, the compound of Formula (I) is a compound of Formula (Id):

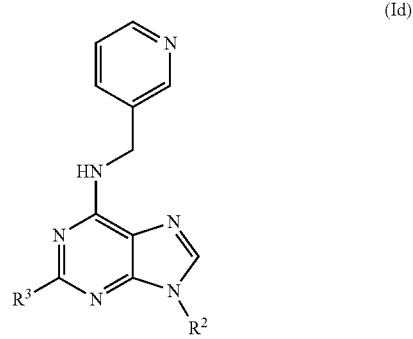

(Id)

or a pharmaceutically acceptable salt thereof.

In some embodiments, the compound of Formula (I) is a compound of Formula

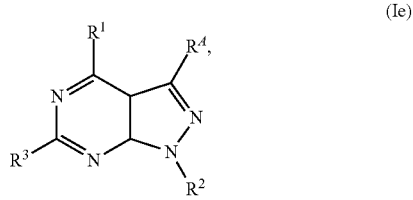

(Ie)

or a pharmaceutically acceptable salt thereof.

In some embodiments, the compound of Formula (I) is a compound of Formula (If):

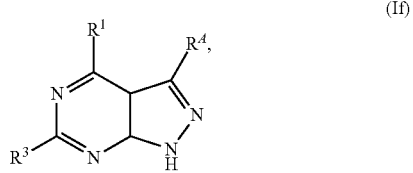

(If)

or a pharmaceutically acceptable salt thereof.

In some embodiments, the compound of Formula (I) is a compound of Formula (Ig):

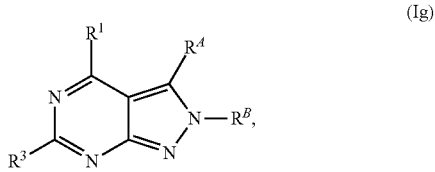

(Ig)

or a pharmaceutically acceptable salt thereof.

In some embodiments, the compound of Formula (I) is selected from the group consisting of:

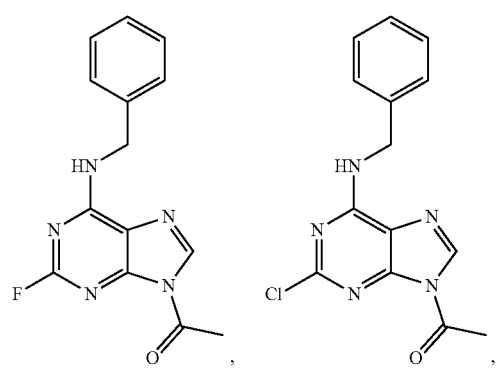
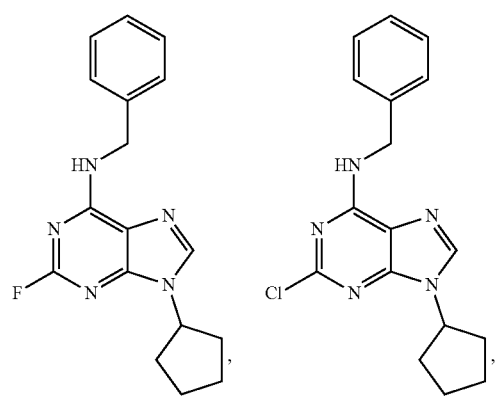
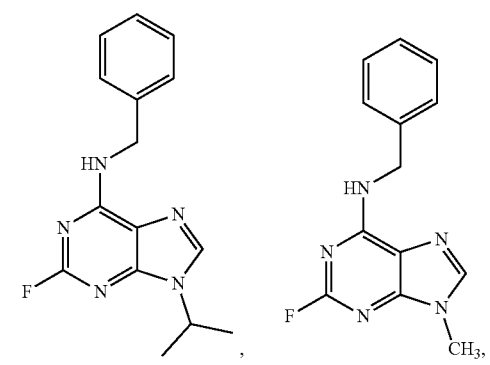
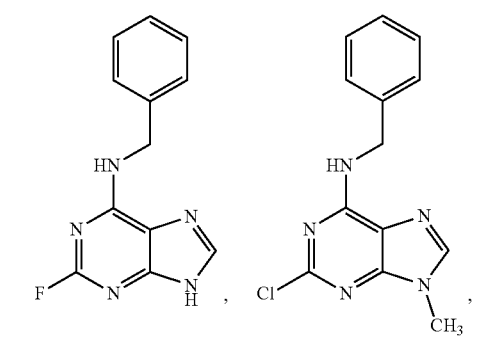
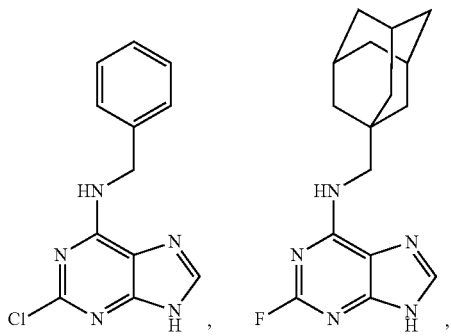
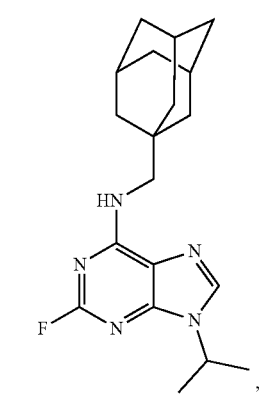
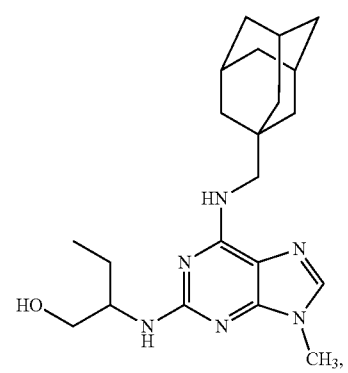
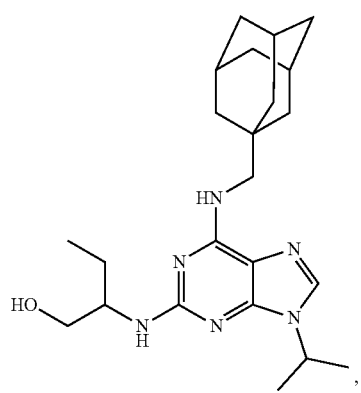

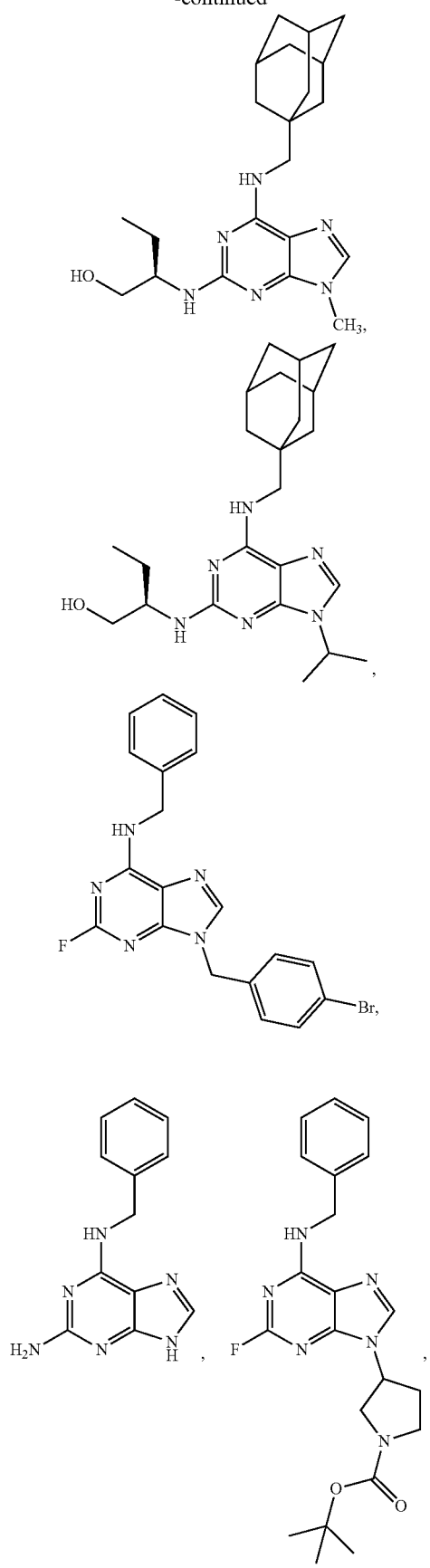
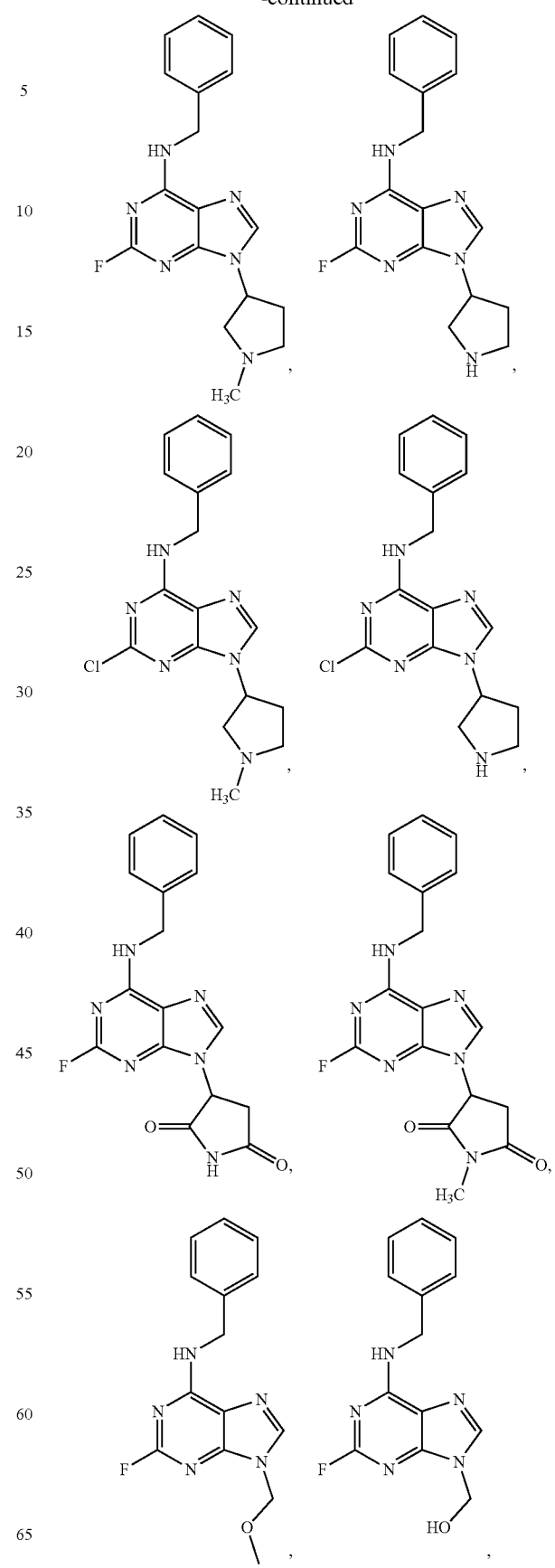

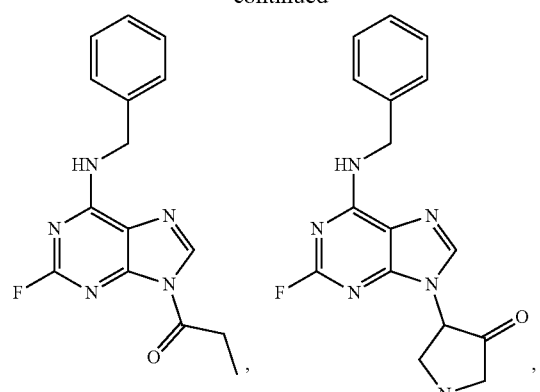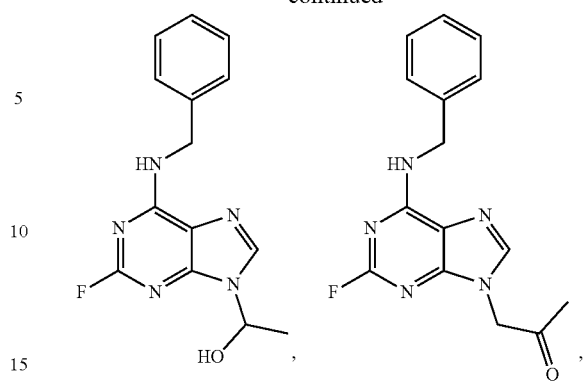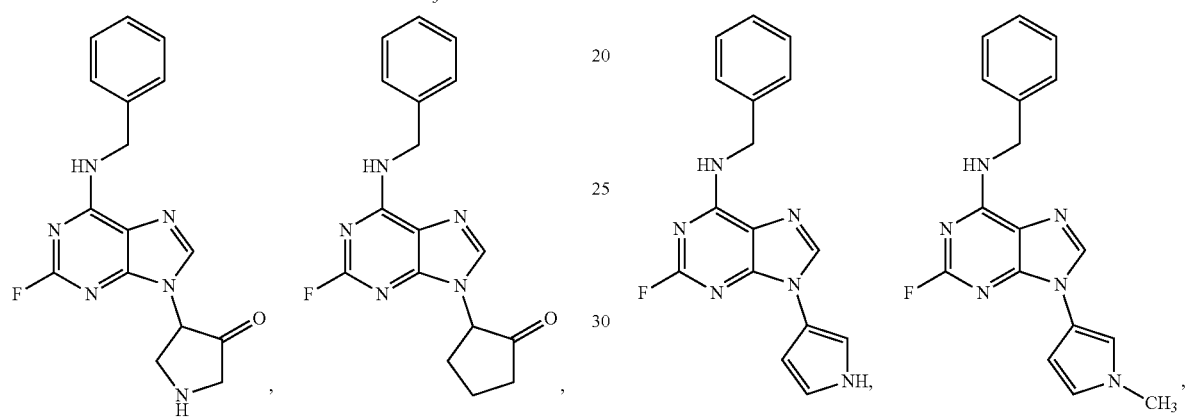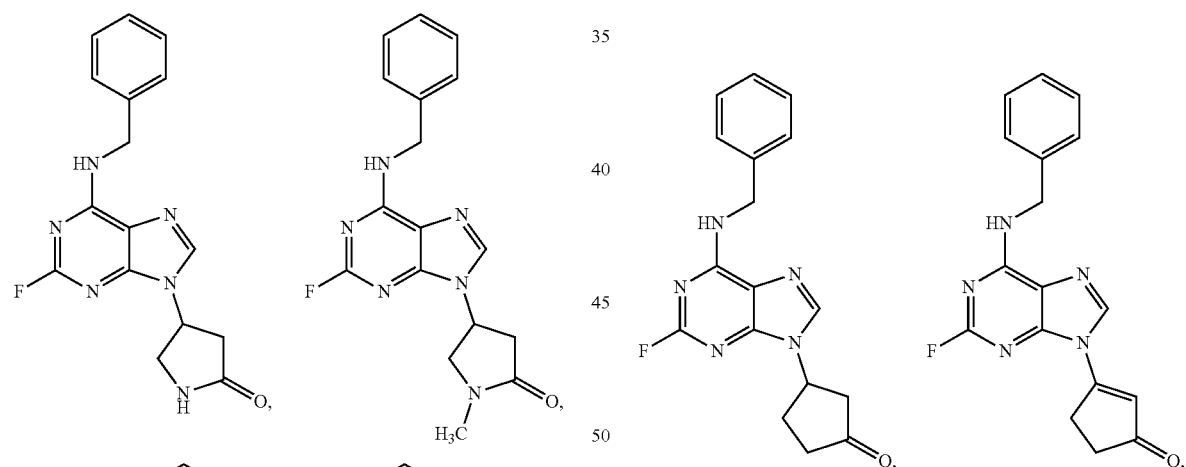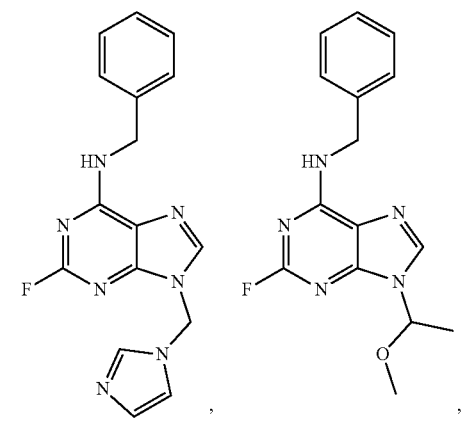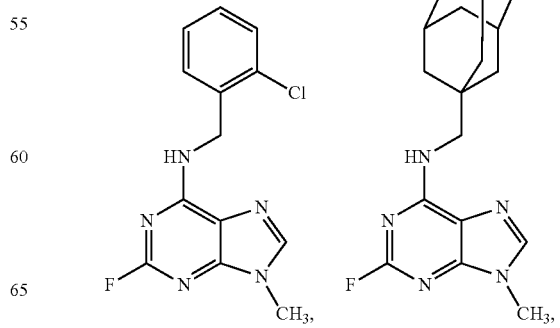

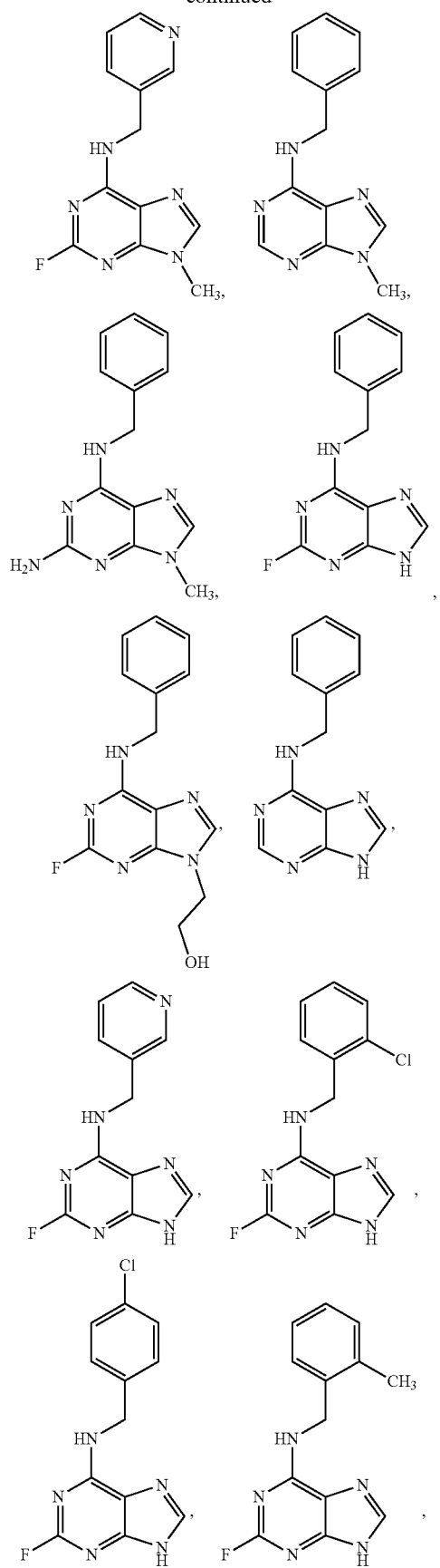
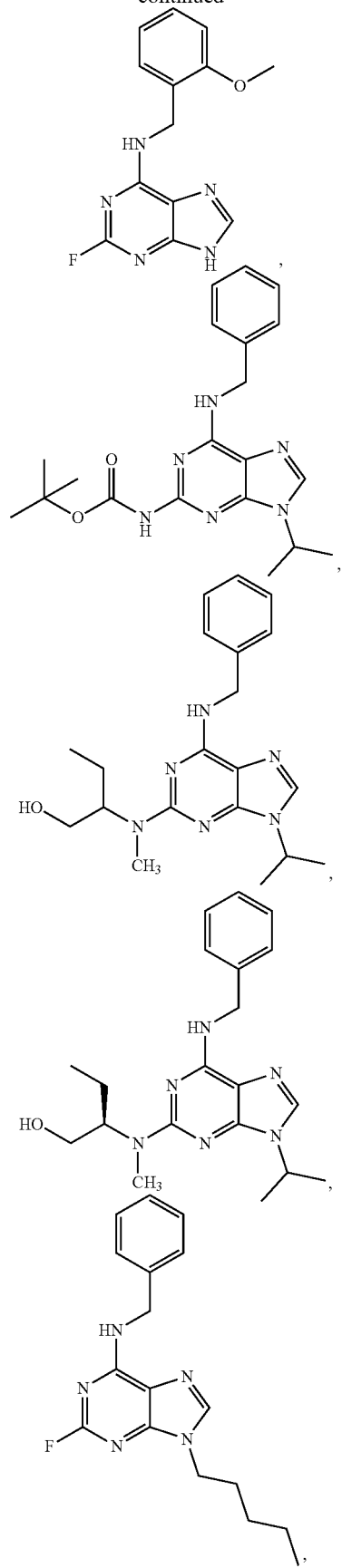

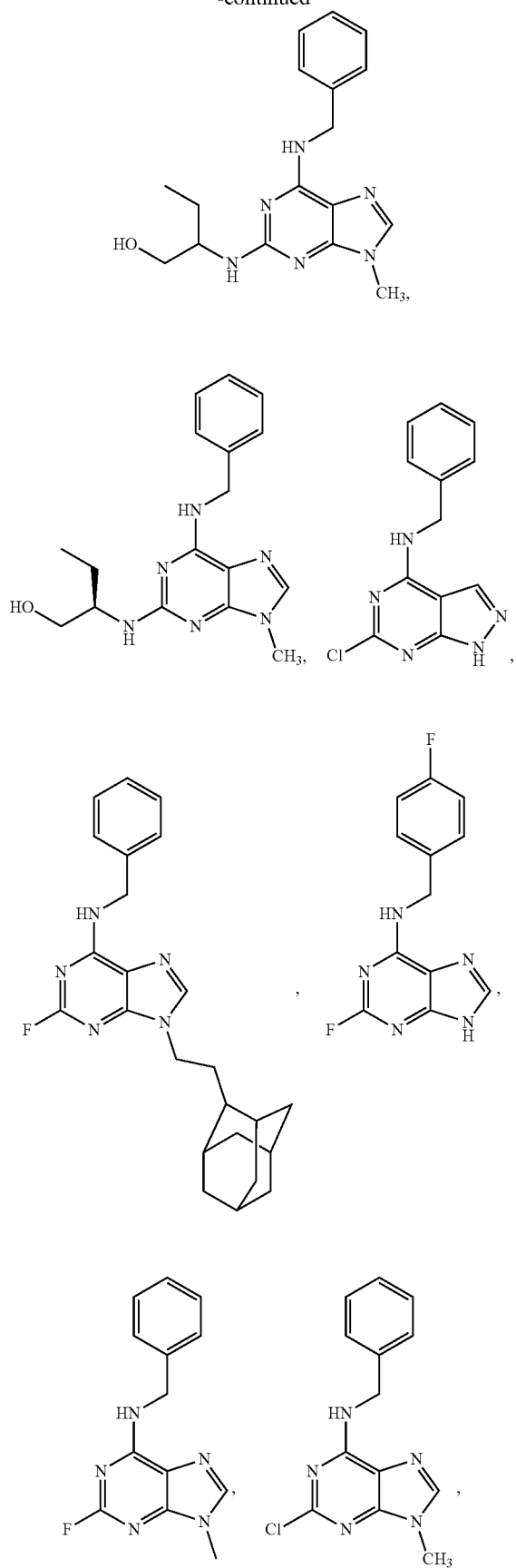

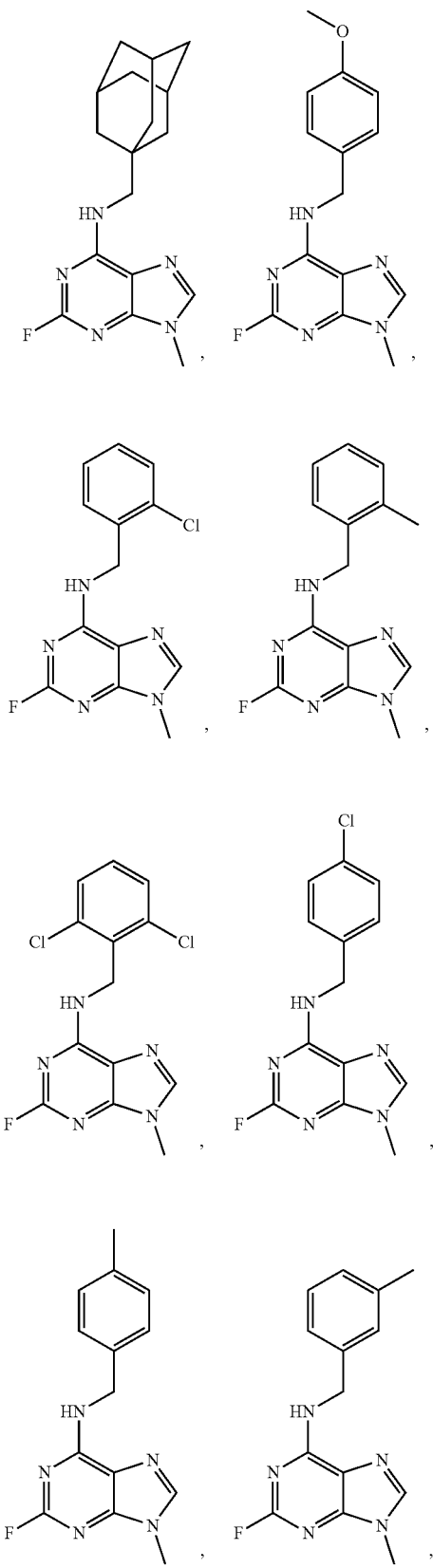
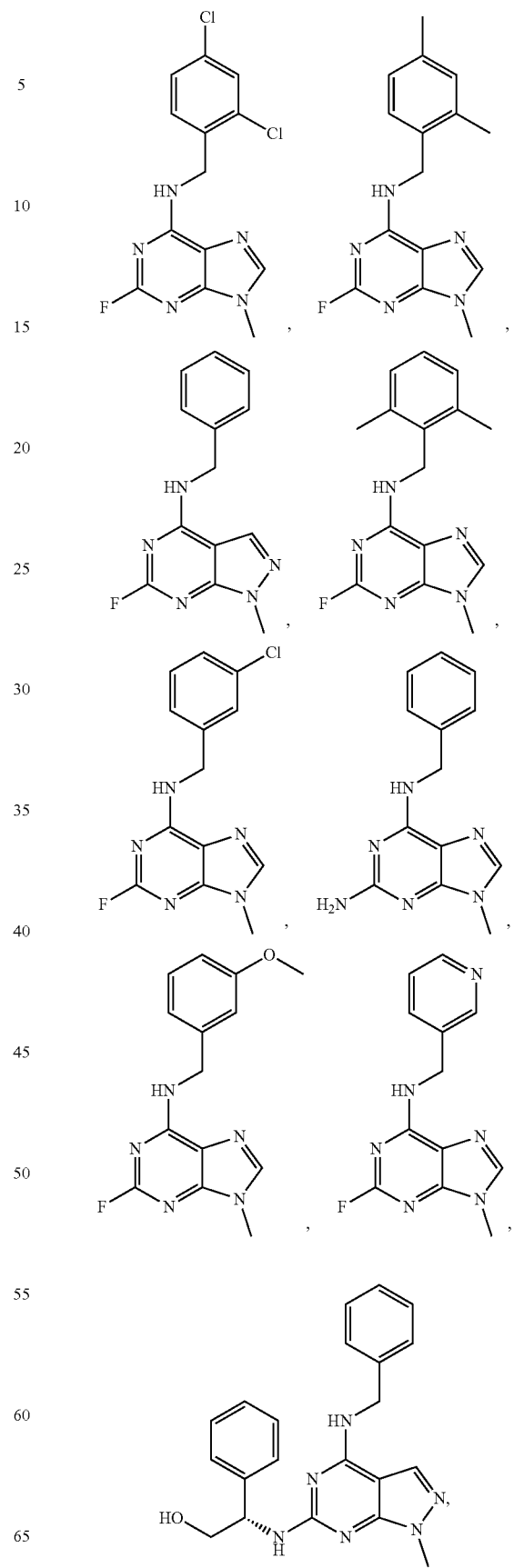

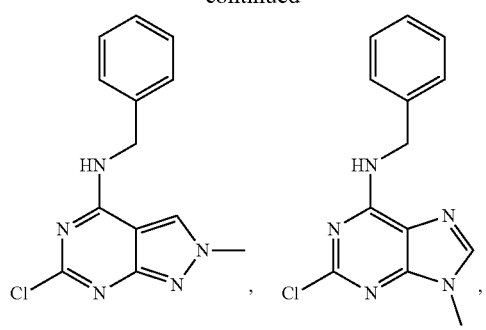
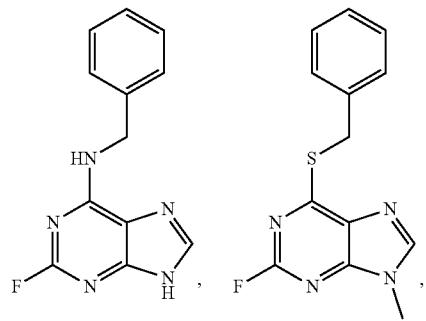
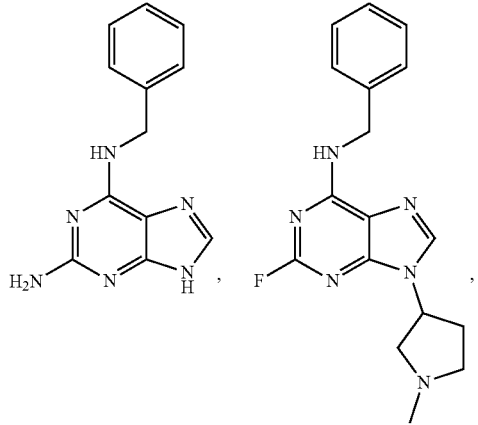
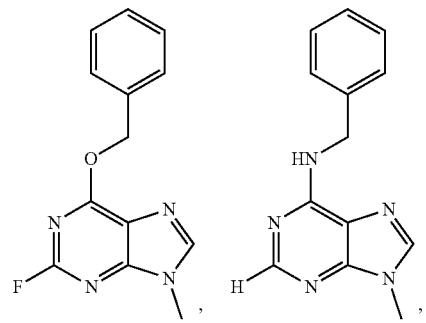
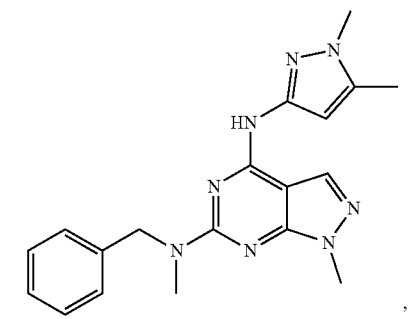
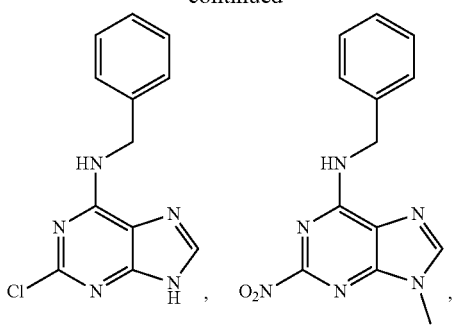
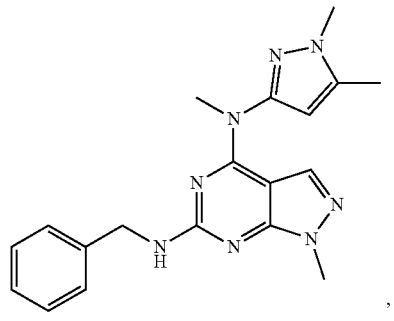
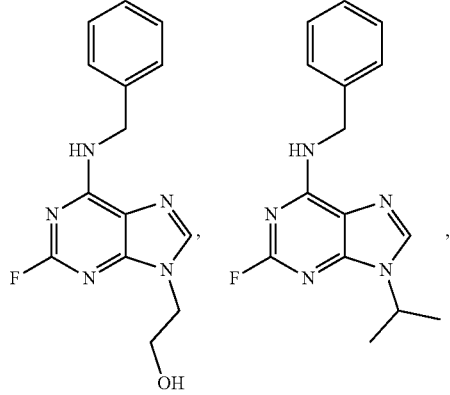
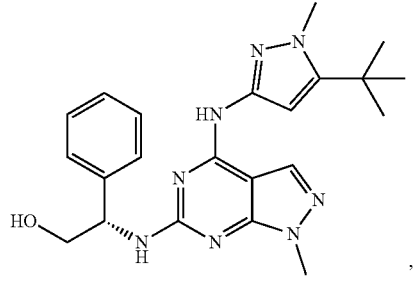
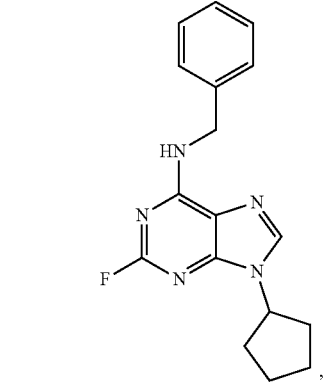

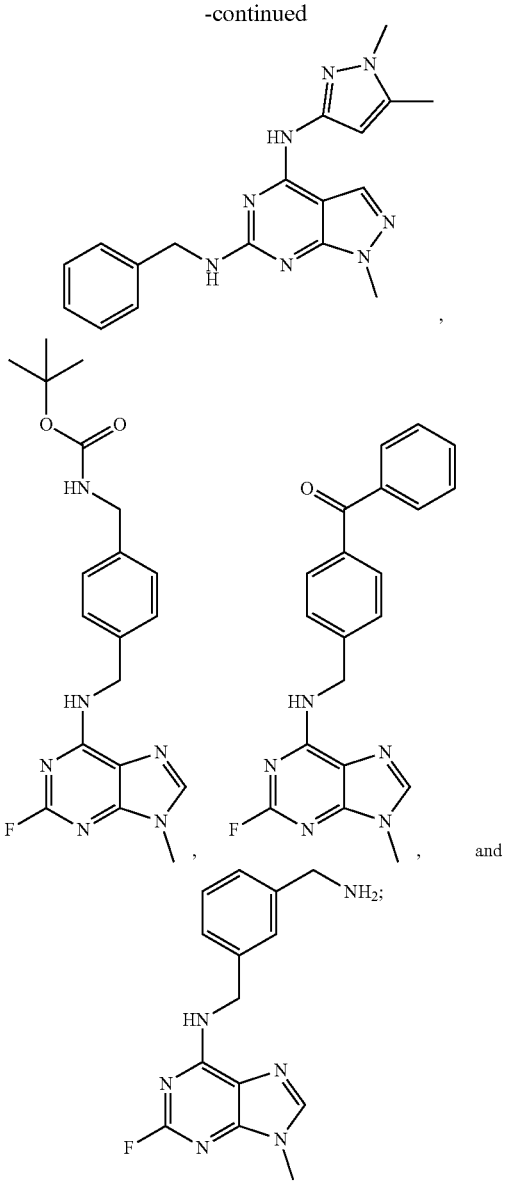

or a pharmaceutically acceptable salt thereof.

The present application further provides a pharmaceutical composition comprising a compound of Formula (I), or a pharmaceutically acceptable salt thereof, and at least one pharmaceutically acceptable carrier.

The present application further provides a method of monitoring treatment of a disease of the central nervous system or the disease of the peripheral nervous system in a subject, comprising:

i) imaging a cell or tissue with an imaging technique;

ii) administering to the subject an effective amount of a therapeutic compound to treat the disease;

iii) waiting a time sufficient to allow the compound to accumulate at a tissue or cell site associated with the disease;

iv) imaging the cell or tissue with an imaging technique; and v) comparing the image of step i) and the image of step iv).

In some embodiments, the therapeutic compound is a compound of Formula (I), or a pharmaceutically acceptable salt thereof.

In some embodiments, the disease of the central nervous system or the disease of the peripheral nervous system comprises a neurodegenerative disease. In some embodiments, the disease of the central nervous system or the disease of the peripheral nervous system is a neurodegenerative disease. In some embodiments, the disease of the central nervous system is selected from the group consisting of schizophrenia, major depressive disorder, depression, dementia, Alzheimer's disease, Huntington's disease, and Parkinson's disease. In some embodiments, the disease of the peripheral nervous system is selected from the group consisting of accessory nerve disorder, autonomic dysreflexia, peripheral neuropathy, mononeuropathy, polyneuropathy, radial neuropathy, ulnar neuropathy, Villaret's syndrome, Charcot-Marie-Tooth disease, diabetic neuropathy, nerve paralysis, and Horner's syndrome. In some embodiments, the disease of the central nervous system or the disease of the peripheral nervous system is associated with hyposmia or anosmia.

In some embodiments, the imaging technique is selected from the group consisting of magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of positron emission tomography imaging, positron emission tomography with computed tomography imaging, or positron emission tomography with magnetic resonance imaging.

In some embodiments, the time sufficient is from about 30 seconds to about 60 minutes. In some embodiments, the time sufficient is from about 30 seconds to about 48 hours.

The present application further provides a method of treating a disease of the central nervous system or the disease of the peripheral nervous system in a subject in need thereof, the method comprising administering to the subject a therapeutically effective amount of a compound of Formula (I), or a pharmaceutically acceptable salt thereof. In some embodiments, the disease of the central nervous system or the disease of the peripheral nervous system comprises a neurodegenerative disease. In some embodiments, the disease of the central nervous system or the disease of the peripheral nervous system is a neurodegenerative disease. In some embodiments, the disease of the central nervous system is selected from the group consisting of schizophrenia, major depressive disorder, depression, dementia, Alzheimer's disease, Huntington's disease, and Parkinson's disease. In some embodiments, the disease of the peripheral nervous system is selected from the group consisting of accessory nerve disorder, autonomic dysreflexia, peripheral neuropathy, mononeuropathy, polyneuropathy, radial neuropathy, ulnar neuropathy, Villaret's syndrome, Charcot-Marie-Tooth disease, diabetic neuropathy, nerve paralysis, and Horner's syndrome. In some embodiments, the disease of the central nervous system or the disease of the peripheral nervous system is associated with hyposmia or anosmia.

In some embodiments, the disease of the central nervous system or the disease of the peripheral nervous system is associated with abnormal neural density. In some embodiments, the abnormal neural density comprises a decrease in neural density compared to normal neural density. In some embodiments, the abnormal neural density comprises about 5% decrease in neural density compared to normal neural density. In some embodiments, the abnormal neural density comprises about 15% decrease in neural density compared to normal neural density. In some embodiments, the abnormal neural density comprises about 25% decrease in neural density compared to normal neural density. In some embodiments, the abnormal neural density comprises about 35% decrease in neural density compared to normal neural density. In some embodiments, the abnormal neural density comprises about 45% decrease in neural density compared to normal neural density. In some embodiments, the abnormal neural density comprises about 55% decrease in neural density compared to normal neural density. In some embodiments, the abnormal neural density comprises about 65% decrease in neural density compared to normal neural density. In some embodiments, the abnormal neural density comprises about 75% decrease in neural density compared to normal neural density. In some embodiments, the abnormal neural density comprises about 85% decrease in neural density compared to normal neural density. In some embodiments, the abnormal neural density comprises about 95% decrease in neural density compared to normal neural density. In some embodiments, the abnormal neural density comprises about 99% decrease in neural density compared to normal neural density.

In some embodiments, the abnormal neural density comprises an increase in neural density compared to normal neural density. In some embodiments, the abnormal neural density comprises about 5% increase in neural density compared to normal neural density. In some embodiments, the abnormal neural density comprises about 15% increase in neural density compared to normal neural density. In some embodiments, the abnormal neural density comprises about 25% increase in neural density compared to normal neural density. In some embodiments, the abnormal neural density comprises about 35% increase in neural density compared to normal neural density. In some embodiments, the abnormal neural density comprises about 45% increase in neural density compared to normal neural density. In some embodiments, the abnormal neural density comprises about 55% increase in neural density compared to normal neural density. In some embodiments, the abnormal neural density comprises about 65% increase in neural density compared to normal neural density. In some embodiments, the abnormal neural density comprises about 75% increase in neural density compared to normal neural density. In some embodiments, the abnormal neural density comprises about 85% increase in neural density compared to normal neural density. In some embodiments, the abnormal neural density comprises about 95% increase in neural density compared to normal neural density. In some embodiments, the abnormal neural density comprises about 99% increase in neural density compared to normal neural density.

In some embodiments, the abnormal neural density comprises a 5 fold decrease in neural density compared to normal neural density. In some embodiments, the abnormal neural density comprises a 10 fold decrease in neural density compared to normal neural density. In some embodiments, the abnormal neural density comprises a 50 fold decrease in neural density compared to normal neural density. In some embodiments, the abnormal neural density comprises a 100 fold decrease in neural density compared to normal neural density. In some embodiments, the abnormal neural density comprises a 250 fold decrease in neural density compared to normal neural density. In some embodiments, the abnormal neural density comprises a 500 fold decrease in neural density compared to normal neural density. In some embodiments, the abnormal neural density comprises a 750 fold decrease in neural density compared to normal neural density. In some embodiments, the abnormal neural density comprises a 1000 fold decrease in neural density compared to normal neural density.

In some embodiments, the abnormal neural density comprises a 5 fold increase in neural density compared to normal neural density. In some embodiments, the abnormal neural density comprises a 10 fold increase in neural density compared to normal neural density. In some embodiments, the abnormal neural density comprises a 50 fold increase in neural density compared to normal neural density. In some embodiments, the abnormal neural density comprises a 100 fold increase in neural density compared to normal neural density. In some embodiments, the abnormal neural density comprises a 250 fold increase in neural density compared to normal neural density. In some embodiments, the abnormal neural density comprises a 500 fold increase in neural density compared to normal neural density. In some embodiments, the abnormal neural density comprises a 750 fold increase in neural density compared to normal neural density. In some embodiments, the abnormal neural density comprises a 1000 fold increase in neural density compared to normal neural density.

In some embodiments, the abnormal neural density comprises abnormal synaptic density. In some embodiments, the abnormal neural density is abnormal synaptic density. In some embodiments, the abnormal neural density is localized in the olfactory epithelium. In some embodiments, the abnormal neural density comprises a decrease in olfactory sensory neurons. In some embodiments, the abnormal neural density comprises an increase in olfactory sensory neurons.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 2A shows a representative treatment and imaging paradigm for saline and zinc sulfate treatment.

FIG. 2B shows summed PET images of Sprague-Dawley rats imaged with [$^{11}$C] radiolabeled N-benzyl-2-fluoro-9-methyl-9H-purin-6-amine after saline treatment.

FIG. 2C shows summed PET images of Sprague-Dawley rats imaged with [$^{11}$C] radiolabeled N-benzyl-2-fluoro-9-methyl-9H-purin-6-amine after zinc sulfate treatment.

FIG. 4A shows averaged PET images of SUV changes in Sprague-Dawley rats.

FIG. 4B shows a Logan Analysis of Sprague-Dawley rats at 2 months and 3 months.

FIG. 9 shows results of a blocking assay using [$^{11}$C] radiolabeled N-benzyl-2-fluoro-9-methyl-9H-purin-6-amine (Compound A) and roscovitine.

FIG. 10B shows peak normalized results of a self-blocking assay (brain) using [$^{11}$C] radiolabeled Compound K.

FIG. 11 shows results of a blocking assay using unlabeled Compound A and [$^{11}$C] radiolabeled Compound L.

FIG. 12A shows results of a self-blocking assay (olfactory epithelium) using unlabeled Compound M.

FIG. 12B shows results of a blocking assay using [$^{11}$C] radiolabeled N-benzyl-2-fluoro-9-methyl-9H-purin-6-amine (Compound A) and unlabeled Compound M.

FIG. 13B shows results of a self-blocking assay (olfactory epithelium) using [$^{11}$C] radiolabeled Compound N and unlabeled Compound N.

FIG. 13C shows results of a blocking assay using [$^{11}$C] radiolabeled N-benzyl-2-fluoro-9-methyl-9H-purin-6-amine (Compound A) and unlabeled Compound N.

FIG. 14B shows results of a self-blocking assay (olfactory epithelium) using [$^{11}$C] radiolabeled Compound O and unlabeled Compound O.

FIG. 14C shows results of a blocking assay using [$^{11}$C] radiolabeled N-benzyl-2-fluoro-9-methyl-9H-purin-6-amine (Compound A) and unlabeled Compound O.

FIG. 15 shows a table that summarizes results of the blocking assays using [$^{11}$C] radiolabeled compounds.

FIG. 16A shows a computational model of Synapsin 1-ATP.

FIG. 16B shows the energy minimum of Synapsin 1-N-benzyl-2-fluoro-9-methyl-9H-purin-6-amine.

FIG. 18A shows a representative PET-MR image of [$^{18}$F] radiolabeled N-benzyl-2-fluoro-9-methyl-9H-purin-6-amine in a rhesus macaque.

FIG. 18B shows a time-activity curve for the olfactory epithelium in a rhesus macque after injection of [$^{18}$F] radiolabeled N-benzyl-2-fluoro-9-methyl-9H-purin-6-amine.

FIG. 20A-B shows results of imaging neuron density changes during neurodevelopment and age-associated neurodegeneration in mice.

FIG. 21A-B show results of monitoring central nervous system damage following anterior bulbectomy.

FIG. 22A-B shows results of imaging neurodegeneration in tau model of Alzheimer's/Frontotemporal Dementia.

DETAILED DESCRIPTION

Figure 1A:
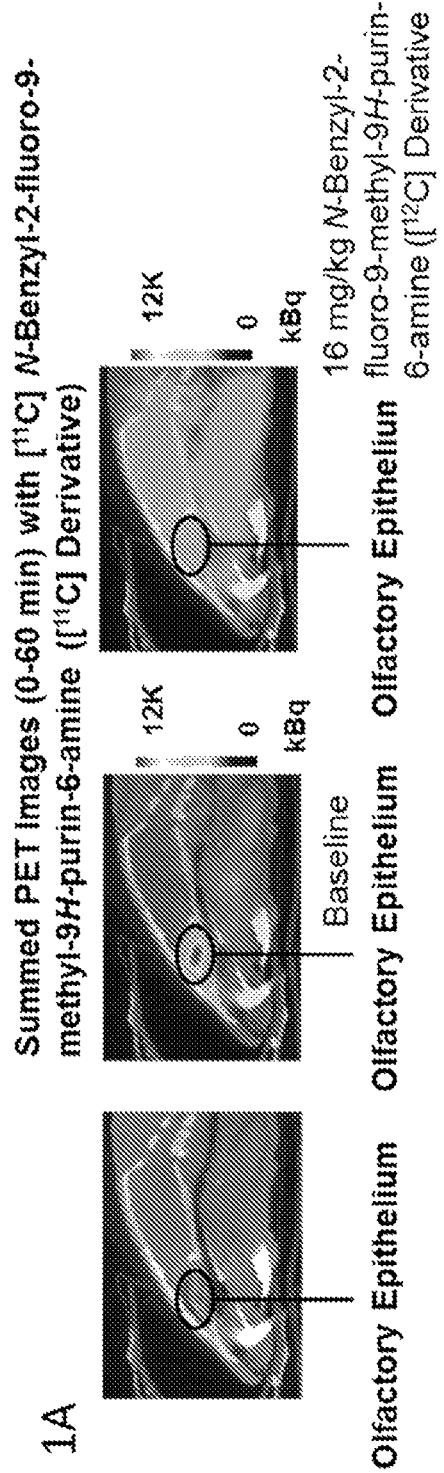
FIG. 1A shows specific binding of [$^{11}$C] radiolabeled N-benzyl-2-fluoro-9-methyl-9H-purin-6-amine in the olfactory epithelium of a Sprague-Dawley rat using summed positron emission tomography (PET) images.
Figure 1B:
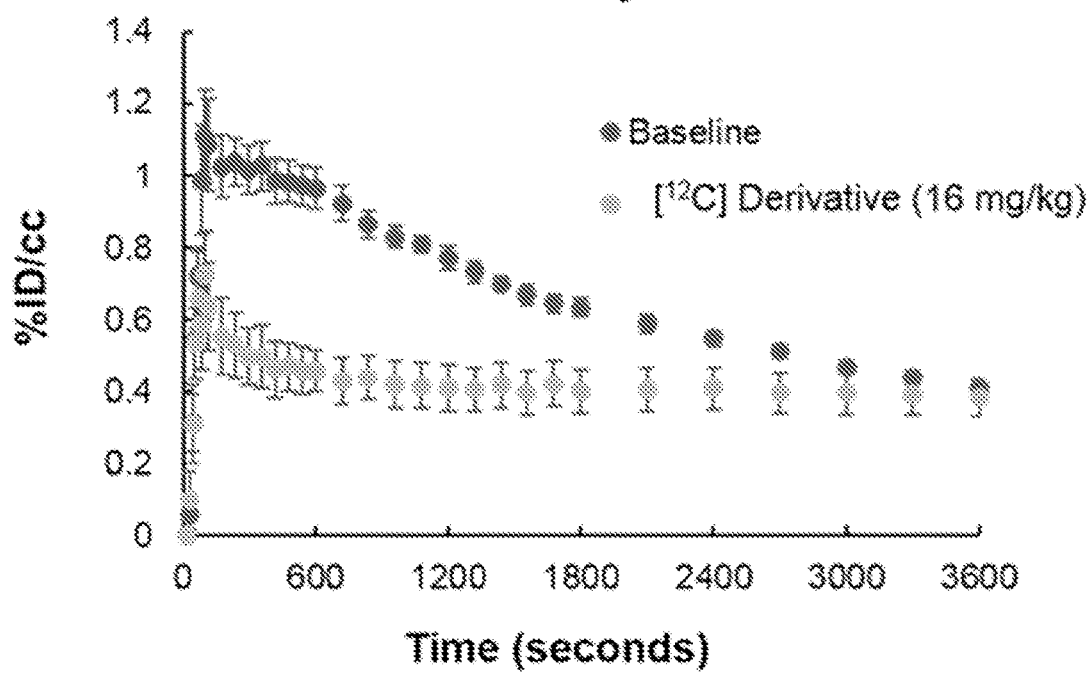
FIG. 1B shows a time-activity curve in the presence of unlabeled N-benzyl-2-fluoro-9-methyl-9H-purin-6-amine (i.e. [$^{12}$C] Derivative).
Figure 1C:
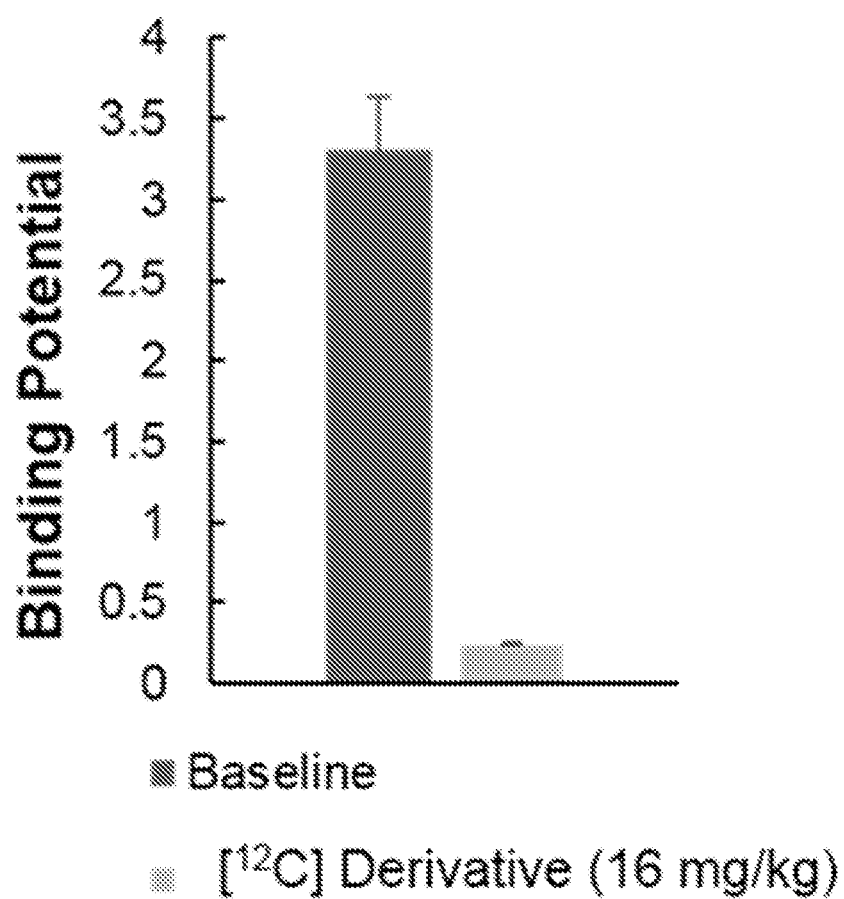
FIG. 1C shows a Logan Analysis in the presence of unlabeled N-benzyl-2-fluoro-9-methyl-9H-purin-6-amine.
Figure 1D:
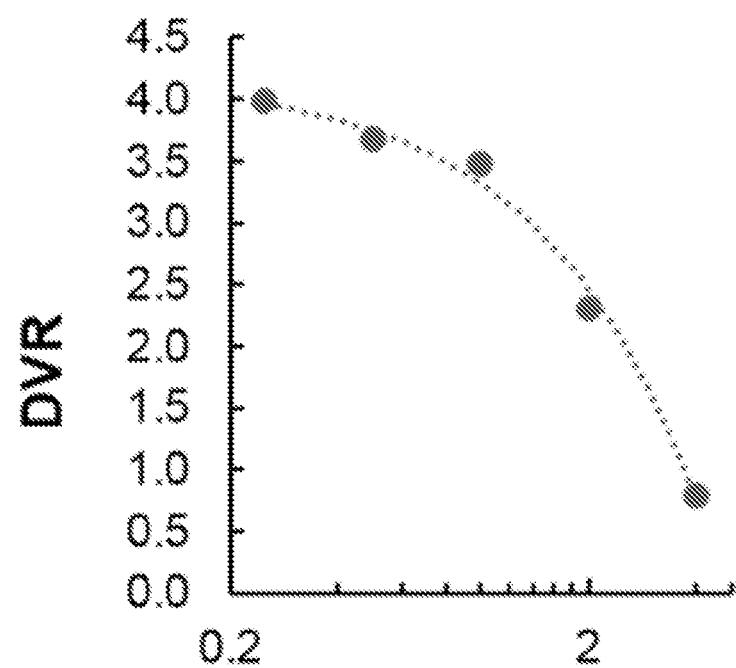
FIG. 1D shows a dose response in the presence of unlabeled N-benzyl-2-fluoro-9-methyl-9H-purin-6-amine.
Figure 3:
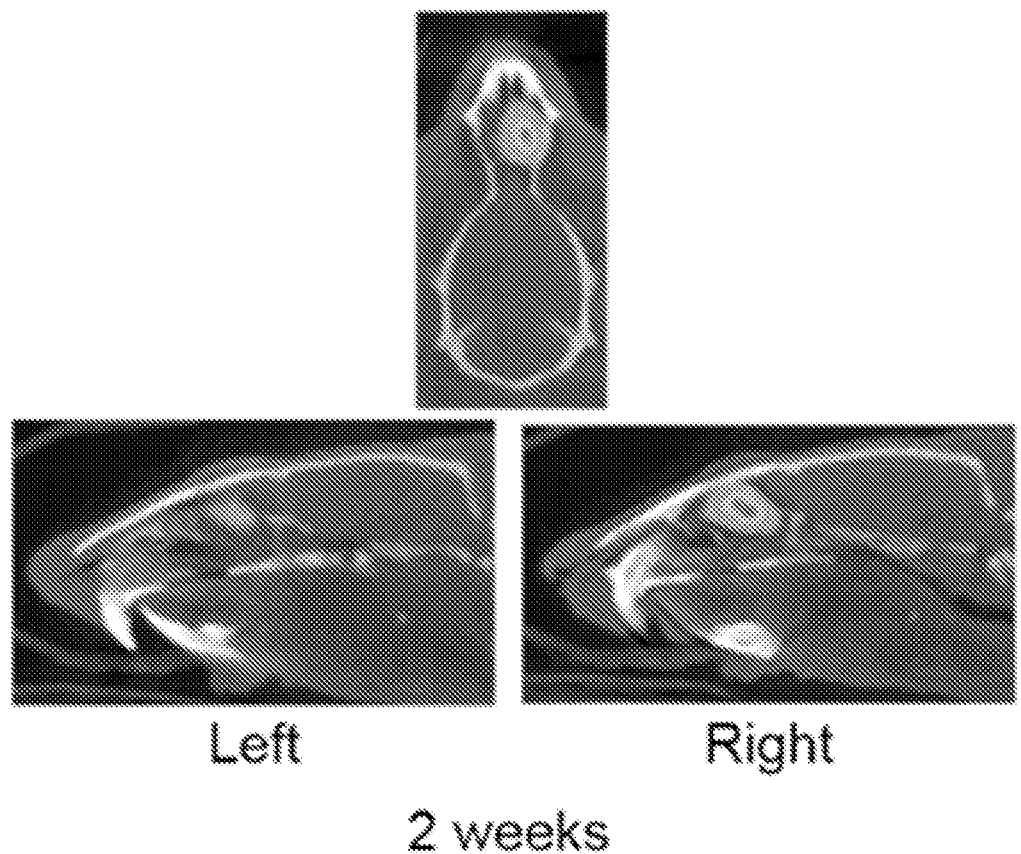
FIG. 3 shows summed PET images of a single-side tissue ablation in a Sprague-Dawley rat.

The olfactory epithelium (OE) houses the olfactory sensory neurons (OSNs), which detect small molecules in the air we breathe and transmit their presence to our brain through their dendritic connections with the olfactory bulb. The OE shows high rates of neurogenesis throughout life and exhibits alterations, or flux, in cell (e.g., neuron, sustentacular, stem cell, glandular cell, glial cell and/or other cell) density (see e.g., Graziadei et al., J. Neurocytol, 1979, 8, 1-18; Hinds et al., J. Comp. Neurol. 1981, 203, 441-453) in part due to its neurogenic capacity. To the extent that cell (neuron, sustentacular, stem cell, glandular cell, glial cell and/or other cell) density is involved in the anosmic process that predicts mortality, a non-invasive, objective measure of the OE's cell (neuron, sustentacular, stem cell, glandular cell, glial cell and/or other cell) density could become a method for measuring overall human health. Additionally, imaging neurogenesis and cell (neuron, sustentacular, stem cell, glandular cell, glial cell and/or other cell) density relatively non-invasively, longitudinally, and without tissue biopsy would also provide a method for monitoring the effects of new therapeutics on a patient's OE cell (neuron, sustentacular, stem cell, glandular cell, glial cell and/or other cell) population. This may be beneficial for diseases that have a suspected impact on OE neurons and that have no or limited existing treatments (e.g. Alzheimer's disease).

Accordingly, the present application provides novel positron emission tomography (PET) radiotracers (e.g., N-benzyl-2-fluoro-9-methyl-9H-purin-6-amine), which monitor cell (e.g., neuron, sustentacular, stem cell, glandular cell, glial cell and/or other cell) density. In some embodiments, the cell density is located within the olfactory epithelium (OE). The present application further provides compounds useful in the treatment of diseases of the central nervous system and peripheral nervous system, in addition to methods of treatment, and diagnostic methods.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Compounds

The present application provides, inter alia, a compound of Formula (I):

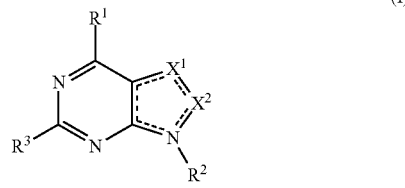

or a pharmaceutically acceptable salt thereof, wherein:
=== represents a single- or double-bond;
$X^1$ is $CR^A$ or $NR^B$;
$X^2$ is $CR^A$ or $NR^B$; wherein
one of $X^1$ and $X^2$ is $CR^A$ and the other is $NR^B$;
$R^A$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;
$R^B$ is absent; or
$R^B$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;
$R^1$ is selected from the group consisting of $NR^NR^{N'}$, —($C_{1-6}$ alkylene)-$NR^NR^{N'}$, —($C_{2-6}$ alkenylene)-$NR^NR^{N'}$, —($C_{2-6}$ alkynylene)-$NR^NR^{N'}$, —O-Cy, —O—($C_{1-6}$ alkylene)-Cy, —S-Cy, and —S—($C_{1-6}$ alkylene)-Cy;
$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;
$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;
$R^2$ is absent; or
$R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

wherein at least two of $R^A$, $R^B$, and $R^2$ are independently H or absent;

$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$, and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

each $R^{a2}$, $R^{b2}$, $R^{c2}$, and $R^{d2}$ is independently selected from the group consisting of H, $C_{1-6}$ alkyl, $C_{2-6}$ alkenyl, and $C_{2-6}$ alkynyl;

$R^{c3}$ and $R^{d3}$ are each independently selected from the group consisting of H, $C_{1-6}$ alkyl, $C_{2-6}$ alkenyl, $C_{2-6}$ alkynyl, and $C(=O)OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, when $X^1$ is N, $X^2$ is CH, $R^2$ is isopropyl and $R^1$ is —N(H)$CH_2$-phenyl, then $R^3$ cannot form the group:

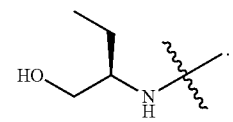

In some embodiments, the compound of Formula (I) is not:

In some embodiments, the compound of Formula (I) is not:

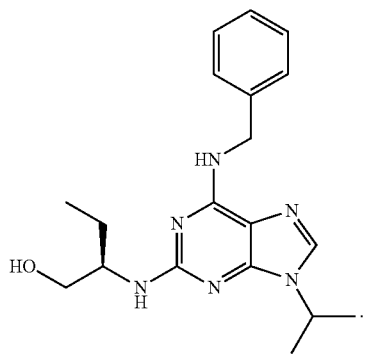 [SMILES: CC[C@H](CO)Nc1nc(NCc2ccccc2)c2ncn(C(C)C)c2n1]

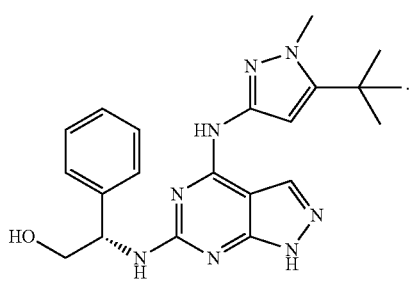 [SMILES: Cn1nc(Nc2nc(N[C@H](CO)c3ccccc3)nc3[nH]ncc23)cc1C(C)(C)C]

In some embodiments, the ring comprising $X^1$ and $X^2$ forms a heteroaromatic ring. In some embodiments, the ring comprising $X^1$ and $X^2$ forms a heterocycloalkyl ring.

In some embodiments, $R^A$ is H or $C_{1-6}$ alkyl. In some embodiments, $R^A$ is H.

In some embodiments, $R^B$ is H or $C_{1-6}$ alkyl. In some embodiments, $R^B$ is methyl. In some embodiments, $R^B$ is absent when the bond between $X^1$ and $X^2$ is a double bond. In some embodiments, $R^B$ is H or $C_{1-6}$ alkyl when the bond between $X^1$ and $X^2$ is a single bond. In some embodiments, $R^B$ is methyl when the bond between $X^1$ and $X^2$ is a single bond.

In some embodiments, $R^1$ is $NR^N R^{N'}$. In some embodiments, $R^N$ is H or $C_{1-6}$ alkyl. In some embodiments, $R^N$ is H. In some embodiments, $R^{N'}$ is selected from the group consisting of $C_{3-10}$ cycloalkyl, $C_{6-10}$ aryl, 4-10 membered heteroaryl, 4-10 membered heterocycloalkyl, and —($C_{1-6}$ alkylene)-$Cy^1$. In some embodiments, $R^{N'}$ is —($C_{1-6}$ alkylene)-$Cy^1$. In some embodiments, $R^{N'}$ is —($CH_2$)—$Cy^1$.

In some embodiments, $Cy^1$ is selected from the group consisting of $C_{3-10}$ cycloalkyl, $C_{6-10}$ aryl, and 4-10 membered heteroaryl, and each is optionally substituted by 1, 2, 3, or 4 independently selected $R^4$ groups. In some embodiments, $Cy^1$ is selected from the group consisting of $C_{3-10}$ cycloalkyl, $C_{6-10}$ aryl, and 4-10 membered heteroaryl, wherein the $C_{6-10}$ aryl is optionally substituted by one substituent selected from the group consisting of halo, $C_{1-6}$ alkyl, and $C_{1-6}$ alkoxy. In some embodiments, $Cy^1$ is selected from the group consisting of adamantyl, phenyl, 2-methylphenyl, 2-methoxyphenyl, 2-chlorophenyl, 4-chlorophenyl, 4-fluorophenyl, and pyridin-3-yl.

In some embodiments, $R^2$ is absent. In some embodiments, $R^2$ is absent when the bond between the nitrogen to which $R^2$ is attached forms a double bond with an adjacent atom (e.g., an adjacent carbon atom or an adjacent $X^2$ atom).

In some embodiments, $R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups. In some embodiments, $R^2$ is selected from the group consisting of H, $C_{1-6}$ alkyl, —C(=O)($C_{1-6}$ alkyl), and $NH_2$, wherein the $C_{1-6}$ alkyl is optionally substituted by one substituent selected from the group consisting of OH, —$OCH_3$, —C(=O)$CH_3$. In some embodiments, $R^2$ is selected from the group consisting of H, methyl, isopropyl, pentyl, —$CH_2OH$, —$CH_2CH_2OH$, —$CH_2OCH_3$, —$CH(OH)CH_3$, —$CH(OCH_3)CH_3$, —$CH_2C(=O)CH_3$, —C(=O)$CH_3$, and —C(=O)$CH_2CH_3$. In some embodiments, $R^2$ is selected from the group consisting of —($C_{1-6}$ alkylene)-$Cy^2$, $C_{3-10}$ cycloalkyl, $C_{6-10}$ aryl, 4-10 membered heteroaryl, and 4-10 membered heterocycloalkyl, wherein the 4-10 membered heteroaryl and 4-10 membered heterocycloalkyl are each optionally substituted by one or two substituents independently selected from the group consisting of halo, oxo, $C_{1-3}$ alkyl, and $C_{1-6}$ alkoxycarbonyl. In some embodiments, $R^2$ is selected from the group consisting of:

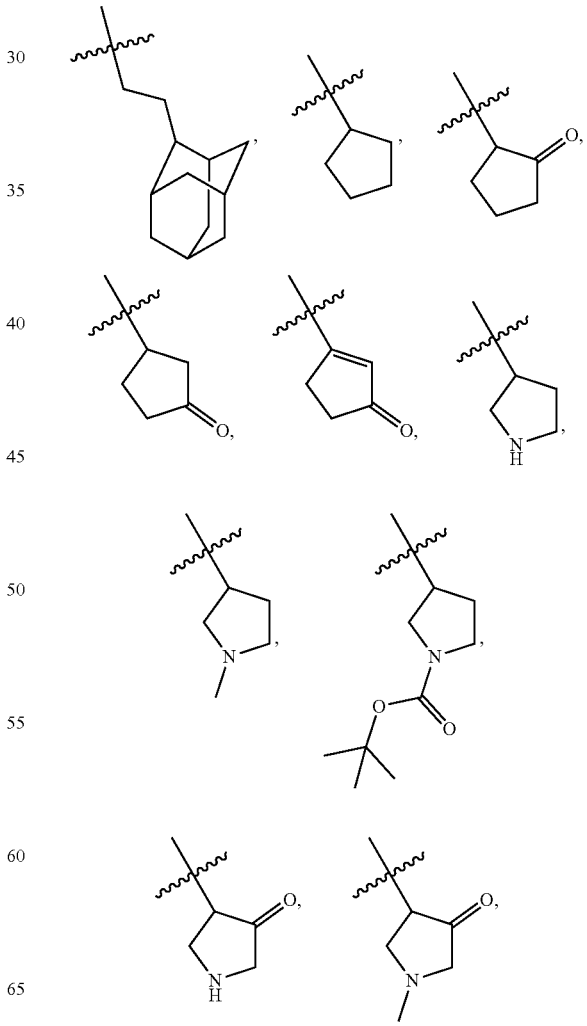

-continued

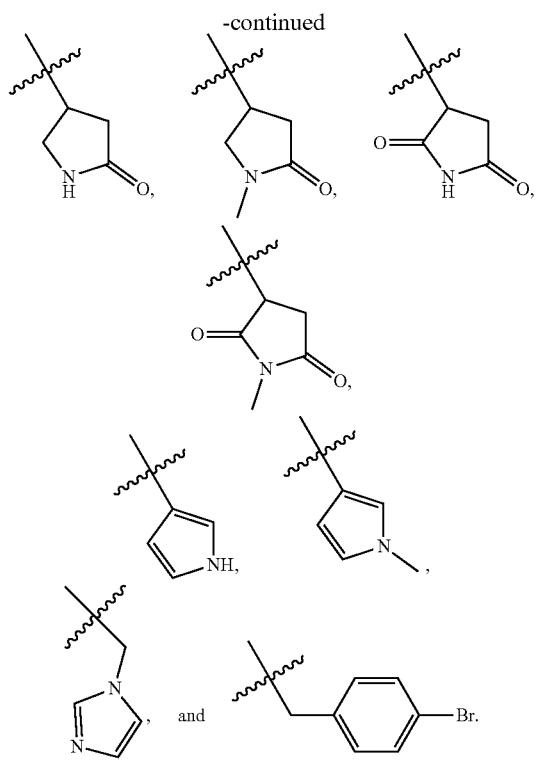

In some embodiments, R³ is selected from the group consisting of H, halo, NR^{c3}R^{d3}, and NO₂. In some embodiments, R³ is selected from the group consisting of H, fluoro, chloro, NH₂, —NHC(=O)O-tert-butyl, and NO₂. In some embodiments, R³ forms a group selected from:

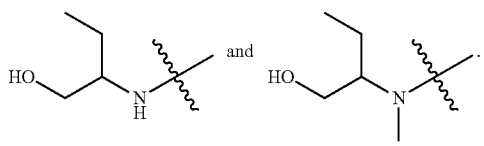

In some embodiments, R³ forms a group selected from:

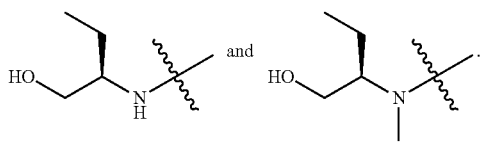

In some embodiments, R¹ is NR^{N}R^{N'}; R^{N} is H; R^{N'} is —(C_{1-6} alkylene)-Cy¹; R² is selected from the group consisting of H, C_{1-6} alkyl, C_{3-10} cycloalkyl, C_{6-10} aryl, 4-10 membered heteroaryl, 4-10 membered heterocycloalkyl, —(C_{1-6} alkylene)-Cy², C(=O)R^{b2}, and NR^{c2}R^{d2}, wherein the C_{1-6} alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR^{c3}R^{d3}, and NO₂.

In some embodiments, R¹ is NR^{N}R^{N'}; R^{N} is H; R^{N'} is selected from the group consisting of —(C_{1-6} alkylene)-phenyl, —(C_{1-6} alkylene)adamantyl, and —(C_{1-6} alkylene)-pyridin-3-yl, wherein said phenyl is optionally substituted by 1, 2, 3, or 4 independently selected R⁴ groups; R² is selected from the group consisting of H, C_{1-6} alkyl, C_{3-10} cycloalkyl, C_{6-10} aryl, 4-10 membered heteroaryl, 4-10 membered heterocycloalkyl, —(C_{1-6} alkylene)-Cy², C(=O)R^{b2}, and NR^{c2}R^{d2}, wherein the C_{1-6} alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR^{c3}R^{d3}, and NO₂.

In some embodiments, the compound of Formula (I) is a compound of Formula (Ia):

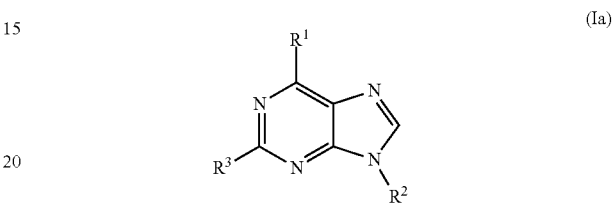

(Ia)

or a pharmaceutically acceptable salt thereof, wherein:

R¹ is selected from the group consisting of NR^{N}R^{N'}, —(C_{1-6} alkylene)-NR^{N}R^{N'}, —(C_{2-6} alkenylene)-NR^{N}R^{N'}, —(C_{2-6} alkynylene)-NR^{N}R^{N'}, —O-Cy, —O—(C_{1-6} alkylene)-Cy, —S-Cy, and —S—(C_{1-6} alkylene)-Cy;

R^{N} is selected from the group consisting of H, C_{1-6} alkyl, C_{2-6} alkenyl, C_{2-6} alkynyl, C_{3-10} cycloalkyl, C_{6-10} aryl, 4-10 membered heteroaryl, and 4-10 membered heterocycloalkyl;

R^{N'} is selected from the group consisting of C_{1-6} alkyl, C_{2-6} alkenyl, C_{2-6} alkynyl, C_{3-10} cycloalkyl, C_{6-10} aryl, 4-10 membered heteroaryl, 4-10 membered heterocycloalkyl, and —(C_{1-6} alkylene)-Cy¹, wherein the C_{3-10} cycloalkyl, C_{6-10} aryl, 4-10 membered heteroaryl, and 4-10 membered heterocycloalkyl are each optionally substituted by 1, 2, 3, or 4 independently selected R⁴ groups;

R² is selected from the group consisting of H, C_{1-6} alkyl, C_{1-6} haloalkyl, C_{2-6} alkenyl, C_{2-6} alkynyl, C_{3-10} cycloalkyl, C_{6-10} aryl, 4-10 membered heteroaryl, 4-10 membered heterocycloalkyl, —(C_{1-6} alkylene)-Cy², OR^{a2}, C(=O)R^{b2}, C(=O)OR^{b2}, NR^{c2}R^{d2}, C(=O)NR^{c2}R^{d2}, NR^{c2}C(=O)R^{b2}, NR^{c2}C(=O)OR^{b2}, NR^{c2}C(=O)NR^{c2}R^{d2}, NR^{c2}S(=O)₂R^{b2}, NR^{c2}S(=O)₂NR^{c2}R^{d2}, S(O)R^{a2}, S(O)₂R^{a2}, S(O)NR^{c2}R^{d2}, and S(O)₂NR^{c2}R^{d2}, wherein the C_{1-6} alkyl, C_{3-10} cycloalkyl, C_{6-10} aryl, 4-10 membered heteroaryl, and 4-10 membered heterocycloalkyl are each optionally substituted by 1, 2, 3, or 4 independently selected R⁴ groups;

R³ is selected from the group consisting of H, C_{1-6} alkyl, C_{2-6} alkenyl, C_{2-6} alkynyl, C_{3-10} cycloalkyl, C_{6-10} aryl, 4-10 membered heteroaryl, 4-10 membered heterocycloalkyl, halo, NR^{c3}R^{d3}, and NO₂, wherein the C_{3-10} cycloalkyl, C_{6-10} aryl, 4-10 membered heteroaryl, and 4-10 membered heterocycloalkyl are each optionally substituted by 1, 2, 3, or 4 independently selected R⁴ groups;

each R^{a2}, R^{b2}, R^{c2}, and R^{d2} is independently selected from the group consisting of H, C_{1-6} alkyl, C_{2-6} alkenyl, and C_{2-6} alkynyl;

R^{c3} and R^{d3} are each independently selected from the group consisting of H, C_{1-6} alkyl, C_{2-6} alkenyl, C_{2-6} alkynyl, and C(=O)OR^{a2}, wherein the C_{1-6} alkyl is optionally substituted by 1, 2, 3, or 4 independently selected R⁴ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, when $R^2$ is isopropyl and $R^3$ is —N(H)$CH_2$-phenyl, then $R^1$ cannot form the group:

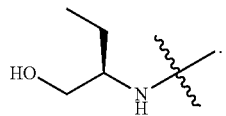

In some embodiments, the compound of Formula (Ia) is not:

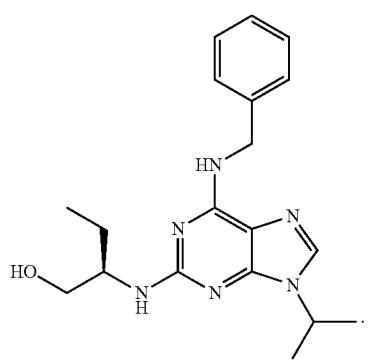 [SMILES: CC[C@H](CO)Nc1nc(NCc2ccccc2)c2ncn(C(C)C)c2n1]

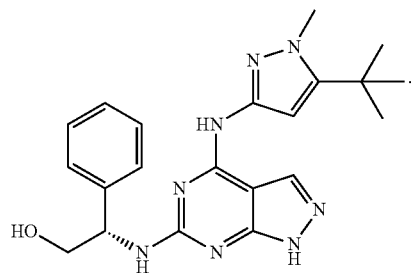 [SMILES: Cn1nc(Nc2nc(N[C@H](CO)c3ccccc3)nc3[nH]ncc23)cc1C(C)(C)C]

In some embodiments, $R^1$ is $NR^NR^{N'}$. In some embodiments, $R^N$ is H or $C_{1-6}$ alkyl. In some embodiments, $R^N$ is H. In some embodiments, $R^{N'}$ is selected from the group consisting of $C_{3-10}$ cycloalkyl, $C_{6-10}$ aryl, 4-10 membered heteroaryl, 4-10 membered heterocycloalkyl, and —($C_{1-6}$ alkylene)-$Cy^1$. In some embodiments, $R^{N'}$ is —($C_{1-6}$ alkylene)-$Cy^1$. In some embodiments, $R^{N'}$ is —($CH_2$)—$Cy^1$.

In some embodiments, $Cy^1$ is selected from the group consisting of $C_{3-10}$ cycloalkyl, $C_{6-10}$ aryl, and 4-10 membered heteroaryl, and each is optionally substituted by 1, 2, 3, or 4 independently selected $R^4$ groups. In some embodiments, $Cy^1$ is selected from the group consisting of $C_{3-10}$ cycloalkyl, $C_{6-10}$ aryl, and 4-10 membered heteroaryl, wherein the $C_{6-10}$ aryl is optionally substituted by one substituent selected from the group consisting of halo, $C_{1-6}$ alkyl, and $C_{1-6}$ alkoxy. In some embodiments, $Cy^1$ is selected from the group consisting of adamantyl, phenyl, 2-methylphenyl, 2-methoxyphenyl, 2-chlorophenyl, 4-chlorophenyl, 4-fluorophenyl, and pyridin-3-yl.

In some embodiments, $R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups. In some embodiments, $R^2$ is selected from the group consisting of H, $C_{1-6}$ alkyl, —C(=O)($C_{1-6}$ alkyl), and $NH_2$, wherein the $C_{1-6}$ alkyl is optionally substituted by one substituent selected from the group consisting of OH, —$OCH_3$, —C(=O)$CH_3$. In some embodiments, $R^2$ is selected from the group consisting of H, methyl, isopropyl, pentyl, —$CH_2OH$, —$CH_2CH_2OH$, —$CH_2OCH_3$, —CH(OH)$CH_3$, —CH($OCH_3$)$CH_3$, —$CH_2$C(=O)$CH_3$, —C(=O)$CH_3$, and —C(=O)$CH_2CH_3$. In some embodiments, $R^2$ is selected from the group consisting of —($C_{1-6}$ alkylene)-$Cy^2$, $C_{3-10}$ cycloalkyl, $C_{6-10}$ aryl, 4-10 membered heteroaryl, and 4-10 membered heterocycloalkyl, wherein the 4-10 membered heteroaryl and 4-10 membered heterocycloalkyl are each optionally substituted by one or two substituents independently selected from the group consisting of halo, oxo, $C_{1-3}$ alkyl, and $C_{1-6}$ alkoxycarbonyl. In some embodiments, $R^2$ is selected from the group consisting of:

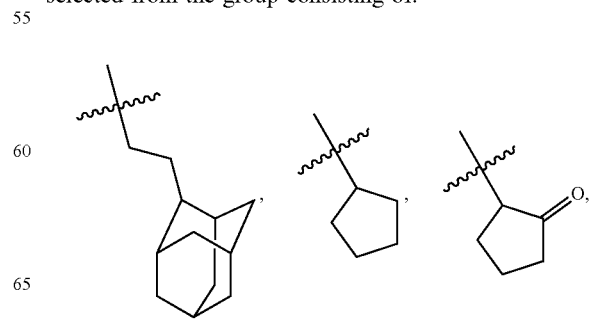

-continued

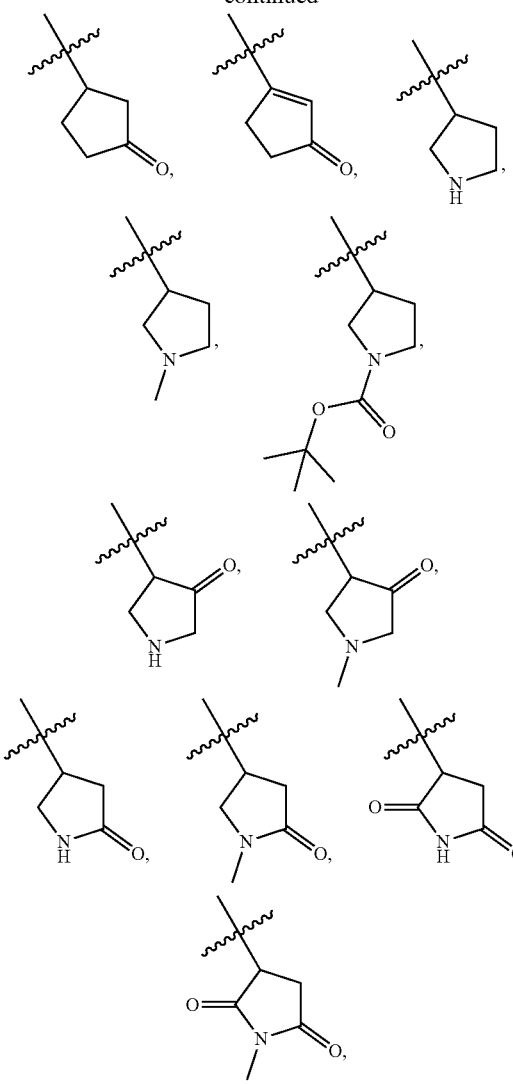

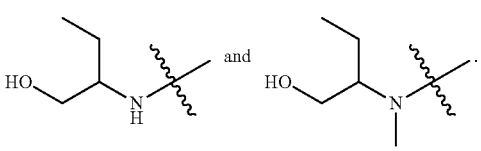

In some embodiments, R³ forms a group selected from:

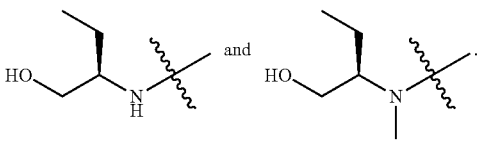

In some embodiments, R¹ is $NR^{N}R^{N'}$; $R^{N}$ is H; $R^{N'}$ is —($C_{1-6}$ alkylene)-Cy¹; R² is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-Cy², C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected R⁴ groups; and R³ is selected from the group consisting of H, halo, $NR^{c3}R^{d3}$, and NO₂.

In some embodiments, R¹ is $NR^{N}R^{N'}$; $R^{N}$ is H; $R^{N'}$ is selected from the group consisting of —($C_{1-6}$ alkylene)-phenyl, —($C_{1-6}$ alkylene)adamantyl, and —($C_{1-6}$ alkylene)-pyridin-3-yl, wherein said phenyl is optionally substituted by 1, 2, 3, or 4 independently selected R⁴ groups; R² is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-Cy², C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected R⁴ groups; and R³ is selected from the group consisting of H, halo, $NR^{c3}R^{d3}$, and NO₂.

In some embodiments, the compound of Formula (I) is a compound of Formula (Ib):

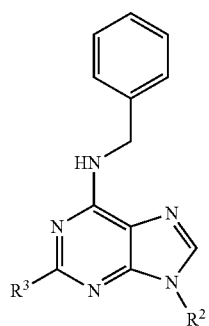

(Ib)

or a pharmaceutically acceptable salt thereof, wherein variables R² and R³ are defined according to the definitions described herein for compounds of Formula (I).

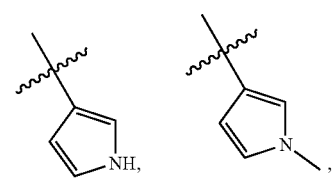

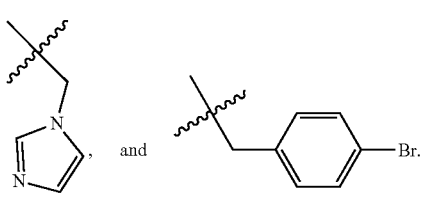

In some embodiments, R³ is selected from the group consisting of H, halo, $NR^{c3}R^{d3}$, and NO₂. In some embodiments, R³ is selected from the group consisting of H, fluoro, chloro, NH₂, —NHC(=O)O-tert-butyl, and NO₂. In some embodiments, R³ forms a group selected from:

In some embodiments, the compound of Formula (I) is a compound of Formula (Ic):

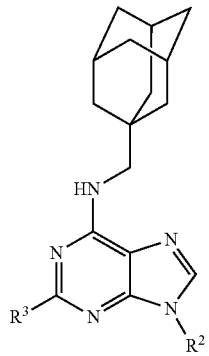
(Ic)

or a pharmaceutically acceptable salt thereof, wherein variables $R^2$ and $R^3$ are defined according to the definitions described herein for compounds of Formula (I).

In some embodiments, the compound of Formula (I) is a compound of Formula (Id):

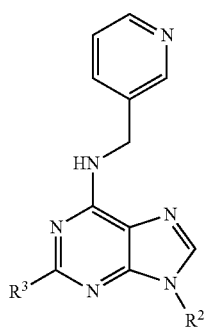
(Id)

or a pharmaceutically acceptable salt thereof, wherein variables $R^2$ and $R^3$ are defined according to the definitions described herein for compounds of Formula (I).

In some embodiments, the compound of Formula (I) is a compound of Formula (Ie):

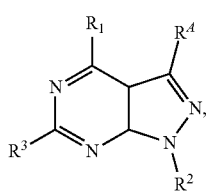
(Ie)

or a pharmaceutically acceptable salt thereof, wherein variables $R^1$, $R^2$, $R^3$, and $R^A$ are defined according to the definitions described herein for compounds of Formula (I).

In some embodiments, the compound of Formula (Ie) is not:

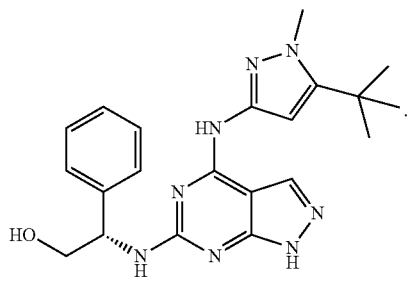 [SMILES: Cn1nc(Nc2nc(N[C@H](CO)c3ccccc3)nc3[nH]ncc23)cc1C(C)(C)C]

In some embodiments, the compound of Formula (I) is a compound of Formula (If):

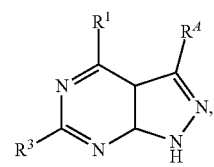
(If)

or a pharmaceutically acceptable salt thereof, wherein variables $R^1$, $R^3$, and $R^A$ are defined according to the definitions described herein for compounds of Formula (I).

In some embodiments, the compound of Formula (If) is not:

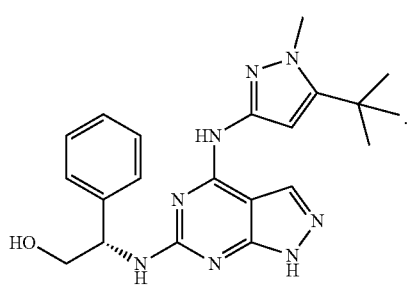 [SMILES: Cn1nc(Nc2nc(N[C@H](CO)c3ccccc3)nc3[nH]ncc23)cc1C(C)(C)C]

In some embodiments, the compound of Formula (I) is a compound of Formula (Ig):

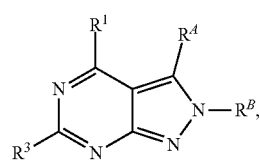
(Ig)

or a pharmaceutically acceptable salt thereof, wherein variables $R^1$, $R^3$, $R^A$, and $R^B$ are defined according to the definitions described herein for compounds of Formula (I).

In some embodiments, the compound of Formula (I) is selected from the group consisting of:

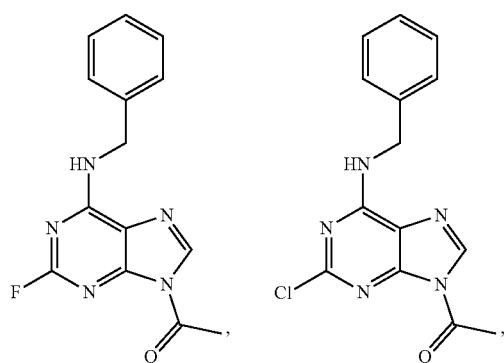 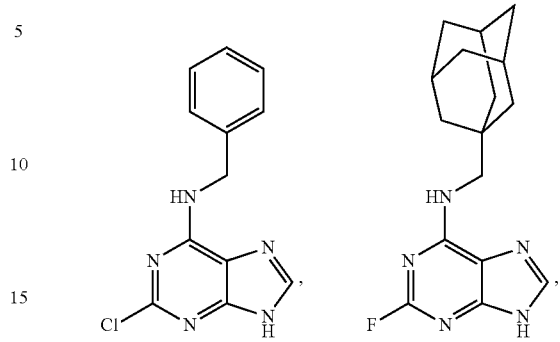 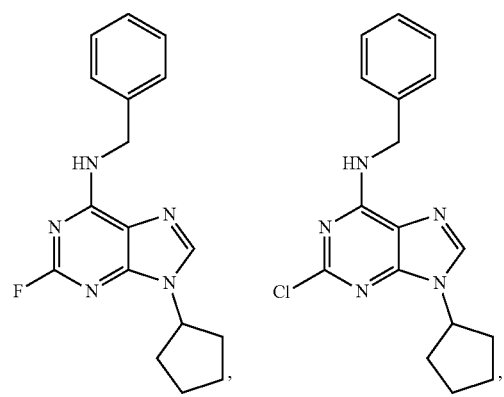 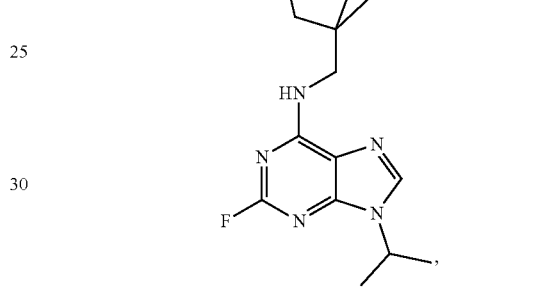 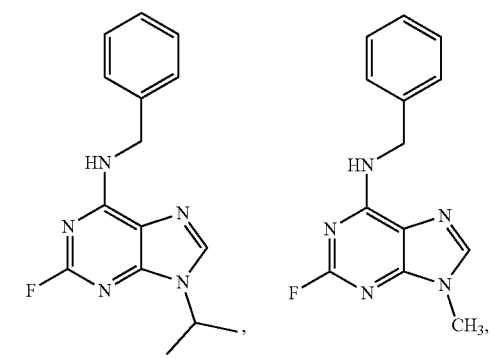 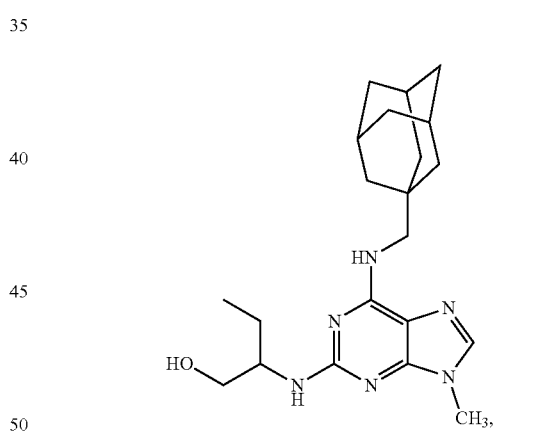 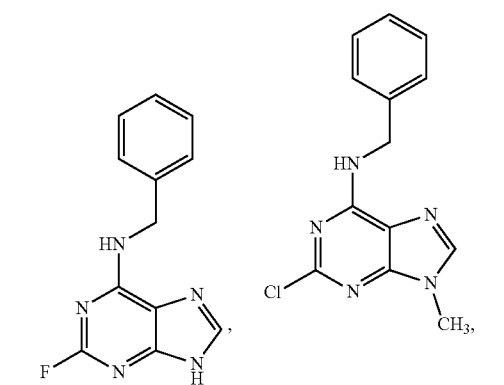 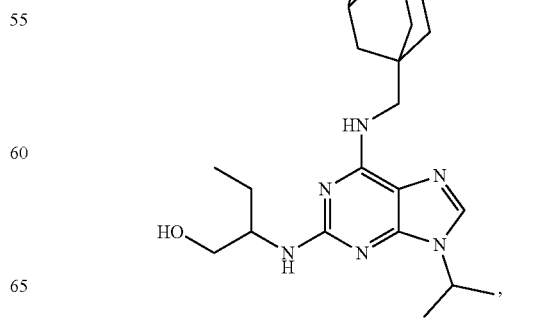

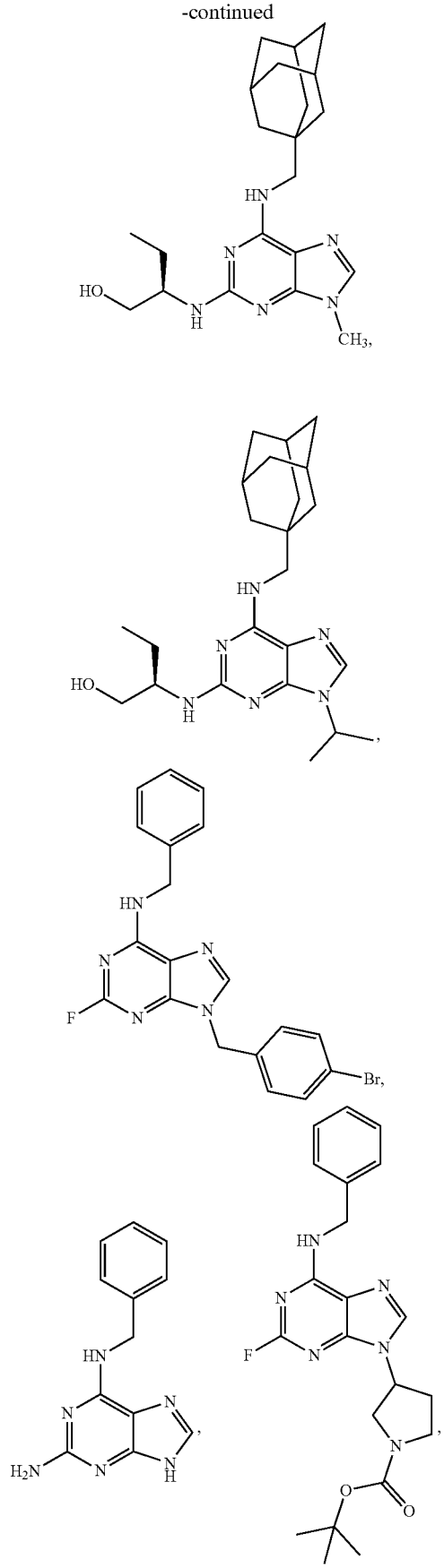

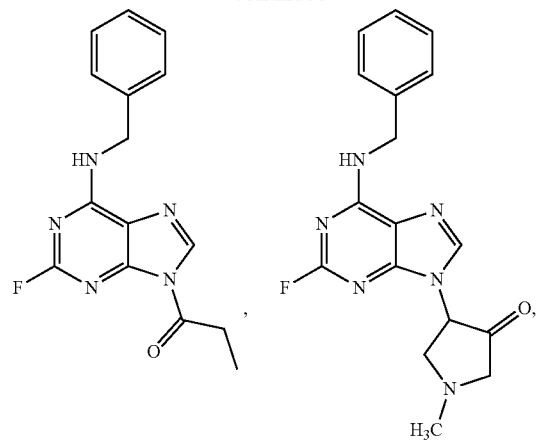
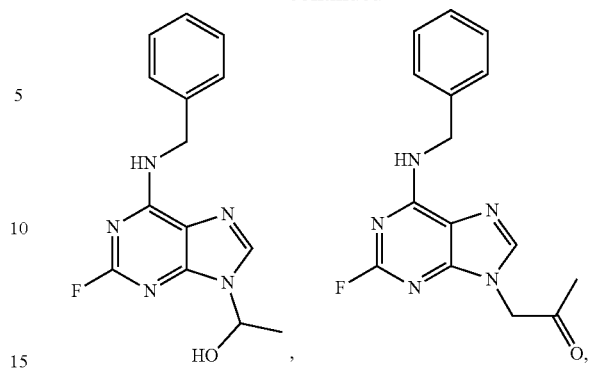
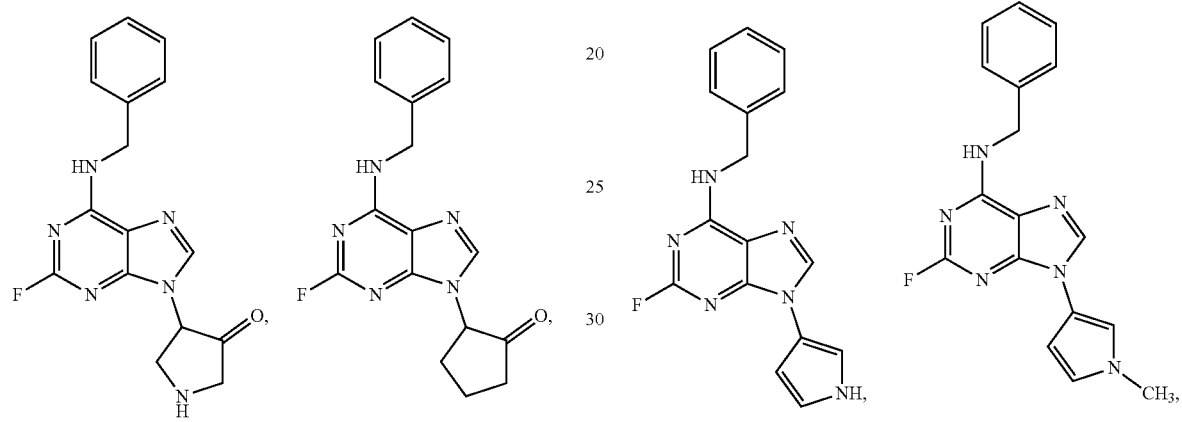
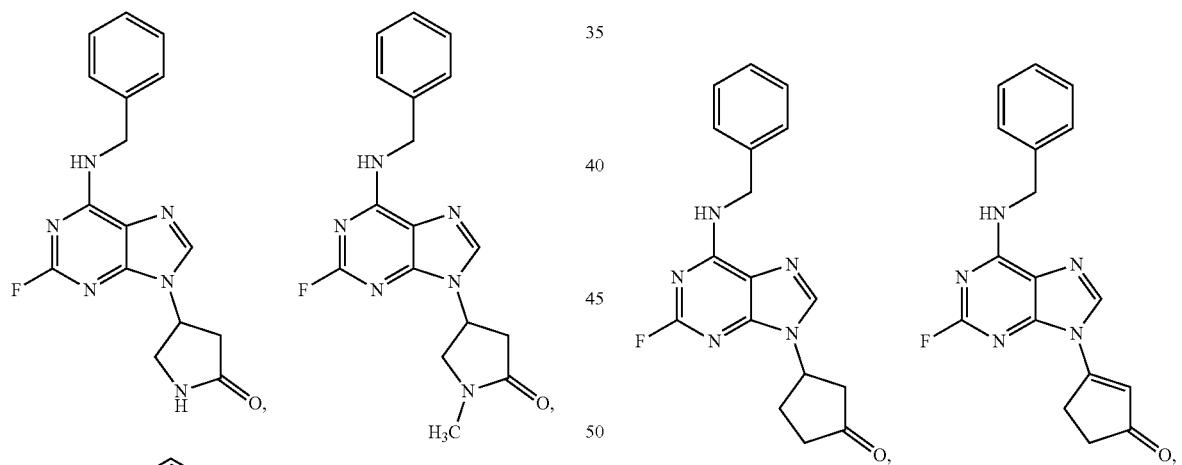
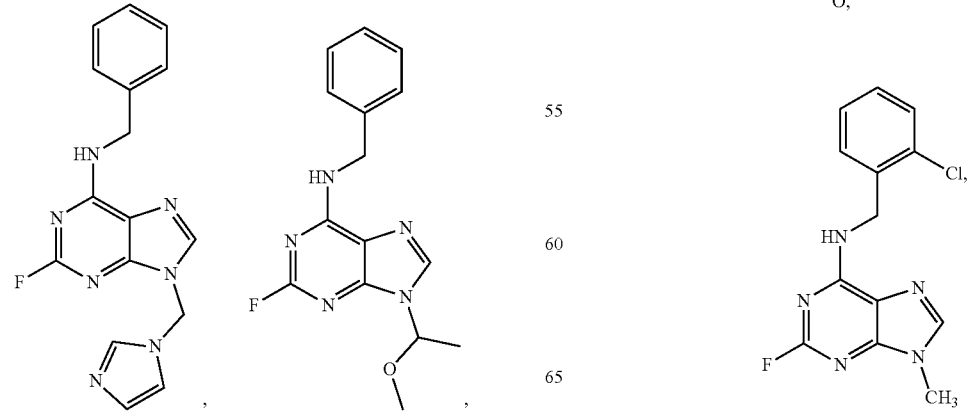

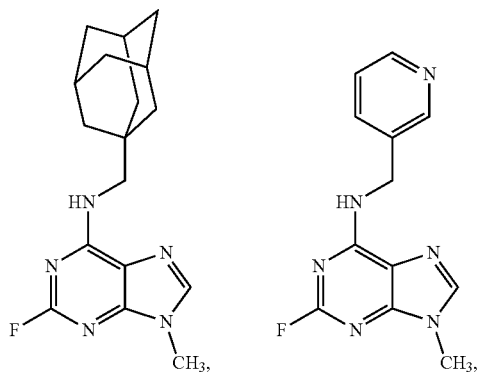
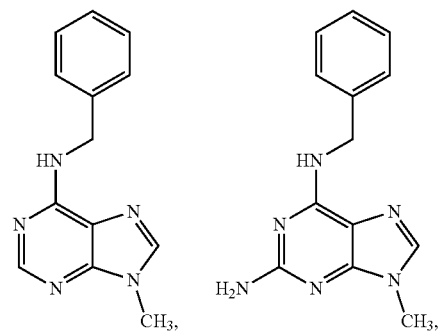
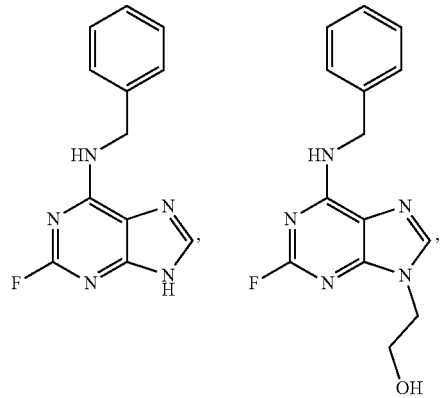
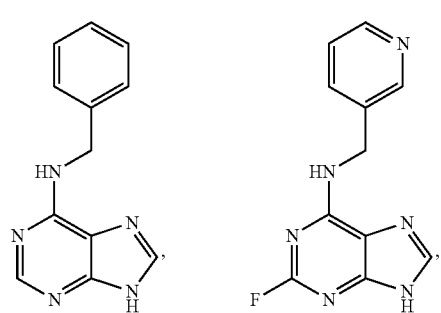
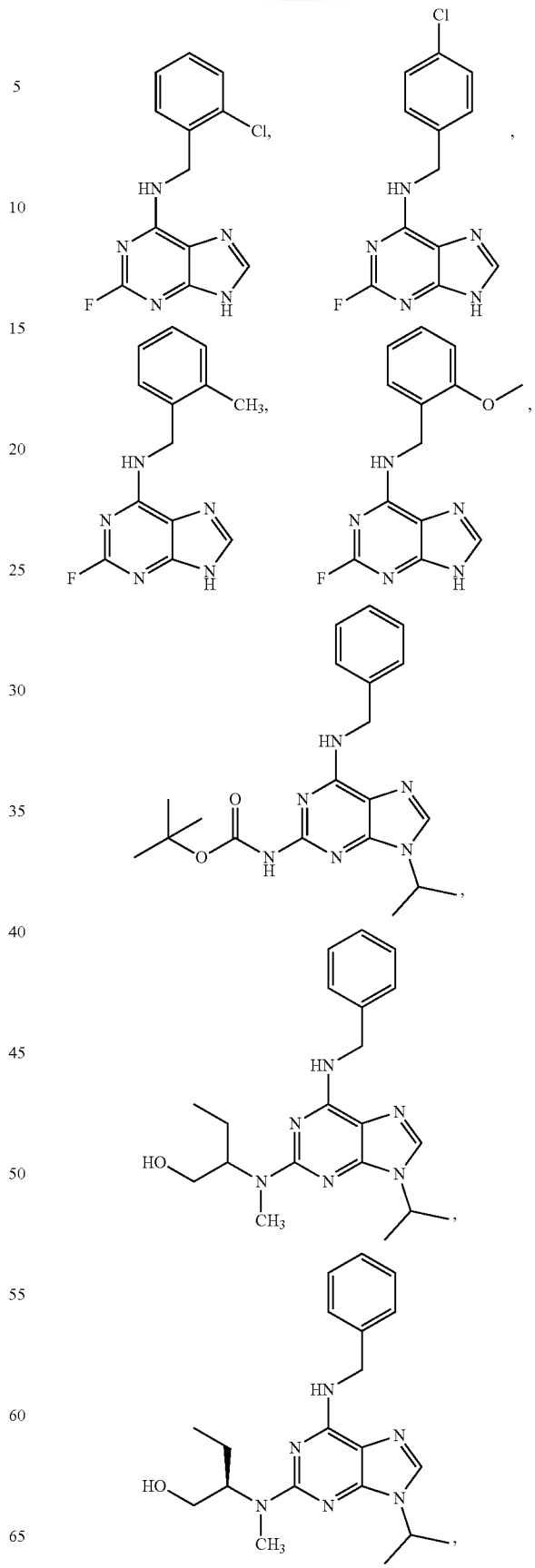

59
-continued
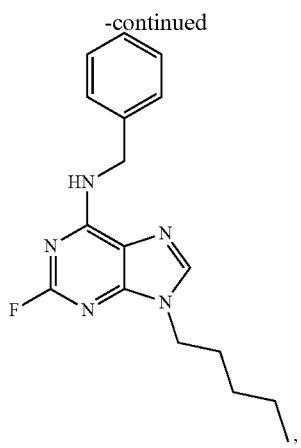
60
-continued
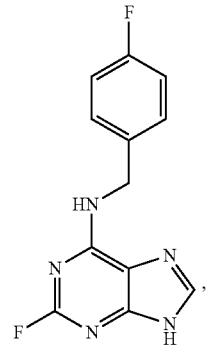
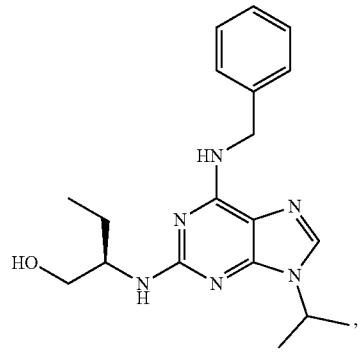
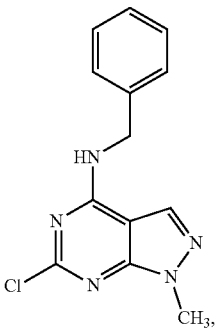
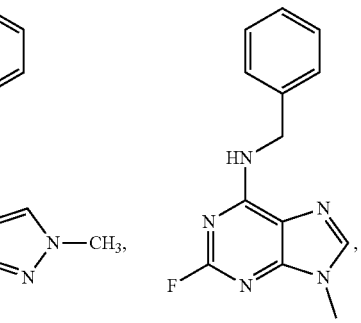
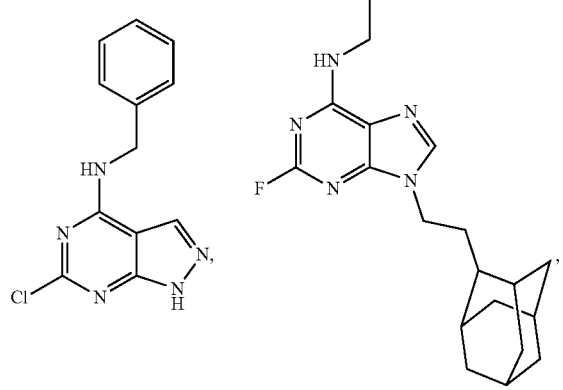

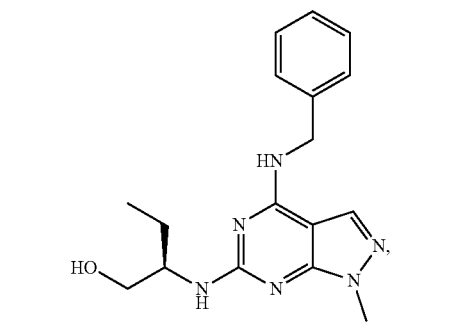
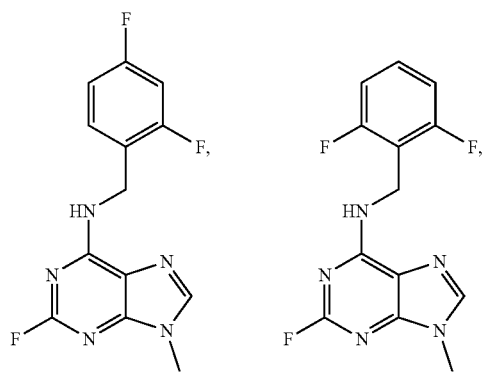
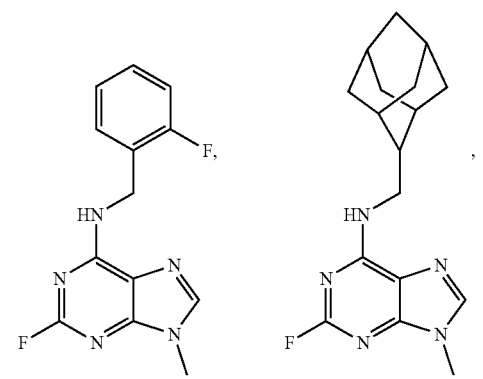
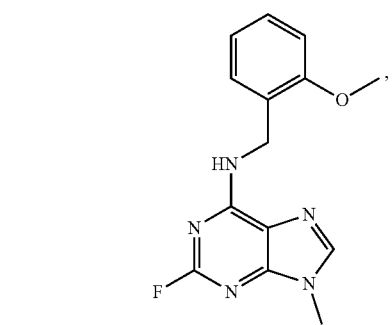
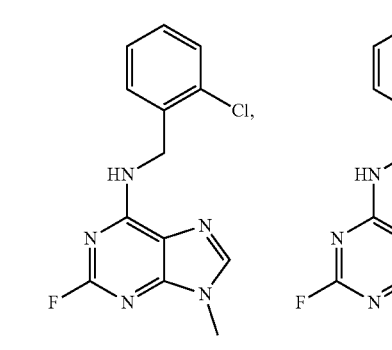
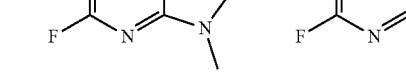
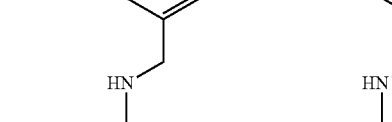
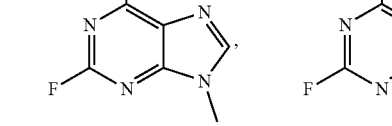
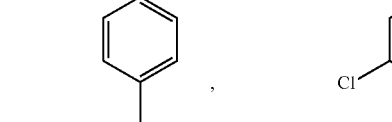
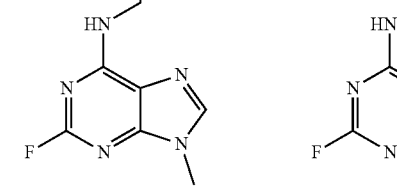

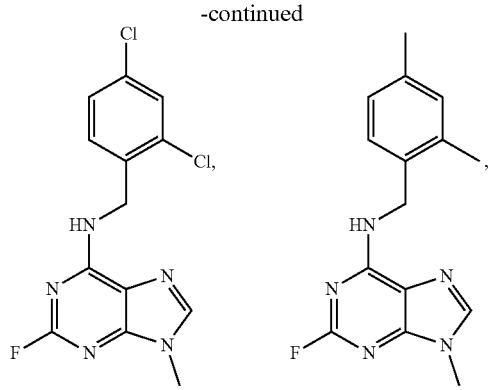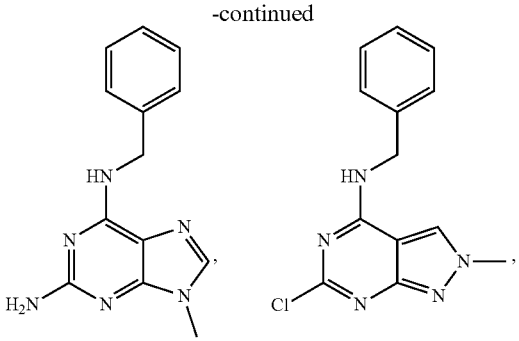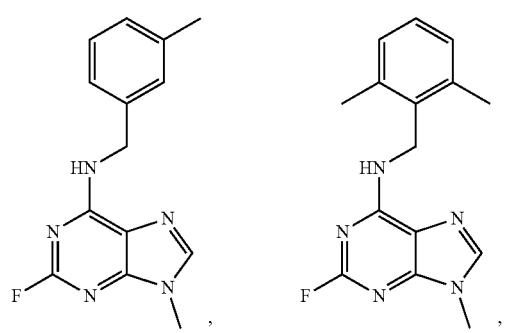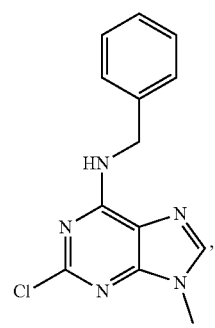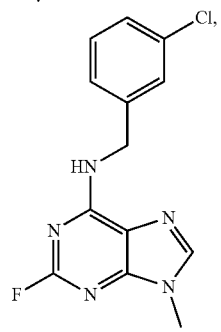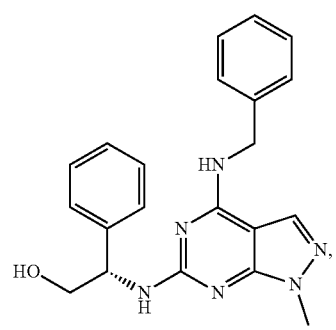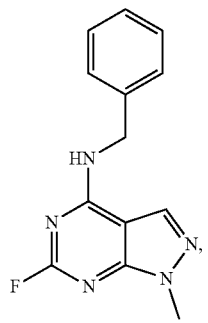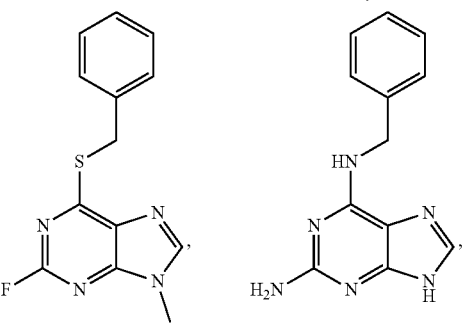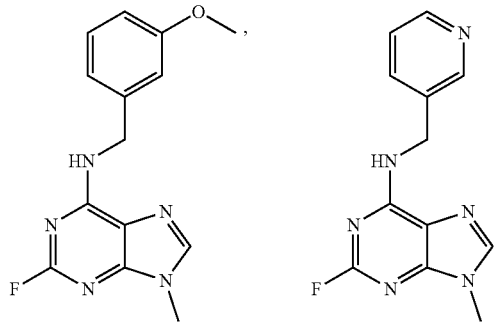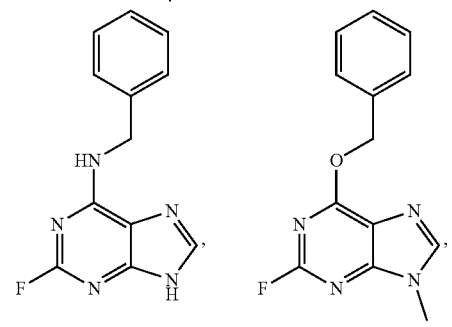

65
-continued
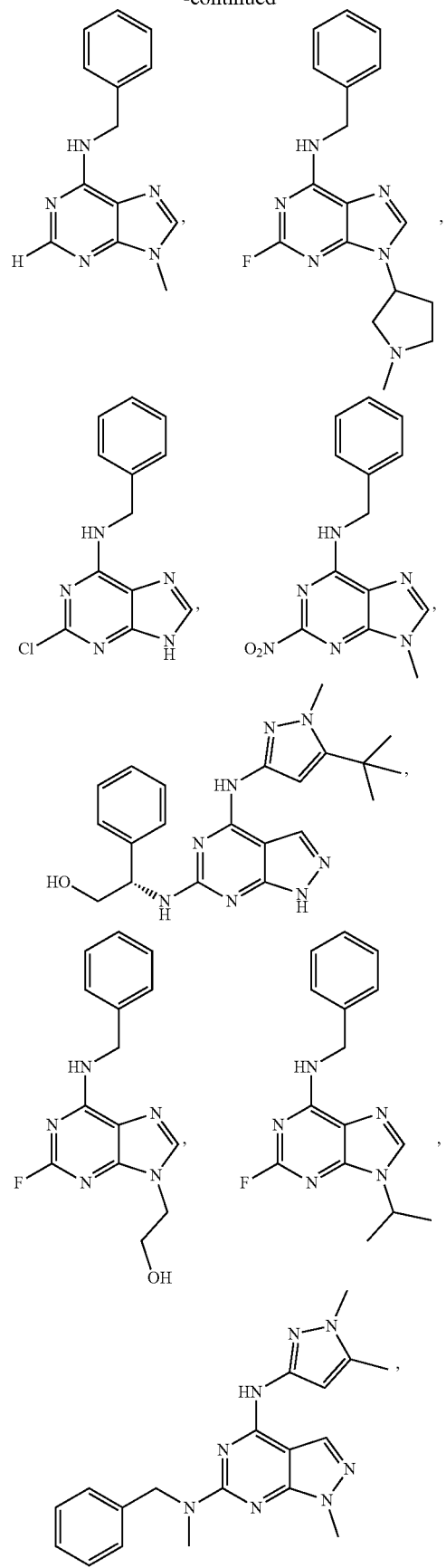
66
-continued
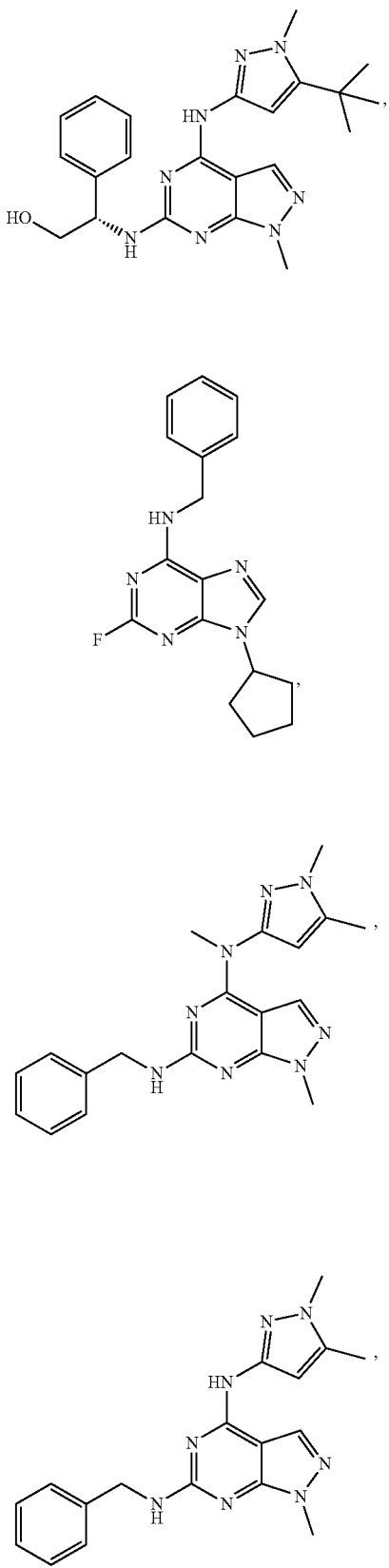

-continued

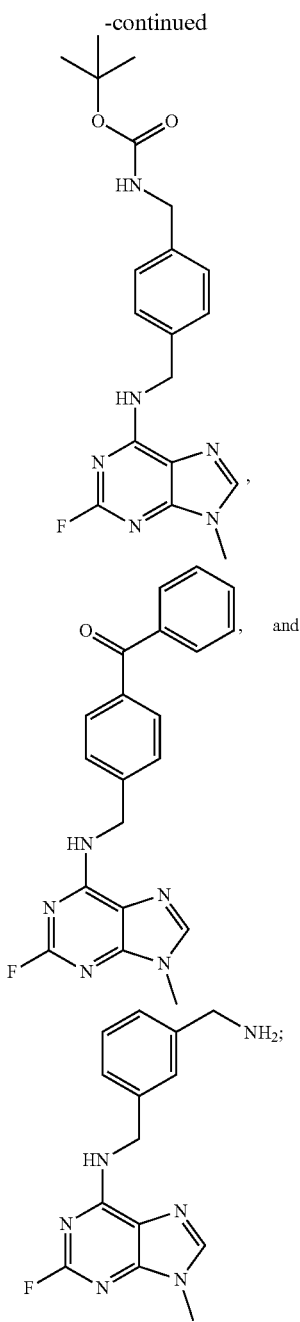

or a pharmaceutically acceptable salt thereof.

The following abbreviations may be used herein: aq. (aqueous); n-BuOH (n-butanol); calc. (calculated); d (doublet); dd (doublet of doublets); DCM (dichloromethane); DIPEA (N,N-diisopropylethylamine); DMA (dimethylacetamide); DMF (N,N-dimethylformamide); eq. (equivalents); Et (ethyl); EtOAc (ethyl acetate); EtOH (ethanol); g (gram(s)); h (hour(s)); HPLC (high performance liquid chromatography); Hz (hertz); IPA (isopropyl alcohol); J (coupling constant); KOH (potassium hydroxide); LCMS (liquid chromatography-mass spectrometry); m (multiplet); M (molar); Me (methyl); MeI (methyl iodide); MeCN (acetonitrile); MeOH (methanol); mg (milligram(s)); min. (minutes(s)); mL (milliliter(s)); mmol (millimole(s)); MS (Mass spectrometry); $Na_2SO_4$ (sodium sulfate); nM (nanomolar); NMR (nuclear magnetic resonance spectroscopy); OMP(s) (olfactory marker protein(s)); OSN(s) (olfactory sensory neuron(s)); PET (positron emission tomography); t (triplet or tertiary); TEA (triethylamine); THF (tetrahydrofuran); TLC (thin layer chromatography); μg (microgram(s)); μL (microliter(s)); μM (micromolar); wt % (weight percent).

Labeled Compounds

Another aspect of the present application relates to labeled compounds of Formula (II) that would be useful not only in imaging techniques but also in assays, both in vitro and in vivo, for identifying (e.g., locating, labeling), measuring (e.g., quantitative or non-quantitative measuring) and quantitating neural density in tissue samples, including human tissue samples.

The present application further includes isotopically-labeled compounds of Formula (II):

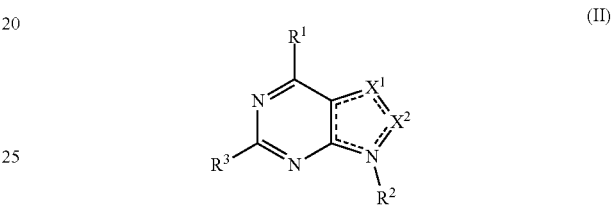

(II)

or a pharmaceutically acceptable salt thereof, wherein:
≡ represents a single- or double-bond;
$X^1$ is $CR^A$ or $NR^B$;
$X^2$ is $CR^A$ or $NR^B$; wherein
one of $X^1$ and $X^2$ is $CR^A$ and the other is $NR^B$;
$R^A$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;
$R^B$ is absent; or
$R^B$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;
$R^1$ is selected from the group consisting of $NR^N R^{N'}$, —($C_{1-6}$ alkylene)-$NR^N R^{N'}$, —($C_{2-6}$ alkenylene)-$NR^N R^{N'}$, —($C_{2-6}$ alkynylene)-$NR^N R^{N'}$, —O-Cy, —O—($C_{1-6}$ alkylene)-Cy, —S-Cy, and —S—($C_{1-6}$ alkylene)-Cy;
$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;
$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^2$ is absent; or $R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

wherein at least two of $R^A$, $R^B$, and $R^2$ are independently H or absent;

$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$, and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

each $R^{a2}$, $R^{b2}$, $R^{c2}$, and $R^{d2}$ is independently selected from the group consisting of H, $C_{1-6}$ alkyl, $C_{2-6}$ alkenyl, and $C_{2-6}$ alkynyl;

$R^{c3}$ and $R^{d3}$ are each independently selected from the group consisting of H, $C_{1-6}$ alkyl, $C_{2-6}$ alkenyl, $C_{2-6}$ alkynyl, and $C(=O)OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^2$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

wherein the compound of Formula (II) comprises at least one radioisotope.

In some embodiments, $R^1$ is $NR^NR^{N'}$.

In some embodiments, $R^N$ is H or $C_{1-6}$ alkyl. In some embodiments, $R^N$ is H.

In some embodiments, $R^{N'}$ is selected from the group consisting of $C_{3-10}$ cycloalkyl, $C_{6-10}$ aryl, 4-10 membered heteroaryl, 4-10 membered heterocycloalkyl, and —($C_{1-6}$ alkylene)-$Cy^1$. In some embodiments, $R^{N'}$ is —($C_{1-6}$ alkylene)-$Cy^1$. In some embodiments, $R^{N'}$ is —($CH_2$)—$Cy^1$.

In some embodiments, $Cy^1$ is selected from the group consisting of $C_{3-10}$ cycloalkyl, $C_{6-10}$ aryl, and 4-10 membered heteroaryl, and each is optionally substituted by 1, 2, 3, or 4 independently selected $R^4$ groups. In some embodiments, $Cy^1$ is selected from the group consisting of $C_{3-10}$ cycloalkyl, $C_{6-10}$ aryl, and 4-10 membered heteroaryl, wherein the $C_{6-10}$ aryl is optionally substituted by one substituent selected from the group consisting of halo, $C_{1-6}$ alkyl, and $C_{1-6}$ alkoxy. In some embodiments, $Cy^1$ is selected from the group consisting of adamantyl, phenyl, 2-methylphenyl, 2-methoxyphenyl, 2-chlorophenyl, 4-chlorophenyl, 4-fluorophenyl, and pyridin-3-yl.

In some embodiments, $R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $C(=O)R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups. In some embodiments, $R^2$ is selected from the group consisting of H, $C_{1-6}$ alkyl, —C(=O)($C_{1-6}$ alkyl), and $NH_2$, wherein the $C_{1-6}$ alkyl is optionally substituted by one substituent selected from the group consisting of OH, —$OCH_3$, —$C(=O)CH_3$. In some embodiments, $R^2$ is selected from the group consisting of H, methyl, isopropyl, pentyl, —$CH_2OH$, —$CH_2CH_2OH$, —$CH_2OCH_3$, —$CH(OH)CH_3$, —$CH(OCH_3)CH_3$, —$CH_2C(=O)CH_3$, —$C(=O)CH_3$, and —$C(=O)CH_2CH_3$. In some embodiments, $R^2$ is selected from the group consisting of —($C_{1-6}$ alkylene)-$Cy^2$, $C_{3-10}$ cycloalkyl, $C_{6-10}$ aryl, 4-10 membered heteroaryl, and 4-10 membered heterocycloalkyl, wherein the 4-10 membered heteroaryl and 4-10 membered heterocycloalkyl are each optionally substituted by one or two substituents independently selected from the group consisting of halo, oxo, $C_{1-3}$ alkyl, and $C_{1-6}$ alkoxycarbonyl. In some embodiments, $R^2$ is selected from the group consisting of:

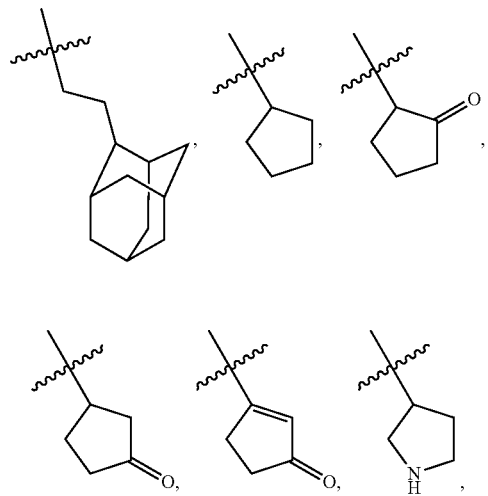

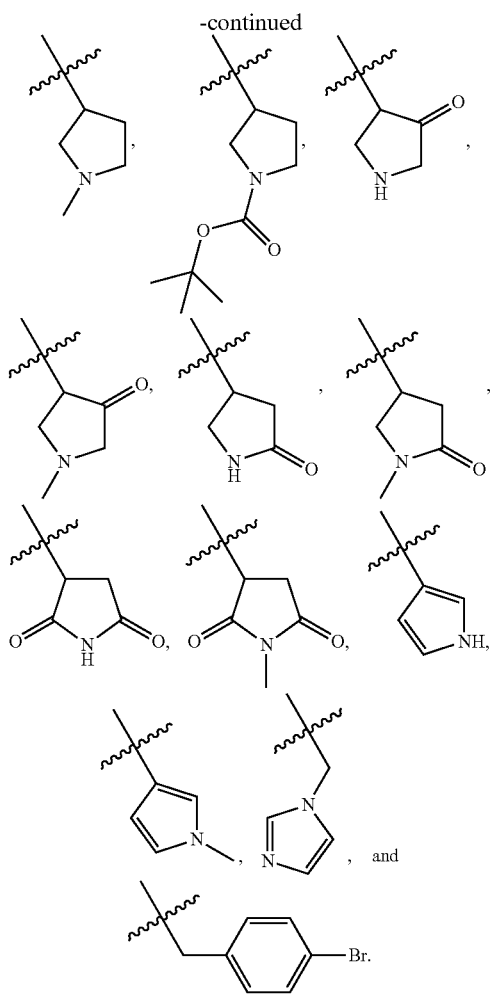

In some embodiments, R³ is selected from the group consisting of H, halo, NR^{c3}R^{d3}, and NO₂. In some embodiments, R³ is selected from the group consisting of H, fluoro, chloro, NH₂, —NHC(=O)O-tert-butyl, and NO₂. In some embodiments, R³ forms a group selected from:

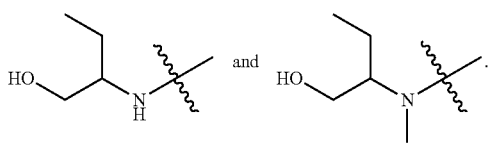

In some embodiments, R³ forms a group selected from:

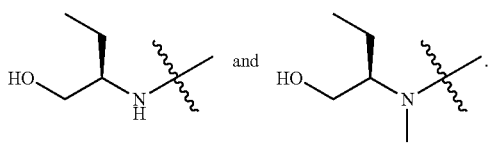

In some embodiments, R¹ is NR^{N}R^{N'}; R^{N} is H; R^{N'} is —(C_{1-6} alkylene)-Cy¹; R² is selected from the group consisting of H, C_{1-6} alkyl, C_{3-10} cycloalkyl, C_{6-10} aryl, 4-10 membered heteroaryl, 4-10 membered heterocycloalkyl, —(C_{1-6} alkylene)-Cy², C(=O)R^{b2}, and NR^{c2}R^{d2}, wherein the C_{1-6} alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR^{c3}R^{d3}, and NO₂.

In some embodiments, R¹ is NR^{N}R^{N'}; R^{N} is H; R^{N'} is selected from the group consisting of —(C_{1-6} alkylene)-phenyl, —(C_{1-6} alkylene)adamantyl, and —(C_{1-6} alkylene)-pyridin-3-yl, wherein said phenyl is optionally substituted by 1, 2, 3, or 4 independently selected R⁴ groups; R² is selected from the group consisting of H, C_{1-6} alkyl, C_{3-10} cycloalkyl, C_{6-10} aryl, 4-10 membered heteroaryl, 4-10 membered heterocycloalkyl, —(C_{1-6} alkylene)-Cy², C(=O)R^{b2}, and NR^{c2}R^{d2}, wherein the C_{1-6} alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR^{c3}R^{d3}, and NO₂.

In some embodiments, the isotopically-labeled compound of Formula (II) is a compound of Formula (IIa):

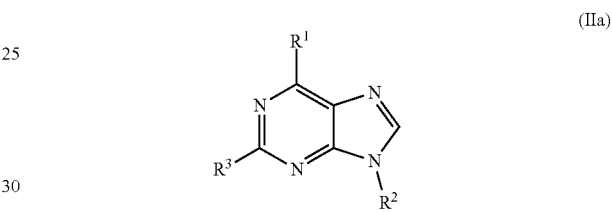

(IIa)

or a pharmaceutically acceptable salt thereof, wherein variables R¹, R², and R³ of Formula (IIa) are defined according to the definitions described herein for compounds of Formula (I); and wherein the compound of Formula (IIa) comprises at least one radioisotope.

In some embodiments, R¹ is NR^{N}R^{N'}.

In some embodiments, R^{N} is H or C_{1-6} alkyl. In some embodiments, R^{N} is H.

In some embodiments, R^{N'} is selected from the group consisting of C_{3-10} cycloalkyl, C_{6-10} aryl, 4-10 membered heteroaryl, 4-10 membered heterocycloalkyl, and —(C_{1-6} alkylene)-Cy¹. In some embodiments, R^{N'} is —(C_{1-6} alkylene)-Cy¹. In some embodiments, R^{N'} is —(CH₂)—Cy¹.

In some embodiments, Cy¹ is selected from the group consisting of C_{3-10} cycloalkyl, C_{6-10} aryl, and 4-10 membered heteroaryl, and each is optionally substituted by 1, 2, 3, or 4 independently selected R⁴ groups. In some embodiments, Cy¹ is selected from the group consisting of C_{3-10} cycloalkyl, C_{6-10} aryl, and 4-10 membered heteroaryl, wherein the C_{6-10} aryl is optionally substituted by one substituent selected from the group consisting of halo, C_{1-6} alkyl, and C_{1-6} alkoxy. In some embodiments, Cy¹ is selected from the group consisting of adamantyl, phenyl, 2-methylphenyl, 2-methoxyphenyl, 2-chlorophenyl, 4-chlorophenyl, 4-fluorophenyl, and pyridin-3-yl.

In some embodiments, R² is selected from the group consisting of H, C_{1-6} alkyl, C_{3-10} cycloalkyl, C_{6-10} aryl, 4-10 membered heteroaryl, 4-10 membered heterocycloalkyl, —(C_{1-6} alkylene)-Cy², C(=O)R^{b2}, and NR^{c2}R^{d2}, wherein the C_{1-6} alkyl, 4-10 membered heteroaryl, and 4-10 membered heterocycloalkyl are each optionally substituted by 1, 2, 3, or 4 independently selected R⁴ groups. In some embodiments, R² is selected from the group consisting of H, C_{1-6} alkyl, —C(=O)(C_{1-6} alkyl), and NH₂, wherein the C_{1-6} alkyl is optionally substituted by one substituent selected from the group consisting of OH, —OCH₃, —C(=O)CH₃. In some embodiments, R² is selected from the group consisting of H, methyl, isopropyl, pentyl, —CH₂OH, —CH₂CH₂OH, —CH₂OCH₃, —CH(OH)CH₃, —CH(OCH₃)CH₃, —CH₂C(=O)CH₃, —C(=O)CH₃, and —C(=O)CH₂CH₃. In some embodiments, R² is selected from the group consisting of —(C₁₋₆ alkylene)-Cy², C₃₋₁₀ cycloalkyl, C₆₋₁₀ aryl, 4-10 membered heteroaryl, and 4-10 membered heterocycloalkyl, wherein the 4-10 membered heteroaryl and 4-10 membered heterocycloalkyl are each optionally substituted by one or two substituents independently selected from the group consisting of halo, oxo, C₁₋₃ alkyl, and C₁₋₆ alkoxycarbonyl. In some embodiments, R² is selected from the group consisting of:

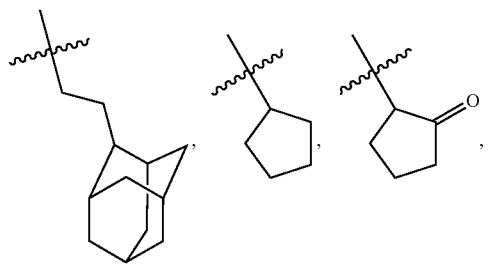

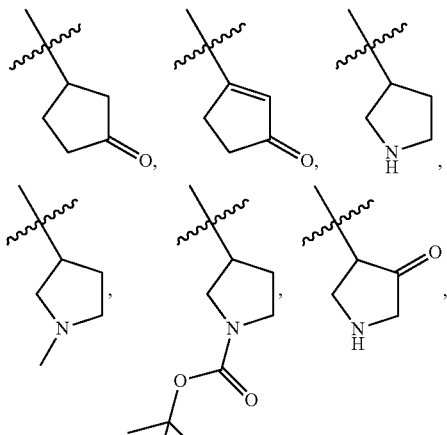

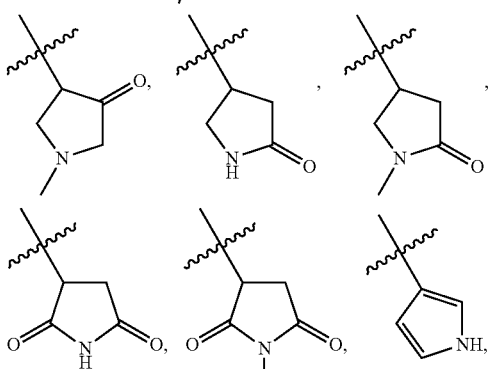

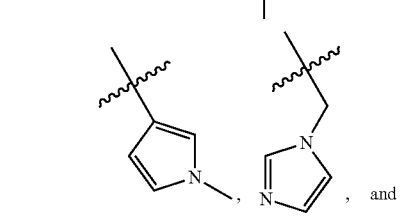

, and

-continued

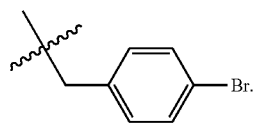

In some embodiments, R³ is selected from the group consisting of H, halo, NR^{c3}R^{d3}, and NO₂. In some embodiments, R³ is selected from the group consisting of H, fluoro, chloro, NH₂, —NHC(=O)O-tert-butyl, and NO₂. In some embodiments, R³ forms a 5 group selected from:

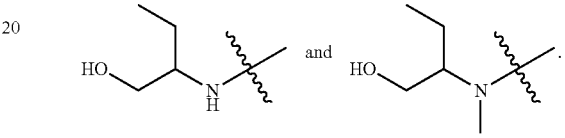

In some embodiments, R³ forms a group selected from:

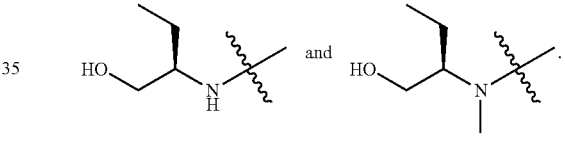

In some embodiments, R¹ is NR^{N}R^{N'}; R^{N} is H; R^{N'} is —(C₁₋₆ alkylene)-Cy¹; R² is selected from the group consisting of H, C₁₋₆ alkyl, C₃₋₁₀ cycloalkyl, C₆₋₁₀ aryl, 4-10 membered heteroaryl, 4-10 membered heterocycloalkyl, —(C₁₋₆ alkylene)-Cy², C(=O)R^{b2}, and NR^{c2}R^{d2}, wherein the C₁₋₆ alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR^{c3}R^{d3}, and NO₂.

In some embodiments, R¹ is NR^{N}R^{N'}; R^{N} is H; R^{N'} is selected from the group consisting of —(C₁₋₆ alkylene)-phenyl, —(C₁₋₆ alkylene)adamantyl, and —(C₁₋₆ alkylene)-pyridin-3-yl, wherein said phenyl is optionally substituted by 1, 2, 3, or 4 independently selected R⁴ groups; R² is selected from the group consisting of H, C₁₋₆ alkyl, C₃₋₁₀ cycloalkyl, C₆₋₁₀ aryl, 4-10 membered heteroaryl, 4-10 membered heterocycloalkyl, —(C₁₋₆ alkylene)-Cy², C(=O)R^{b2}, and NR^{c2}R^{d2}, wherein the C₁₋₆ alkyl, 4-10 membered heteroaryl, and 4-10 membered heterocycloalkyl are each optionally substituted by 1, 2, 3, or 4 independently selected R⁴ groups; and R³ is selected from the group consisting of H, halo, NR^{c3}R^{d3}, and NO₂.

In some embodiments, the compound of Formula (II) is a compound of Formula (IIb):

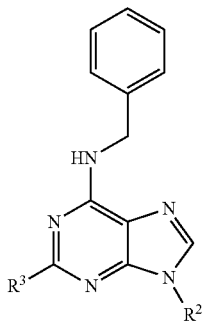

(IIb)

or a pharmaceutically acceptable salt thereof, and wherein variables $R^2$ and $R^3$ of Formula (IIb) are defined according to the definitions described herein for compounds of Formula (II); and wherein the compound of Formula (IIb) comprises at least one radioisotope.

In some embodiments, the compound of Formula (II) is a compound of Formula (IIc):

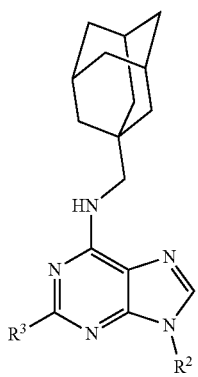

(IIc)

or a pharmaceutically acceptable salt thereof, wherein variables $R^2$ and $R^3$ of Formula (IIc) are defined according to the definitions described herein for compounds of Formula (II); and wherein the compound of Formula (IIc) comprises at least one radioisotope.

In some embodiments, the compound of Formula (II) is a compound of Formula (IId):

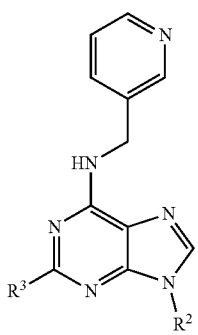

(IId)

or a pharmaceutically acceptable salt thereof, wherein variables $R^2$ and $R^3$ of Formula (IId) are defined according to the definitions described herein for compounds of Formula (II); and wherein the compound of Formula (IId) comprises at least one radioisotope.

In some embodiments, the compound of Formula (II) is a compound of Formula (IIe):

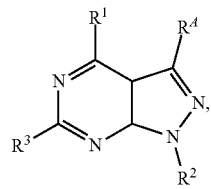

(IIe)

or a pharmaceutically acceptable salt thereof, wherein variables $R^1$, $R^2$, $R^3$, and $R^A$ of Formula (IIe) are defined according to the definitions described herein for compounds of Formula (II); and wherein the compound of Formula (IIe) comprises at least one radioisotope.

In some embodiments, the compound of Formula (II) is a compound of Formula (IIf):

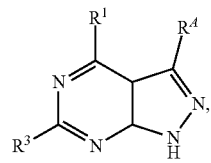

(IIf)

or a pharmaceutically acceptable salt thereof, wherein variables $R^1$, $R^3$, and $R^A$ of Formula (IIf) are defined according to the definitions described herein for compounds of Formula (II); and wherein the compound of Formula (IIf) comprises at least one radioisotope.

In some embodiments, the compound of Formula (II) is a compound of Formula (IIg):

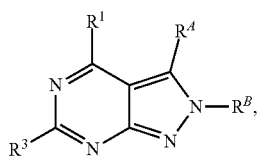

(IIg)

or a pharmaceutically acceptable salt thereof, wherein variables $R^1$, $R^3$, $R^A$, and $R^B$ of Formula (IIg) are defined according to the definitions described herein for compounds of Formula (II); and wherein the compound of Formula (IIg) comprises at least one radioisotope.

In some embodiments, the compound of Formula (II) is selected from the group consisting of:

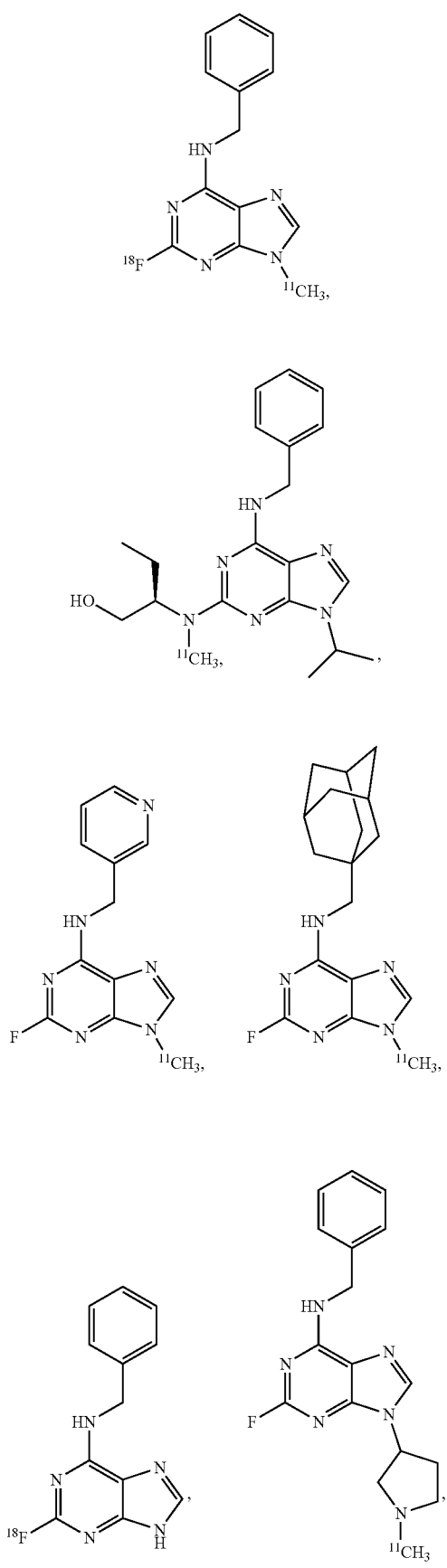
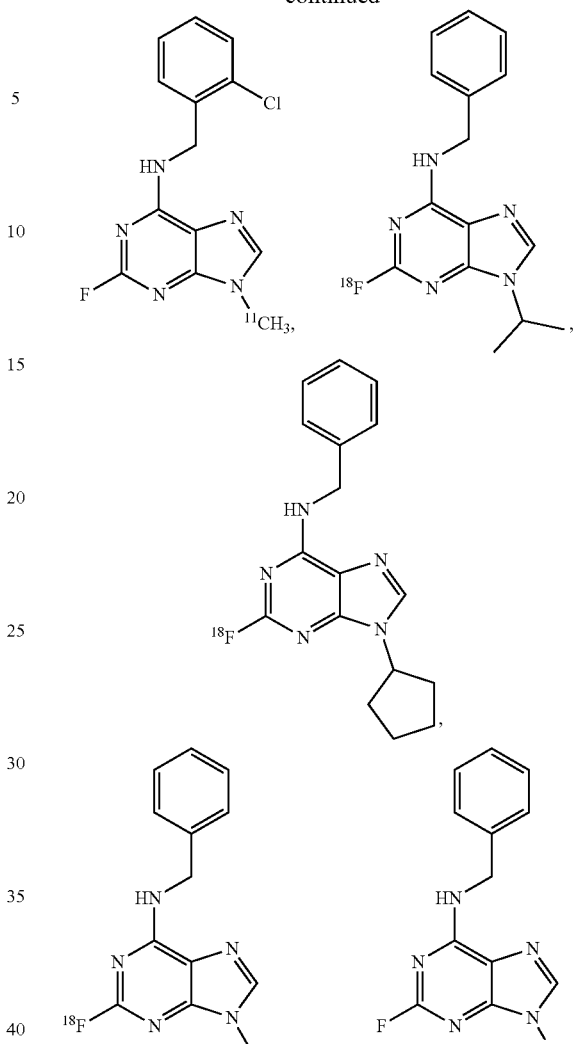

or a pharmaceutically acceptable salt thereof.

In some embodiments, a compound of Formula (I) (e.g., a compound of Formula (Ia), a compound of Formula (Ib), a compound of Formula (Ic), a compound of Formula (Id), a compound of Formula (Ie), a compound of Formula (If), or a compound of Formula (Ig)), or a pharmaceutically acceptable salt thereof, can be labeled with one or more radioisotopes to result in a compound of Formula (II), or a pharmaceutically acceptable salt thereof. In some embodiments, the radioisotope is a carbon atom or a fluorine atom. In some embodiments, the radioisotope is a [$^{11}$C] or a [$^{18}$F] atom. In some embodiments, the radioisotope is a [$^{11}$C] atom. In some embodiments, the radioisotope is a [$^{18}$F] atom.

As used herein, the term "radioisotope" refers to an atom having an atomic mass or mass number different from the atomic mass or mass number typically found in nature (i.e., naturally occurring). An "isotopically" or "radio-labeled" compound is a compound provided herein where one or more atoms are replaced or substituted by an atom having an atomic mass or mass number different from the atomic mass or mass number typically found in nature (i.e., naturally occurring). Example radioisotopes include, but are not limited to, $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{67}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{99m}$Tc, $^{110m}$In, $^{111}$In, $^{118}$Sb, $^{120}$I, $^{121}$I, $^{122}$I, $^{123}$I, $^{124}$I, $^{124}$I, $^{131}$I, and $^{201}$Tl.

In some embodiments, the compounds of Formula (II) includes one radioisotope. In some embodiments, the compound of Formula (II) includes two independently selected radioisotopes. In some embodiments, the compound of Formula (II) includes three independently selected radioisotopes. In some embodiments, $R^1$ comprises at least one of the at least one radioisotopes. In some embodiments, $R^1$ comprises one radioisotope. In some embodiments, $R^1$ comprises one radioisotope selected from [$^{11}$C] and [$^{18}$F]. In some embodiments, $R^2$ comprises at least one of the at least one radioisotopes. In some embodiments, $R^2$ comprises one radioisotope. In some embodiments, $R^2$ comprises one radioisotope selected from [$^{11}$C] and [$^{18}$F]. In some embodiments, $R^2$ comprises two independently selected radioisotopes. In some embodiments, $R^2$ comprises two radioisotopes independently selected from [$^{11}$C] and [$^{18}$F]. In some embodiments, $R^3$ comprises at least one of the at least one radioisotopes. In some embodiments, $R^3$ comprises one radioisotope. In some embodiments, $R^3$ comprises one radioisotope selected from [$^{11}$C] and [$^{18}$F]. In some embodiments, $R^1$ and $R^2$ each comprise at least one of at least one radioisotopes. In some embodiments, $R^1$ and $R^2$ each comprise one independently selected radioisotope. In some embodiments, $R^1$ and $R^2$ each comprise one radioisotope independently selected from [$^{11}$C] and [$^{18}$F]. In some embodiments, $R^1$ and $R^3$ each comprise at least one of at least one radioisotopes. In some embodiments, $R^1$ and $R^3$ each comprise one independently selected radioisotope. In some embodiments, $R^1$ and $R^3$ each comprise one radioisotope independently selected from [$^{11}$C] and [$^{18}$F]. In some embodiments, $R^2$ and $R^3$ each comprise at least one of at least one radioisotopes. In some embodiments, $R^2$ and $R^3$ each comprise one independently selected radioisotope. In some embodiments, $R^2$ and $R^3$ each comprise one radioisotope independently selected from [$^{11}$C] and [$^{18}$F].

In some embodiments, the radioisotope is selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$CU, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, 86Y, $^{89}$Zr, $^{90}$Nb, $^{94m}$Tc, $^{110m}$In, $^{118}$Sb, $^{120}$I, $^{121}$I, $^{122}$I, and $^{124}$I. In some embodiments, the radioisotope is a positron emitter. As used herein the term "positron emitter" refers to a radioisotope wherein a proton is converted to a neutron, thereby releasing a positron and an electron neutrino. In some embodiments, the positron emitter is $^{11}$C or $^{18}$F.

As used herein, the term "Ci", used alone or in combination with other terms, refers to "Curie", a unit of radioactivity.

As used herein, the term "specific activity", used alone or in combination with other terms, refers to the activity of a given radioisotope per unit mass, for example, Ci/g.

Synthesis

As will be appreciated, the compounds provided herein, including salts thereof, can be prepared using known organic synthesis techniques and can be synthesized according to any of numerous possible synthetic routes.

The compounds of Formula (I) and Formula (II) provided herein can be prepared using methods analogous to those shown below in Scheme I, by substituting the appropriate starting materials. For example, reacting purine derivative (i) wherein $X^1$ is halo (e.g., chloro or bromo) with a primary or secondary amine (e.g., benzylamine) in the presence of a base (e.g., triethylamine or diisopropylethylamine) affords purine derivative (ii), which is subsequently reacted with an appropriately substituted $R^2$—$X^2$ group, wherein $X^2$ is halo (e.g. chloro, bromo, or iodo) in the presence of a base (e.g., potassium carbonate) to afford the trisubstituted purine derivative (iii).

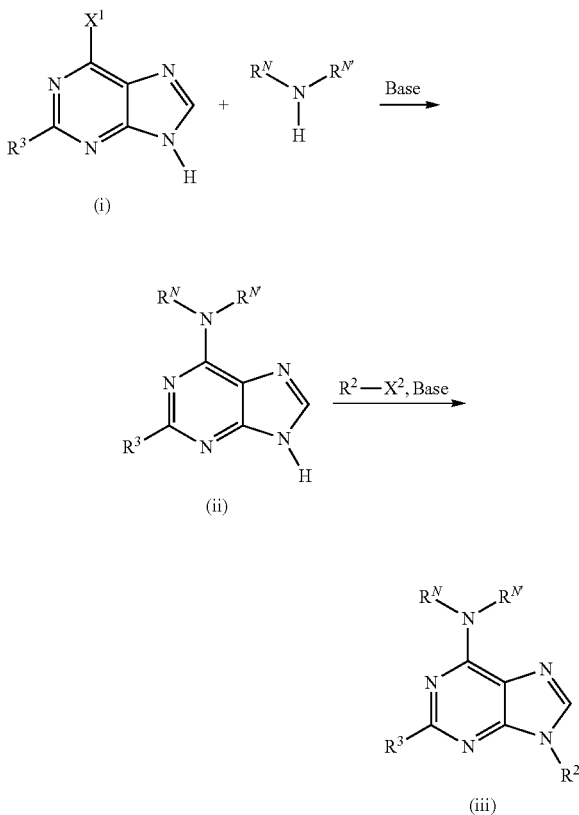

The compounds of Formula (II) provided herein can also be prepared, for example, using methods analogous to those shown below in Scheme II, by substituting the appropriate starting materials. For example, reacting purine derivative (i) wherein $X^1$ is halo, (e.g., chloro or bromo) with an appropriately substituted $R^2$—$X^2$, wherein $X^2$ is halo (e.g., chloro, bromo, or iodo) in the presence of a base (e.g., potassium carbonate) affords purine derivative (iv), which is subsequently reacted with a primary or secondary amine (e.g., benzylamine) in the presence of a base (e.g., triethylamine or diisopropylethylamine) to afford the trisubstituted purine derivative (iii).

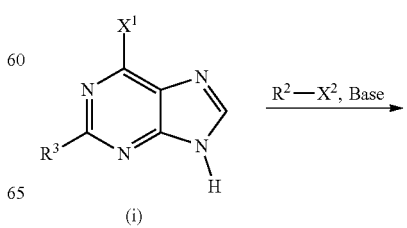

-continued

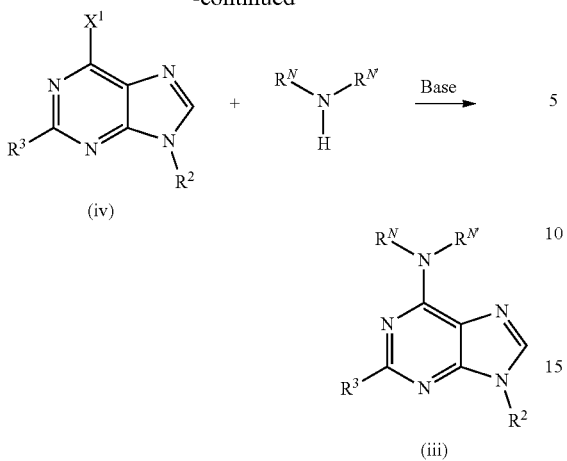

The present application also provides synthetic methods for incorporating radioisotopes into the compounds provided herein (e.g., preparing a compound of Formula (II). The compounds of Formula (II) provided herein can be prepared using methods analogous to those shown below in Scheme III, by substituting the appropriate starting materials. For example, reacting purine derivative (i) wherein $X^1$ is halo (e.g., chloro or bromo) with a primary or secondary amine (e.g., benzylamine) in the presence of a base (e.g., triethylamine or diisopropylethylamine) affords purine derivative (ii), which is subsequently reacted with an appropriately substituted $R^{2*}$—$X^2$ group, wherein $R^{2*}$ is a group comprising at least one radioisotope and $X^2$ is halo (e.g. chloro, bromo, or iodo) in the presence of a base (e.g., potassium hydroxide) to afford the radiolabeled purine derivative (v).

Scheme III

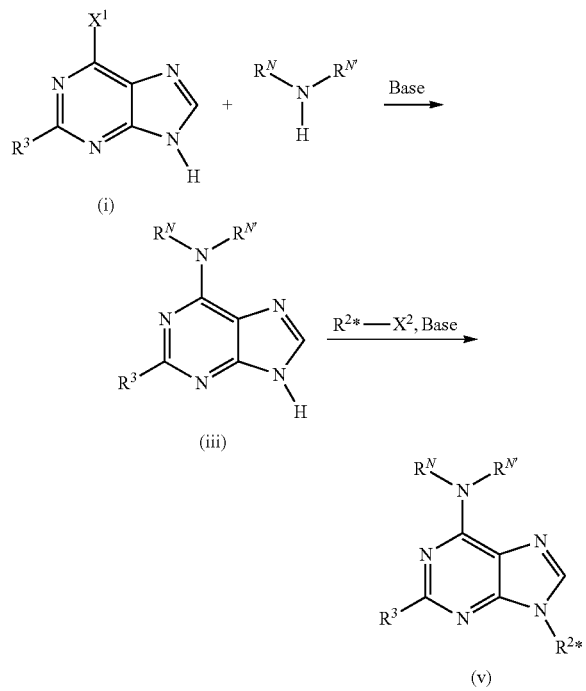

The compounds of Formula (II) provided herein can also be prepared, for example, using methods analogous to those shown below in Scheme IV, by substituting the appropriate starting materials. For example, reacting purine derivative (i) wherein $X^1$ is halo, (e.g., chloro or bromo) with an appropriately substituted $R^{2*}$—$X^2$, wherein $R^{2*}$ is a group comprising at least one radioisotope and $X^2$ is halo (e.g., chloro, bromo, or iodo) in the presence of a base (e.g., potassium hydroxide) affords the radiolabeled purine derivative (vi), which is subsequently reacted with a primary or secondary amine (e.g., benzylamine) in the presence of a base (e.g., triethylamine or diisopropylethylamine) to afford the radiolabeled purine derivative (v).

Scheme IV

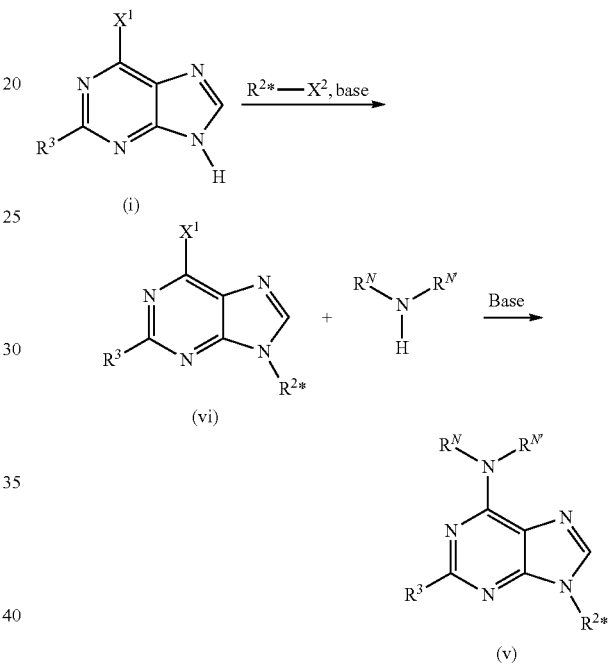

Synthetic methods for incorporating radioisotopes into organic compounds are well known in the art, and one of ordinary skill in the art will readily recognize other methods applicable for the compounds provided herein.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "purine" refers to a group of the following formula:

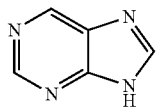

wherein the purine may be optionally substituted at any position allowed by valency. For example, a purine group may be selected from a mono-substituted purine of the following formulae:

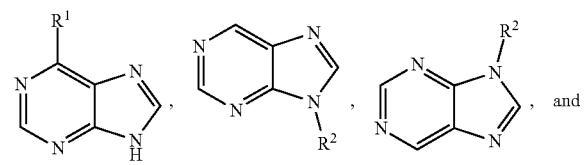

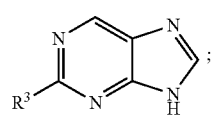

a di-substituted purine of the following formulae:

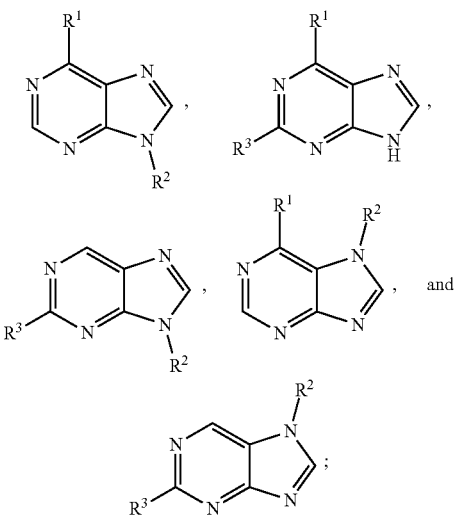

or a tri-substituted purine of the following formulae:

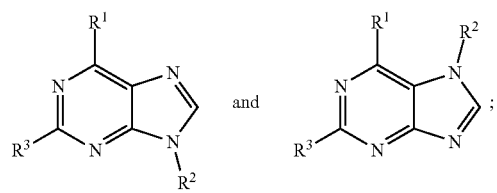

wherein variables $R^1$, $R^2$, and $R^3$ are defined according to the definitions described herein for compounds of Formula (I) and/or Formula (II). In some embodiments, a purine group is a tri-substituted purine group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Assay Methods

The present application further provides methods of imaging neural density in a subject, comprising:

i) administering to the subject a compound provided herein (e.g., a compound of Formula (II)), or a pharmaceutically acceptable salt thereof; and ii) imaging the cell or tissue with an imaging technique.

In some embodiments, the method further comprises imaging the subject prior to administration of the compound. In some embodiments, the method further comprises imaging the subject concurrently with administration of the compound. In some embodiments, the method further comprises imaging the subject prior to administration of the compound and imaging the subject concurrently with administration of the compound. In some embodiments, the imaging comprises longitudinal imaging (i.e., imaging the subject multiple times to determine a rate of change of neural density). In some embodiments, steps i) and ii) are repeated multiple times.

The present application further provides methods of imaging neural density in a subject, comprising:

i) administering to the subject a compound provided herein (e.g., a compound of Formula (II)), or a pharmaceutically acceptable salt thereof);

ii) waiting a time sufficient to allow the compound to accumulate at a tissue or cell site to be imaged; and iii) imaging the cell or tissue with an imaging technique.

In some embodiments, the method further comprises imaging the subject prior to administration of the compound. In some embodiments, the method further comprises imaging the subject concurrently with administration of the compound. In some embodiments, the method further comprises imaging the subject prior to administration of the compound and imaging the subject concurrently with administration of the compound. In some embodiments, the imaging comprises longitudinal imaging (i.e., imaging the subject multiple times to determine a rate of change of neural density). In some embodiments, steps i) to iii) are repeated multiple times.

In some embodiments, the imaging technique is a non-invasive imaging technique. In some embodiments, the imaging technique is a minimally invasive imaging technique. As used herein, the term "minimally invasive imaging technique" comprises imaging techniques employing the use of an internal probe or injection of a compound or radiotracer via syringe. Example imaging techniques include, but are not limited to, fluoroscopic imaging, X-ray imaging, magnetic resonance imaging (MRI), scintigraphic imaging, ultrasound imaging, elastographic imaging, tactile imaging, photoacoustic imaging, thermographic imaging, tomographic imaging, echocardiographic imaging, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of fluoroscopic imaging, X-ray imaging, magnetic resonance imaging (MRI), scintigraphic imaging, ultrasound imaging, elastographic imaging, tactile imaging, photoacoustic imaging, thermographic imaging, tomographic imaging, echocardiographic imaging, positron emission tomography imaging, positron emission tomography with computed tomography imaging, positron emission tomography with magnetic resonance imaging, and Cerenkov imaging. In some embodiments, the imaging technique is selected from the group consisting of positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of positron emission tomography imaging, positron emission tomography with computed tomography imaging, and positron emission tomography with magnetic resonance imaging.

In some embodiments, the neural density comprises synaptic density. In some embodiments, the neural density comprises neuron cell density (e.g. immature neural cell density, mature neural cell density), epithelial cell density, sustentacular cell density, stem cell density (e.g., horizontal basal cell density, globose basal cell density), glandular cell density, glial cell density (e.g. olfactory ensheathing glial cell density), microglia cell density, brush cell density, endothelial cell density, blood cell density, density of cells of the central nervous system, density of cells of the peripheral nervous system, or any combination thereof. In some embodiments, the neuron cell density comprises mature epithelial neuron density. In some embodiments, the neural density is synaptic density.

In some embodiments, the cell or tissue is localized in the olfactory epithelium. In some embodiments, the cell is selected from the group consisting of a neuron cell (e.g. an immature neural cell and/or a mature neural cell), an epithelial cell (e.g. a sustentacular cell), a stem cell (e.g., a horizontal basal cell, a globose basal cell), a glandular cell, a glial cell (e.g. an olfactory ensheathing glial cell), a microglia cell, a brush cell, an endothelial cell, a blood cell, and/or other cells of the central nervous system or peripheral nervous system. In some embodiments, the cell is selected from a cell located in the human body, for example, a bacterial cell, a viral cell, an epithelial cell, a hormone secreting cell, a barrier function cell, and the like. In some embodiments, the cell is a cell of the central nervous system or peripheral nervous system. In some embodiments, the neuron cell is a mature epithelial neuron cell. In some embodiments, the cell or tissue comprises olfactory sensory neurons.

In some embodiments, the time sufficient is from about 30 seconds to about 48 hours, for example, from about 30 seconds to about 5 minutes, about 30 seconds to about 15 minutes, about 30 seconds to about 25 minutes, about 30 seconds to about 35 minutes, about 30 seconds to about 45 minutes, about 30 seconds to about 1 hour, about 30 seconds to about 2 hours, about 30 seconds to about 5 hours, about 30 seconds to about 10 hours, about 30 seconds to about 15 hours, about 30 seconds to about 20 hours, about 30 seconds to about 24 hours, about 30 seconds to about 30 hours, about 30 seconds to about 35 hours, about 30 seconds to about 42 hours, about 30 minutes to about 1 hour, about 30 minutes to about 2 hours, about 30 minutes to about 5 hours, about 30 minutes to about 10 hours, about 30 minutes to about 15 hours, about 30 minutes to about 20 hours, about 30 minutes to about 24 hours, about 30 minutes to about 30 hours, about 30 minutes to about 35 hours, about 30 minutes to about 42 hours, about 1 hour to about 2 hours, about 1 hour to about 5 hours, about 1 hour to about 10 hours, about 1 hour to about 15 hours, about 1 hour to about 20 hours, about 1 hour to about 24 hours, about 1 hour to about 30 hours, about 1 hour to about 35 hours, or about 1 hour to about 42 hours.

In some embodiments, the neural density comprises synaptic density. In some embodiments, the neural density comprises neuron cell density (e.g. immature neural cell density, mature neural cell density), epithelial cell density, sustentacular cell density, stem cell density (e.g., horizontal basal cell density, globose basal cell density), glandular cell density, glial cell density (e.g. olfactory ensheathing glial cell density), microglia cell density, brush cell density, endothelial cell density, blood cell density, density of cells of the central nervous system, density of cells of the peripheral nervous system, or any combination thereof. In some embodiments, the neuron cell density comprises mature epithelial neuron density. In some embodiments, the neural density is synaptic density.

In some embodiments, the cell or tissue is localized in the olfactory epithelium. In some embodiments, the cell is selected from the group consisting of a neuron cell (e.g. an immature neural cell and/or a mature neural cell), an epithelial cell (e.g. a sustentacular cell), a stem cell (e.g., including a horizontal basal cell and/or a globose basal cells), a glandular cell, a glial cell (e.g. an olfactory ensheathing glial cell), a microglia cell, a brush cell, an endothelial cell, a blood cell, and/or other cells located in the olfactory epithelium. In some embodiments, the cell is a cell of the central nervous system or peripheral nervous system. In some embodiments, the neuron cell is a mature epithelial neuron cell. In some embodiments, the cell or tissue comprises olfactory sensory neurons.

In some embodiments, imaging neural density further comprises quantitatively measuring the neural density. In some embodiments, imaging neural density further comprises non-quantitatively measuring the neural density. In some embodiments, imaging neural density further comprises identifying olfactory sensory neurons. In some embodiments, imaging neural density further comprises identifying and quantitatively measuring olfactory sensory neurons. In some embodiments, imaging neural density further comprises identifying neuron cell density (e.g. immature neural cell density, mature neural cell density), epithelial cell density, sustentacular cell density, stem cell density (e.g., horizontal basal cell density, globose basal cell density), glandular cell density, glial cell density (e.g. olfactory ensheathing glial cell density), microglia cell density, brush cell density, endothelial cell density, blood cell density, density of cells of the central nervous system, density of cells of the peripheral nervous system, or any combination thereof. In some embodiments, imaging neural density further comprises identifying and quantitatively measuring neuron cell density (e.g. immature neural cell density, mature neural cell density), epithelial cell density, sustentacular cell density, stem cell density (e.g., horizontal basal cell density, globose basal cell density), glandular cell density, glial cell density (e.g. olfactory ensheathing glial cell density), microglia cell density, brush cell density, endothelial cell density, blood cell density, density of cells of the central nervous system, density of cells of the peripheral nervous system, or any combination thereof. In some embodiments, the neuron cell density comprises mature epithelial neuron density.

The present application also provides methods of diagnosing a disease of the central nervous system or a disease of the peripheral nervous system in a subject, comprising:

i) administering to the subject a compound provided herein; and ii) imaging the cell or tissue with an imaging technique.

In some embodiments, the method further comprises administering a compound of Formula (II), or a pharmaceutically acceptable salt thereof, prior to the imaging (e.g., prior to the imaging of step ii). In some embodiments, the method further comprises imaging the subject prior to administration of the compound. In some embodiments, the method further comprises imaging the subject concurrently with administration of the compound. In some embodiments, the method further comprises imaging the subject prior to administration of the compound and imaging the subject concurrently with administration of the compound. In some embodiments, the imaging comprises longitudinal imaging (i.e., imaging the subject multiple times to diagnose a disease of the central nervous system or a disease of the peripheral nervous system). In some embodiments, steps i) and ii) are repeated multiple times.

The present application also provides methods of diagnosing a disease of the central nervous system or a disease of the peripheral nervous system in a subject, comprising:

i) administering to the subject a compound provided herein;

ii) waiting a time sufficient to allow the compound to accumulate at a tissue or cell site associated with the disease; and iii) imaging the cell or tissue with an imaging technique.

In some embodiments, the method further comprises administering a compound of Formula (II), or a pharmaceutically acceptable salt thereof, prior to the imaging (e.g., prior to the imaging of step iii). In some embodiments, the method further comprises imaging the subject prior to administration of the compound. In some embodiments, the method further comprises imaging the subject concurrently with administration of the compound. In some embodiments, the method further comprises imaging the subject prior to administration of the compound and imaging the subject concurrently with administration of the compound. In some embodiments, the imaging comprises longitudinal imaging (i.e., imaging the subject multiple times to diagnose a disease of the central nervous system or a disease of the peripheral nervous system). In some embodiments, steps i) to iii) are repeated multiple times.

In some embodiments, the subject is pre-symptomatic or prodromal. In some embodiments, the subject is pre-symptomatic. In some embodiments, the subject is prodromal. In some embodiments, the subject has a predisposition or suspicion of having a disease of the central nervous system or a disease of the peripheral nervous system, for example, the subject has a genetic disposition for a disease of the central nervous system or a disease of the peripheral nervous system, the subject is an elderly subject, or the subject exhibits hyposmia or anosmia. In some embodiments, the subject exhibits hyposmia or anosmia. In some embodiments, the subject exhibits hyposmia. In some embodiments, the subject exhibits anosmia.

In some embodiments, the disease of the central nervous system or the disease of the peripheral nervous system comprises a neurodegenerative disease. In some embodiments, the disease of the central nervous system or the disease of the peripheral nervous system is a neurodegenerative disease. In some embodiments, the disease of the central nervous system or the disease of the peripheral nervous system comprises a neurodevelopmental disease. In some embodiments, the disease of the central nervous system or the disease of the peripheral nervous system is selected from the group consisting of schizophrenia, major depressive disorder, depression, dementia, Alzheimer's disease, Huntington's disease, and Parkinson's disease. In some embodiments, the disease of the central nervous system or the disease of the peripheral nervous system is associated with hyposmia or anosmia.

In some embodiments, the imaging technique is selected from the group consisting of fluoroscopic imaging, X-ray imaging, magnetic resonance imaging (MRI), scintigraphic imaging, ultrasound imaging, elastographic imaging, tactile imaging, photoacoustic imaging, thermographic imaging, tomographic imaging, echocardiographic imaging, positron emission tomography imaging, positron emission tomography with computed tomography imaging, positron emission tomography with magnetic resonance imaging, Cerenkov imaging. In some embodiments, the imaging technique is selected from the group consisting of magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of positron emission tomography imaging, positron emission tomography with computed tomography imaging, or positron emission tomography with magnetic resonance imaging.

In some embodiments, diagnosing comprises quantitatively measuring the neural density. In some embodiments, diagnosing comprises non-quantitatively measuring the neural density. In some embodiments, diagnosing comprises identifying changes in neural density. In some embodiments, diagnosing comprises identifying a decrease neural density compared to a normal or healthy subject. In some embodiments, diagnosing comprises identifying an increase in neural density compared to a normal or healthy subject. In some embodiments, diagnosing comprises identifying and quantitatively measuring olfactory sensory neurons.

In some embodiments, diagnosing comprises identifying and quantitatively measuring changes in one or more cells selected from the group consisting of a neuron cell, a sustentacular, a stem cell, a glandular cell, a glial cell, a microglia cell, and/or other cells of the central or peripheral nervous system in a single patient over time. In some embodiments, diagnosing comprises identifying and qualitatively measuring changes in one or more cells selected from the group consisting of a neuron cell, a sustentacular, a stem cell, a glandular cell, a glial cell, a microglia cell, and/or other cells of the central or peripheral nervous system in a single patient. In some embodiments, the neuron cell is a mature epithelial neuron cell. In some embodiments, the measured changes include, but are not limited to measuring changes in the amount of cells (e.g., an increase or decrease in the amount of cells), measuring changes in cellular density (e.g., an increase or decrease in cellular density), the rate of change of cellular growth (e.g., an increased or decreased rate of cellular growth), the rate of change of cellular death (e.g., an increased or decreased rate of cellular death) measuring changes in the amount of one or more cellular components (e.g., an increase or decrease in one or more cellular components), measuring changes in the density of one or more cellular components (e.g., an increase or decrease in one or more cellular components), the rate of change of growth of one or more cellular components (e.g., an increased or decreased rate of growth of one or more cellular components), the rate of change of death of one or more cellular components (e.g., an increased or decreased rate of death of one or more cellular components cellular), measuring changes in the expression of one or more cellular components, measuring changes in the rate of production of one or more cellular components, measuring changes in the rate of degradation of one or more cellular components, or any combination thereof. In some embodiments, each of the cellular components is independently selected from the group consisting of a protein, a DNA molecule, an RNA molecule, a lipid molecule, and a carbohydrate.

Methods of Treatment

Provided herein are methods of treating a disease in a subject in need thereof. As used herein, the term "subject," refers to any animal, including mammals. For example, mice, rats, other rodents, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of Formula (I)), or a pharmaceutically acceptable salt thereof.

In some embodiments, the disease is a disease of the central nervous system or a disease of the peripheral nervous system. Examples of diseases of the central nervous system, but are not limited to, Alzheimer's disease, autism spectrum disorders, attention deficit/hyperactivity disorder (ADHD), Bell's Palsy, bipolar disorder, catalepsy, Cerebal Palsy, depression, dementia, epilepsy, encephalitis, Huntington's disease, locked-in syndrome, major depressive disorder, meningitis, migraine, multiple sclerosis (MS), Parkinson's disease, Rett syndrome, schizophrenia, tropical spastic paraparesis, and Tourette's syndrome. Examples of diseases of the peripheral nervous system include, but are not limited to accessory nerve disorder, autonomic dysreflexia, peripheral neuropathy, mononeuropathy, polyneuropathy, radial neuropathy, ulnar neuropathy, Villaret's syndrome, Charcot-Marie-Tooth disease, diabetic neuropathy, nerve paralysis, and Horner's syndrome. In some embodiments, the disease of the central nervous system or the disease of the peripheral nervous system comprises a neurodegenerative disease. In some embodiments, the disease of the central nervous system or the disease of the peripheral nervous system is a neurodegenerative disease. In some embodiments, the disease of the central nervous system or the disease of the peripheral nervous system comprises a neurodevelopmental disease (e.g., Rett's syndrome, autism spectrum disorders, and the like). In some embodiments, the disease of the central nervous system or the disease of the peripheral nervous system is a neurodevelopmental disease. In some embodiments, the disease of the central nervous system is selected from the group consisting of schizophrenia, major depressive disorder, depression, dementia, Alzheimer's disease, Huntington's disease, and Parkinson's disease. In some embodiments, the disease of the peripheral nervous system is selected from the group consisting of accessory nerve disorder, autonomic dysreflexia, peripheral neuropathy, mononeuropathy, polyneuropathy, radial neuropathy, ulnar neuropathy, Villaret's syndrome, Charcot-Marie-Tooth disease, diabetic neuropathy, nerve paralysis, and Horner's syndrome. In some embodiments, the disease is a disease associated with hyposmia or anosmia. In some embodiments, the disease is a disease associated with hyposmia. In some embodiments, the disease is a disease associated with anosmia. In some embodiments, the disease is hyposmia. In some embodiments, the disease is anosmia. In some embodiments, the disease of the central nervous system or the disease of the peripheral nervous system is associated with hyposmia or anosmia. In some embodiments, the disease is a disease of the central nervous system or the disease of the peripheral nervous system associated with hyposmia or anosmia. In some embodiments, the disease is a disease of the central nervous system associated with hyposmia. In some embodiments, the disease is a disease of the central nervous system associated with anosmia. In some embodiments, the disease is a disease of the peripheral nervous system associated with hyposmia. In some embodiments, the disease is a disease of the peripheral nervous system associated with anosmia. In some embodiments, the disease is associated with acute or chronic rhinosinusitis. In some embodiments, the disease is associated with acute rhinosinusitis. In some embodiments, the disease is associated with chronic rhinosinusitis. In some embodiments, the disease is acute rhinosinusitis. In some embodiments, the disease is chronic rhinosinusitis.

In some embodiments, the disease is a disease associated with abnormal neural density. In some embodiments, the disease is a disease associated with abnormal neuron cell density (e.g. abnormal immature neural cell density, abnormal mature neural cell density), abnormal epithelial cell density, abnormal sustentacular cell density, abnormal stem cell density (e.g., abnormal horizontal basal cell density, abnormal globose basal cell density), abnormal glandular cell density, abnormal glial cell density (e.g. olfactory ensheathing glial cell density), abnormal microglia cell density, abnormal brush cell density, abnormal endothelial cell density, abnormal blood cell density, abnormal density of cells of the central nervous system, abnormal density of cells of the peripheral nervous system, or any combination thereof. In some embodiments, the disease is a disease associated with abnormal mature epithelial neuron density. In some embodiments, the disease is a disease associated with abnormal synaptic density. In some embodiments, the disease is a disease of the central nervous system or a disease of the peripheral nervous system associated with abnormal neural density. In some embodiments, the disease of the central nervous system or a disease of the peripheral nervous system is associated with abnormal synaptic density.

In some embodiments, the abnormal neural density comprises abnormal neuron cell density (e.g. abnormal immature neural cell density, abnormal mature neural cell density), abnormal epithelial cell density, abnormal sustentacular cell density, abnormal stem cell density (e.g., abnormal horizontal basal cell density, abnormal globose basal cell density), abnormal glandular cell density, abnormal glial cell density (e.g. olfactory ensheathing glial cell density), abnormal microglia cell density, abnormal brush cell density, abnormal endothelial cell density, abnormal blood cell density, abnormal density of cells of the central nervous system, abnormal density of cells of the peripheral nervous system, or any combination thereof. In some embodiments, the abnormal neuron cell density comprises abnormal mature epithelial neuron density. In some embodiments, the abnormal neural density comprises abnormal synaptic density. In some embodiments, the abnormal neural density is abnormal synaptic density. As used herein, the terms "abnormal neural density" and "abnormal synaptic density" refers to a change (e.g. increased or decreased) in neural density or synaptic density in a subject compared to the neural density or synaptic density in a normal or healthy subject or as compared to the measured neural or synaptic density in the subject over time. For example, abnormal neural density can refer to an increased or decreased neural density or synaptic density in a subject exhibiting symptoms associated with a disease of the central nervous system or a disease of the peripheral nervous system compared to a subject not exhibiting symptoms associated with a disease of the central nervous system or a disease of the peripheral nervous system. The term "abnormal neural density" also refers to a measurable increase or decrease in neural density or synaptic density in a subject monitored over time (e.g., quantitatively or qualitatively measured).

In some embodiments, a "normal" or "healthy" subject is determined using an age-matched control or age-matched controls. As used herein, the term "age-matched control" and "age-matched controls" refers to a subject or subjects within about 2.5 years in age compared to a test subject (e.g., +2.5 or −2.5 years). In some embodiments, a normal or healthy subject is determined using age-matched binning, for example, a subject or subjects ranging from about 20 to about 25 years old, from about 25 to about 30 years old, from about 30 to about 35 years old, from about 35 to about 40 years old, and the like. In some embodiments, a normal or healthy subject may be monitored over time to measure an increase or decrease in neural density or synaptic density (e.g., quantitatively or qualitatively measure). In some embodiments, the abnormal neural density refers to about 5% decreased neural density to about 99% decreased in neural density in a subject compared to the neural density in a normal or healthy subject, for example, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% decreased neural density.

In some embodiments, the abnormal neural density refers to about 5% increased neural density to about 99% increased neural density in a subject compared to the neural density in a normal or healthy subject, for example, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% increased neural density.

In some embodiments, the abnormal neural density refers to from about 5% to about 99% decreased neural density in a subject compared to a normal or healthy subject. In some embodiments, the abnormal neural density refers to from about 5% to about 99% decreased neural density in a subject monitored over time, compared to an initial measurement of the neural density of the subject. In some embodiments, the abnormal neural density refers to, for example, from about 5% to about 95%, from about 5% to about 90%, from about 5% to about 85%, from about 5% to about 80%, from about 5% to about 75%, from about 5% to about 70%, from about 5% to about 65%, from about 5% to about 60%, from about 5% to about 55%, from about 5% to about 50%, from about 5% to about 45%, from about 5% to about 40%, from about 5% to about 35%, from about 5% to about 30%, from about 5% to about 25%, from about 5% to about 20%, from about 5% to about 15%, from about 5% to about 10%, from about 10% to about 95%, from about 10% to about 90%, from about 10% to about 85%, from about 10% to about 80%, from about 10% to about 75%, from about 10% to about 70%, from about 10% to about 65%, from about 10% to about 60%, from about 10% to about 55%, from about 10% to about 50%, from about 10% to about 45%, from about 10% to about 40%, from about 10% to about 35%, from about 10% to about 30%, from about 10% to about 25%, from about 10% to about 20%, from about 10% to about 15%, from about 25% to about 95%, from about 25% to about 90%, from about 25% to about 85%, from about 25% to about 80%, from about 25% to about 75%, from about 25% to about 70%, from about 25% to about 65%, from about 25% to about 60%, from about 25% to about 55%, from about 25% to about 50%, from about 25% to about 45%, from about 25% to about 40%, from about 25% to about 35%, from about 25% to about 30%, from about 35% to about 95%, from about 35% to about 90%, from about 35% to about 85%, from about 35% to about 80%, from about 35% to about 75%, from about 35% to about 70%, from about 35% to about 65%, from about 35% to about 60%, from about 35% to about 55%, from about 35% to about 50%, from about 35% to about 45%, from about 35% to about 40%, from about 45% to about 95%, from about 45% to about 90%, from about 45% to about 85%, from about 45% to about 80%, from about 45% to about 75%, from about 45% to about 70%, from about 45% to about 65%, from about 45% to about 60%, from about 45% to about 55%, from about 45% to about 50%, from about 55% to about 95%, from about 55% to about 90%, from about 55% to about 85%, from about 5% to about 80%, from about 55% to about 75%, from about 55% to about 70%, from about 55% to about 65%, from about 55% to about 60%, from about 65% to about 95%, from about 65% to about 90%, from about 65% to about 85%, from about 65% to about 80%, from about 65% to about 75%, from about 65% to about 70%, from about 70% to about 95%, from about 70% to about 90%, from about 70% to about 85%, from about 70% to about 80%, from about 70% to about 75%, from about 75% to about 95%, from about 75% to about 90%, from about 75% to about 85%, from about 75% to about 80%, from about 85% to about 95%, from about 85% to about 90%, or from about 90% to about 95% decreased neural density.

In some embodiments, the abnormal neural density refers to from about 5% to about 99% increased neural density in a subject compared to a normal or healthy subject. In some embodiments, the abnormal neural density refers to from about 5% to about 99% increased neural density in a subject monitored over time, compared to an initial measurement of the neural density of the subject. In some embodiments, the abnormal neural density refers to, for example, from about 5% to about 95%, from about 5% to about 90%, from about 5% to about 85%, from about 5% to about 80%, from about 5% to about 75%, from about 5% to about 70%, from about 5% to about 65%, from about 5% to about 60%, from about 5% to about 55%, from about 5% to about 50%, from about 5% to about 45%, from about 5% to about 40%, from about 5% to about 35%, from about 5% to about 30%, from about 5% to about 25%, from about 5% to about 20%, from about 5% to about 15%, from about 5% to about 10%, from about 10% to about 95%, from about 10% to about 90%, from about 10% to about 85%, from about 10% to about 80%, from about 10% to about 75%, from about 10% to about 70%, from about 10% to about 65%, from about 10% to about 60%, from about 10% to about 55%, from about 10% to about 50%, from about 10% to about 45%, from about 10% to about 40%, from about 10% to about 35%, from about 10% to about 30%, from about 10% to about 25%, from about 10% to about 20%, from about 10% to about 15%, from about 25% to about 95%, from about 25% to about 90%, from about 25% to about 85%, from about 25% to about 80%, from about 25% to about 75%, from about 25% to about 70%, from about 25% to about 65%, from about 25% to about 60%, from about 25% to about 55%, from about 25% to about 50%, from about 25% to about 45%, from about 25% to about 40%, from about 25% to about 35%, from about 25% to about 30%, from about 35% to about 95%, from about 35% to about 90%, from about 35% to about 85%, from about 35% to about 80%, from about 35% to about 75%, from about 35% to about 70%, from about 35% to about 65%, from about 35% to about 60%, from about 35% to about 55%, from about 35% to about 50%, from about 35% to about 45%, from about 35% to about 40%, from about 45% to about 95%, from about 45% to about 90%, from about 45% to about 85%, from about 45% to about 80%, from about 45% to about 75%, from about 45% to about 70%, from about 45% to about 65%, from about 45% to about 60%, from about 45% to about 55%, from about 45% to about 50%, from about 55% to about 95%, from about 55% to about 90%, from about 55% to about 85%, from about 5% to about 80%, from about 55% to about 75%, from about 55% to about 70%, from about 55% to about 65%, from about 55% to about 60%, from about 65% to about 95%, from about 65% to about 90%, from about 65% to about 85%, from about 65% to about 80%, from about 65% to about 75%, from about 65% to about 70%, from about 70% to about 95%, from about 70% to about 90%, from about 70% to about 85%, from about 70% to about 80%, from about 70% to about 75%, from about 75% to about 95%, from about 75% to about 90%, from about 75% to about 85%, from about 75% to about 80%, from about 85% to about 95%, from about 85% to about 90%, or from about 90% to about 95% increased neural density.

In some embodiments, the abnormal neural density refers to about 5 to about 1000 fold increased neural density in a subject compared to the neural density in a normal or healthy subject. In some embodiments, the abnormal neural density refers to from about 5 to about 1000 fold increased neural density in a subject monitored over time, compared to an initial measurement of the neural density of the subject, for example, from about 5 to about 1000 fold increased neural density in a subject compared to a normal or healthy subject, for example, about 5 fold, about 10 fold, about 20 fold, about 50 fold, about 100 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, or about 1000 fold increased neural density.

In some embodiments, the abnormal neural density refers to from about 5 to about 1000 fold decreased neural density in a subject compared to a normal or healthy subject. In some embodiments, the abnormal neural density refers to from about 5 to about 1000 fold decreased neural density in a subject monitored over time, compared to an initial measurement of the neural density of the subject, for example, about 5 fold, about 10 fold, about 20 fold, about 50 fold, about 100 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, or about 1000 fold decreased neural density.

In some embodiments, the abnormal neural density comprises abnormal neuron cell density (e.g. abnormal immature neural cell density, abnormal mature neural cell density), abnormal epithelial cell density, abnormal sustentacular cell density, abnormal stem cell density (e.g., abnormal horizontal basal cell density, abnormal globose basal cell density), abnormal glandular cell density, abnormal glial cell density (e.g. olfactory ensheathing glial cell density), abnormal microglia cell density, abnormal brush cell density, abnormal endothelial cell density, abnormal blood cell density, abnormal density of cells of the central nervous system, abnormal density of cells of the peripheral nervous system, or any combination thereof. In some embodiments, the abnormal neural density comprises abnormal synaptic density. In some embodiments, the abnormal neural density is abnormal synaptic density. In some embodiments, the abnormal neural density is localized in the olfactory epithelium.

The present application also provides methods of monitoring treatment of a disease of the central nervous system or a disease of the peripheral nervous system in a subject, comprising:
i) imaging a cell or tissue with an imaging technique;
ii) administering to the subject an effective amount of a therapeutic compound to treat the disease (e.g., a compound provided herein);
iii) imaging the cell or tissue in the subject with an imaging technique; and iv) comparing the image of step i) and the image of step iii).

In some embodiments, the method further comprises administering a compound of Formula (II), or a pharmaceutically acceptable salt thereof, prior to the imaging (e.g., prior to the imaging of step i) and/or prior to the imaging of step iii). In some embodiments, the method further comprises imaging the subject concurrently with administration of the therapeutic compound. In some embodiments, the imaging comprises longitudinal imaging (i.e., imaging the subject multiple times to monitor treatment of a disease of the central nervous system or a disease of the peripheral nervous system). In some embodiments, steps i) to iv) are repeated multiple times.

The present application also provides methods of monitoring treatment of a disease of the central nervous system or a disease of the peripheral nervous system in a subject, comprising:
i) imaging a cell or tissue with an imaging technique;
ii) administering to the subject an effective amount of a therapeutic compound to treat the disease (e.g., a compound provided herein);
iii) waiting a time sufficient to allow the compound to accumulate at a tissue or cell site associated with the disease;

iv) imaging the cell or tissue in the subject with an imaging technique; and v) comparing the image of step i) and the image of step iv).

In some embodiments, the method further comprises administering a compound of Formula (II), or a pharmaceutically acceptable salt thereof, prior to the imaging (e.g., prior to the imaging of step i) and/or prior to the imaging of step iv). In some embodiments, the method further comprises imaging the subject concurrently with administration of the therapeutic compound. In some embodiments, the imaging comprises longitudinal imaging (i.e., imaging the subject multiple times to monitor treatment of a disease of the central nervous system or a disease of the peripheral nervous system). In some embodiments, steps i) to v) are repeated multiple times.

In some embodiments, monitoring treatment comprises monitoring a change in the rate of neural density change in a subject (e.g., change in the rate of loss of neural density or change in the rate of increase of neural density). In some embodiments, the neural density comprises neuron cell density (e.g. immature neural cell density, mature neural cell density), epithelial cell density, sustentacular cell density, stem cell density (e.g., horizontal basal cell density, globose basal cell density), glandular cell density, glial cell density (e.g. olfactory ensheathing glial cell density), microglia cell density, brush cell density, endothelial cell density, blood cell density, density of cells of the central nervous system, density of cells of the peripheral nervous system, or any combination thereof. In some embodiments, the neuron cell density comprises mature epithelial neuron density.

In some embodiments, following administering to the subject an effective amount of a therapeutic compound, the neural or synaptic density of the subject changes (e.g., increases or decreases) by about 5 to about 1000 fold, for example, about 5 fold, about 10 fold, about 20 fold, about 50 fold, about 100 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, or about 1000 fold. In some embodiments, the change in neural or synaptic density is a decrease in neural or synaptic density. In some embodiments, the change in neural or synaptic density is an increase in neural or synaptic density.

In some embodiments, following administering to the subject an effective amount of a therapeutic compound, the neural or synaptic density of the subject approaches or is about the neural or synaptic density of a normal or healthy subject. In some embodiments, the normal or healthy subject is determined by age matched controls, as defined herein. In some embodiments, the neural or synaptic density of the subject is about +10% (e.g., about −10% or about +10%) of a normal or healthy subject. In some embodiments, the neural or synaptic density of the subject is about +5% (e.g., about −5% or about +5%) of a normal or healthy subject.

In some embodiments, the therapeutic compound is any one of the compounds provided herein (e.g., a compound of Formula (I) or a compound of Formula (II)), or a pharmaceutically acceptable salt thereof.

In some embodiments, the disease of the central nervous system or the disease of the peripheral nervous system comprises a neurodegenerative disease. In some embodiments, the disease of the central nervous system or the disease of the peripheral nervous system is a neurodegenerative disease. In some embodiments, the disease of the central nervous system or the disease of the peripheral nervous system comprises a neurodevelopmental disease. In some embodiments, the disease of the central nervous system or the disease of the peripheral nervous system is a neurodevelopmental disease.

In some embodiments, the disease of the central nervous system is selected from the group consisting of schizophrenia, major depressive disorder, depression, dementia, Alzheimer's disease, Huntington's disease, and Parkinson's disease. In some embodiments, the disease of the peripheral nervous system is selected from the group consisting of accessory nerve disorder, autonomic dysreflexia, peripheral neuropathy, mononeuropathy, polyneuropathy, radial neuropathy, ulnar neuropathy, Villaret's syndrome, Charcot-Marie-Tooth disease, diabetic neuropathy, nerve paralysis, and Horner's syndrome. In some embodiments, the disease of the central nervous system or the disease of the peripheral nervous system is associated with hyposmia or anosmia. In some embodiments, the disease of the central nervous system or the disease of the peripheral nervous system associated with hyposmia. In some embodiments, the disease of the central nervous system or the disease of the peripheral nervous system associated with anosmia.

In some embodiments, the imaging technique is selected from the group consisting of fluoroscopic imaging, X-ray imaging, magnetic resonance imaging (MRI), scintigraphic imaging, ultrasound imaging, elastographic imaging, tactile imaging, photoacoustic imaging, thermographic imaging, tomographic imaging, echocardiographic imaging, positron emission tomography imaging, positron emission tomography with computed tomography imaging, positron emission tomography with magnetic resonance imaging, Cerenkov imaging. In some embodiments, the imaging technique is selected from the group consisting of magnetic resonance imaging, optical imaging, single-photon emission computed tomography, positron emission tomography imaging, positron emission tomography with computed tomography imaging, positron emission tomography with magnetic resonance imaging, Cerenkov imaging, and ultrasound imaging. In some embodiments, the imaging technique is selected from the group consisting of positron emission tomography imaging, positron emission tomography with computed tomography imaging, or positron emission tomography with magnetic resonance imaging.

In some embodiments, the time sufficient is from about 30 seconds to about 48 hours, for example, from about 30 seconds to about 5 minutes, about 30 seconds to about 15 minutes, about 30 seconds to about 25 minutes, about 30 seconds to about 35 minutes, about 30 seconds to about 45 minutes, about 30 seconds to about 1 hour, about 30 seconds to about 2 hours, about 30 seconds to about 5 hours, about 30 seconds to about 10 hours, about 30 seconds to about 15 hours, about 30 seconds to about 20 hours, about 30 seconds to about 24 hours, about 30 seconds to about 30 hours, about 30 seconds to about 35 hours, about 30 seconds to about 42 hours, about 30 minutes to about 1 hour, about 30 minutes to about 2 hours, about 30 minutes to about 5 hours, about 30 minutes to about 10 hours, about 30 minutes to about 15 hours, about 30 minutes to about 20 hours, about 30 minutes to about 24 hours, about 30 minutes to about 30 hours, about 30 minutes to about 35 hours, about 30 minutes to about 42 hours, about 1 hour to about 2 hours, about 1 hour to about 5 hours, about 1 hour to about 10 hours, about 1 hour to about 15 hours, about 1 hour to about 20 hours, about 1 hour to about 24 hours, about 1 hour to about 30 hours, about 1 hour to about 35 hours, or about 1 hour to about 42 hours.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a subject or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional pharmaceutical agents such as, for example, anti-inflammatory agents, steroids, immunosuppressants, or other agents such as therapeutic antibodies, can be used in combination with the compounds of the present application for treatment of the diseases provided herein.

Example antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20) and antibodies directed to c-MET.

Example steroids include corticosteroids such as cortisone, dexamethasone, hydrocortisone, methylprednisolone, prednisolone, and prednisone.

Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example immunosuppressants include azathioprine, chlorambucil, cyclophosphamide, cyclosporine, daclizumab, infliximab, methotrexate, and tacrolimus.

One or more of the following agents may be used in combination with the compounds provided herein and are presented as a non-limiting list: a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Sml1, triapine, didox, trimidox, amidox, 3-AP, MDL-101,731, bendamustine, ofatumumab, and GS-1101 (also known as CAL-101).

Pharmaceutical Formulations and Formulations

When employed as pharmaceuticals, the compounds provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein (e.g., compounds of Formula (II)) are suitable for parenteral administration. In some embodiments, the compounds provided herein (e.g., the compounds of Formula (II)) are suitable for intravenous administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the compositions provided herein are suitable for intravenous administration.

Also provided are pharmaceutical compositions which contain, as the active ingredient, a compound provided herein (e.g., a compound of Formula (I) or a compound of Formula (II)), or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

General Materials and Characterization Methods

All chemical reagents were of ACS grade purity or higher, purchased from commercial sources, and used as received without further purification. Reactions were performed using standard techniques, including inert atmosphere of nitrogen with standard Schlenk technique, when necessary. Glassware was oven-dried at 150° C. overnight. Analytical thin layer chromatography (TLC) was performed on Sili-Cycle TLC silica Gel 60-F254 plates with visualization by ultraviolet (UV) irradiation at 254 nm. Purifications were performed using HP silica chromatography column by Teledyne Isco. The elution system for each purification was determined by TLC analysis. Chromatography solvents were purchased from commercial sources and used without distillation. NMR spectra were recorded at 22° C. on a Varian 500 MHz spectrometer. Proton chemical shifts are reported as δ in units of parts per million (ppm) relative to chloroform-d (δ 7.27, singlet), methanol-d4 (δ 3.31, pentet), or dimethylsulfoxide-d6 (δ 2.50, pentet). Multiplicities are reported as follows: s (singlet), d (doublet), t (triplet), q (quartet), dd (doublet of doublets), dt (doublet of triplets), dq (doublet of quartet) or m (multiplet). Coupling constants are reported as a J value in Hertz (Hz). HPLC-analysis of organic synthetic reactions was conducted on an Agilent 1100 series HPLC fitted with a diode-array detector, quaternary pump, vacuum degasser, and autosampler. Mass spectrometry data were recorded on an Agilent 6310 ion trap mass spectrometer (ESI source) connected to an Agilent 1200 series HPLC with quaternary pump, vacuum degasser, diode-array detector, and autosampler.

Male Sprague-Dawley rats were purchased from Charles River Labs and imaged between 2 and 15 months of age. Animals were pair housed until they reached a weight of 500 g, and they were kept on a 12 h: 12 h light-dark cycle, switching at 7 am and pm. All treatment and imaging was performed according to procedures approved by the Institutional Animal Care and Use Committee (IACUC).

General Imaging Procedures

Prior to imaging, animals were anesthetized with isoflurane and a catheter was placed in a lateral tail vein. An extension line was used to attach the catheter to a syringe with heparinized saline, which was used to prevent clotting of the line and catheter. Animals were then placed in one of two instruments (a GammeMedicaTriumph PET/CT/SPECT scanner or a Siemens R4 PET scanner) and maintained under isoflurane anesthesia for the imaging period. For scans completed in the Triumph scanner, CT images of the animals were taken for PET image attenuation. For animals imaged in the R4, a Germanium (Ge) 68 or a Cobalt (Co) 57 line source was used to create an attenuation correction map. Following imaging, animals were placed in their cages and monitored until they recovered from the anesthesia.

Brain and Olfactory Epithelium Dissection

After euthanasia, brains were first dissected from the skull using standard procedures, rinsed with cold DI water, and placed on dry ice to freeze. Brains were stored at −80° C. In some cases, the brains were immediately dissected prior to being frozen to remove particular regions of interest (e.g., frontal cortex, hippocampus, cerebellum, and pons). These tissues were kept moist with cold DI water and placed on ice until being stored at −80° C. Following brain dissection, all skin and tissue was removed from the skull to provide access to the olfactory epithelium. Bone rongeurs were used to pry open the skull lateral to the septum for access to the epithelium. Small forceps were used to pull out the turbinate bones and associated olfactory epithelium, which were placed in an Eppendorf and frozen on dry ice. The olfactory epithelium located on the septum was then carefully removed and placed in a separate Eppendorf and frozen on dry ice.

Example 1. N-benzyl-2-fluoro-9H-purin-6-amine

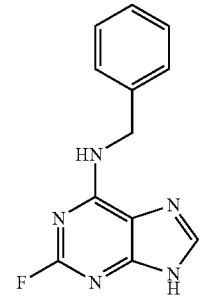

The title compound was synthesized according to previously published procedures (see Wilson et al. *Bioorg. Med. Chem.* 2011, 19, 6949) using modified conditions. 6-Chloro-2-fluoro-9H-purine (750 mg, 4.35 mmol, 1 eq.) was dissolved in n-butanol (n-BuOH, 50 mL) prior to addition of diisopropylethylamine (DIPEA, 0.575 mL, 5.22 mmol, 1.21 eq.). The resulting solution was cooled in an ice-water bath and benzylamine (2 mL, 11.5 mmol, 2.64 eq.) was added dropwise over 25 min. The reaction mixture was stirred in the ice-water bath until the ice melted, and then the reaction mixture was stirred at room temperature overnight. After 24 h, the reaction mixture was heated to 60° C. for 6 h. The mixture was cooled to room temperature before being added to a mixture of ethyl acetate (EtOAc, 150 mL) and deionized (DI) water (100 mL). After mixing, the water layer was collected and the organic phase was washed once with DI water (100 mL), followed by brine (75 mL). The organic phase was dried over sodium sulfate and concentrated to give the pure product (970 mg, 92%) as a pale yellow solid. LCMS [M+1]: 244. 1H NMR (500 MHz, DMF-d7): 4.97 (d, 2H, J=4.5), 7.41-7.62 (m, 5H), 8.27 (s, 1H), 8.91 (s, 1H). 13C NMR (126 MHz, DMF-d7): 43.8, 127.1, 127.7, 128.5, 139.9, 142.1.

Example 2. N-Benzyl-2-chloro-9H-purin-6-amine

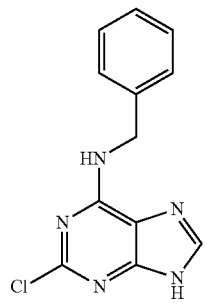 [SMILES: Clc1nc(NCc2ccccc2)c2nc[nH]c2n1]

2,6-Dichloro-9H-purine (500 mg, 2.46 mmol, 1 eq.) was dissolved in n-BuOH (4 mL), and benzylamine (322 μL, 2.95 mmol, 1.2 eq.) and triethylamine (TEA, 549 μL, 3.94 mmol, 1.6 eq.) were added to the solution. The solution was heated at reflux (110° C.) for 3 h, and then cooled to room temperature. The product, which precipitated from the reaction solution, was filtered under vacuum and washed with cold n-BuOH. The precipitate was vacuum dried and a colorless solid was obtained. LCMS [M+1]: 260. ¹H NMR (500 MHz, DMSO-d6): 4.65 (s, 2H), 7.23-7.34 (m, 5H), 8.13 (s, 1H), 8.71 (s, 1H).

Example 3. N-Benzyl-2-chloro-9-methyl-9H-purin-6-amine

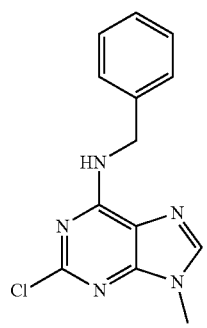

N-Benzyl-2-chloro-9H-purin-6-amine (200 mg, 0.77 mmol, 1 eq.) was dissolved in DMF (800 μL) prior to addition of potassium carbonate (532.5 mg, 3.85 mmol, 5 eq.) and methyl iodide (112 μL, 0.77 mmol, 1 eq.). The reaction mixture was stirred at room temperature for 105 min, and then the DMF was removed under vacuum. The resultant solid was dissolved in dichloromethane and the mixture filtered to remove the potassium carbonate. The product was purified via flash chromatography (1:1 DCM: EtOAc with 0.5% methanol) to provide the pale yellow product (93 mg, 44%). LCMS [M+1]: 273.7.

Example 4. N-benzyl-9-(4-bromobenzyl)-2-fluoro-9H-purin-6-amine

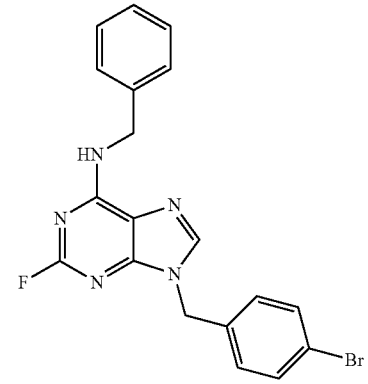 [SMILES: Fc1nc(NCc2ccccc2)c2ncn(Cc3ccc(Br)cc3)c2n1]

N-Benzyl-2-fluoro-9H-purin-6-amine (100 mg, 0.41 mmol, 1 eq.) was dissolved in dimethylacetamide prior to the addition of potassium carbonate (1.12 g, 4.1 mmol, 10 eq.) and 4-bromobenzyl bromide (512.38 mg, 2.05 mmol, 5 eq.). The reaction was stirred under nitrogen overnight. The reaction mixture was filtered and the solvents were removed in vacuo. The obtained solid was redissolved in DCM, washed with brine, dried with anhydrous Na₂SO₄, and concentrated to obtain the product. LCMS—[M+1]: 414.1.

Example 5. N-((3r,5r,7r)-adamantan-1-ylmethyl)-2-fluoro-9H-purin-6-amine

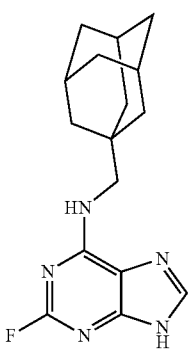 [SMILES: Fc1nc(NCC23CC4CC(CC(C4)C2)C3)c2nc[nH]c2n1]

6-Chloro-2-fluoro-9H-purine (305 mg, 1.77 mmol, 1 eq.) was dissolved in n-butanol (800 μL) prior to addition of diisopropylethylamine (813 uL, 4.67 mmol, 2.64 eq.). Adamantylamine (380 uL, 2.14 mmol, 1.21 eq.) was then added slowly at 0° C. and the reaction was then brought to 40° C. and stirred overnight. Solvents were removed to get a solid which was re-dissolved in DCM and washed with water and brine. Organic layer dried over anhyd. Na₂SO₄, and was concentrated to get the target compound. LCMS—[M+1]: 302.2.

Example 6. N-((3r,5r,7r)-adamantan-1-ylmethyl)-2-fluoro-9-methyl-9H-purin-6-amine

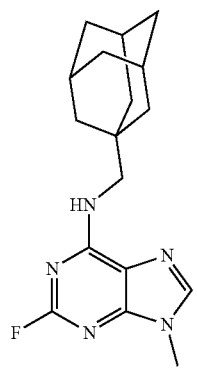

N-(((3r,5r,7r)-adamantan-1-yl)methyl)-2-fluoro-9H-purin-6-amine (100 mg, 0.33 mmol, 1 eq.) was dissolved in DMF (400 µL) prior to addition of potassium carbonate (230 mg, 1.66 mmol, 5 eq.) and methyl iodide (225 µL, 3.30 mmol, 1 eq.). The reaction was stirred at room temperature overnight, and then the DMF was removed under vacuum. The resulting solid was dissolved in dichloromethane and the mixture filtered to remove the potassium carbonate and the mixture was concentrated in vacuo. The resulting residue was redissolved in DCM, washed with water and brine, dried with anhydrous $Na_2SO_4$. Organic layer was concentrated to afford a solid product. LCMS—[M+1]: 316.2.

Example 7. $N^6$-benzyl-9H-purine-2,6-diamine

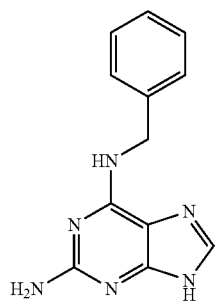 [SMILES: Nc1nc(NCc2ccccc2)c2nc[nH]c2n1]

6-chloro-9H-purin-2-amine (200 mg, 1.18 mmol, 1 eq.) was dissolved in DMF prior to addition of diisopropylethylamine (543 µL, 3.12 mmol, 2.64 eq.). The benzyl amine (156 µL, 1.43 mmol, 1.21 eq.) was then added slowly at 0° C., the reaction was brought to 90° C. and stirred overnight. LCMS—[M+1]: 241.1.

Example 8. N-Benzyl-2-fluoro-9-methyl-9H-purin-6-amine

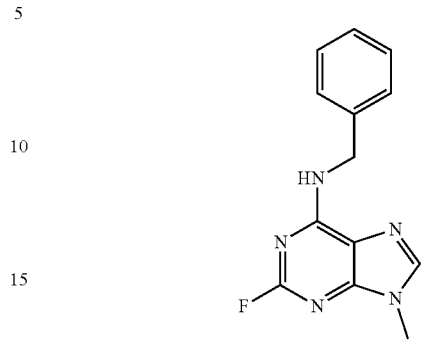

N-Benzyl-2-fluoro-9H-purin-6-amine (300 mg, 1.23 mmol, 1 eq.), potassium carbonate (852.4 mg, 6.17 mmol, 5 eq.), and methyl iodide (374 µL, 6.01 mmol, 4.89 eq.) were added to dimethylacetamide (DMA, 3.5 mL) and the reaction was stirred at room temperature for 7 h. Excess methyl iodide was removed by first passing $N_2$ (gas) through the solution for 15 min and then removing residual methyl iodide under vacuum. The reaction was then added to EtOAc (50 mL) and the resulting mixture was washed with DI water (100 mL). The aqueous phase was collected and washed with EtOAc (3×50 mL). The combined organic phases were then washed with brine (50 mL), dried over sodium sulfate, and concentrated. After column chromatography (DCM:EtOAc:MeOH, 49:49:2), of the purified title product was obtained as a pale yellow solid (215.5 mg, 68%). LCMS [M+1]: 258. 1H, 13C.

Example 9. 2-Fluoro-N-(pyridin-3-ylmethyl)-9H-purin-6-amine

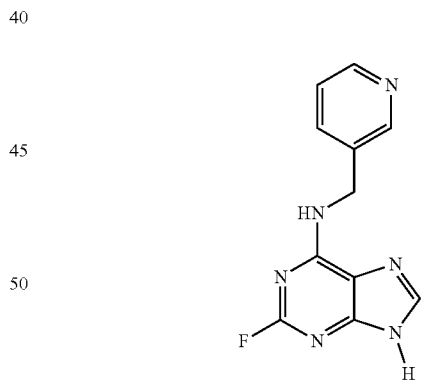

To a solution of 6-chloro-2-fluoro-9H-purine (0.5 g, 2.9 mmol) and DIEA (0.7 mL, 7.5 mmol) in nBuOH (40 mL) at 0° C. was gradually added pyridin-3-ylmethanamine (0.4 mL, 3.5 mmol). The reaction mixture was stirred for 17 h at RT, before heating to 40° C. for 1.5 h. After cooling on ice, the reaction mixture was diluted in 70 mL $H_2O$ and extracted with 100 mL EtOAc. The organic phase was washed with 70 mL $H_2O$, 50 mL brine, dried over $Na_2SO_4$ and concentrated under reduced pressure. Purification of the crude product by manual flash column chromatography (DCM/EtOAc/MeOH 45:45:10→0:80:20) gave the desired 2-fluoro-N-(pyridin-3-ylmethyl)-9H-purin-6-amine in 42% yield (0.3 g, 1.2 mmol)

as yellow solid. $R_f$: 0.20 (DCM/EtOAc/MeOH 45:45:10). LCMS (ESI): calculated for $[C_{11}H_9FN_6+H]^+$: 245, found 245 $[M+H]^+$.

Example 10. 2-Fluoro-9-methyl-N-(pyridin-3-ylmethyl)-9H-purin-6-amine

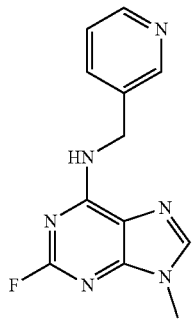

To a suspension of 2-fluoro-N-(pyridin-3-ylmethyl)-9H-purin-6-amine (50.0 mg, 0.19 mmol) and $K_2CO_3$ (36.3 mg, 0.95 mmol) in DMF (10 mL) at RT was gradually added methyl iodide (10.6 µL, 0.17 mmol). The reaction mixture was stirred for 3.5 h at RT and finally stopped by dilution in EtOAc. The suspension was filtrated, the residue washed with EtOAc and the filtrate concentrated under reduced pressure. Purification of the orange crude product by manual flash column chromatography (DCM/EtOAc/MeOH 50:50:0→45:45:10) gave the desired methylated purine 2-fluoro-9-methyl-N-(pyridin-3-ylmethyl)-9H-purin-6-amine in 89% yield (43.9 mg, 0.17 mmol) as dark red solid. $R_f$: 0.30 (DCM/EtOAc/MeOH 45:45:10). LCMS (ESI): calculated for $[C_{12}H_{11}FN_6+H]^+$: 259, found 259 $[M+H]^+$.

Example 11. N-(2-Chlorobenzyl)-2-fluoro-9H-purin-6-amine

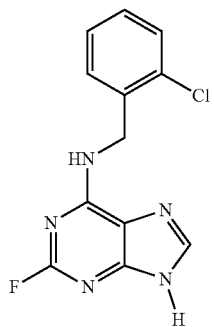 [SMILES: Fc1nc(NCc2ccccc2Cl)c2nc[nH]c2n1]

To a solution of 6-chloro-2-fluoro-9H-purine (200 mg, 1.16 mmol) and DIEA (525 µL, 3.01 mmol) in nBuOH (10 mL) at 0° C. was gradually added (2-chlorophenyl)methanamine (154 µL, 1.28 mmol). The reaction mixture was stirred for 18 h at RT, 1 h at 65° C., 2 h at 50° C., and finally 4 h at 65° C. Subsequent cooling to 0° C. for 12 h gave a colorless precipitant, which was filtrated, washed with 10 mL ice-cold MeOH and dried in vacuo. The desired N-(2-chlorobenzyl)-2-fluoro-9H-purin-6-amine was obtained in 88% yield (283 mg, 1.02 mmol) as colorless solid. $R_f$: 0.40 (DCM/EtOAc/MeOH 49:49:2). LCMS (ESI): calculated for $[C_{12}H_9ClFN_5+H]^+$: 278, found 278 $[M+H]^+$.

Example 12. N-Benzyl-9H-purin-6-amine

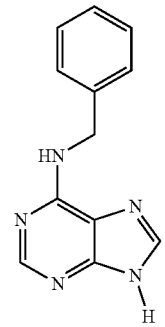 [SMILES: c1ccc(CNc2ncnc3[nH]cnc23)cc1]

To a solution of 6-chloro-9H-purine (112 mg, 0.72 mmol) and TEA (161 µL, 1.15 mmol) in nBuOH (6 mL) at RT was gradually added benzyl amine (95.6 µL, 0.86 mmol). The reaction mixture was stirred for 3 h at 110° C. and subsequently cooled to 0° C. The colorless precipitant was filtrated, washed with 10 mL ice-cold MeOH and dried in vacuo. The desired N-Benzyl-9H-purin-6-amine was obtained in 69% yield (112 mg, 0.49 mmol) as colorless solid. $R_f$: 0.15 (DCM/EtOAc/MeOH 49:49:2). LCMS (ESI): calculated for $[C_{12}H_{11}N_5+H]^+$: 226, found 226 $[M+H]^+$.

Example 13. 2-Fluoro-N-(2-methylbenzyl)-9H-purin-6-amine

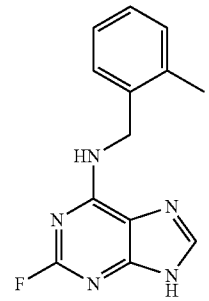 [SMILES: Cc1ccccc1CNc1nc(F)nc2[nH]cnc12]

To a solution of 6-chloro-2-fluoro-9H-purine (200 mg, 1.16 mmol) and DIEA (525 µL, 3.01 mmol) in nBuOH (6 mL) at 0° C. was gradually added o-tolylmethanamine (158 µL, 1.28 mmol). The reaction mixture was stirred for 2.5 h at RT and 4 h at 50° C. Subsequent cooling to 0° C. for 13 h gave a colorless precipitant, which was filtrated, washed with 10 mL ice-cold MeOH and dried in vacuo. The desired 2-Fluoro-N-(2-methylbenzyl)-9H-purin-6-amine was obtained in 56% yield (167 mg, 0.65 mmol) as colorless solid. $R_f$: 0.40 (DCM/EtOAc/MeOH 49.5:49.5:1). LCMS (ESI): calculated for $[C_{13}H_{12}FN_5+H]^+$: 258, found 258 $[M+H]^+$.

Example 14.
2-Fluoro-N-(2-methoxybenzyl)-9H-purin-6-amine

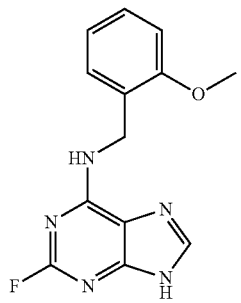 [SMILES: COc1ccccc1CNc1nc(F)nc2[nH]cnc12]

To a solution of 6-chloro-2-fluoro-9H-purine (200 mg, 1.16 mmol) and DIEA (525 µL, 3.01 mmol) in nBuOH (6 mL) at 0° C. was gradually added (2-methoxyphenyl)methanamine (166 µL, 1.28 mmol). The reaction mixture was stirred for 2.5 h at RT and 4 h at 50° C. Subsequent cooling to 0° C. for 13 h gave a colorless precipitant, which was filtered, washed with 10 mL ice-cold MeOH and dried in vacuo. The desired 2-Fluoro-N-(2-methoxybenzyl)-9H-purin-6-amine was obtained in 60% yield (190 mg, 0.70 mmol) as colorless solid. $R_f$: 0.30 (DCM/EtOAc/MeOH 48:48:4). LCMS (ESI): calculated for $[C_{13}H_{12}FN_5O+H]^+$: 274, found 274 $[M+H]^+$.

Example 15.
N-(4-Chlorobenzyl)-2-fluoro-9H-purin-6-amine

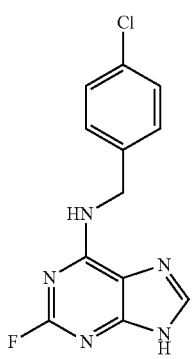 [SMILES: Fc1nc(NCc2ccc(Cl)cc2)c2nc[nH]c2n1]

To a solution of 6-chloro-2-fluoro-9H-purine (200 mg, 1.16 mmol) and DIEA (525 µL, 3.01 mmol) in nBuOH (6 mL) at 0° C. was gradually added (4-chlorophenyl)methanamine (155 µL, 1.28 mmol). The reaction mixture was stirred for 2.5 h at RT and 4 h at 50° C. Subsequent cooling to 0° C. for 13 h gave a colorless precipitant, which was filtered, washed with 10 mL ice-cold MeOH and dried in vacuo. The desired N-(4-Chlorobenzyl)-2-fluoro-9H-purin-6-amine was obtained in 78% yield (251 mg, 0.91 mmol) as colorless solid. $R_f$: 0.25 (DCM/EtOAc/MeOH 49.5:49.5:1). LCMS (ESI): calculated for $[C_{12}H_9ClFN_5+H]^+$: 278, found 278 $[M+H]^+$.

Example 16.
2-Fluoro-N-(4-fluorobenzyl)-9H-purin-6-amine

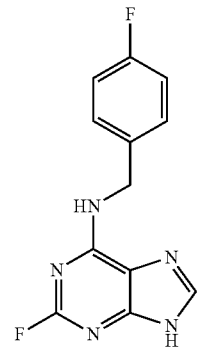 [SMILES: Fc1ccc(CNc2nc(F)nc3[nH]cnc23)cc1]

To a solution of 6-chloro-2-fluoro-9H-purine (200 mg, 1.16 mmol) and DIEA (525 µL, 3.01 mmol) in nBuOH (6 mL) at 0° C. was gradually added (4-fluorophenyl)methanamine (146 µL, 1.28 mmol). The reaction mixture was stirred for 0.5 h at RT and 3.5 h at 50° C. Subsequent cooling to 0° C. for 48 h gave a colorless precipitant, which was filtered, washed with 10 mL ice-cold MeOH and dried in vacuo. The desired 2-Fluoro-N-(4-fluorobenzyl)-9H-purin-6-amine was obtained in 65% yield (197 mg, 0.75 mmol) as colorless solid. $R_f$: 0.30 (DCM/EtOAc/MeOH 49:49:2). LCMS (ESI): calculated for $[C_{12}H_9F_2N_5+H]^+$: 262, found 262 $[M+H]^+$.

Example 17. (R)-2-((6-(((3R,5R,7R)-adamantan-1-ylmethyl)amino)-9-methyl-9H-purin-2-yl)amino)butan-1-ol

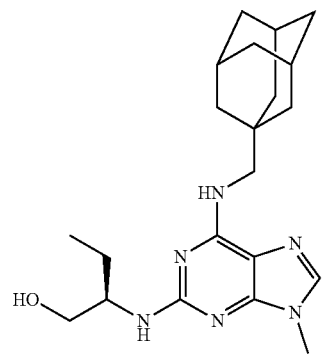 [SMILES: CC[C@H](CO)Nc1nc(NCC23CC4CC(CC(C4)C2)C3)c2ncn(C)c2n1]

N-(((3r,5r,7r)-adamantan-1-yl)methyl)-2-fluoro-9-methyl-9H-purin-6-amine (35 mg, 0.12 mmol, 1 equiv.) was dissolved in a mixture of n-butanol (1 mL) and DMSO (0.3 mL) prior to addition of diisopropylethylamine (209 uL, 1.2 mmol, 10 equiv.). The amine (110 uL, 1.15 mmol, 9.6 equiv.) was then added and the reaction was brought to 135 C and stirred for 48 hours. Silica flash chromatography provided 34 mg pure product. LCMS—M+1: 385.

Example 18. 2-(6-(Benzylamino)-2-fluoro-9H-purin-9-yl)ethan-1-ol

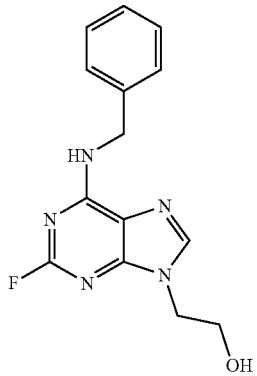 [SMILES: OCCn1cnc2c(NCc3ccccc3)nc(F)nc21]

To a suspension of N-benzyl-2-fluoro-9H-purin-6-amine (75.0 mg, 0.31 mmol) and KOH (96.2 mg, 1.23 mmol) in DMF (2 mL) at room temperature was gradually added 2-chloroethan-1-ol (207 µL, 3.08 mmol). The reaction mixture was stirred for 20 h at 70° C., followed by concentration under reduced pressure. Purification by manual flash column chromatography (DCM/EtOAc/MeOH 60:40:0→48:48:4) yielded 68% of the desired product (60.0 mg, 0.21 mmol) as colorless solid. LCMS (ESI): calculated for $[C_{14}H_{14}FN_5O+H]^+$: 288, found 288 $[M+H]^+$.

Example 19. N-benzyl-6-chloro-1H-pyrazolo[3,4-d]pyrimidin-4-amine

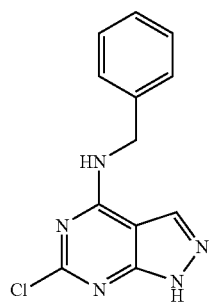 [SMILES: Clc1nc(NCc2ccccc2)c2cn[nH]c2n1]

To a solution of 4,6-dichloro-1H-pyrazolo[3,4-d]pyrimidine (0.50 g, 2.65 mmol) and TEA (0.59 mL, 4.23 mmol) in nBuOH (10 mL) at 0° C. was gradually added benzyl amine (0.30 mL, 2.78 mmol). The orange reaction mixture was stirred for 18 h at RT and finally stopped by addition of 100 mL EtOAc. The organic phase was washed with 2×30 mL H$_2$O, 5 mL brine, dried over Na$_2$SO$_4$ and concentrated under reduced pressure. Purification of the crude product by manual flash column chromatography (DCM/EtOAc/MeOH 50:50:0→45:45:10) gave the desired N-Benzyl-6-chloro-1H-pyrazolo[3,4-d]pyrimidin-4-amine in 94% yield (0.64 mg, 2.48 mmol) as orange solid. R$_f$: 0.60 (DCM/EtOAc/MeOH 49.5:49.5:1). LCMS (ESI): calculated for $[C_{12}H_{11}FN_6+H]^+$: 259, found 259 $[M+H]^+$.

Example 20. N-benzyl-6-chloro-1-methyl-1H-pyrazolo[3,4-d]pyrimidin-4-amine and N-benzyl-6-chloro-2-methyl-2H-pyrazolo[3,4-d]pyrimidin-4-amine

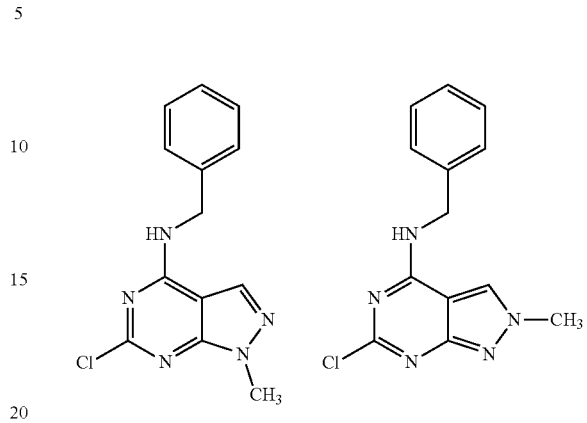

To a suspension of N-Benzyl-6-chloro-1H-pyrazolo[3,4-d]pyrimidin-4-amine (100 mg, 0.39 mmol) and K$_2$CO$_3$ (267 mg, 1.93 mmol) in DMF (500 µL) at 0° C. was gradually added methyl iodide (23.2 µL, 0.37 mmol). The reaction mixture was stirred for 1 h at RT. The reaction mixture was concentrated under reduced pressure and redissolved in 5 mL EtOAc. The resulting suspension was filtrated, washed with 5 mL EtOAc and the filtrate concentrated under reduced pressure. Purification of the yellow crude product by manual flash column chromatography (DCM/EtOAc/MeOH 60:40:0→48:48:2) gave two different yellow crystalline solids. N-Benzyl-6-chloro-1-methyl-1H-pyrazolo[3,4-d]pyrimidin-4-amine was obtained in 64% yield (67.4 g, 0.25 mmol) and N-benzyl-6-chloro-2-methyl-1H-pyrazolo[3,4-d]pyrimidin-4-amine in 13% yield (13.5 mg, 0.05 mmol).

N-benzyl-6-chloro-1-methyl-1H-pyrazolo[3,4-d]pyrimidin-4-amine: R$_f$: 0.75 (DCM/EtOAc/MeOH 49:49:2). LCMS (ESI): calculated for $[C_{12}H_{11}FN_6+H]^+$: 274, found 274 $[M+H]^+$.

N-benzyl-6-chloro-2-methyl-1H-pyrazolo[3,4-d]pyrimidin-4-amine: R$_f$: 0.5 (DCM/EtOAc/MeOH 49:49:2). LCMS (ESI): calculated for $[C_{12}H_{11}FN_6+H]^+$: 274, found 274 $[M+H]^+$.

Example 21. [$^{11}$C] Radiolabeled N-benzyl-2-fluoro-9-methyl-9H-purin-6-amine

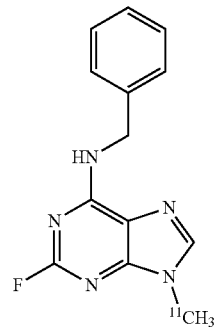

DMSO (300 μL) was added to a vial containing N-benzyl-2-fluoro-9H-purin-6-amine (1-2 mg) and potassium hydroxide (2-8 mg, powdered). The solution was transferred to a reaction vessel with a stir bar, and the reaction vessel was placed in an automated radiosynthesis instrument. The automated system was used to add [$^{11}$C]methyl iodide (100-400 mCi), and the resulting solution was stirred at 80° C. for 5 min.

Quenching solution was then added (1.7 mL 35% MeCN and 65% H$_2$O with 0.065% formic acid), and the solution (2 mL total) was injected onto a Phenomenex Luna C18 semi-preparative column. The product was purified via HPLC at a flow rate of 5 mL/min using isocratic conditions (35% MeCN and 65% H$_2$O with 0.065% formic acid). The identity of the product was confirmed using LCMS under standard gradient conditions with a co-injection of the radioactive product and a standard solution containing the [$^{12}$C] labeled version of the product.

Example 22. [$^{18}$F] Radiolabeled N-benzyl-2-fluoro-9-methyl-9H-purin-6-amine

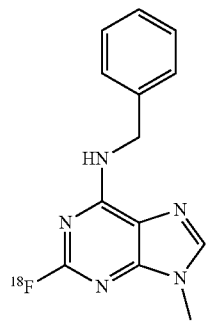

This synthesis was automated using an Explora GN radiochemistry unit. A solution of potassium kryptofix (800 μL, 6.25 mg/mL in MeCN) and potassium carbonate (200 μL, 5 mg/mL) and $^{18}$F— was dried at 110° C. for 3 min. Then 500 μL MeCN was added and the solution was dried at about 110-115° C. for 3 min. This process was repeated a second time. A precursor solution of N-benzyl-2-chloro-9-methyl-9H-purin-6-amine (1.5 mg in 500 μL DMSO) was added to the dried $^{18}$F—, and the solution was heated at 140° C. for 10 min under N$_2$ gas. The reaction was cooled, diluted with 4 mL of HPLC mobile phase (mixture of MeCN, H$_2$O, and formic acid) and passed through an Alumina cartridge before purification by HPLC. The HPLC mobile phase consisted of 280 g MeCN, 720 g H$_2$O, and 720 μL formic acid. The identity of the product was confirmed using LCMS under standard gradient conditions with a co-injection of the radioactive product and a standard solution containing the [$^{12}$C] labeled version of the product.

Example 23. 2-Fluoro-9-(methyl-$^{11}$C)—N-(pyridin-3-ylmethyl)-9H-purin-6-amine

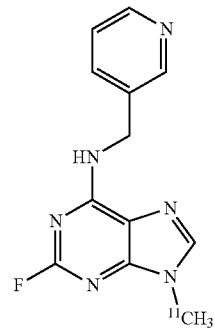

To a vial containing 2-fluoro-N-(pyridin-3-ylmethyl)-9H-purin-6-amine (1-2 mg) and KOH (2-8 mg, powdered), DMSO (300 μL) was added. The solution was transferred to a reaction vessel with a stir bar, and the reaction vessel was placed in an automated radiosynthesis instrument. The automated system was used to add [$^{11}$C]-methyl iodide (100-400 mCi), and the resultant solution was stirred at 80° C. for 5 min. Quenching solution (1.7 mL 35% MeCN, 65% H$_2$O, with 0.065% formic acid) was then added, and the complete solution (2 mL total) was injected onto a Phenomenex Luna C18 semi-preparative column. The product was purified via HPLC at a flow rate of 5 mL/min using isocratic conditions (18% MeCN, 65% H$_2$O, with 0.065% formic acid). The identity of the product was confirmed using LCMS under standard gradient conditions with a co-injection of the radioactive product and a standard solution containing the [$^{12}$C]methylated version.

Example 24. N-Benzyl-2-fluoro-9-(1-(methyl-$^{11}$C)pyrrolidin-3-yl)-9H-purin-6-amine

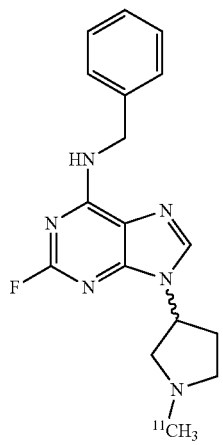 [SMILES: [11CH3]N1CCC(n2cnc3c(NCc4ccccc4)nc(F)nc32)C1]

To a vial containing N-benzyl-2-fluoro-9-(pyrrolidin-3-yl)-9H-purin-6-amine (1-2 mg) and KOH (2-8 mg, powdered), DMSO (300 μL) was added. The solution was transferred to a reaction vessel with a stir bar, and the reaction vessel was placed in an automated radiosynthesis instrument. The automated system was used to add [$^{11}$C] methyl iodide (100-400 mCi), and the resultant solution was stirred at 40° C. for 5 min. Quenching solution (1.7 mL 35% MeCN, 65% H₂O, with 0.065% formic acid) was then added, and the complete solution (2 mL total) was injected onto a Phenomenex Luna C18 semi-preparative column. The product was purified via HPLC at a flow rate of 5 mL/min using isocratic conditions (23% MeCN, 77% H₂O, with 0.077% formic acid). The identity of the product was confirmed using LCMS under standard gradient conditions with a co-injection of the radioactive product and a standard solution containing the [$^{12}$C]methylated version.

Example 25. N-(2-Chlorobenzyl)-2-fluoro-9-(methyl-$^{11}$C)-9H-purin-6-amine

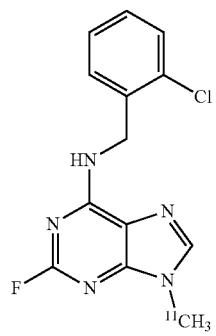 [SMILES: [11CH3]n1cnc2c(NCc3ccccc3Cl)nc(F)nc21]

To a vial containing N-(2-chlorobenzyl)-2-fluoro-9H-purin-6-amine (1-2 mg) and K₂CO₃ (2-8 mg, powdered), DMSO (300 µL) was added. The solution was transferred to a reaction vessel with a stir bar, and the reaction vessel was placed in an automated radiosynthesis instrument. The automated system was used to add [$^{11}$C] methyl iodide (100-400 mCi), and the resultant solution was stirred at 25° C. for 5 min. Quenching solution (1.7 mL 35% MeCN, 65% H₂O, with 0.065% formic acid) was then added, and the complete solution (2 mL total) was injected onto a Phenomenex Luna C18 semi-preparative column. The product was purified via HPLC at a flow rate of 5 mL/min using isocratic conditions (42% MeCN, 58% H₂O, with 0.058% formic acid). The identity of the product was confirmed using LCMS under standard gradient conditions with a co-injection of the radioactive product and a standard solution containing the [$^{12}$C]methylated version.

Example 26. N-Benzyl-2-(fluoro-$^{18}$F)-9-isopropyl-9H-purin-6-amine

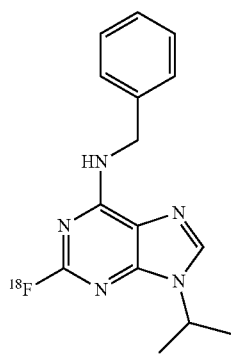 [SMILES: CC(C)n1cnc2c(NCc3ccccc3)nc([18F])nc21]

The synthesis was automated using an Explora GN radiochemistry unit. A mixed solution of K₂₂₂ (800 µL, 5 mg/mL in MeCN), K₂CO₃ (200 µL, 5 mg/mL in H₂O) and [$^{18}$F]—KF was dried at 109-110° C. for 3 min under N₂ gas. Then additional MeCN (500 µL) was added and the solution was dried again at 109-110° C. for 3 min. The last step was repeated a second time. A solution of N-benzyl-2-chloro-9-isopropyl-9H-purin-6-amine (1.5-2 mg in 500 µL DMSO) was added to the dried $^{18}$F⁻, and the solution was stirred at 155° C. for 10 min under N₂ gas. The reaction was cooled, diluted with 4 mL of HPLC mobile phase (40% MeCN, 60% H₂O, with 0.06% formic acid) and passed through an Alumina cartridge before purification by HPLC at a flow rate of 5 mL/min. The identity of the product was confirmed using LCMS under standard gradient conditions with a co-injection of the radioactive product and a standard solution containing the [$^{12}$C] methylated version.

Example 27. N-Benzyl-9-cyclopentyl-2-(fluoro-$^{18}$F)-9H-purin-6-amine

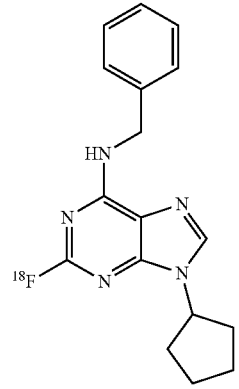 [SMILES: [18F]c1nc(NCc2ccccc2)c2ncn(C3CCCC3)c2n1]

The synthesis was automated using an Explora GN radiochemistry unit. A mixed solution of K₂₂₂ (800 µL, 5 mg/mL in MeCN), K₂CO₃ (200 µL, 5 mg/mL in H₂O) and [$^{18}$F]—KF was dried at 109-110° C. for 3 min under N₂ gas. Then additional MeCN (500 µL) was added and the solution was dried again at 109-110° C. for 3 min. The last step was repeated a second time. A solution of N-benzyl-2-chloro-9-cyclopentyl-9H-purin-6-amine (1.5-2 mg in 500 µL DMSO) was added to the dried $^{18}$F⁻, and the solution was stirred at 155° C. for 10 min under N₂ gas. The reaction was cooled, diluted with 4 mL of HPLC mobile phase (45% MeCN, 55% H₂O, with 0.055% formic acid) and passed through an Alumina cartridge before purification by HPLC at a flow rate of 5 mL/min. The identity of the product was confirmed using LCMS under standard gradient conditions with a co-injection of the radioactive product and a standard solution containing the [$^{12}$C] methylated version.

Example 28. 6-Chloro-2-fluoro-9-methyl-9H-purine

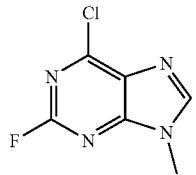

To a solution of 6-chloro-2-fluoro-9H-purine (500 mg, 2.9 mmol) in dimethylformamide (DMF), potassium carbonate (K$_2$CO$_3$, 2 g, 14.5 mmol) was added. After 10 min at room temperature, the suspension was cooled to 0° C. and methyl iodide (181 µL, 2.9 mmol) was added gradually over 5 min. The reaction mixture was stirred for 10 min at room temperature, before the DMF was removed under reduced pressure. The crude product was dissolved in ethyl acetate (EtOAc, 10 mL) and washed with deionized water (50 mL). The aqueous phase was re-extracted with EtOAc (30 mL), and the combined organic phases were dried over sodium sulfate (Na$_2$SO$_4$), and concentrated under reduced pressure. Purification of the crude product by manual flash column chromatography (DCM→DCM/EtOAc 75:25→50:50) gave 6-chloro-2-fluoro-9-methyl-9H-purine in 50% yield (269 mg, 1.44 mmol) as a colorless solid. R$_f$: 0.3 (DCM/EtOAc/MeOH 49:49:2). LCMS (ESI): calculated for [C$_6$H$_4$ClFN$_4$+H]$^+$: 187, found 187 [M+H]$^+$.

Example 29. t-Butyl 4-(((2-fluoro-9-methyl-9H-purin-6-yl)amino)methyl)benzylcarbamate

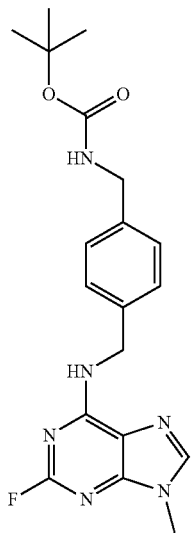 [SMILES: Cn1cnc2c(NCc3ccc(CNC(=O)OC(C)(C)C)cc3)nc(F)nc21]

To a solution of 6-chloro-2-fluoro-9-methyl-9H-purine (150 mg, 0.80 mmol) and diisopropylethylamine (DIPEA, 225 µL, 1.29 mmol) in n-butanol/ethanol (n-BuOH/EtOH, 50:50, 14 mL) at 0° C. was gradually added t-butyl 4-(aminomethyl)-benzylcarbamate (209 mg, 0.88 mmol). The reaction mixture was stirred for 19 h at room temperature, and subsequently concentrated under reduced pressure. The crude product was purified by manual flash column chromatography (DCM/EtOAc 85:15→DCM/EtOAc/MeOH 49:49:2) to give t-butyl 4-(((2-fluoro-9-methyl-9H-purin-6-yl)amino)methyl)benzylcarbamate in 69% yield (174 mg, 0.45 mmol) as a colorless solid. R$_f$: 0.20 (DCM/EtOAc/MeOH 49:49:2). LCMS (ESI): calculated for [C$_{19}$H$_{23}$FN$_6$O$_2$+H]$^+$: 387, found 387 [M+H]$^+$.

Example 30. (4-(((2-Fluoro-9-methyl-9H-purin-6-yl)amino)methyl)phenyl)(phenyl)methanone

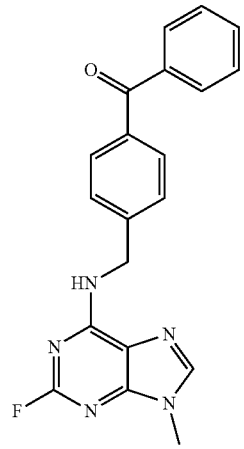 [SMILES: Cn1cnc2c(NCc3ccc(C(=O)c4ccccc4)cc3)nc(F)nc21]

To a solution of 6-chloro-2-fluoro-9-methyl-9H-purine (27 mg, 0.14 mmol) and DIPEA (67 µL, 0.37 mmol) in n-BuOH/EtOH (50:50, 2 mL) at 0° C. was gradually added 4-benzoylbenzylamine hydrochloride (40 mg, 0.16 mmol). The reaction mixture was stirred in the dark for 12 h at room temperature. Subsequent cooling to 4° C. for 6 h gave a colorless precipitate, which was filtered, washed with MeOH (5 mL, 0° C.), and dried under reduced pressure to provide pure (4-(((2-fluoro-9-methyl-9H-purin-6-yl)amino)methyl)phenyl)(phenyl)methanone as a colorless solid. LCMS (ESI): calculated for [C$_{20}$H$_{16}$FN$_5$O+H]$^+$: 362, found 362 [M+H]$^+$.

Example 31. N-(3-(Aminomethyl)benzyl)-2-fluoro-9-methyl-9H-purin-6-amine

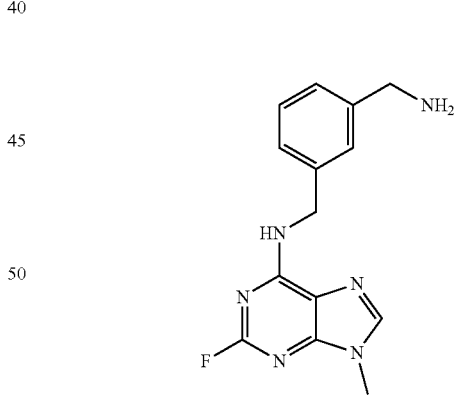

To a solution of 6-chloro-2-fluoro-9-methyl-9H-purine (50 mg, 27 mmol) and DIPEA (56 µL, 0.32 mmol) in n-BuOH/EtOH (50:50, 3 mL) at 0° C. was gradually added 1,3-phenylenedimethanamine (40 mg, 0.30 mmol). The reaction mixture was stirred for 12 h at room temperature. Subsequent cooling to 4° C. for 6 h gave a colorless precipitate, which was filtered, washed with methanol (MeOH, 5 mL, 0° C.) and dried under reduced pressure to provide pure N-(3-(aminomethyl)benzyl)-2-fluoro-9-methyl-9H-purin-6-amine as a colorless solid. LCMS (ESI): calculated for [C$_{14}$H$_{15}$FN$_6$+H]$^+$: 287, found 287 [M+H]$^+$.

Example 32. Specific Binding of N-Benzyl-2-fluoro-9-methyl-9H-purin-6-amine

Male Sprague-Dawley rats were imaged with [$^{11}$C] radiolabeled N-benzyl-2-fluoro-9-methyl-9H-purin-6-amine following treatment with [$^{12}$C] radiolabeled N-benzyl-2-fluoro-9-methyl-9H-purin-6-amine to determine the specific binding of the radiotracer in the olfactory epithelium. Animals were injected with [$^{12}$C] radiolabeled N-benzyl-2-fluoro-9-methyl-9H-purin-6-amine (i.v.; 16 mg/kg; 4 mg/mL in 10% DMSO, 10% Tween 20, and 80% saline). After 5 min, animals were injected with [$^{11}$C] radiolabeled N-benzyl-2-fluoro-9-methyl-9H-purin-6-amine (0.3-1.5 mCi), in 10% ethanol, 90% saline). Animals were imaged for up to 60 min to monitor the radiotracer uptake, and are shown in FIG. 1A. [$^{11}$C] Radiolabeled N-benzyl-2-fluoro-9-methyl-9H-purin-6-amine shows high initial uptake in the brain with fast removal from the brain and low non-specific binding. Although [$^{11}$C] N-benzyl-2-fluoro-9-methyl-9H-purin-6-amine exhibits limited specific binding in the brain, there is specific binding in the nasal cavity, where the olfactory receptor neurons are located. This area of specific binding is present in the nasal cavity of rats and NHPs, as demonstrated by a decrease in [$^{11}$C] N-benzyl-2-fluoro-9-methyl-9H-purin-6-amine binding in the presence of unlabeled N-benzyl-2-fluoro-9-methyl-9H-purin-6-amine, shown in FIG. 1A-1D.

Example 33. Zinc Sulfate Treatment and Imaging

Animals were anesthetized with isoflurane prior to placement on their backs for intranasal administration of either zinc sulfate (10% in saline, 100 µL per nostril) or vehicle (saline, 100 µL per nostril). Zinc sulfate and vehicle were administered bilaterally, with injection in the right nostril occurring 15 minutes prior to injection of the left nostril. For the injection, anesthetized animals were placed on their backs and slightly shifted toward the opposite side of the nostril being injected. PE 10 tubing attached to a syringe containing the zinc sulfate or vehicle dose was then inserted about 14 mm into the nostril, and the solution was quickly expunged into the nasal cavity. The rats head was held at a 45 degree angle for 1-2 seconds and then the head was placed nose-down to allow excess solution to drain out of the nostril. Animals were allowed to wake between injections to assist with clearing of the nasal passages, before being anesthetized for injection of the second (left) nostril. Using this procedure, there was no animal mortality. Following intranasal treatment, animals were imaged with [$^{11}$C] radiolabeled N-benzyl-2-fluoro-9-methyl-9H-purin-6-amine (0.3-1.5 mCi, in 10% ethanol, 90% saline) at 1-74 days after treatment to monitor synapsin density. After the final imaging session, animals were euthanized and their brains and olfactory epithelium were dissected for Western Blot analysis. Results of the zinc sulfate and saline treatments are shown in FIG. 2A-2C and FIG. 3.

Example 34. Imaging Neural Density During Development and Aging

Sprague-Dawley Rats

Figure 4C:
FIG. 4C shows averaged PET images of SUV changes in mice.

At the specified ages, male Sprague-Dawley rats were imaged with [$^{11}$C] radiolabeled N-benzyl-2-fluoro-9-methyl-9H-purin-6-amine to monitor changes in the N-benzyl-2-fluoro-9-methyl-9H-purin-6-amine signal in the olfactory epithelium. Animals were injected with vehicle (4 mL/kg; 10% DMSO, 10% Tween 20, and 80% saline). After 5 min, animals were injected with [$^{11}$C] radiolabeled N-benzyl-2-fluoro-9-methyl-9H-purin-6-amine (0.3-1.5 mCi), in 10% ethanol, 90% saline). Animals were imaged for up to 60 min to monitor the radiotracer uptake, and are shown in FIG. 4A. Statistical analyses were completed with a two-tailed student's t-test, p=0.019 (n=3, 2 months; n=4, 3 months), and are shown in FIG. 4B.

B6C31 Mice

Figure 4D:
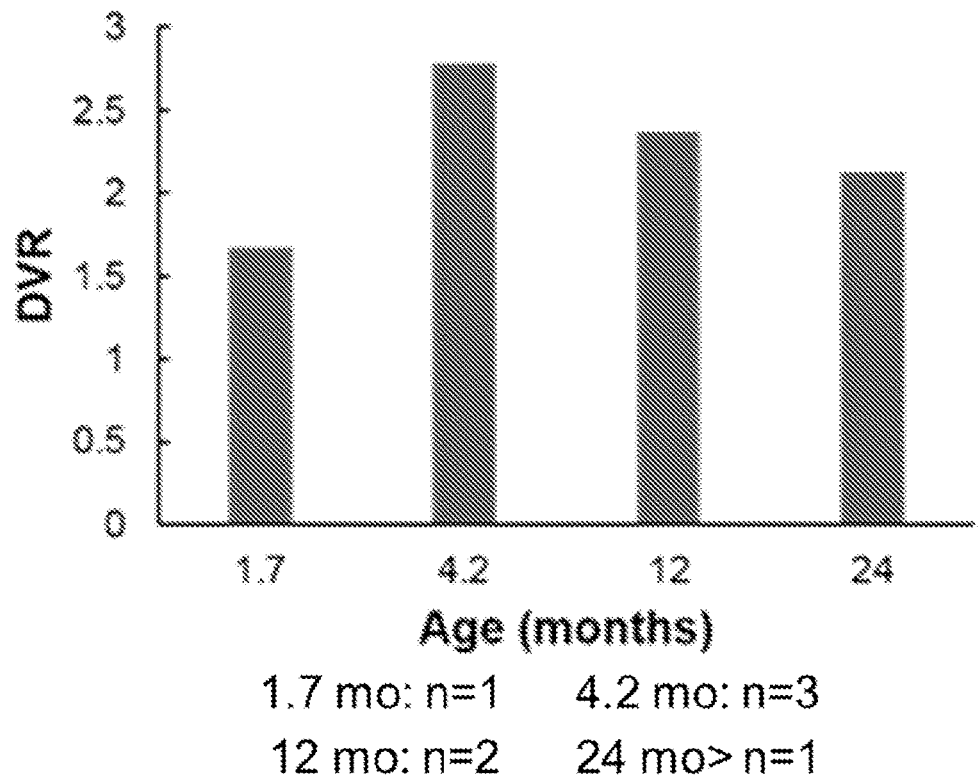
FIG. 4D shows a Logan Analysis of mice at 1.7 months, 4.2 months, 12 months, and 24 months.

At the specified ages, nude or B6C31 mice (male and female) were imaged with [$^{11}$C] radiolabeled N-benzyl-2-fluoro-9-methyl-9H-purin-6-amine to monitor changes in the N-benzyl-2-fluoro-9-methyl-9H-purin-6-amine signal in the olfactory epithelium. Some animals were injected with vehicle (4 mL/kg; 10% DMSO, 10% Tween 20, and 80% saline) 5 min prior to the radiotracer; others did not receive a vehicle injection. Animals were injected with [$^{11}$C] radiolabeled N-benzyl-2-fluoro-9-methyl-9H-purin-6-amine (0.1-1.3 mCi, in 10% ethanol, 90% saline). Animals were imaged for up to 60 min to monitor the radiotracer uptake, shown in FIG. 4C. Results of the statistical analysis is shown in FIG. 4D.

Example 35. Alzheimer's Disease Model

Figure 5:
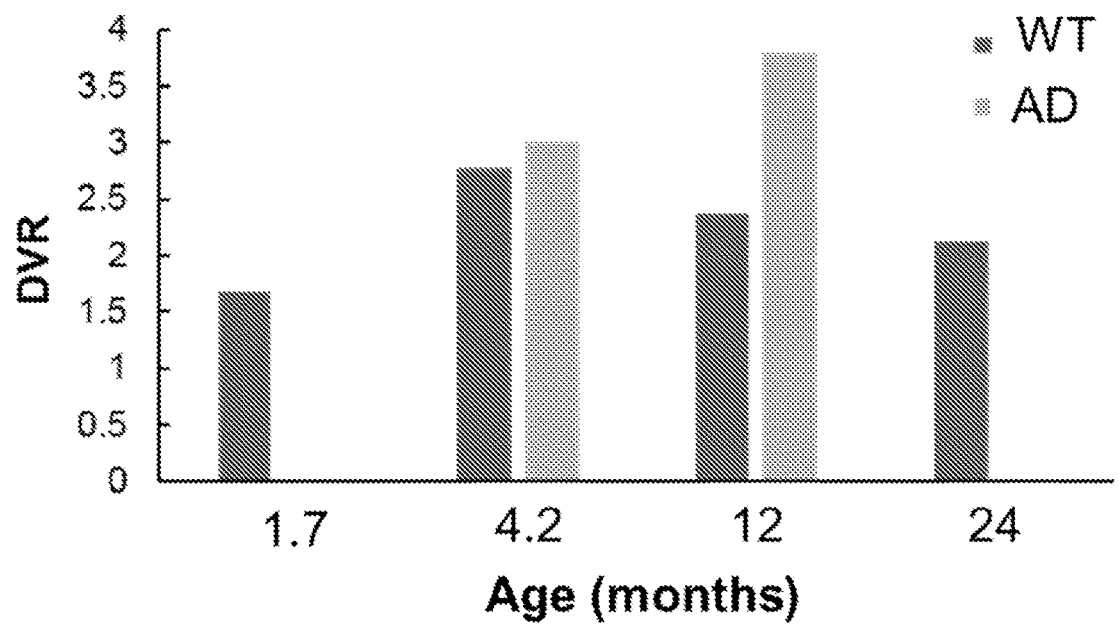
FIG. 5 shows results of an Alzheimer's disease model using wild type (WT) and APPsw mice at 1.7 months, 4.2 months, 12 months, and 24 months.
Figure 6:
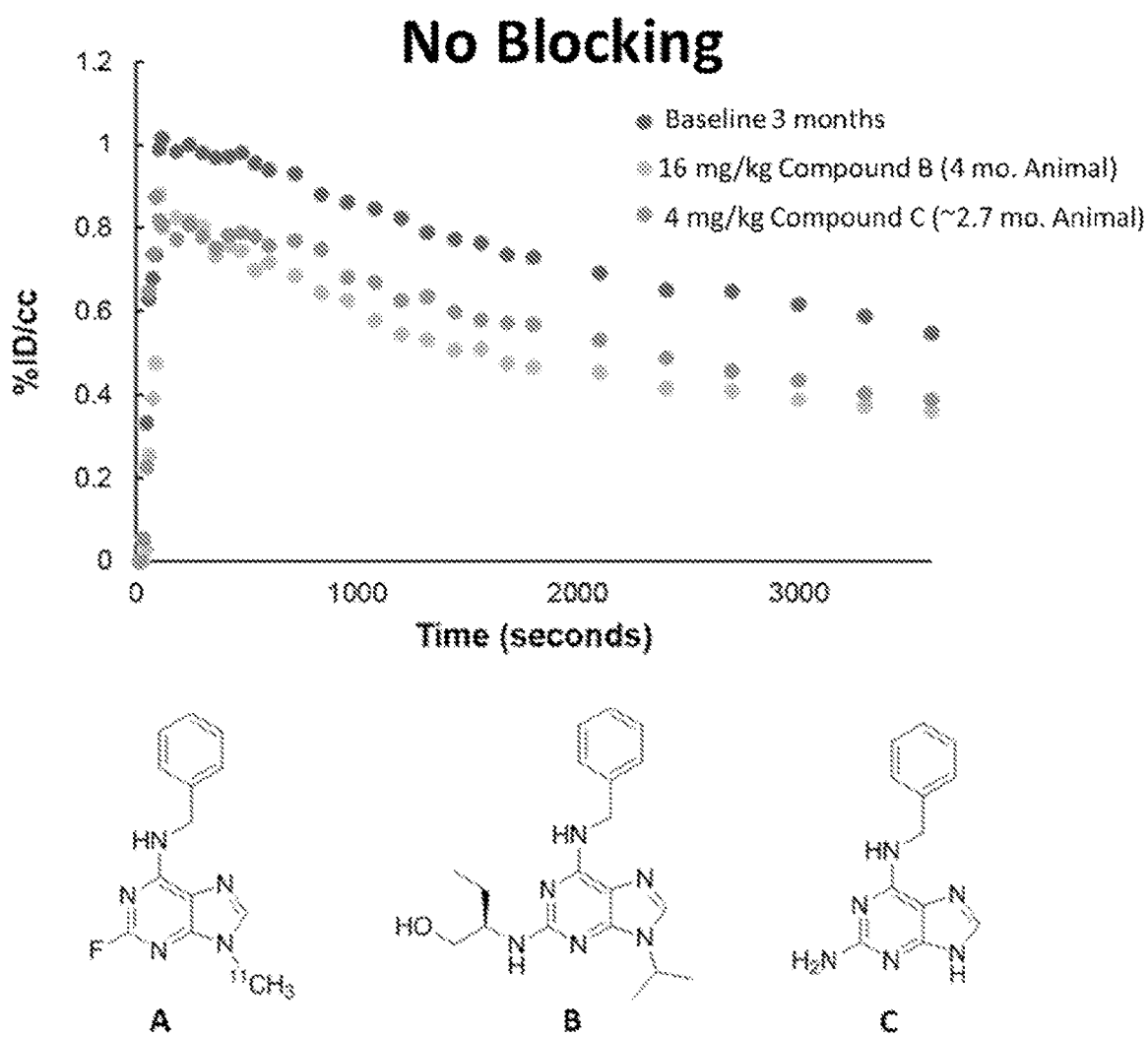
FIG. 6 shows results of blocking assay using [$^{11}$C] radiolabeled N-benzyl-2-fluoro-9-methyl-9H-purin-6-amine (Compound A) and unlabeled Compounds B and C.
Figure 7:
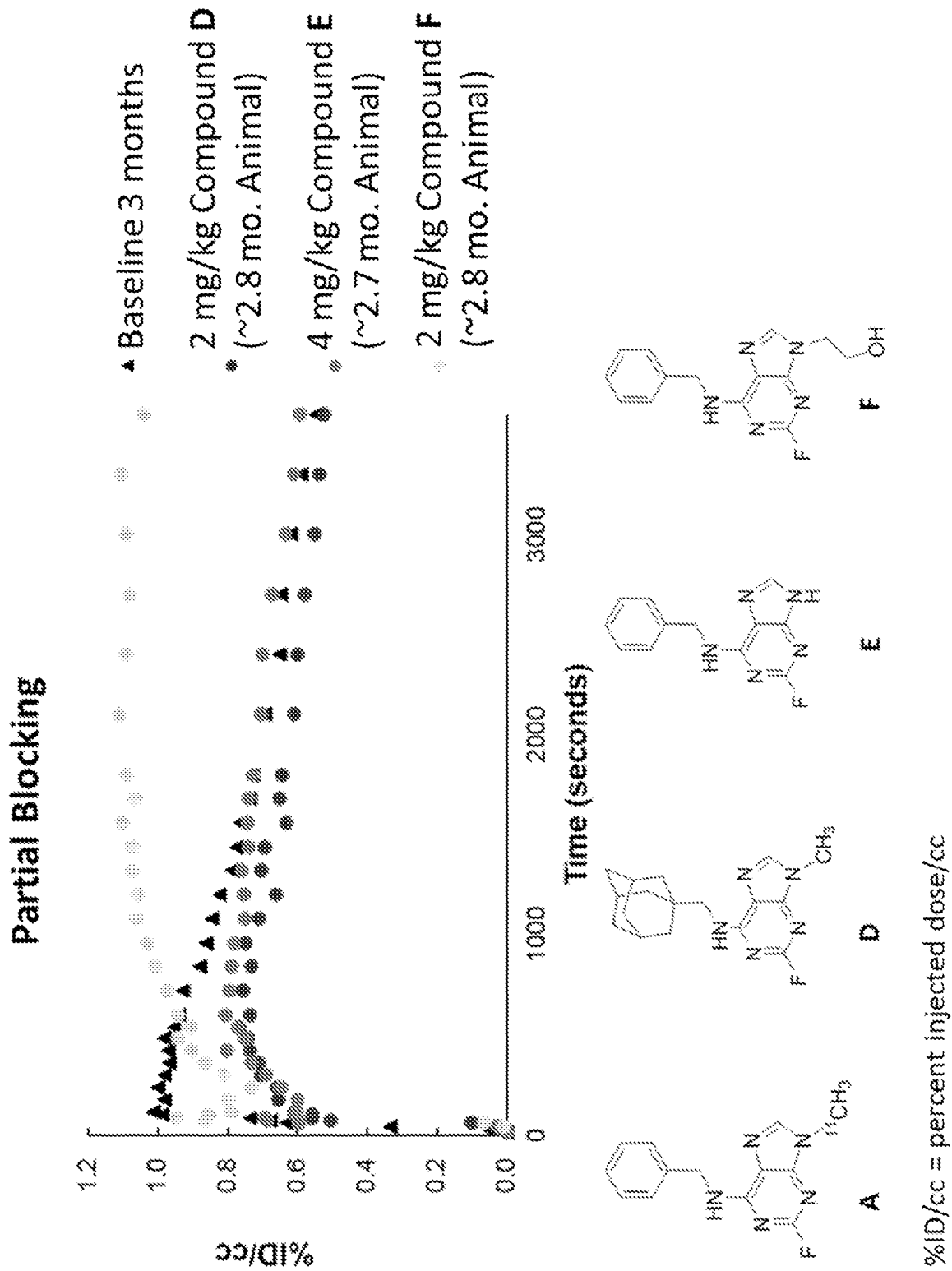
FIG. 7 shows results of a blocking assay using [$^{11}$C] radiolabeled N-benzyl-2-fluoro-9-methyl-9H-purin-6-amine (Compound A) and unlabeled Compounds D, E, F, and P.
Figure 8:
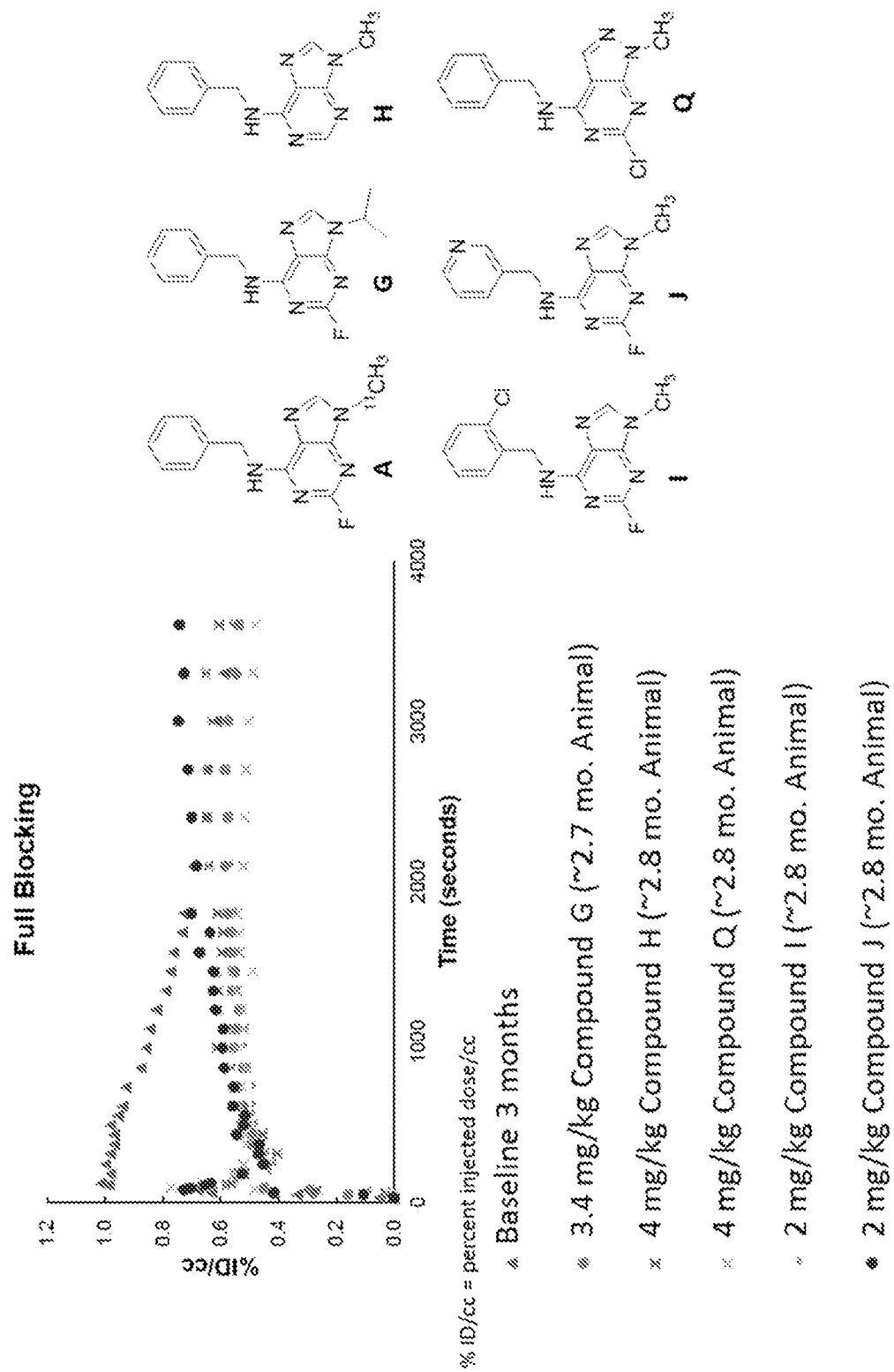
FIG. 8 shows results of a blocking assay using [$^{11}$C] radiolabeled N-benzyl-2-fluoro-9-methyl-9H-purin-6-amine (Compound A) and unlabeled Compounds G, H, I, J, and Q.
Figure 10A:
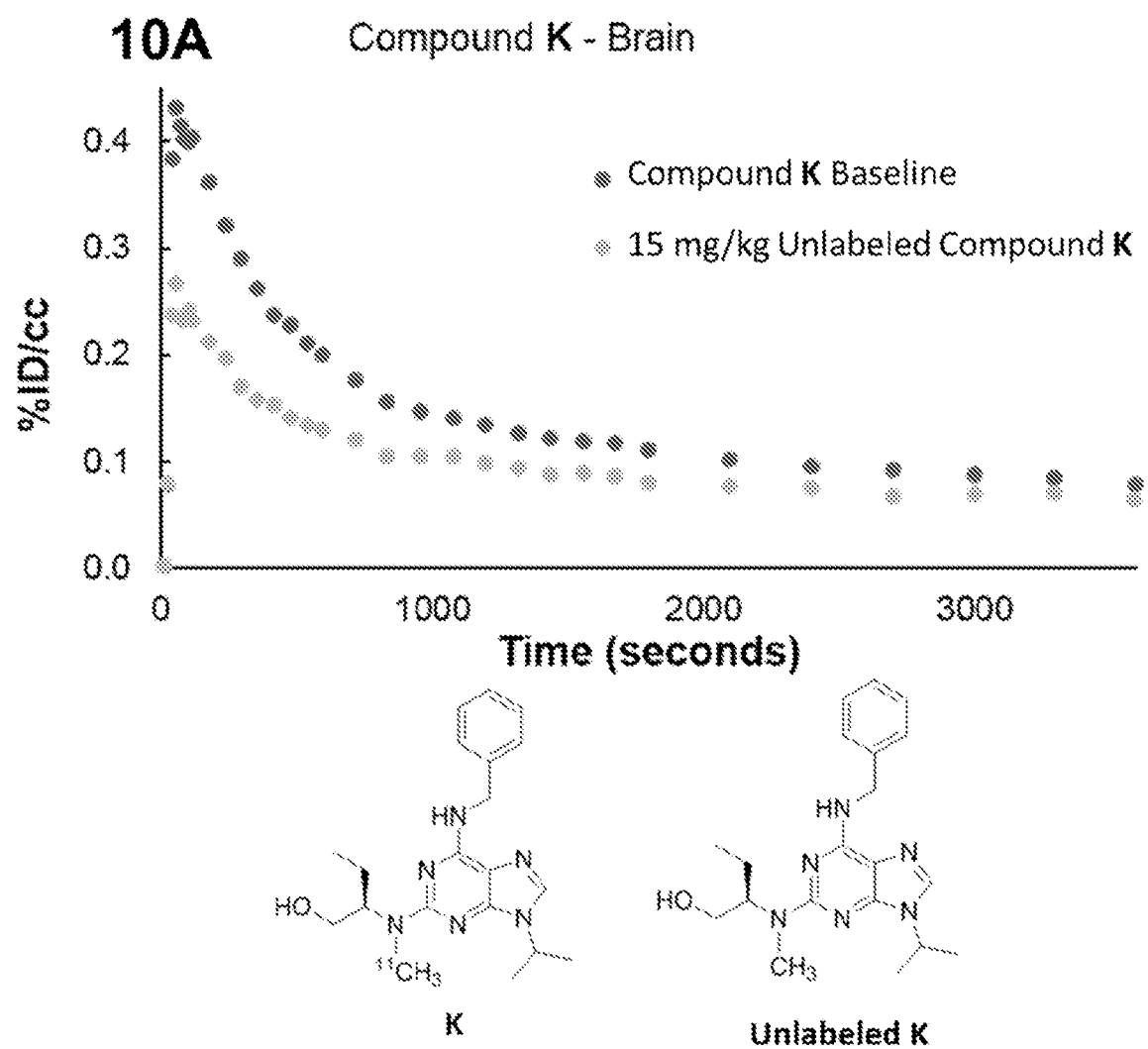
FIG. 10A shows results of a self-blocking assay (brain) using unlabeled Compound K.
Figure 13A:
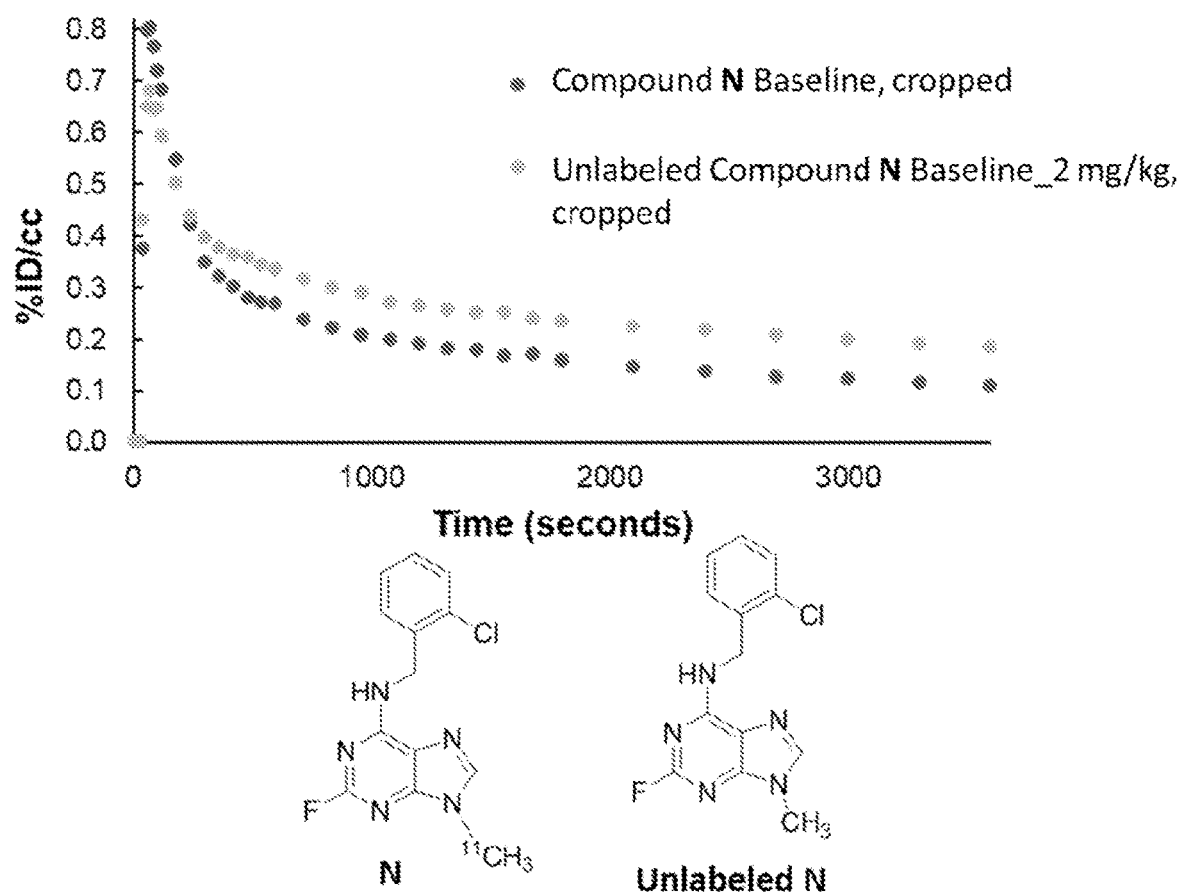
FIG. 13A shows results of a self-blocking assay (brain) using [$^{11}$C] radiolabeled compound N and unlabeled Compound N.
Figure 14A:
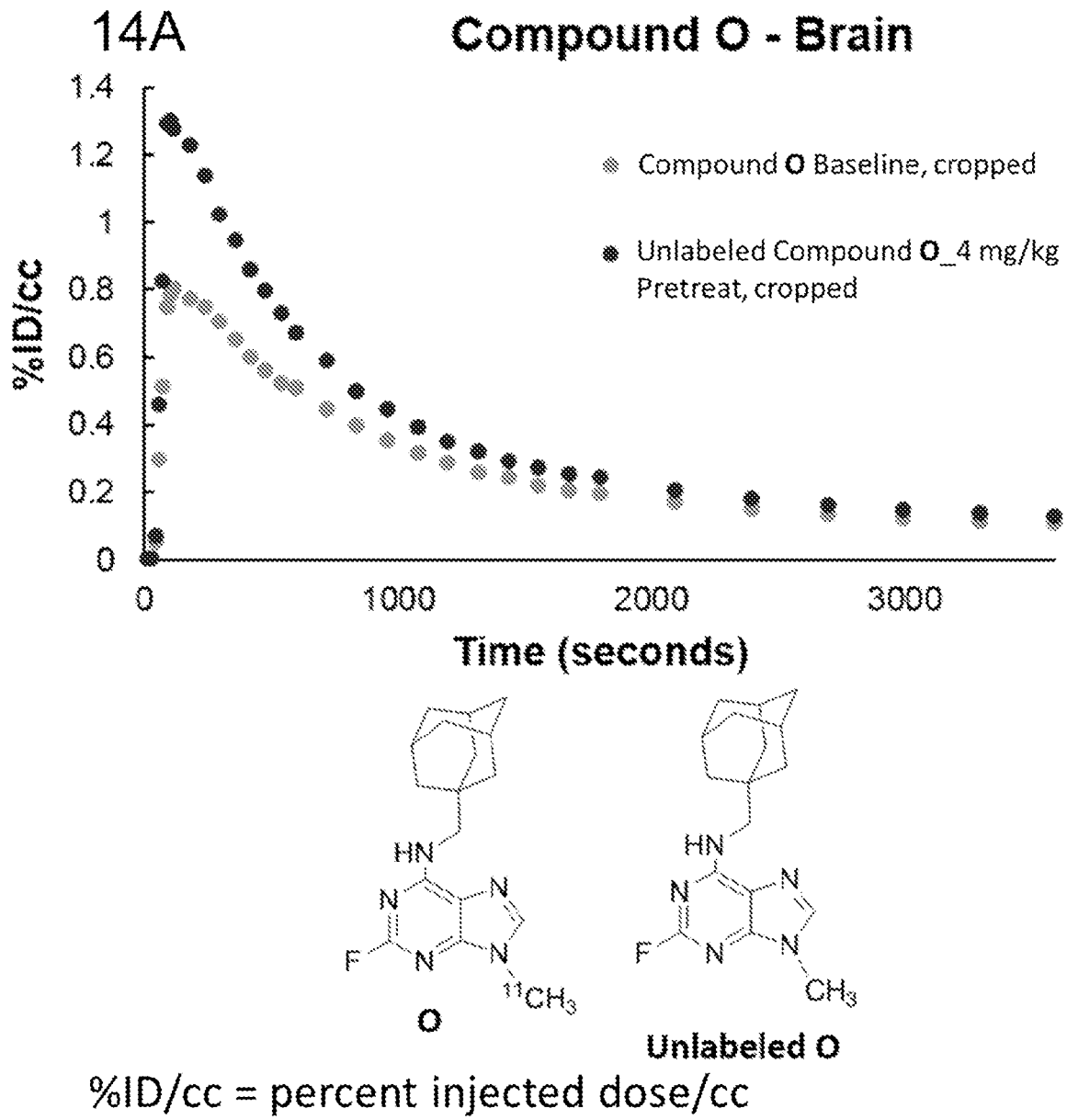
FIG. 14A shows results of a self-blocking assay (brain) using [$^{11}$C] radiolabeled Compound O and unlabeled Compound O.

At 4.2 and 12 months, female AD mice B6C3-Tg (APPswe,PSEN1dE9)85Dbo or WT controls (B6C3F1) were imaged with [$^{11}$C] radiolabeled N-benzyl-2-fluoro-9-methyl-9H-purin-6-amine. Animals were injected with [$^{11}$C] radiolabeled N-benzyl-2-fluoro-9-methyl-9H-purin-6-amine (0.4-1.3 mCi, in 10% ethanol, 90% saline). Animals were imaged for up to 60 min to monitor the radiotracer uptake. Results of the Alzheimer's disease model are shown in FIG. 5.

Example 36. Blocking Studies

Self Blocking with N-benzyl-2-fluoro-9-methyl-9H-purin-6-amine and [$^{11}$C] Radiolabeled N-benzyl-2-fluoro-9-methyl-9H-purin-6-amine Animals were injected with an unlabeled N-benzyl-2-fluoro-9-methyl-9H-purin-6-amine (0.1-16 mg/kg in 10% DMSO, 10% Tween 20, and 80% saline). Following this, animals were injected with [$^{11}$C] radiolabeled N-benzyl-2-fluoro-9-methyl-9H-purin-6-amine (0.3-1.5 mCi, in 10% ethanol, 90% saline). For the self-blocking dose-response study, the animals were co-administered with N-benzyl-2-fluoro-9-methyl-9H-purin-6-amine and [$^{11}$C] radiolabeled N-benzyl-2-fluoro-9-methyl-9H-purin-6-amine in 10% DMSO, 10% Tween 20, 10% ethanol and 70% saline in 1 mL.

Self Blocking with Unlabeled Compounds and Corresponding Radiolabeled Compounds

Animals were injected with the unlabeled $^{12}$C- or $^{19}$F-labeled derivative of a radiotracer (i.v., 2-16 mg/kg in 10% DMSO, 10% Tween 20, and 80% saline). After 2-5 min, animals were injected with the respective [$^{11}$C]- or [$^{18}$F]-labeled radiotracer (i.v., 0.15-1.5 mCi, in 10% ethanol, 90% saline) and imaged.

Blocking with Radiolabeled Compounds and [$^{11}$C] Radiolabeled N-benzyl-2-fluoro-9-methyl-9H-purin-6-amine Animals were injected with radiolabeled purine derivatives (i.v., 2-16 mg/kg in 10% DMSO, 10% Tween 20, and 80% saline) 2-5 min prior to injection of [$^{11}$C]radiolabeled N-benzyl-2-fluoro-9-methyl-9H-purin-6-amine (i.v., 0.2-1.5 mCi, in 10% ethanol, 90% saline). Radiotracer injection was followed by imaging.

Results of all blocking and self-blocking assays are shown in FIG. 6-14C. A summary of blocking and self-blocking assay data comparing radiolabeled compounds and [$^{11}$C] radiolabeled N-benzyl-2-fluoro-9-methyl-9H-purin-6-amine is shown in FIG. 15.

Example 37. Computational Molecular Modeling

Figure 16C:
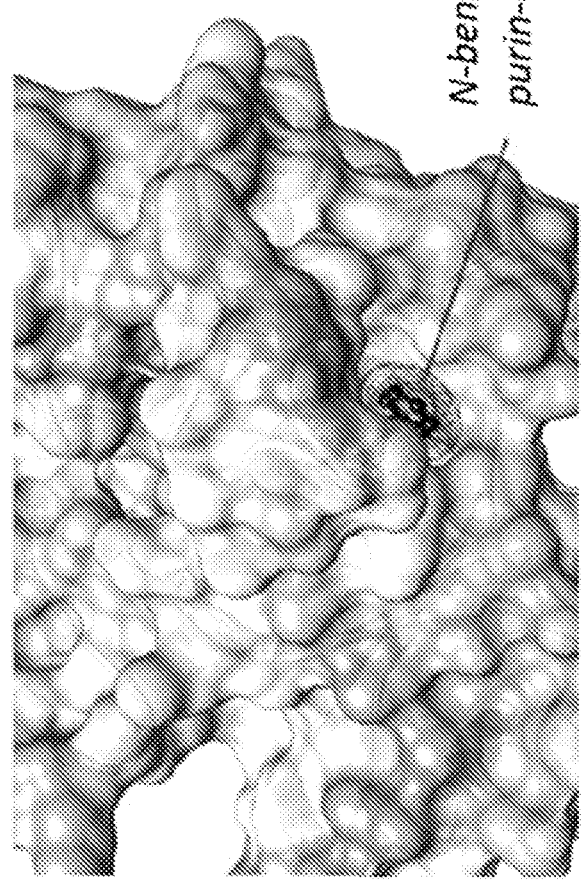
FIG. 16C shows a space-filling model of the putative binding pocket of Synapsin 1-N-benzyl-2-fluoro-9-methyl-9H-purin-6-amine.

Computational molecular modeling was used to assess in silico the docking of a N-benzyl-2-fluoro-9-methyl-9H-purin-6-amine to the synapsin I ATP-grasp site. For this purpose, AutoDock Vina (v1.1.2) was used. The boundary of the search space was defined by the coordinates of ATP complexed and co-crystalized with a monomer of the rat synapsin I C domain (PDB: 1PK8, chain A). As an initial validation, the ATP was removed from the structure and then used AutoDock Vina to model ATP without constraints within an expanded boundary box. AutoDock Vina ranked 5 primary conformations of ATP (all similar) into apo-synapsin I and these conformations (and the resulting protein interactions) showed excellent agreement with the experimentally-determined (crystallographic) conformation. Docked poses were visualized with Vina using UCSF Chimera (v1.8), and the hydrophobicity surface plot was constructed based on the Kyte-Doolittle scale. When applying the validated method to N-benzyl-2-fluoro-9-methyl-9H-purin-6-amine for synapsin I, several energy-minimized conformations of N-benzyl-2-fluoro-9-methyl-9H-purin-6-amine were calculated. Each of these conformations generally featured alignment of the purine core with that of ATP and protrusion of the phenyl ring into a hydrophobic groove. On the basis of this conformation class, it was determined that SAR efforts should include substitution on the phenyl ring to maximize hydrophobic interactions in this groove. Furthermore, additions to the purine core could fill the polar cavity typically occupied by the triphosphate component of ATP. Representative computational models are shown in FIG. 16A-C.

Example 38. Cellular Thermal Shift Assay (CETSA)

Figure 17:
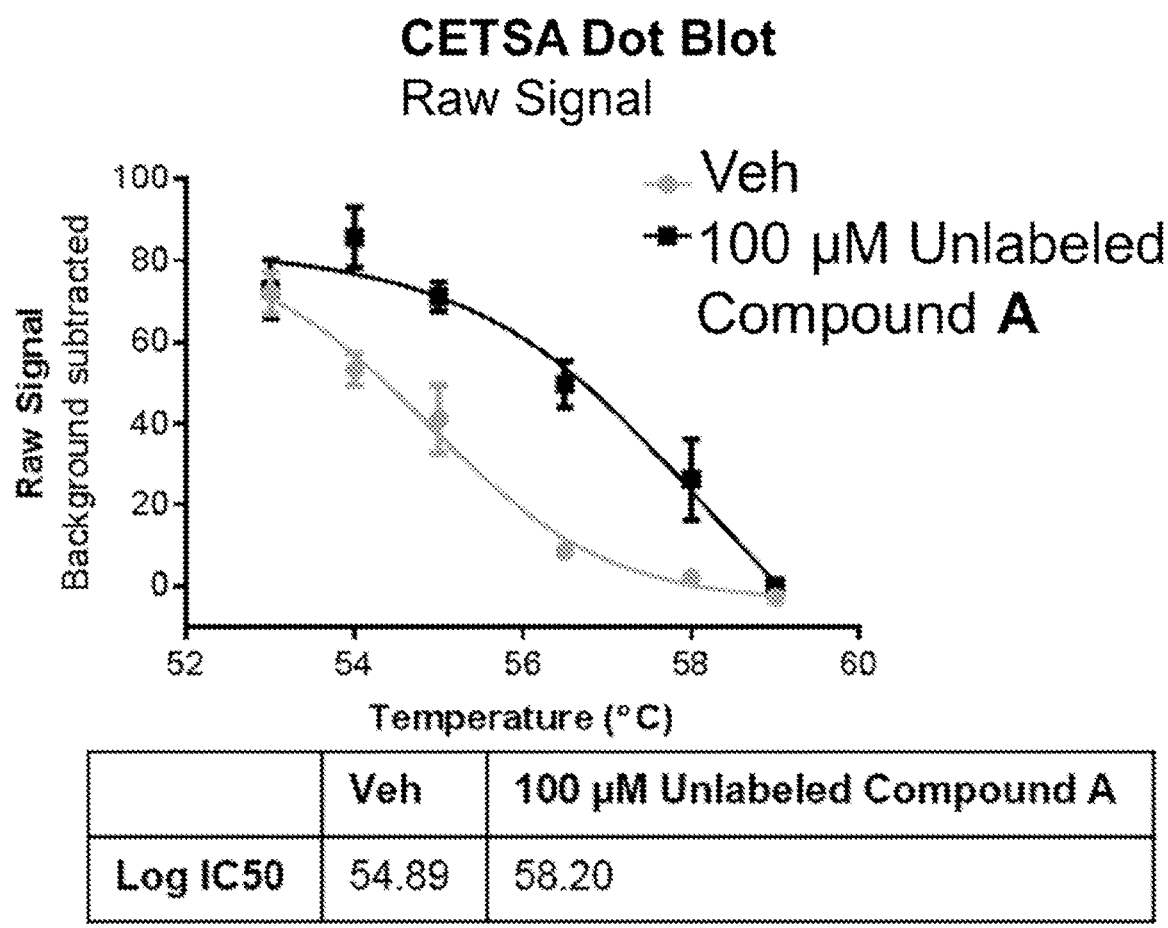
FIG. 17 shows the raw signal of a Synapsin Cell Thermal Shift Assay using unlabeled Compound A.

Methods for this assay were based on those described by Larsson, E. A. et al. *Science,* 2013, 341, 84-87. The experiment used brain lysate and a dot blot for the analysis, which is shown in FIG. 17.

Example 39. Uptake of [$^{11}$C] Radiolabeled N-benzyl-2-fluoro-9-methyl-9H-purin-6-amine in the Olfactory Epithelium of a Rhesus Macaque The non-human primates were initially anesthetized with ketamine, followed by maintenance with isoflurane. Animals were placed on the imaging bed and two lines were inserted, an IV line for tracer administration and an arterial line for blood sampling. The animals were scanned for 90 minutes, including time for the MR structural scan. During the scan and tracer injection, the heart and breathing rate of the animal were monitored. Tracer doses were 4-6 mCi (bolus or bolus-plus-infusion) with or without treatment with study compounds (nonradioactive 'blocking agent'). Prior to tracer injection, the purified tracer was analyzed on an analytical HPLC instrument to determine the purity (must be >95% chemical purity, must be >99% radiochemical purity) and specific activity (must be >1.0 Ci·μmol$^{-1}$ of the compound). As standard practice for all NHP work, pyrogenicity, chemical and radiochemical stability, residual solvents, pH, and sterility (post injection) were tested for. For [$^{11}$C] radiolabeled compounds, paired studies were performed with radiotracer injections spaced >2.5 h apart. For [$^{18}$F] studies, paired studies were performed by assessing baseline and pretreatment effect on two separate days. A high-resolution anatomical scan using multi-echo MPRAGE sequence (TR=2530 ms, TE1/TE2/TE3/TE4=1.64/3.5/5.36/7.22 ms, TI=1200 ms, flip angle=7°, and 1 mm isotropic) was simultaneously acquired during each scan. Results of the PET-MR imaging of a rhesus macaque are shown in FIG. 18A-B.

Figure 19A:
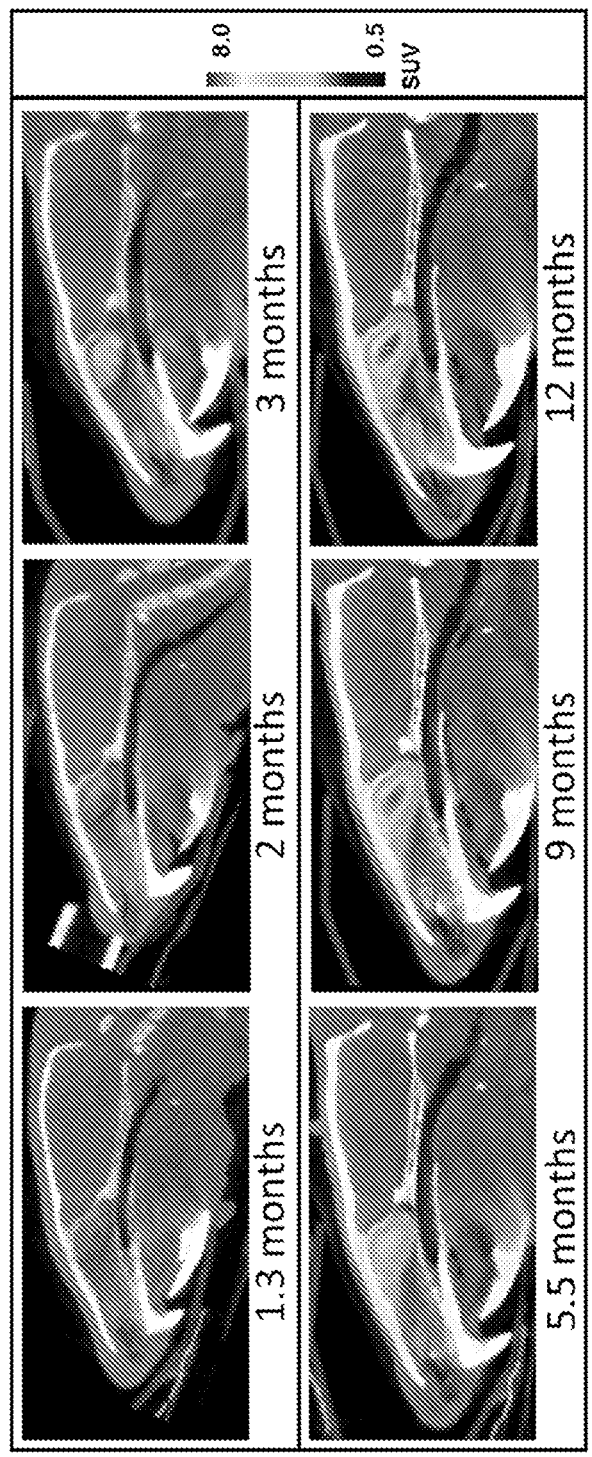
FIG. 19A-B show results of imaging neuron density changes during neurodevelopment in rat.
Figure 19B:
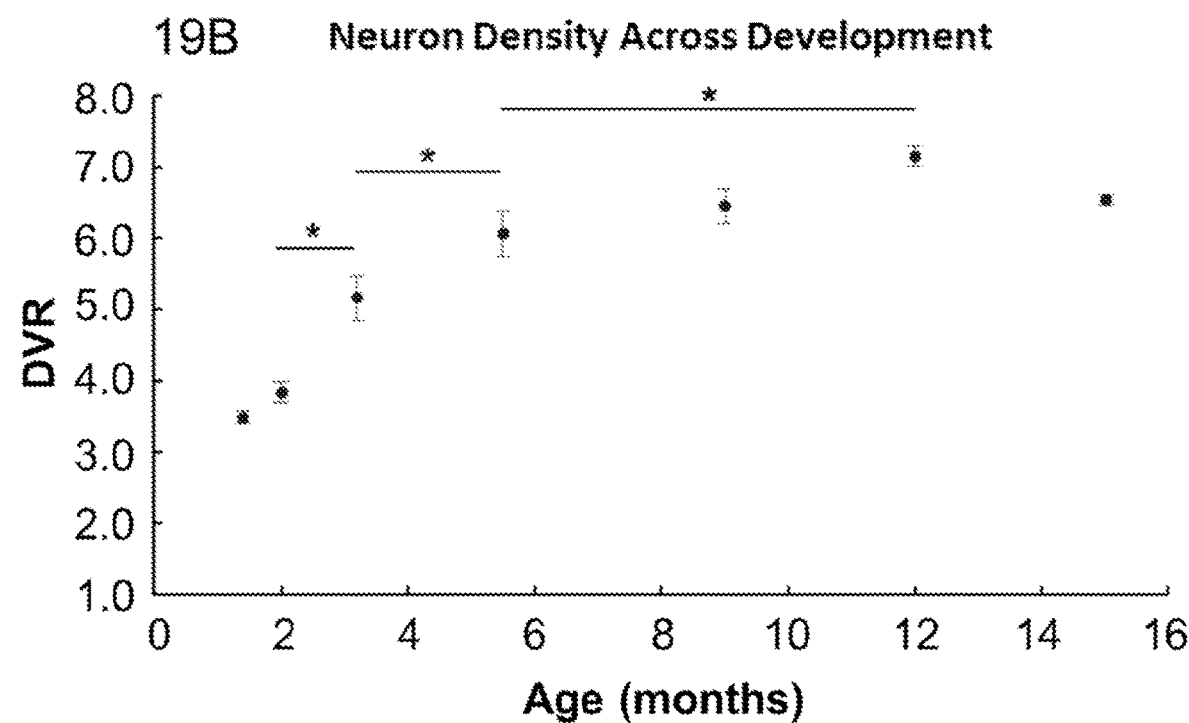

Example 40. Imaging Neuron Density Changes During Neurodevelopment in Rat and Neurodevelopment and Neurodegeneration in Mice FIGS. 19A-20B show changes in olfactory neuron density/number across age in rat and mouse. In FIGS. 19A-B, the neuron density has been monitored in male Sprague Dawley rats between 1.3 and 15 months and shows a general increase in neuron density/number (i.e., neuron influx) during the post-natal developmental period. The neuron density/number increases to the age of 12 months, then levels off (or slightly decreases) by 15 months of age. FIG. 19A-B shows results of monitoring neural density changes during postnatal development. Male Sprague Dawley rats imaged at specified ages. Images of FIG. 19A show SUV, averaged over 3-45 minutes. The graph of FIG. 19B depicts average DVR values for each age. Error bars are ±sem; n=3-9 per age. *$p<0.05$ using a two-tailed Student's t-test.

In female mice, a similar trend was observed, with an increasing neuron density/number (or neuron influx) detected during postnatal development between 3 and 7 months of age. This is followed by image-guided detection of a decreased neuron density/number (or neuron efflux) during aging, beginning after 7 months of age. FIG. 20A-B shows results of monitoring neural density changes during postnatal development and aging in mice. Female C57BL/6 or B6C3 mice were imaged at specified ages. Images of FIG. 20A show SUV, averaged over 3-45 minutes. The graph of FIG. 20 B depicts average DVR values for each age. Error bars are ±sem; n=6 at 3 months, n=2 at 4 months, n=3 at 7 months, n=5 at 12 months, n=3 at 23 months. **$p<0.01$ using a two-tailed Student's t-test.

Example 41. Monitoring Central Nervous System Damage from Anterior Bulbectomy

FIGS. 21A-B demonstrates a decrease in radiotracer uptake following an anterior bulbectomy, which causes damage to the axons of mature (or nearly mature) olfactory sensory neurons, resulting in their death. The neuron death is greatest 2-3 days after the anterior bulbectomy, at which point the animals were imaged using a neuron density radiotracer. The radiotracer uptake shows a decrease after a unilateral bulbectomy, and a further decrease (significant from control) after bilateral anterior bulbectomy, indicating that the radiotracer is sensitive to mature neuron cell death caused by olfactory bulb damage. Further, this study demonstrates the ability of this neuron radiotracer to detect damage within the central nervous system, although the radiotracer uptake is outside the central nervous system, in the olfactory epithelium. FIG. 21A-B shows results of monitoring neural density changes following anterior bulbectomy. Female C57BL/6 mice imaged 2-3 days after anterior bulbectomy. Images of FIG. 21A show SUV, averaged over 3-45 minutes. The graph of FIG. 21B depicts individual and average DVR values for control, unilateral (right side) anterior bulbectomy, and bilateral anterior bulbectomy. Unilateral and bilateral animals were imaged 3 days post-bulbectomy, except for the bilateral animal with highest DVR, which was imaged 2 days post-bulbectomy. Error bars are ±sem. *p<0.05 using a two-tailed Student's t-test.

Example 42. Imaging Neurodegeneration in Tau Model of Alzheimer's/Frontotemporal Dementia FIGS. 22A-B shows the detection of decreased neuron density/number in a murine tauopathy model of Alzheimer's disease/frontotemporal dementia. These animals were monitored at a relatively early stage of the disease (3.7 months) as well as a more severe stage of the disease (7 months). At both ages, our neuron density radiotracer showed a decreased uptake in the transgenic animal model compared to non-carrier control animals, indicating a decrease in neuron density/number (i.e., neuron efflux) in the transgenic animals. This data indicates that our neuron density radiotracers are adept at monitoring neuron density/number changes that occur in tauopathy. FIGS. 22A-B shows results of monitoring neurodegeneration in a murine model of Alzheimer's disease/Frontotemporal Dementia. Female rTg4510 and WT (within colony) mice imaged at 3.7 and 7 months. Images of FIG. 22A show SUV, averaged over 3-45 minutes. The graph of FIG. 22B depicts individual and average DVR values for WT control and rTg4510 animals. Error bars are ±sem. *p<0.05 using a two-tailed Student's t-test. **p<0.005 using a two-tailed Student's t-test.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of Formula (II):

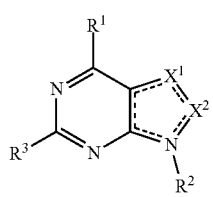

(II)

or a pharmaceutically acceptable salt thereof, wherein:
=== represents a single- or double-bond;
$X^1$ is $CR^A$ or $NR^B$;
$X^2$ is $CR^A$ or $NR^B$; wherein
one of $X^1$ and $X^2$ is $CR^A$ and the other is $NR^B$;
$R^A$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)$ $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^B$ is absent; or
$R^B$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)OR^{b2}$, $NR^{c2}R^{d2}$, $C(=O)$ $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^1$ is $NR^N R^{N'}$;
$R^N$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, and 4-10 membered heterocycloalkyl;
$R^{N'}$ is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, and —($C_{1-6}$ alkylene)-$Cy^1$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

$R^2$ is absent; or
$R^2$ is selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, $OR^{a2}$, $C(=O)R^{b2}$, $C(=O)R^{b2}$, $NR^{c2}R^{d2}$, $C(=O)$ $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)R^{a2}$, $S(O)_2R^{a2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;

wherein at least two of $R^A$, $R^B$, and $R^2$ are independently H or absent;
$R^3$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heteroaryl, 4-10 membered heterocycloalkyl, halo, $NR^{c3}R^{d3}$ and $NO_2$, wherein the $C_{3-10}$ cycloalkyl, $C_{6-10}$ aryl, 4-10 membered heteroaryl, and 4-10 membered heterocycloalkyl are each optionally substituted by 1, 2, 3, or 4 independently selected $R^4$ groups;
each $R^{a2}$, $R^{b2}$, $R^{c2}$, and $R^{d2}$ is independently selected from the group consisting of H, $C_{1-6}$ alkyl, $C_{2-6}$ alkenyl, and $C_{2-6}$ alkynyl;
$R^{c3}$ and $R^{d3}$ are each independently selected from the group consisting of H, $C_{1-6}$ alkyl, $C_{2-6}$ alkenyl, $C_{2-6}$ alkynyl, and $C(=O)OR^{a2}$, wherein the $C_{1-6}$ alkyl is optionally substituted by 1, 2, 3, or 4 independently selected $R^4$ groups;

each Cy is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy^1$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups;

each $Cy'$ is independently selected from the group consisting of $C_{3-10}$ cycloalkyl, $C_{6-10}$ aryl, 4-10 membered heteroaryl, and 4-10 membered heterocycloalkyl, each optionally substituted by 1, 2, 3, or 4 independently selected $R^4$ groups; and each $R^4$ is independently selected from the group consisting of OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkoxy)-($C_{1-6}$ alkoxy), $C_{1-6}$ haloalkoxy, $C_{3-10}$ cycloalkyl, phenyl, amino, $C_{1-6}$ alkylamino, di($C_{1-6}$ alkyl)amino, —($C_{1-6}$ alkylene)-amino, —($C_{1-6}$ alkylene)-$C_{1-6}$ alkylamino, —($C_{1-6}$ alkylene)-di($C_{1-6}$ alkyl)amino, carbamyl, $C_{1-6}$ alkylcarbamyl, di($C_{1-6}$ alkyl)carbamyl, —($C_{1-6}$ alkylene)-$C_{1-6}$ alkyoxycarbamyl, $C_{1-6}$ alkylcarbonyl, $C_{1-6}$ alkoxycarbonyl, $C_{6-10}$ arylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

wherein the compound of Formula (II) comprises at least one radioisotope.

2. The compound of claim 1, wherein $R^N$ is H or $C_{1-6}$ alkyl.

3. The compound of claim 1, wherein $R^{N'}$ is selected from the group consisting of $C_{3-10}$ cycloalkyl, $C_{6-10}$ aryl, 4-10 membered heteroaryl, 4-10 membered heterocycloalkyl, and —($C_{1-6}$ alkylene)-$Cy^1$.

4. The compound of claim 1, wherein $Cy^1$ is selected from the group consisting of $C_{3-10}$ cycloalkyl, $C_{6-10}$ aryl, and 4-10 membered heteroaryl, and each is optionally substituted by 1, 2, 3, or 4 independently selected $R^4$ groups.

5. The compound of claim 1, wherein $R^2$ is selected from the group consisting of H, $C_{1-6}$ alkyl, $C_{3-10}$ cycloalkyl, $C_{6-10}$ aryl, 4-10 membered heteroaryl, 4-10 membered heterocycloalkyl, —($C_{1-6}$ alkylene)-$Cy^2$, C(=O)$R^{b2}$, and $NR^{c2}R^{d2}$, wherein the $C_{1-6}$ alkyl, 4-10 membered heteroaryl, and 4-10 membered heterocycloalkyl are each optionally substituted by 1, 2, 3, or 4 independently selected $R^4$ groups.

6. The compound of claim 1, wherein $R^3$ is selected from the group consisting of H, halo, $NR^{c3}R^{d3}$, and $NO_2$.

le;2q7. The compound of claim 1, wherein the radioisotope is selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$ $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$.

8. The compound of claim 1, wherein the compound of Formula (II) is selected from the group consisting of:

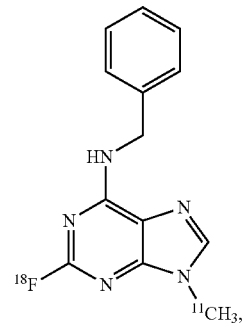

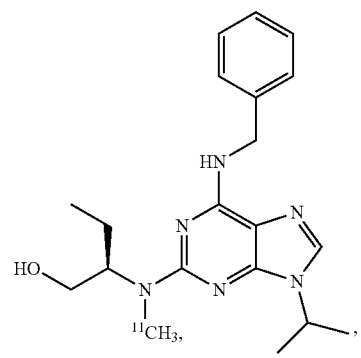

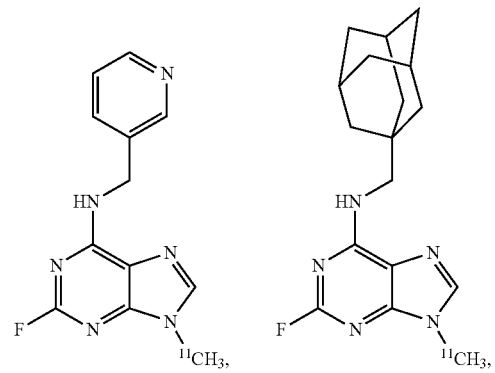

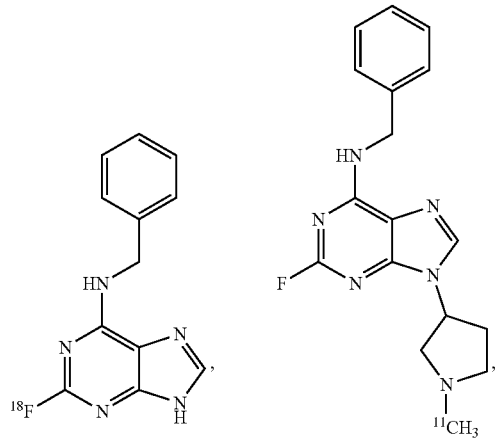

131
-continued
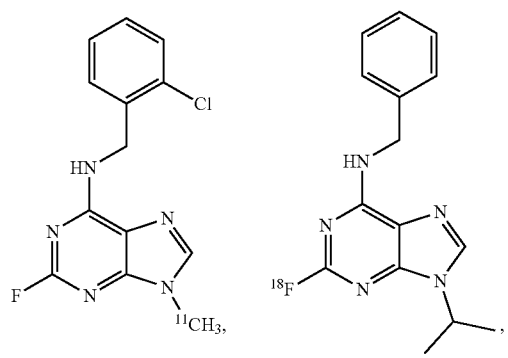
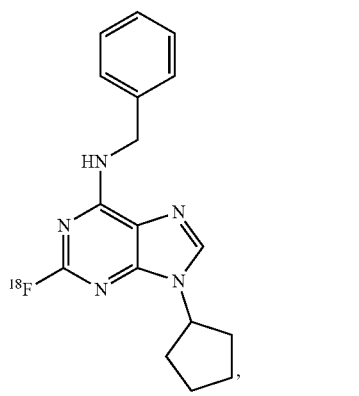
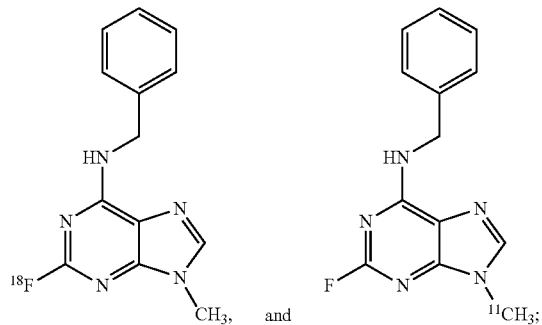
or a pharmaceutically acceptable salt thereof.
9. A pharmaceutical composition comprising a compound of claim 1, or a pharmaceutically acceptable salt thereof, and at least one pharmaceutically acceptable carrier.
10. A compound, which is selected from the group consisting of:
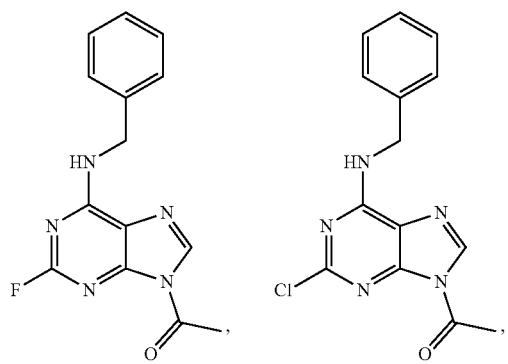
132
-continued
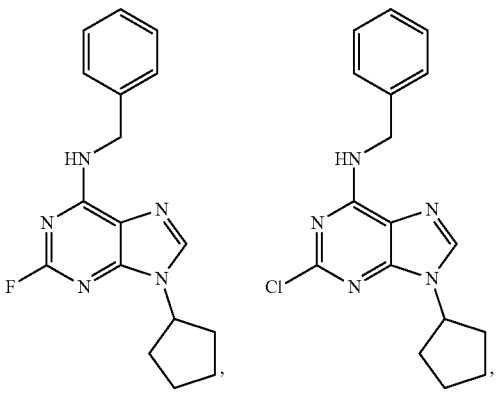
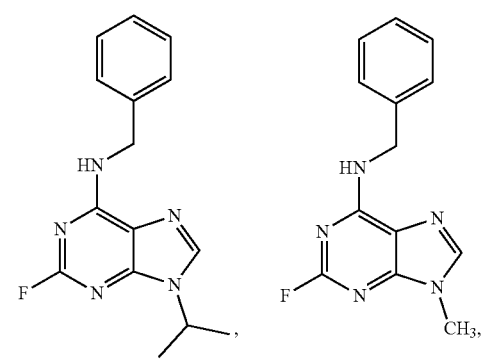
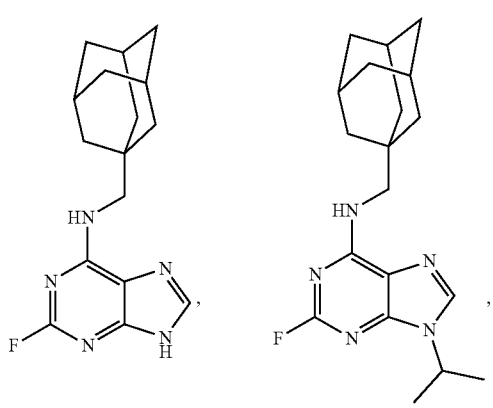
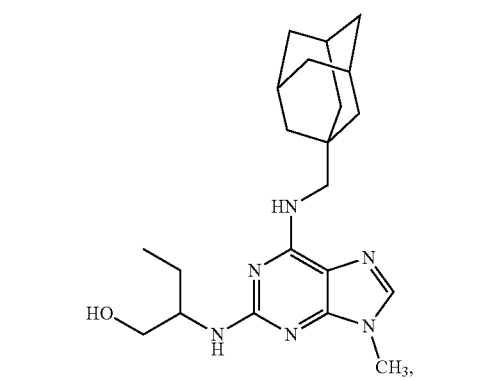

133
-continued
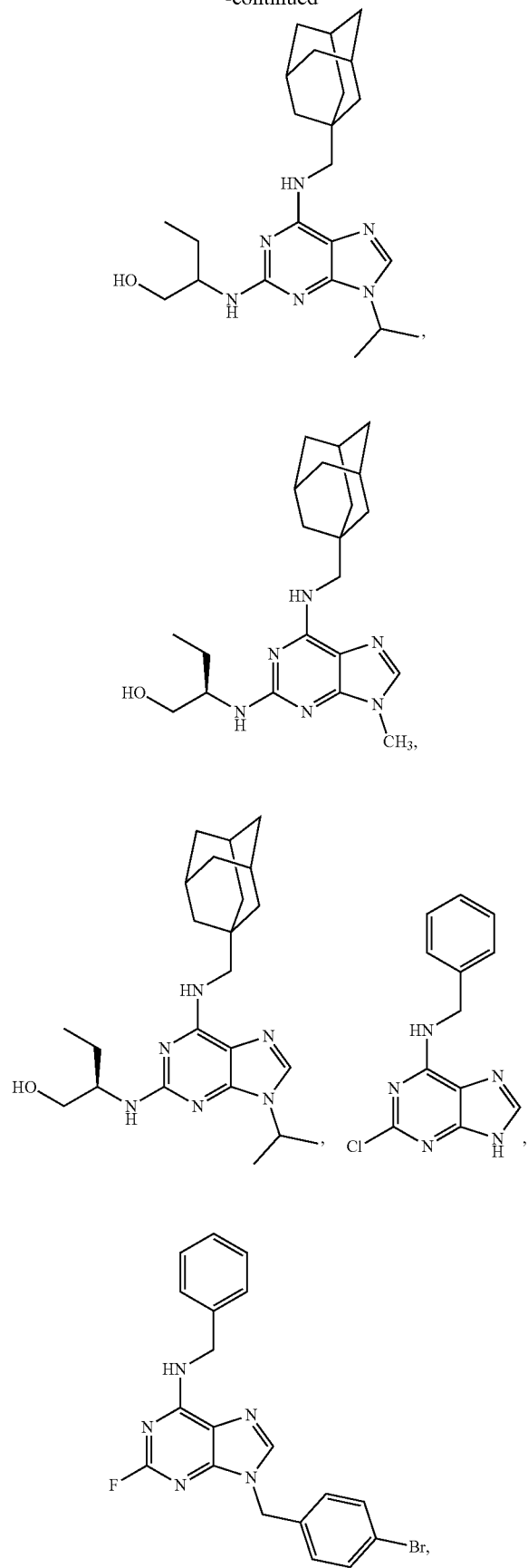
134
-continued
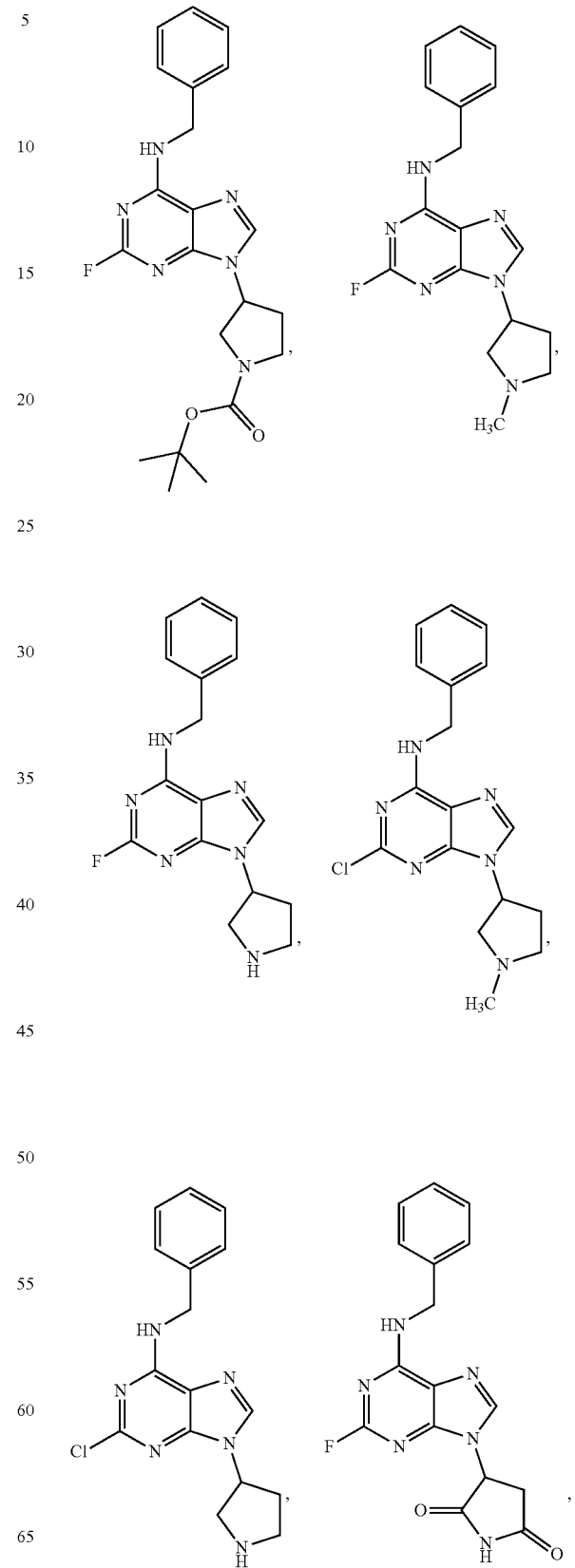

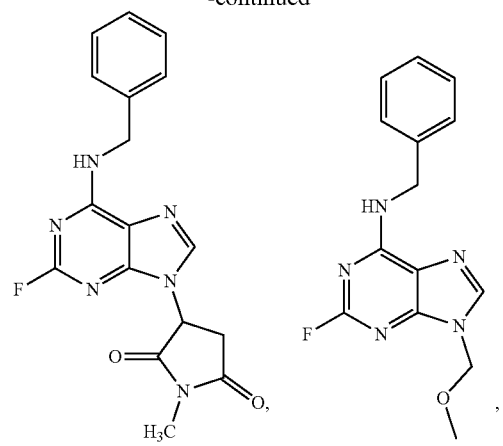
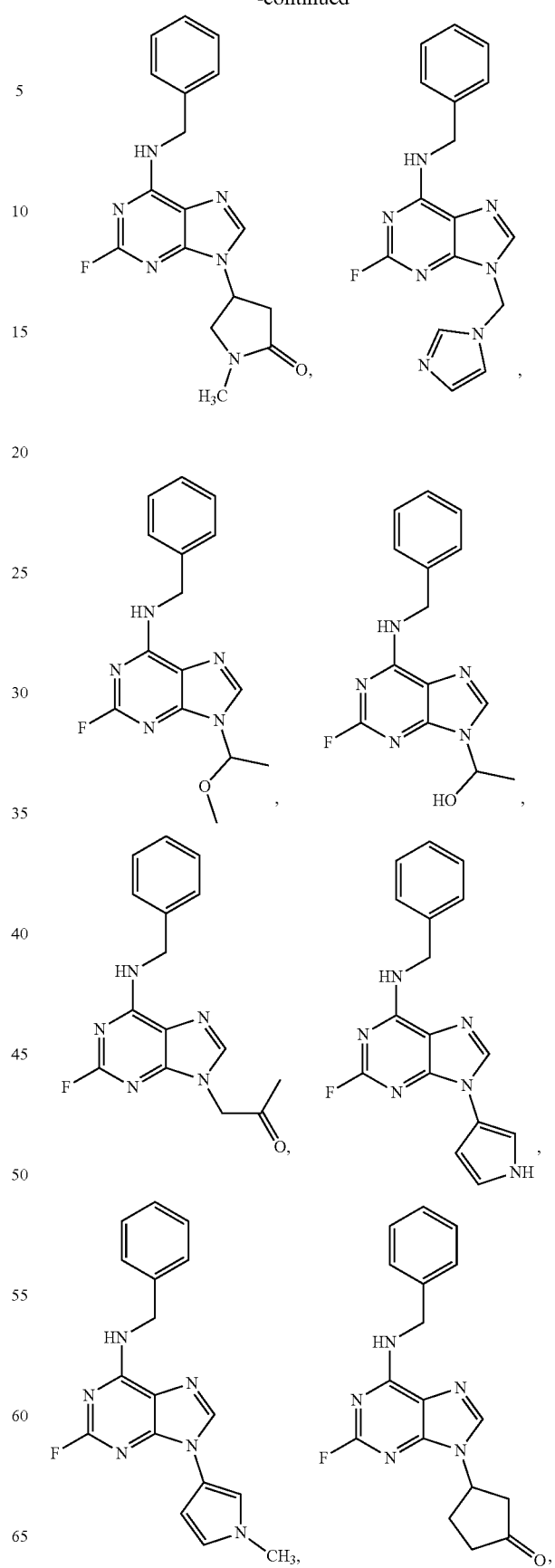

137
-continued
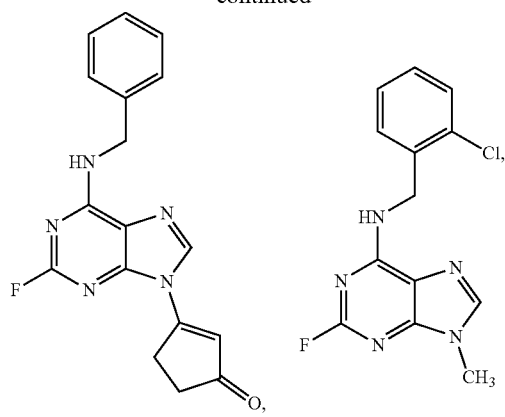
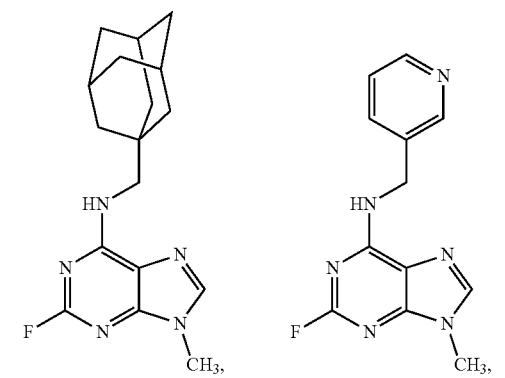
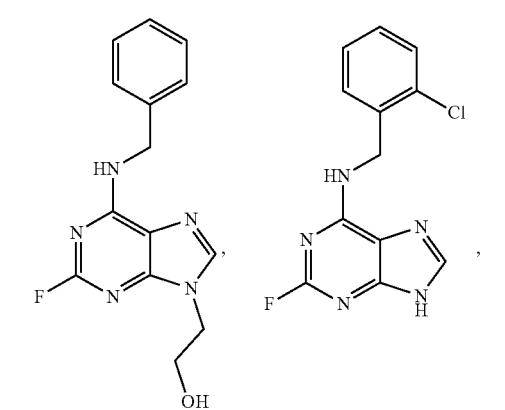
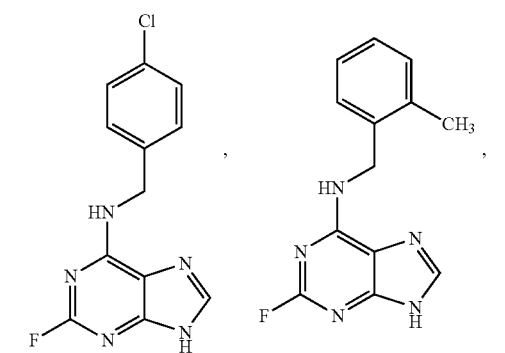
138
-continued
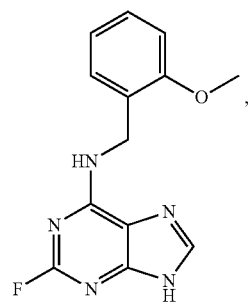
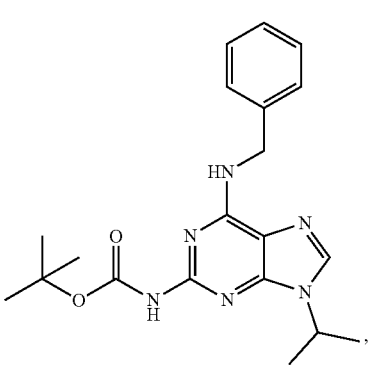
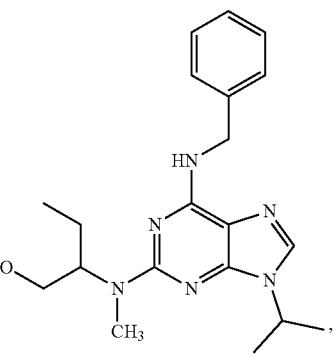
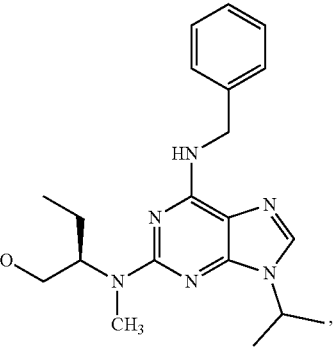

139
-continued
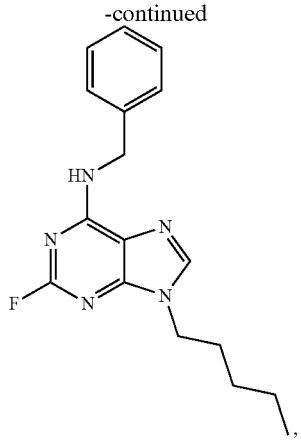
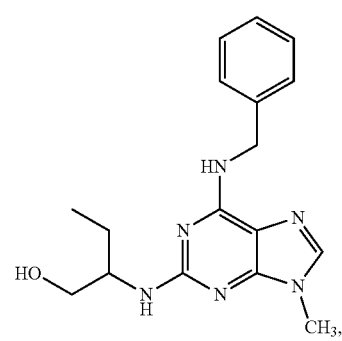
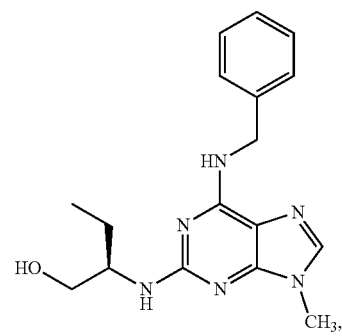
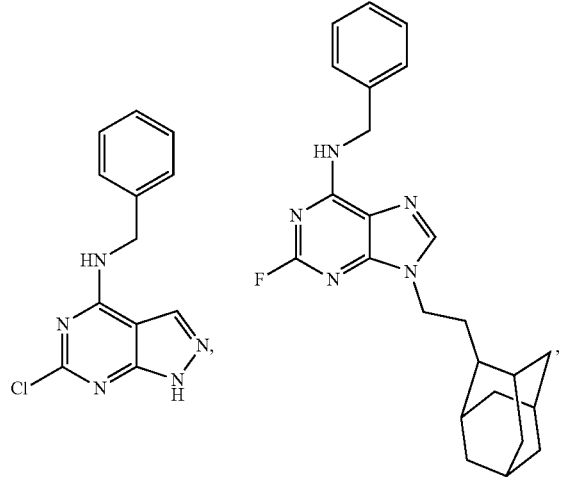
140
-continued
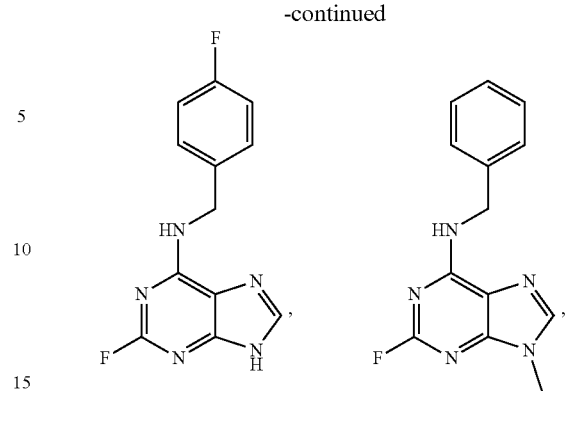
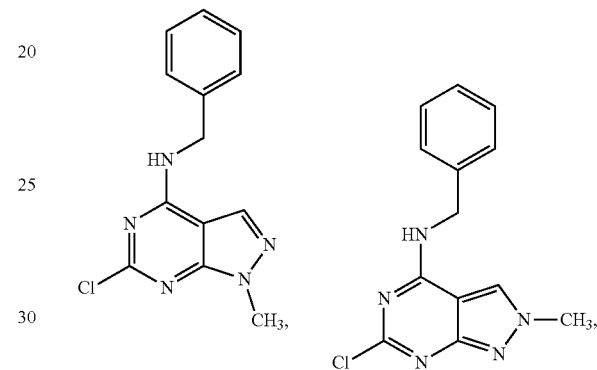
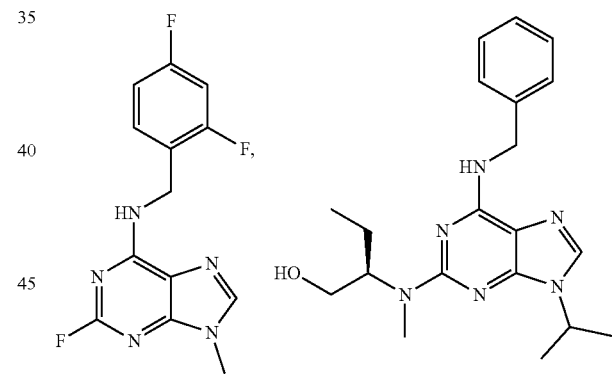
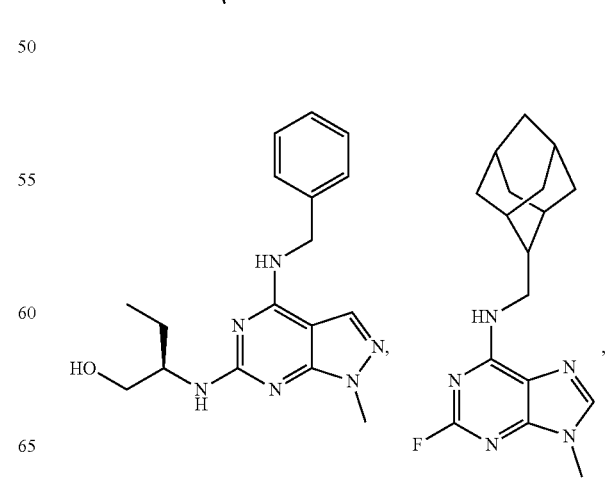

141
-continued
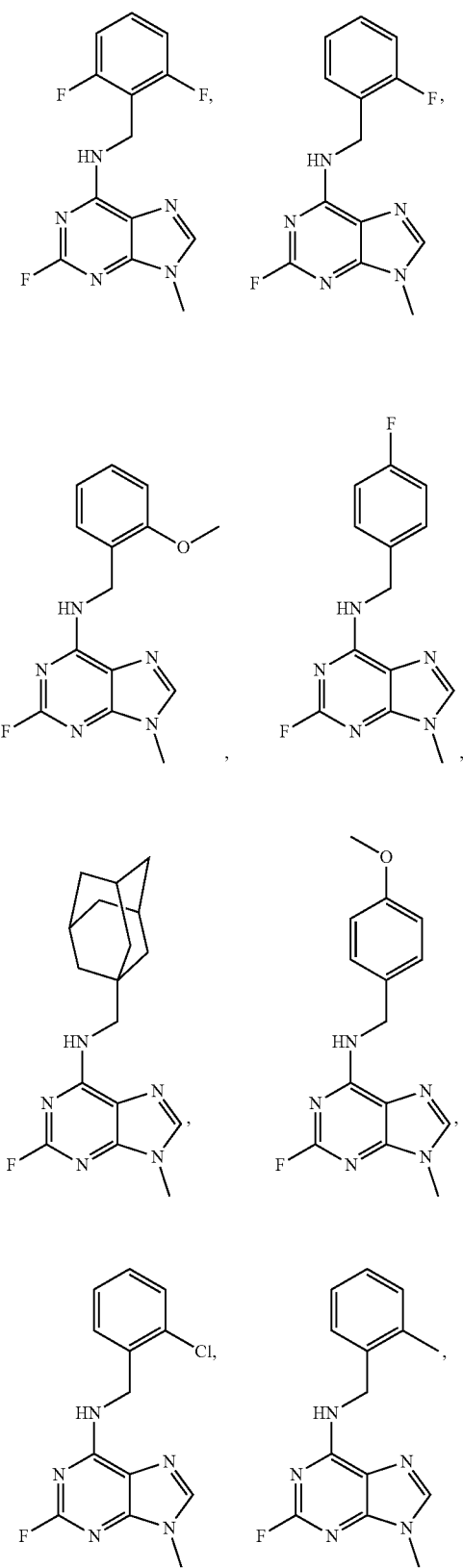
142
-continued
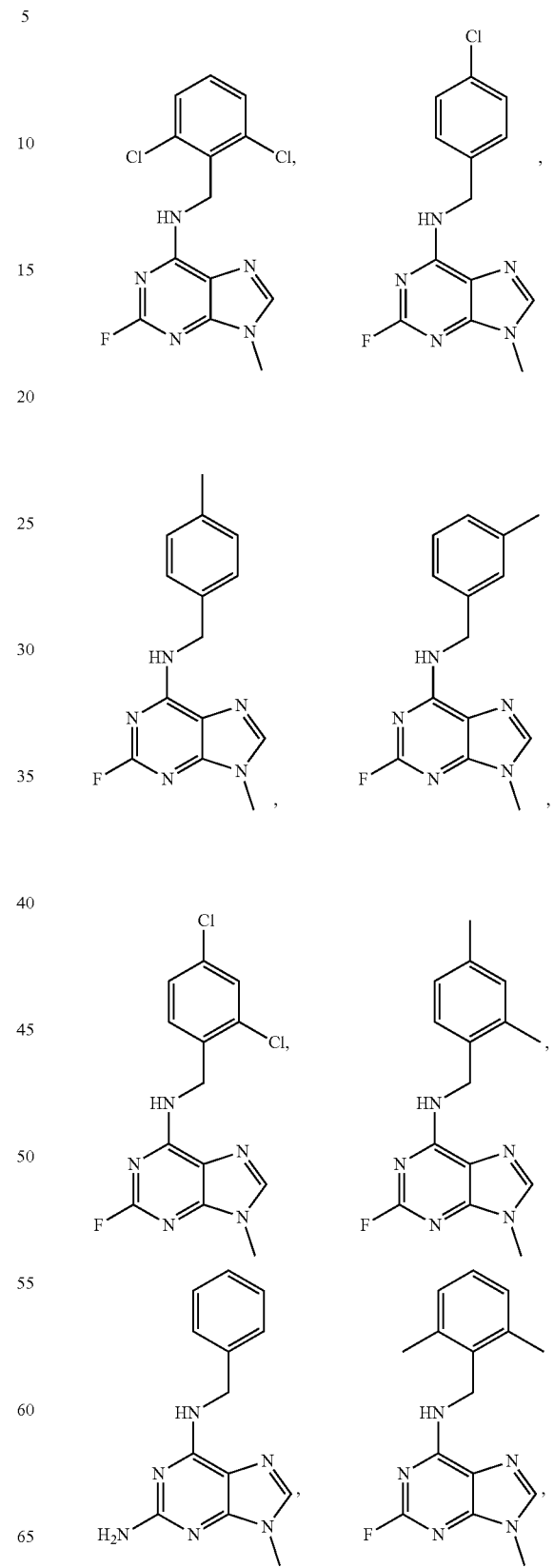

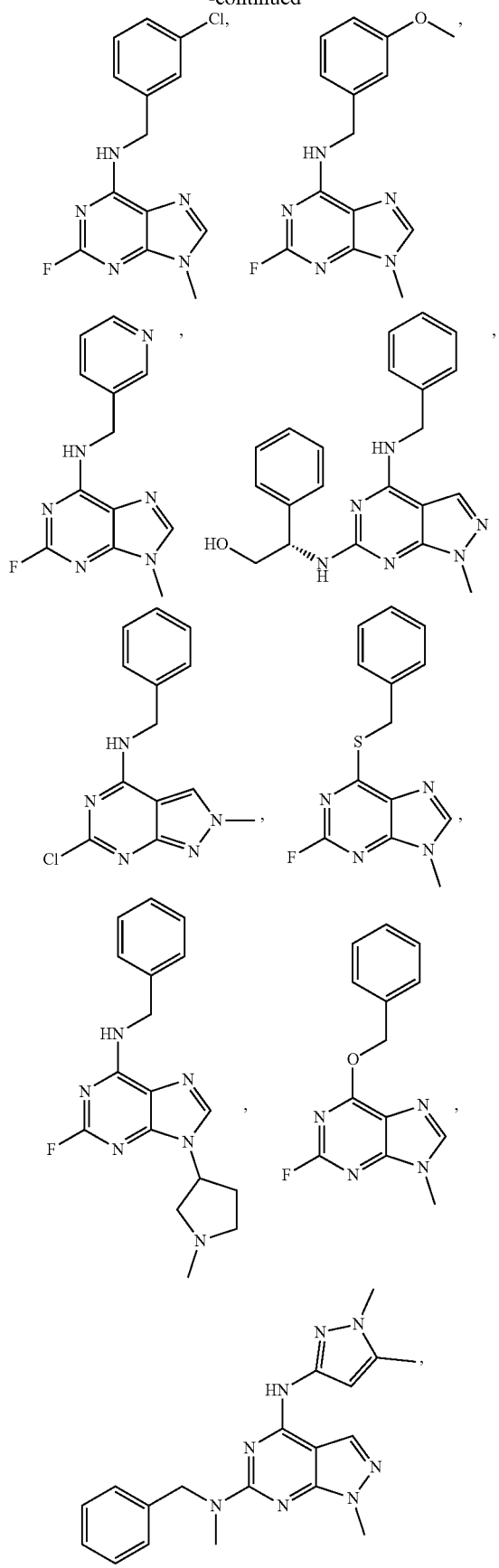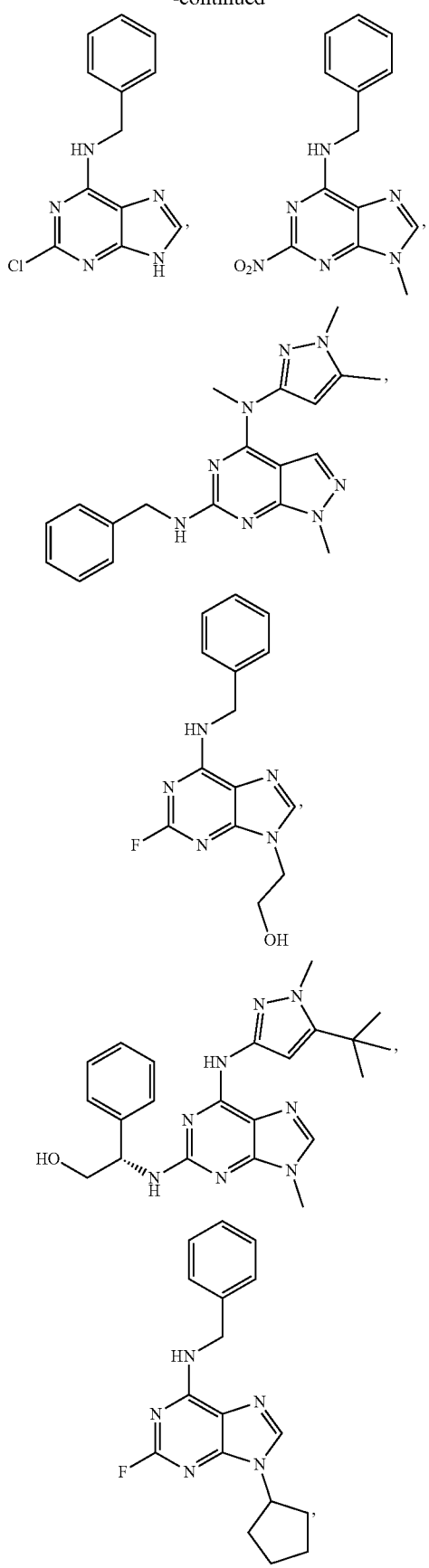

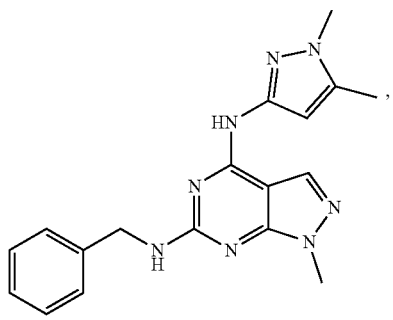
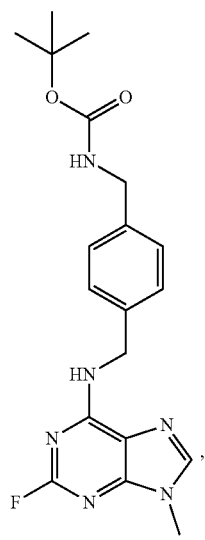
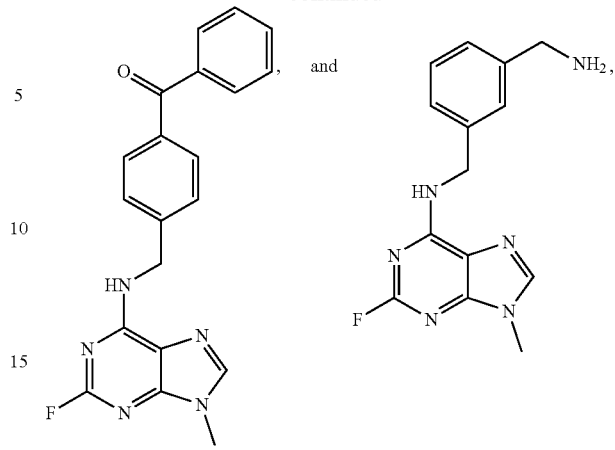
or a pharmaceutically acceptable salt thereof.
11. A pharmaceutical composition comprising a compound of claim 10, or a pharmaceutically acceptable salt thereof, and at least one pharmaceutically acceptable carrier.
12. A compound, which is:
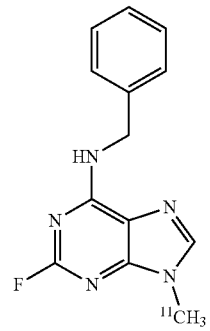 [SMILES: [11CH3]n1cnc2c(NCc3ccccc3)nc(F)nc21]
or a pharmaceutically acceptable salt thereof.
* * * * *

UNITED STATES PATENT AND TRADEMARK OFFICE
CERTIFICATE OF CORRECTION

PATENT NO. : 10,519,160 B2
APPLICATION NO. : 15/326890
DATED : December 31, 2019
INVENTOR(S) : Genevieve Van de Bittner and Jacob Hooker Page 1 of 2

It is certified that error appears in the above-identified patent and that said Letters Patent is hereby corrected as shown below:

On the Title Page

Item [56], Column 2, Line 2, delete "6-oyridylmethylaminopurines" and insert -- 6-pyridylmethylaminopurines --

Item [56], Column 2, Line 21, delete "ofNuclear" and insert -- of Nuclear --

Item [56], Column 2, Line 31, delete "measurments,"" and insert -- measurements," --

In the Claims

Column 128, Line 41, Claim 1, delete "$R^{b2}$," and insert -- $OR^{b2}$, --

Column 129, Line 12, Claim 1, delete "$Cy^{t}$" and insert -- $Cy^2$ --

Column 129, Line 62, Claim 7, before "7." delete "le;2q"

Column 129, Line 65, Claim 7, delete "$^{76}Br$" and insert -- $^{76}Br$, --

Column 142, Lines 55-65, Claim 10, delete " 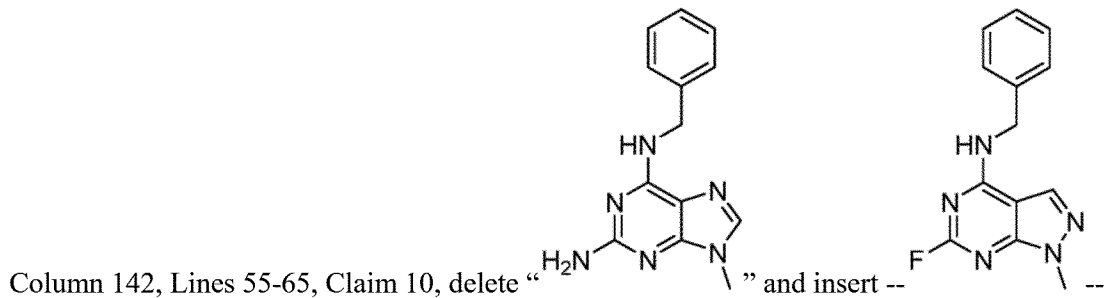 " and insert --

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,519,160 B2

Column 144, Lines 42-50, Claim 10, delete " 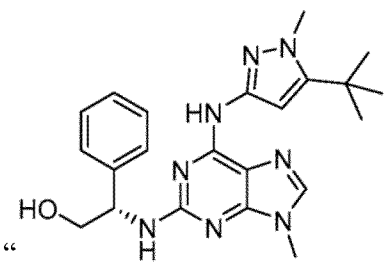 " and insert

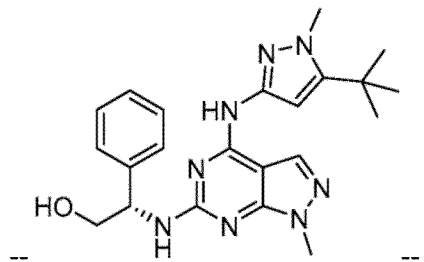

-- --